(12) United States Patent
Alberti et al.

(10) Patent No.: US 7,034,030 B2
(45) Date of Patent: Apr. 25, 2006

(54) PYRALOPYRIDINES, PROCESS FOR THEIR PREPARATION AND USE AS THERAPEUTIC COMPOUNDS

(75) Inventors: Michael John Alberti, Durham, NC (US); Stanley D. Chamberlain, Durham, NC (US); Mui Cheung, Durham, NC (US); Kristjan Gudmundsson, Durham, NC (US); Philip Anthony Harris, Durham, NC (US); Brian A. Johns, Durham, NC (US); David Kendall Jung, Durham, NC (US); Michael Robert Peel, Durham, NC (US); Jennifer Badiang Stanford, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 162 days.

(21) Appl. No.: 10/473,196

(22) PCT Filed: Mar. 20, 2002

(86) PCT No.: PCT/US02/08524

§ 371 (c)(1),
(2), (4) Date: Sep. 24, 2003

(87) PCT Pub. No.: WO02/078700

PCT Pub. Date: Oct. 10, 2002

(65) Prior Publication Data

US 2005/0059677 A1   Mar. 17, 2005

Related U.S. Application Data

(60) Provisional application No. 60/315,090, filed on Aug. 27, 2001, provisional application No. 60/307,786, filed on Jul. 25, 2001, provisional application No. 60/307,189, filed on Jul. 23, 2001, provisional application No. 60/280,047, filed on Mar. 30, 2001.

(51) Int. Cl.
*C07D 403/04* (2006.01)
*A61K 31/505* (2006.01)

(52) U.S. Cl. ............... 514/256; 514/269; 514/275; 544/333

(58) Field of Classification Search ............ 544/333; 514/256, 269, 275
See application file for complete search history.

(56) References Cited

U.S. PATENT DOCUMENTS

| 4,576,952 A | 3/1986 | Hurst et al. |
| 4,621,089 A | 11/1986 | Ward et al. |
| 4,670,432 A | 6/1987 | Ward et al. |
| 4,985,444 A | 1/1991 | Shiokawa et al. |
| 5,155,114 A | 10/1992 | Shiokawa et al. |
| 5,204,346 A | 4/1993 | Shiokawa et al. |
| 5,234,930 A | 8/1993 | Shiokawa et al. |
| 5,296,490 A | 3/1994 | Shiokawa et al. |
| 5,300,478 A | 4/1994 | Michaely et al. |
| 5,498,774 A | 3/1996 | Mitsudera et al. |
| 5,552,422 A | 9/1996 | Gauthier et al. |
| 5,700,816 A | 12/1997 | Isakson et al. |
| 5,990,148 A | 11/1999 | Isakson et al. |
| 6,136,839 A | 10/2000 | Isakson et al. |
| 6,207,675 B1 | 3/2001 | Carry et al. |

FOREIGN PATENT DOCUMENTS

| EP | 0 404 190 A1 | 6/1990 |
| EP | 0 404 190 B1 | 6/1990 |
| EP | 0 379 979 | 8/1990 |
| EP | 0 467 248 B1 | 7/1991 |
| EP | 0 497 258 A2 | 1/1992 |
| WO | 0 364 204 A1 | 10/1989 |
| WO | WO 91 00092 | 1/1991 |
| WO | WO 91 19497 | 12/1991 |
| WO | WO 95 00501 | 1/1995 |
| WO | WO 96 06840 | 3/1996 |
| WO | WO 96 21667 | 7/1996 |
| WO | WO 96 31509 | 10/1996 |
| WO | WO 96 41625 | 12/1996 |
| WO | WO 96 41626 | 12/1996 |
| WO | WO 96 41645 | 12/1996 |
| WO | WO 98 56377 | 12/1998 |
| WO | WO 99 12930 | 3/1999 |
| WO | WO 99/58523 | 11/1999 |
| WO | WO 99/59585 | 11/1999 |
| WO | WO 99 64419 | 12/1999 |
| WO | WO 00/26216 | 5/2000 |
| WO | WO 00/52008 | 9/2000 |
| WO | WO 01/00615 | 1/2001 |
| WO | WO 01 14375 | 3/2001 |
| WO | WO 02/16359 | 2/2002 |
| WO | WO 02 16359 | 2/2002 |
| WO | WO 02 18382 | 3/2002 |
| WO | WO 02/18382 | 3/2002 |

(Continued)

OTHER PUBLICATIONS

Vane, J. et al. "Towards a Better Aspirin." Nature, vol. 367, Jan. 20, 1994, pp. 215-216.

Carter, J. et al. "Recently Reported Inhibitors of Cyclooxygenase-2." Exp. Opin. Ther. Patents (1998), 8(1), pp. 21-29.

Talley, JJ., "Review, Pulmonary-Allergy, Dermatological, Gastrointestinal & Arthritis, Selective Inhibitors of Cyclooxygenase-2." Exp. Opin. Ther. Patents (1997) 7(1), pp. 55-62.

(Continued)

*Primary Examiner*—Zinna Northington Davis
(74) *Attorney, Agent, or Firm*—Lorie Ann Morgan

(57) ABSTRACT

The present invention provides compounds of formula (I): wherein all variables are as defined herein, pharmaceutical compositions containing the same, processes for preparing the same and their use as pharmaceutical agents.

25 Claims, No Drawings

FOREIGN PATENT DOCUMENTS

| | | |
|---|---|---|
| WO | WO 02 48147 | 6/2002 |
| WO | WO 02/048148 | 6/2002 |
| WO | WO 02 066481 | 8/2002 |
| WO | WO 03/00682 | 1/2003 |

OTHER PUBLICATIONS

Roy, P., "A New Series of Selective Cox-2 Inhibitors: 5,6-Diarylthiazolo [3,2-b][1,22,4] Triazoles," *Bioorganiz & Med. Chem. Ltrs.*, vol. 7, No. 1, 1997, pp. 57-62.

Therien, Michael, Synthesis and Biological Evaluation of 5, 6-Diarylimidazo[2.1-b]Thiazole As Selective Cox-2 Inhibitors, *Bioorganic & Med. Chem. Ltrs.*, vol. 7, No. 1, 1997, pp. 47-52.

Akahane, Atsushi, "Discovery of 6-Oxo-3-(2-Phenlypyrazolo[1,5-a]pyridin-3-yl)-1(6H)-pyridazinebutanoic Acid (FR 838): A Novel Xanthine Adenosine $A_1$ Receptor Antagonist with Potent Diuretic Activity," *Journal of Medicinal Chemistry*, vol. 42, No. 5, 1999, pp. 779-783.

Talley, John J., 5 Selective Inhibitors of Cyclooxygenase-2 (COX-2) *Progress in Medicinal Chemistry*, vol. 36, (1999): pp. 201-234.

Boehm, J.C., et al. "1-Substituted 4-Aryl-5-pyridinylimidazoles: A New Class of Cytokine Suppressive Drugs with Low 5-Lipoxygenase and Cyclooxygenase Inhibitory Potency." J. Med. Chem. 1996, 39, pp. 3929-3937.

Hanson, G.J., et al. "Pulmonary-Allergy, Dermatological, Gastrointestinal & Arthritis, Inhibitors of p38 kinase." Expert Opinion Ther. Patents, 1997, 7(7):729-733.

PYRALOPYRIDINES, PROCESS FOR THEIR PREPARATION AND USE AS THERAPEUTIC COMPOUNDS

CROSS REFERENCES TO RELATED APPLICATIONS

This application is a 371 Application of PCT/US02/08524, filed 20 Mar. 2002, which claims priority to U.S. Application Ser. No. 60/280,047, filed 30 Mar. 2001, U.S. Application Ser. No. 60/307,189, filed 23 Jul. 2001, U.S. Application Ser. No. 60/307,786, filed 25 Jul. 2001 and 60/315,090 filed 27 Aug. 2001.

BACKGROUND OF THE INVENTION

The present invention relates to novel compounds, pharmaceutical formulations comprising these compounds, and the use of these compounds in therapy. More particularly, the present invention relates to compounds for the prophylaxis and treatment of herpes viral infections.

Of the DNA viruses, those of the herpes group are the sources of the most common viral illnesses in man. The group includes herpes simplex virus types 1 and 2 (HSV), varicella zoster virus (VZV), cytomegalovirus (CMV), Epstein-Barr virus (EBV), human herpes virus type 6 (HHV-6), human herpes virus type 7 (HHV-7) and human herpes virus type 8 (HHV-8). HSV-1 and HSV-2 are some of the most common infectious agents of man. Most of these viruses are able to persist in the host's neural cells; once infected, individuals are at risk of recurrent clinical manifestations of infection which can be both physically and psychologically distressing.

Herpes simplex viruses (HSV-1 and -2) are the causative agents of herpes labialis and genital herpes. HSV infection is often characterised by extensive and debilitating lesions of the skin, mouth and/or genitals. Primary infections may be subclinical although tend to be more severe than infections in individuals previously exposed to the virus. Ocular infection by HSV can lead to keratitis or cataracts thereby endangering the host's sight Infection in the new-born, in immunocompromised patients or penetration of the infection into the central nervous system can prove fatal. In the US alone, 40 million individuals are infected with HSV-2, a number that is expected to increase to 60 million by 2007. Over 80% of individuals infected with HSV-2 are unaware they carry and spread the virus, and of those diagnosed less than 20% received oral therapies. The net result is that less than 5% of the infected population are treated. Likewise of the 530 million individuals worldwide who carry HSV-1, 81% of the symptomatic population remain untreated. No cure exists for HSV infection, and once infected, individuals carry the virus for life in a dormant state. Reactivation of the virus from latency occurs periodically and may be triggered by stress, environmental factors, and/or suppression of the host immune system. Currently, the use of nucleoside analogs such as valaciclovir (VALTREX®) and aciclovir (ZOVIRAX®) is the standard of care for managing genital herpes virus outbreaks.

Varicella zoster virus (VZV) (also known as herpes zoster virus) is a herpes virus which causes chickenpox and shingles. Chickenpox is the primary disease produced in a host without immunity, and in young children is usually a mild illness characterised by a vesicular rash and fever. Shingles or zoster is the recurrent form of the disease which occurs in adults who were previously infected with VZV. The clinical manifestations of shingles are characterised by neuralgia and a vesicular skin rash that is unilateral and dermatomal in distribution. Spread of inflammation may lead to paralysis or convulsions. Coma can occur if the meninges become affected. VZV is of serious concern in patients receiving immunosuppressive drugs for transplant purposes or for treatment of malignant neoplasia and is a serious complication of AIDS patients due to their impaired immune system.

In common with other herpes viruses, infection with CMV leads to a lifelong association of virus and host. Congenital infection following infection of the mother during pregnancy may give rise to clinical effects such as death or gross disease (microcephaly, hepatosplenomegaly, jaundice, mental retardation), retinitis leading to blindness or, in less severe forms, failure to thrive, and susceptibility to chest and ear infections. CMV infection in patients who are immunocompromised for example as a result of malignancy, treatment with immunosuppressive drugs following transplantation or infection with Human Immunodeficiency Virus, may give rise to retinitis, pneumonitis, gastrointestinal disorders and neurological diseases. CMV infection is also associated with cardiovascular diseases and conditions including restenosis and atherosclerosis.

The main disease caused by EBV is acute or chronic infectious mononucleosis (glandular fever). Examples of other EBV or EBV associated diseases include lymphoproliferative disease which frequently occurs in persons with congenital or acquired cellular immune deficiency, X-linked lymphoproliferative disease which occurs namely in young boys, EBV-associated B-cell tumours, Hodgkin's disease, nasopharyngeal carcinoma, Burkitt lymphoma, non-Hodgkin's lymphoma, thymomas and oral hairy leukoplakia. EBV infections have also been found in association with a variety of epithelial-cell-derived tumours of the upper and lower respiratory tracts including the lung. EBV infection has also been associated with other diseases and conditions including chronic fatigue syndrome, multiple sclerosis and Alzheimer's disease.

HHV-6 has been shown to be a causative agent of infantum subitum in children and of kidney rejection and interstitial pneumonia in kidney and bone marrow transplant patients, respectively, and may be associated with other diseases such as multiple sclerosis. There is also evidence of repression of stem cell counts in bone marrow transplant patients. HHV-7 is of undetermined disease aetiology.

Hepatitis B virus (HBV) is a viral pathogen of world-wide major importance. The virus is aetiologically associated with primary hepatocellular carcinoma and is thought to cause 80% of the world's liver cancer. Clinical effects of infection with HBV range from headache, fever, malaise, nausea, vomiting, anorexia and abdominal pains. Replication of the virus is usually controlled by the immune response, with a course of recovery lasting weeks or months in humans, but infection may be more severe leading to persistent chronic liver disease outlined above.

U.S. Pat. No. 5,498,774 and European Patent No. 0 404 190 to Mitsudera et al., relates to condensed heterocyclic compounds of the general formula (I):

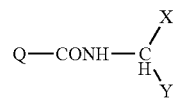

wherein Q is a condensed heterocyclic group having a nitrogen atom in the bridgehead which is unsubstituted or substituted, X is a hydrogen atom or a group attached through C, O, S or N, and Y is an electron attractive group; or its salt which is useful as an agricultural chemical.

BRIEF SUMMARY OF THE INVENTION

According to a first aspect of the invention there is provided a compound of formula (I):

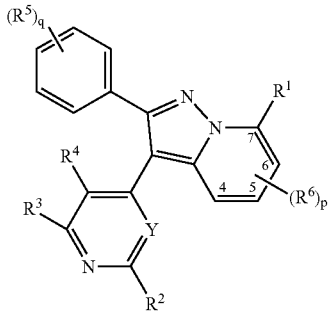

wherein:
R$^1$ is selected from the group consisting of alkyl, alkenyl, alkynyl, cycloalkyl, cycloalkenyl, —R$^{10}$cycloalkyl, —R$^{10}$Ay, —R$^{10}$Het, —OR$^7$, —OAy, —OHet, —OR$^{10}$Ay, —OR$^{10}$ Het, —R$^{10}$R$^9$, —R$^{10}$NR$^7$R$^8$, —R$^{10}$NR$^7$Ay, —R$^{10}$C(O)R$^9$, —C(O)R$^9$, —C(O)Ay, —C(O)Het, —R$^{10}$OC(O)R$^9$, —R$^{10}$OC(O)Ay, —R$^{10}$OC(O)Het, —CO$_2$R$^9$, —R$^{10}$CO$_2$R$^9$, —C(O)NR$^7$R$^8$, —C(O)NR$^7$Ay, —C(O)NHR$^{10}$Ay, —R$^{10}$C(O)NR$^9$R$^{11}$, —C(S)NR$^9$R$^{11}$, —R$^{10}$C(S)NR$^9$R$^{11}$, —R$^{10}$NHC(NH)NR$^9$R$^{11}$, —C(NH) NR$^7$R$^8$, —C(NH)NR$^7$Ay, —R$^{10}$C(N H)NR$^9$R$^{11}$, —S(O)$_2$NR$^7$R$^8$, —S(O)$_2$NR$^7$Ay, —R$^{10}$SO$_2$NHCOR$^9$, —R$^{10}$SO$_2$NR$^9$R$^{11}$, —R$^{10}$SO$_2$R$^9$, —R$^{10}$S(O)$_n$R$^9$, —R$^{10}$NHSO$_2$R$^9$, —R$^{10}$NHCOR$^9$, —S(O)$_n$R$^9$, —S(O)$_n$Ay, —S(O)$_n$Het, cyano, azido and nitro;

each R$^7$ and R$^8$ are the same or different and are independently selected from the group consisting of H, alkyl, cycloalkyl, alkenyl, cycloalkenyl, —R$^{10}$cycloalkyl, —OR$^9$, —R$^{10}$OR$^9$, —R$^{10}$NR$^9$R$^{11}$, —R$^{10}$C(O)R$^9$, —C(O)R$^9$, —CO$_2$R$^9$, —R$^{10}$CO$_2$R$^9$, —C(O)NR$^9$R$^{11}$, —R$^{10}$C(O)NR$^9$R$^{11}$, —C(S)NR$^9$R$^{11}$, —R$^{10}$C(S)NR$^9$R$^{11}$, —R$^{10}$NHC(NH)NR$^9$R$^{11}$, —R$^{10}$C (NH)NR$^9$R$^{11}$, —C(NH)NR$^9$R$^{11}$, —SO$_2$NR$^9$R$^{11}$, —R$^{10}$SO$_2$NR$^9$R$^{11}$, —R$^{10}$NHSO$_2$R$^9$, —SO$_2$R$^{10}$, —R$^{10}$SO$_2$R$^{10}$, —R$^{10}$NHCOR$^9$ and —R$^{10}$SO$_2$NHCOR$^9$;

each R$^9$ and R$^{11}$ are the same or different and are independently selected from the group consisting of H, alkyl, cycloalkyl, —R$^{10}$cycloalkyl, —R$^{10}$OH, —R$_{10}$(OR$^{10}$)$_w$ where w is 1–10, and —R$^{10}$NR$^{10}$R$^{10}$;

each R$^{10}$ is the same or different and is independently selected from the group consisting of alkyl, cycloalkyl, alkenyl, cycloalkenyl and alkynyl;

Ay is an aryl;

Het is a 5- or 6-membered heterocyclic or heteroaryl group;

n is 0, 1 or 2;

R$^2$ is selected from the group consisting of H, halo, alkyl, cycloalkyl, alkenyl, cycloalkenyl, —NR$^7$R$^8$, Ay, —NHR$^{10}$Ay, —OR$^7$, —OAy, —S(O)$_n$R$^9$, —S(O)$_n$Ay, —R$^{10}$NR$^7$R$^8$, —R$^{10}$NR$^7$Ay, Het, —NHHet, —NHR$^{10}$Het, —OHet and —OR$^{10}$Het;

Y is N or CH;

R$^3$ and R$^4$ are the same or different and are independently selected from the group consisting of H, halo, alkyl, cycloalkyl, alkenyl, Ay, —OR$^7$, —OAy, —R$^{10}$R$^7$, —R$^{10}$OAy, —NR$^7$R$^8$, —NR$^7$Ay, —R$^{10}$NR$^7$R$^8$, —R$^{10}$NR$^7$Ay, —C(O)R$^7$, C(O)Ay, —CO$_2$R$^7$, —CO$_2$Ay, —SO$_2$NHR$^9$, Het, —NHHet and —NHR$^{10}$Het;

q is 0, 1, 2, 3, 4 or 5;

each R$^5$ is the same or different and is independently selected from the group consisting of halo, alkyl, alkenyl, alkynyl, cycloalkyl, cycloalkenyl, —R$^{10}$cycloalkyl, Ay, —NHR$^{10}$Ay, —NR$^7$Ay, Het, —NHHet, —NHR$^{10}$Het, —OR$^7$, —OAy, —OHet, —R$^{10}$OR$^9$, —NR$^7$R$^8$, —R$^{10}$NR$^7$R$^8$, —R$^{10}$NR$^7$Ay, —R$^{10}$C(O)R$^9$, —C(O)R$^9$, —C(O)Ay, —C(O)Het, —CO$_2$R$^9$, —R$^{10}$CO$_2$R$^9$, —C(O)NR$^7$R$^8$, —C(O) NR$^7$Ay, —C(O)NHR$^{10}$Het, —R$^{10}$C(O)NR$^9$R$^{11}$, —C(S)NR$^9$R$^{11}$, —R$^{10}$C(S)NR$^9$R$^{11}$, —R$^{10}$NHC(NH) NR$^9$R$^{11}$, —C(NH)NR$^7$R$^8$, —C(NH)NR$^7$Ay, —R$^{10}$C (NH)NR$^9$R$^{11}$, —S(O)$_2$NR$^7$R$^8$, —S(O)$_2$NR$^7$Ay, —R$^{10}$SO$_2$NHCOR$^9$, —R$^{10}$SO$_2$NR$^9$R$^{11}$, —R$^{10}$SO$_2$R$^9$, —S(O)$_n$R$^9$, cyano, azido and nitro; or two adjacent R$^5$ groups together with the atoms to which they are bonded form a $C_{5-6}$ cycloalkyl or aryl;

p is 0, 1, 2 or 3; and each R$^6$ is the same or different and is independently selected from the group consisting of halo, alkyl, alkenyl, alkynyl, cycloalkyl, cycloalkenyl, —R$^{10}$cycloalkyl, Ay, Het, —R$^{10}$Ay, —R$^{10}$Het, —OR$^7$, —OAy, —OHet, —R$^{10}$OR$^9$, —OR$^{10}$Ay, —OR$^{10}$Het, —R$^{10}$NR$^7$R$^8$, —R$^{10}$NR$^7$Ay, —R$^{10}$C(O)R$^9$, —C(O)R$^9$, —C(O)Ay, —C(O)Het, —CO$_2$R$^9$, —R$^{10}$CO$_2$R$^9$, —C(O)NR$^7$R$^8$, —C(O)NR$^7$Ay, —C(O)NHR$^{10}$Het, —R$^{10}$C(O)NR$^9$R$^{11}$, —C(S)NR$^9$R$^{11}$, —R$^{10}$C(S)NR$^9$R$^{11}$, —R$^{10}$NHC(NH)NR$^9$R$^{11}$, —C(NH) NR$^7$R$^8$, —C(NH)NR$^7$Ay, —R$^{10}$C(NH)NR$^9$R$^{11}$, —S(O)$_2$NR$^7$R$^8$, —S(O)$_2$NR$^7$Ay, —R$^{10}$SO$_2$NHCOR$^9$, —R$^{10}$SO$_2$NR$^9$R$^{11}$, —R$^{10}$SO$_2$R$^9$, —S(O)$_n$R$^9$, cyano, azido and nitro; or two adjacent R$^6$ groups together with the atoms to which they are bonded form a $C_{5-6}$ cycloalkyl or a 5- or 6-membered heterocyclic group containing 1 or 2 heteroatoms;

wherein when Y is CH, R$^3$ is not —NR$^7$Ay;

and pharmaceutically acceptable salts, solvates and physiologically functional derivatives thereof.

In another aspect of the invention there is provided a pharmaceutical composition comprising a compound of formula (I). In one preferred embodiment, the pharmaceutical composition further comprises a pharmaceutically acceptable carrier or diluent In one embodiment, the pharmaceutical composition further comprises an antiviral agent selected from the group consisting of aciclovir and valaciclovir.

In a third aspect of the invention, there is provided a method for the prophylaxis or treatment of a herpes viral infection. The method comprises administering a therapeutically effective amount of a compound of formula (I) above or a pharmaceutically acceptable salt, solvate or physiologically functional derivative thereof. The herpes viral infection may be selected from the group consisting of herpes simplex virus 1, herpes simplex virus 2, cytomegalovirus, Epstein Barr virus, varicella zoster virus, human herpes virus 6, human herpes virus 7, and human herpes virus 8.

In a fourth aspect, there is provided a method for the treatment or prophylaxis of conditions or diseases associated with a herpes viral infection in an animal. The method comprises administering to the animal a therapeutically effective amount of the compound of formula (I) above or a pharmaceutically acceptable salt, solvate or physiologically functional derivative thereof.

In another aspect, there is provided a process for preparing compounds of formula (I) wherein Y is N; $R^2$ is selected from the group consisting of H, alkyl, cycloalkyl, alkenyl, cycloalkenyl, —$NR^7R^8$, Ay, —$NHR^{10}$Ay, —$OR^7$, —OAy, —$S(O)_nR^9$, —$S(O)_n$Ay, —$R^{10}NR^7R^8$, —$R^{10}NR^7$Ay, Het, —NHHet, —$NHR^{10}$Het, —OHet and —$OR^{10}$Het; $R^3$ is H; $R^4$ is H and all other variables are as defined above in connection with compounds of formula (I). The process comprises the steps of: a) reacting a compound of formula (IX):

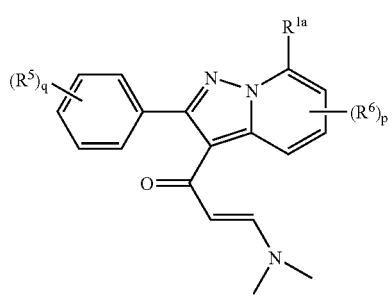

IX wherein $R^{1a}$ is selected from the group consisting of H, halo, alkyl, alkenyl, alkynyl, cycloalkyl, cycloalkenyl, —$R^{10}$cycloalkyl, —$R^{10}$Ay, —$R^{10}$Het, —$OR^7$, —OAy, —OHet, —$OR^{10}$Ay, —$OR^{10}$Het, —$R^{10}OR^9$, —$R^{10}NR^7R^8$, —$R^{10}NR^7$Ay, —$R^{10}C(O)R^9$, —$C(O)R^9$, —C(O)Ay, —C(O)Het, —$R^{10}OC(O)R^9$, —$R^{10}C(O)$Ay, —$R^{10}OC(O)$Het, —$CO_2R^9$, —$R^{10}CO_2R^9$, —C(O)$NR^7R^8$, —C(O)$NR^7$Ay, —C(O)$NHR^{10}$Ay, —$R^{10}C(O)NR^9R^{11}$, —$C(S)NR^9R^{11}$, —$R^{10}C(S)NR^9R^{11}$, —$R^{10}NHC(NH)NR^9R^{11}$, —$C(NH)NR^7R^8$, —C(NH)$NR^7$Ay, —$R^{10}C(NH)NR^9R^{11}$, —$S(O)_2NR^7R^8$, —$S(O)_2NR^7$Ay, —$R^{10}SO_2NHCOR^9$, —$R^{10}SO_2NR^9R^{11}$, —$R^{10}SO_2R^9$, —$R^{10}OS(O)_nR^9$, —$R^{10}NHSO_2R^9$, —$R^{10}NHCOR^9$, —$S(O)_nR^9$, —$S(O)_n$Ay, —$S(O)_n$Het, cyano, azido and nitro;

with a compound of formula (X)

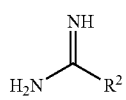

X to prepare a compound of formula (XI):

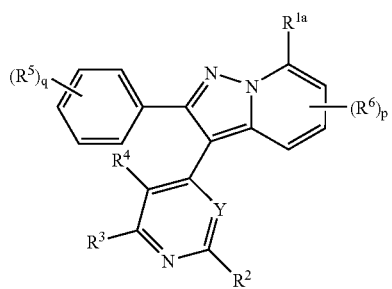

XI and b) when $R^{1a}$ is H or halo, converting the compound of formula (XI) to a compound of formula (I).

As another aspect, the present invention provides another process for preparing compounds of formula (I) wherein Y is N; $R^2$ is selected from the group consisting of H, alkyl, cycloalkyl, alkenyl, cycloalkenyl, —$NR^7R^8$, Ay, —$NHR^{10}$Ay, —$OR^7$, —OAy, —$S(O)_nR^9$, —$S(O)_n$Ay, —$R^{10}NR^7R^8$, —$R^{10}NR^7$Ay, Het, —NHHet, —$NHR^{10}$Het, —OHet and —$OR^{10}$Het; $R^3$ is selected from the group consisting of H, alkyl, cycloalkyl, alkenyl, Ay, —$R^{10}OR^7$, —$R^{10}$OAy, —$NR^7R^8$ where $R^7$ and $R^8$ are not H, —$NR^7$Ay where $R^7$ is not H, —$R^{10}NR^7R^8$, —$R^{10}NR^7$Ay, —$C(O)R^7$, —C(O)Ay, —$CO_2R^7$, —$CO_2$AY, —$SO_2NHR^9$ and Het; $R^4$ is H; and all other variables are as defined above in connection with compounds of formula (I). The process comprises the steps of: a) reacting a compound of formula (XV):

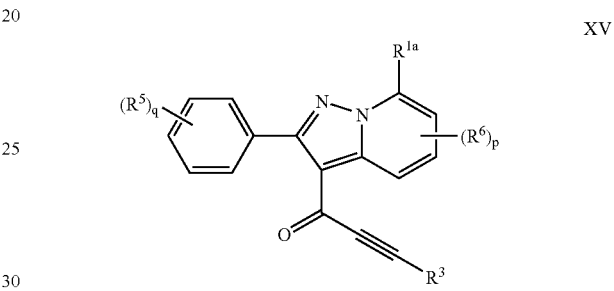

XV wherein $R^{1a}$ is as defined in the process described above;

with a compound of formula (X) to prepare a compound of formula (XI), and b) when $R^{1a}$ is H or halo, converting the compound of formula (XI) to a compound of formula (I).

As another aspect, the present invention provides another process for preparing compounds of formula (I) wherein Y is N; $R^2$ is selected from the group consisting of H, alkyl, cycloalkyl, alkenyl, cycloalkenyl, —$NR^7R^8$, Ay, —$NHR^{10}$Ay, —$OR^7$, —OAy, —$S(O)R^9$, —$S(O)_n$Ay, —$R^{10}NR^7R^8$, —$R^{10}NR^7$Ay, Het, —NHHet, —$NHR^{10}$Het, —OHet and —$OR^{10}$Het; and all other variables are as defined above in connection with compounds of formula (I).

The process comprises the steps of: a) reacting a compound of formula (XVIII):

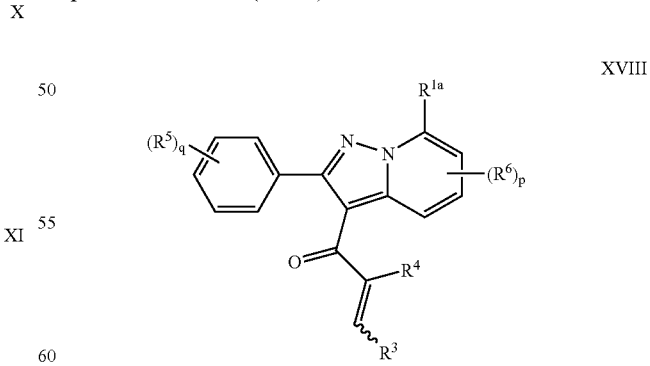

XVIII wherein $R^{1a}$ is as defined in the process described above;

with a compound of formula (X) followed by oxidative aromatization, to prepare a compound of formula (XI), and b) when $R^{1a}$ is H or halo, converting the compound of formula (XI) to a compound of formula (I).

As another aspect, the present invention provides another process for preparing compounds of formula (I). The process comprises the steps of: a) reacting a compound of formula (XIX):

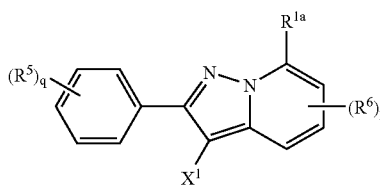

wherein $R^{1a}$ is as defined in the process described above, $X^1$ is halo and q, $R^5$, p
and $R^6$ are as defined above in connection with compounds of formula (I); with a compound of formula (XX)

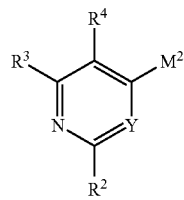

wherein $R^2$, $R^3$, $R^4$ and Y are as defined above in connection with compounds of formula (I) and $M^2$ is —B(OH)$_2$, —B(ORa)$_2$, —B(Ra)$_2$, —Sn(Ra)$_3$, Zn-halide, ZnRa, Mg-halide where Ra is alkyl or cycloalkyl and halide is halo, to prepare a compound of formula (XI), and b) when $R^{1a}$ is H or halo, converting the compound of formula (XI) to a compound of formula (I).

The present invention also provides processes for converting a compound of formula (XI) to a pharmaceutically acceptable salt, solvate or physiologically functional derivative thereof; processes for converting a compound of formula (XI) or a pharmaceutically acceptable salt, solvate or physiologically functional derivative thereof to another compound of formula (XI) or a pharmaceutically acceptable salt, solvate or physiologically functional derivative thereof; processes for converting a compound of formula (I) to a pharmaceutically acceptable salt, solvate or physiologically functional derivative thereof; and processes for converting a compound of formula (I) or a pharmaceutically acceptable salt, solvate or physiologically functional derivative thereof to another compound of formula (I) or a pharmaceutically acceptable salt, solvate or physiologically functional derivative thereof.

In another aspect, the present invention provides a radiolabeled compound of formula (I) or a pharmaceutically acceptable salt, solvate or physiologically functional derivative thereof. In one embodiment, the present invention provides a tritiated compound of formula (I) or a pharmaceutically acceptable salt, solvate or physiologically functional derivative thereof. In another embodiment, the present invention provides a biotinylated compound of formula (I) or a pharmaceutically acceptable salt, solvate or physiologically functional derivative thereof.

In another aspect, the present invention provides a compound of formula (I) for use in therapy.

In yet another aspect, the present invention provides a compound of formula (I) for use in the prophylaxis or treatment of a herpes viral infection.

In another aspect, the present invention provides a pharmaceutical composition comprising a compound of formula (I), for use in the prophylaxis or treatment of a herpes viral infections in an animal, preferably a human.

In yet another aspect, the present invention provides a compound of formula (I) for use in the prophylaxis or treatment of conditions or diseases associated with a herpes viral infection in an animal.

In yet another aspect, the present invention provides a pharmacuetical composition for use in the prophylaxis or treatment of conditions or diseases associated with a herpes viral infection in an animal, comprising a compound of formula (I).

In yet another aspect, the present invention provides the use of a compound of formula (I) for the preparation of a medicament for the prophylaxis or treatment of a herpes viral infection in an animal, preferably a human.

In yet another aspect, the present invention provides the use of a compound of formula (I) for the preparation of a medicament for the treatment or prophylaxis of diseases or conditions associated with a herpes viral infection in an animal, preferably a human. The herpes viral infection may be herpes simplex virus 1, herpes simplex virus 2, cytomegalovirus, Epstein Barr virus, varicella zoster virus, human herpes virus 6, human herpes virus 7, or human herpes virus 8.

DETAILED DESCRIPTION OF THE INVENTION

As used herein, "a compound of the invention" or "a compound of formula (I)" means a compound of formula (I) or a pharmaceutically acceptable salt, solvate, or physiologically functional derivative thereof. Similarly, with respect to isolatable intermediates such as for example, compounds of formula (IX), the phrase "a compound of formula (number)" means a compound of that formula and pharmaceutically acceptable salts, solvates and physiologically functional derivatives thereof.

As used herein, the terms "alkyl" and "alkylene" refer to straight or branched hydrocarbon chains containing from 1 to 8 carbon atoms. Examples of "alkyl" as used herein include, but are not limited to, methyl, ethyl, n-propyl, n-butyl, n-pentyl, isobutyl, isopropyl and tert-butyl. Examples of "alkylene" as used herein include, but are not limited to, methylene, ethylene, propylene, butylene and isobutylene. "Alkyl" and "alkylene" also includes substituted alkyl and substituted alkylene. The alkyl (alkylene) groups may be optionally substituted with one or more substituents selected from the group consisting of mercapto, nitro, cyano, azido and halo. Perhaloalkyl, such as trifluoromethyl is one particularly preferred alkyl group.

As used herein, the term "cycloalkyl" refers to a non-aromatic carbocyclic ring having from 3 to 8 carbon atoms and no carbon-carbon double bonds. "Cycloalkyl" includes by way of example cyclopropyl, cyclobutyl, cyclopentyl, cyclohexyl, cycloheptyl and cyclooctyl. "Cycloalkyl" also includes substituted cycloalkyl. The cycloalkyl may optionally be substituted on an available carbon with one or more substituents selected from the group consisting of mercapto, nitro, cyano, halo, and alkyl.

As used herein, the term "alkenyl" refers to straight or branched hydrocarbon chains containing from 2 to 8 carbon atoms and at least one and up to three carbon-carbon double bonds. Examples of "alkenyl" as used herein include, but are not limited to ethenyl and propenyl. "Alkenyl" also includes substituted alkenyl. The alkenyl groups may optionally be substituted on an available carbon with one or more substituents selected from the group consisting of mercapto, nitro, cyano, halo and alkyl.

As used herein, the term "cycloalkenyl" refers to a non-aromatic carbocyclic ring having from 3 to 8 carbon atoms (unless otherwise specified) and up to 3 carbon-carbon double bonds. "Cycloalkenyl" includes by way of example cyclobutenyl, cyclopentenyl and cyclohexenyl. "Cycloalkenyl" also includes substituted cycloalkenyl. The cycloalkenyl may optionally be substituted on an available carbon with one or more substituents selected from the group consisting of mercapto, nitro, cyano, halo, and alkyl.

As used herein, the term "alkynyl" refers to straight or branched hydrocarbon chains containing from 2 to 8 carbon atoms and at least one and up to three carbon-carbon triple bonds. Examples of "alkynyl" as used herein include, but are not limited to ethynyl and propynyl. "Alkynyl" also includes substituted alkynyl. The alkynyl groups may optionally be substituted on an available carbon with one or more substituents selected from the group consistng of mercapto, nitro, cyano, halo and alkyl.

The term "halo" or "halogen" refers to the elements fluorine, chlorine, bromine and iodine.

The term "Ay" refers to monocyclic carbocyclic groups and fused bicyclic carbocyclic groups having from 5 to 12 carbon atoms and having at least one aromatic ring. Examples of particular aryl groups include but are not limited to phenyl, and naphthyl. "Aryl" also includes substituted aryl. Aryl groups may optionally be substituted on an available carbon with one or more substituents selected from the group consisting of halo, alkyl (including perhaloalkyl), alkenyl, cycloalkyl, cycloalkenyl, alkoxy, cycloalkoxy, amino, mercapto, hydroxy, alkylhydroxy, alkylamine, cycloalkylamine, carboxy, carboxamide, sulfonamide, Het, amidine, cyano, nitro and azido. Preferred aryl groups according to the invention include but are not limited to phenyl and substituted phenyl.

The term "heterocyclic" (or "heterocycle") refers to a monocyclic saturated or unsaturated non-aromatic groups and fused bicyclic non-aromatic groups, having the specified number of members and containing 1, 2, 3 or 4 heteroatoms selected from N, O and S. Examples of particular heterocyclic groups include but are not limited to tetrahydrofuran, dihydropyran, tetrahydropyran, pyran, oxetane, thietane, 1,4-dioxane, 1,3-dioxane, 1,3-dioxalane, piperidine, piperazine, tetrahydropyrimidine, pyrrolidine, morpholine, thiomorpholine, thiazolidine, oxazolidine, tetrahydrothiopyran, tetrahydrothiophene, and the like. "Heterocyclic" also includes substituted heterocyclic. The heterocyclic group may be optionally substituted on an available carbon or heteroatom, with one or more substituents selected from the group consisting of halo, alkyl (including perhaloalkyl), alkenyl, cycloalkyl, cycloalkenyl, alkoxy, cycloalkoxy, amino, mercapto, hydroxy, alkylhydroxy, alkylamine, cycloalkylamine, carboxy, carboxamide, sulfonamide, Het, amidine, cyano, nitro and azido. Preferred heterocyclic groups according to the invention include but are not limited to pyrrolidine, piperidinei morpholine, thiomorpholine and piperazine and substituted variants thereof.

The term "heteroaryl" refers to aromatic monocyclic groups and aromatic fused bicyclic groups having the specified number of members and containing 1, 2, 3, or 4 heteroatoms selected from N. O and S. Examples of particular heteroaryl groups include but are not limited to furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole and indazole. "Heteroaryl" also includes substituted heteroaryl. The heteroaryl group may optionally be substituted on an available carbon or heteroatom with one or more substituents selected from the group consisting of halo, alkyl (perhaloalkyl), alkenyl, cycloalkyl, cycloalkenyl, alkoxy, cycloalkoxy, amino, mercapto, hydroxy, alkylhydroxy, alkylamine, cycloalkylamine, carboxy, carboxamide, sulfonamide, Het, amidine, cyano, nitro and azido. Preferred heteroaryl groups according to the invention include but are not limited to pyridine, furan, thiophene, pyrrole, imidazole, pyrazole, and pyrimidine, and substituted variants thereof.

The term "members" (or variations thereof such as "membered") in the context of heterocyclic and heteroaryl groups refers to the total atoms, carbon and heteroatoms N, O and/or S, which form the ring. Thus, an example of a 6-membered heterocyclic ring is piperidine and an example of a 6-membered heteroaryl ring is pyridine.

As used herein, the term "optionally" means that the subsequently described event(s) may or may not occur, and includes both event(s) that occur and events that do not occur.

The present invention provides compounds of formula (I):

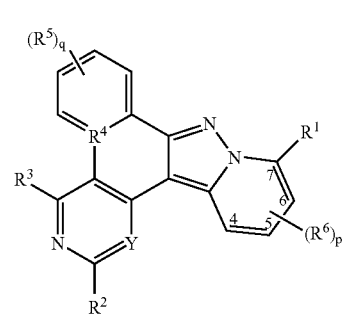

I wherein:
$R^1$ is selected from the group consisting of alkyl, alkenyl, alkynyl, cycloalkyl, cycloalkenyl, —$R^{10}$cycloalkyl, —$R^{10}$Ay, —$R^{10}$Het, —$OR^7$, —OAy, —OHet, —$OR^{10}$Ay, —$OR^{10}$Het, —$R^{10}OR^9$, —$R^{10}NR^7R^8$, —$R^{10}NR^7$Ay, —$R^{10}C(O)R^9$, —$C(O)R^9$, —$C(O)$Ay, —$C(O)$Het, —$R^{10}OC(O)R^9$, —$R^{10}OC(O)$Ay, —$R^{10}OC(O)$Het, —$CO_2R^9$, —$R^{10}CO_2R^9$, —$C(O)NR^7R^8$, —$C(O)NR^7$Ay, —$C(O)NHR^{10}$Ay, —$R^{10}C(O)NR^9R^{11}$, —$C(S)NR^9R^{11}$, —$R^{10}C(S)NR^9R^{11}$, —$R^{10}NHC(NH)NR^9R^{11}$, —$C(NH)NR^7R^8$, —$C(NH)NR^7$Ay, —$R^{10}C(NH)NR^9R^{11}$, —$S(O)_2NR^7R^8$, —$S(O)_2NR^7$Ay, —$R^{10}SO_2NHCOR^9$, —$R^{10}SO_2NR^9R^{11}$, —$R^{10}SO_2R^9$, —$R^{10}OS(O)_nR^9$, —$R^{10}NHSO_2R^9$, —$R^{10}NHCOR^9$, —$S(O)_nR^9$, —$S(O)_n$Ay, —$S(O)_n$Het, cyano, azido and nitro;
each $R^7$ and $R^8$ are the same or different and are independently selected from the group consisting of H, alkyl, alkenyl, cycloalkyl, cycloalkenyl, —$R^{10}$cycloalkyl, —$OR^9$, —$R^{10}OR^9$, —$R^{10}NR^9R^{11}$, —$R^{10}C(O)R^9$, —$C(O)R^9$, —$CO_2R^9$, —$R^{10}CO_2R^9$, —$C(O)NR^9R^{11}$, —$R^{10}C(O)NR^9R^{11}$, —$C(S)NR^9R^{11}$, —$R^{10}C(S)NR^9R^{11}$ —$R^{10}NHC(NH)NR^9R^{11}$, —$R^{10}C$ (NH)NR$^9$R$^{11}$, —C(NH)NR$^9$R$^{11}$, —SO$_2$NR$^9$R$^{11}$, —R$^{10}$SO$_2$NR$^9$R$^{11}$, —R$^{10}$NHSO$_2$R$^9$, —SO$_2$R$^{10}$, —R$^{10}$SO$_2$R$^{10}$, —R$^{10}$NHCOR$^9$ and —R$^{10}$SO$_2$NHCOR$^9$;

each R$^9$ and R$^{11}$ are the same or different and are independently selected from the group consisting of H, alkyl, cycloalkyl, —R$^{10}$cycloalkyl, —R$^{10}$OH, —R$^{10}$(OR$^{10}$)$_w$ where w is 1–10, and —R$^{10}$NR$^{10}$R$^{10}$;

each R$^{10}$ is the same or different and is independently selected from the group consisting of alkyl, cycloalkyl, alkenyl, cycloalkenyl and alkynyl;

Ay is an aryl;

Het is a 5- or 6-membered heterocyclic or heteroaryl group;

n is 0, 1 or 2;

R$^2$ is selected from the group consisting of H, halo, alkyl, cycloalkyl, alkenyl, cycloalkenyl, —NR$^7$R$^8$, Ay, —NHR$^{10}$Ay, —OR$^7$, —OAy, —S(O)$_n$R$^9$, —S(O)$_n$Ay, —R$^{10}$NR$^7$R$^8$, —R$^{10}$NR$^7$Ay, Het, —NHHet, —NHR$^{10}$Het, —OHet and —OR$^{10}$Het;

Y is N or CH;

R$^3$ and R$^4$ are the same or different and are each independently selected from the group consisting of H, halo, alkyl, cycloalkyl, alkenyl, Ay, —OR$^7$, —OAy, —R$^{10}$OR$^7$, —R$^{10}$OAy, —NR$^7$R$^8$, —NR$^7$Ay, —R$^{10}$NR$^7$R$^8$, —R$^{10}$NR$^7$Ay, —C(O)R$^7$, C(O)Ay, —CO$_2$R$^7$, —CO$_2$Ay, —SO$_2$NHR$^9$, Het, —NHHet and —NHR$^{10}$Het;

q is 0, 1, 2, 3, 4 or 5;

each R$^5$ is the same or different and is independently selected from the group consisting of halo, alkyl, alkenyl, alkynyl, cycloalkyl, cycloalkenyl, —R$^{10}$cycloalkyl, Ay, —NHR$^{10}$Ay, —NR$^7$Ay, Het, —NHHet, —NHR$^{10}$Het, —OR$^7$, —OAy, —OHet, —R$^{10}$OR$^9$, —NR$^7$R$^8$, —R$^{10}$NR$^7$R$^8$, —R$^{10}$NR$^7$Ay, —R$^{10}$C(O)R$^9$, —C(O)R$^9$, —C(O)Ay, —C(O)Het, —CO$_2$R$^9$, —R$^{10}$CO$_2$R$^9$, —C(O)NR$^7$R$^8$, —C(O)NR$^7$Ay, —C(O)NHR$^{10}$Het, —R$^{10}$C(O)NR$^9$R$^{11}$, —C(S)NR$^9$R$^{11}$, —R$^{10}$C(S)NR$^9$R$^{11}$, —R$^{10}$NHC(NH)NR$^9$R$^{11}$, —C(NH)NR$^7$R$^8$, —C(NH)NR$^7$Ay, —R$^{10}$C(NH)NR$^9$R$^{11}$, —S(O)$_2$NR$^7$R$^8$, —S(O)$_2$NR$^7$Ay, —R$^{10}$SO$_2$NHCOR$^9$, —R$^{10}$SO$_2$NR$^9$R$^{11}$, —R$^{10}$SO$_2$R$^9$, —S(O)$_n$R$^9$, cyano, azido and nitro; or two adjacent R$^5$ groups together with the atoms to which they are bonded form a C$_{5-6}$ cycloalkyl or aryl;

p is 0, 1, 2 or 3; and each R$^6$ is the same or different and is independently selected from the group consisting of halo, alkyl, alkenyl, alkynyl, cycloalkyl, cycloalkenyl, —R$^{10}$cycloalkyl, Ay, Het, —R$^{10}$Ay, —R$^{10}$Het, —OR$^7$, —OAy, —OHet, —R$^{10}$OR$^9$, —OR$^{10}$Ay, —OR$^{10}$Het, —R$^{10}$NR$^7$R$^8$, —R$^{10}$NR$^7$Ay, —R$^{10}$C(O)R$^9$, —C(O)R$^9$, —C(O)Ay, —C(O)Het, —CO$_2$R$^9$, —R$^{10}$CO$_2$R$^9$, —C(O)NR$^7$R$^8$, —C(O)NR$^7$Ay, —C(O)NHR$^{10}$Het, —R$^{10}$C(O)NR$^9$R$^{11}$, —C(S)NR$^9$R$^{11}$, —R$^{10}$C(S)NR$^9$R$^{11}$, —R$^{10}$NHC(NH)NR$^9$R$^{11}$, —C(NH)NR$^7$R$^8$, —C(NH)NR$^7$Ay, —R$^{10}$C(NH)NR$^9$R$^{11}$, —S(O)$_2$NR$^7$R$^8$, —S(O)$_2$NR$^7$Ay, —R$^{10}$SO$_2$NHCOR$^9$, —R$^{10}$SO$_2$NR$^9$R$^{11}$, —R$^{10}$SO$_2$R$^9$, —S(O)$_n$R$^9$, cyano, azido and nitro; or two adjacent R$^6$ groups together with the atoms to which they are bonded form a C$_{5-6}$ cycloalkyl or a 5- or 6-membered heterocyclic group containing 1 or 2 heteroatoms;

and pharmaceutically acceptable salts, solvates and physiologically functional derivatives thereof.

In one preferred class of compounds of formula (I), Y is CH. In another preferred class of compounds of formula (I), Y is N.

Compounds of formula (I) include those compounds wherein R$^1$ contains an aryl, heterocyclic or heteroaryl moiety. The groups —R$^{10}$Ay, —R$^{10}$Het, —OAy, —OHet, —OR$^{10}$Ay, —OR$^{10}$Het, —R$^{10}$NR$^7$Ay, —C(O)Ay, —C(O)Het, —R$^{10}$OC(O)Ay, —R$^{10}$OC(O)Het, —C(O)NR$^7$Ay, —C(O)NHR$^{10}$Ay, —C(NH)NR$^7$Ay, —SO$_2$NR$^7$Ay, —S(O)$_n$Ay and —S(O)$_n$Het are examples of groups containing an aryl, heterocyclic or heteroaryl moiety. In one embodiment, compounds of the present invention includes those compounds defined wherein R$^1$ does not contain a heterocyclic or heteroaryl moeity.

Preferably, each R$^1$ is the same or different and is independently selected from the group consisting of alkyl, cycloalkyl, —R$^{10}$cycloalkyl, —OR$^7$, —OAy, —R$^{10}$OR$^9$, —R$^{10}$NR$^7$R$^8$, —C(O)R$^9$, —CO$_2$R$^9$, —C(O)NR$^7$R$^8$, —S(O)$_2$NR$^7$R$^8$, —S(O)$_n$R$^9$, cyano, nitro and azido, or any subset thereof.

More preferably, each R$^1$ is the same or different and is independently selected from the group consisting of alkyl, —OR$^7$, —R$^{10}$OR$^9$, —R$^{10}$NR$^7$R$^8$, —C(O)NR$^7$R$^8$ and —S(O)$_n$R$^9$, or any subset thereof. The variable n is preferably O.

In one preferred embodiment, each R$^1$ is the same or different and is independently selected form the group consisting of alkyl, —OR$^7$, —C(O)NR$^7$R$^8$ and S(O)$_n$R$^9$.

In one preferred embodiment, the compounds of formula (I) are defined wherein when Y is —CH and R$^1$ is —CO$_2$R$^9$, R$^9$ is not H. In another preferred embodiment, the compounds of formula (I) are defined wherein when R$^1$ is —CONR$^7$R$^8$ neither R$^7$ nor R$^8$ is H.

In another embodiment, R$^1$ is selected from the group consisting of alkyl, alkenyl, alkynyl, cycloalkyl, cycloalkenyl, —R$^{10}$cycloalkyl, —R$^{10}$Ay, —R$^{10}$Het, —OR$^7$, —OAy, —OHet, —OR$^{10}$Ay, —OR$^{10}$Het, —R$^{10}$OR$^9$, —R$^{10}$NR$^7$R$^8$, —R$^{10}$NR$^7$Ay, —R$^{10}$C(O)R$^9$, —C(O)R$^9$, —C(O)Ay, —C(O)Het, —R$^{10}$OC(O)R$^9$, —R$^{10}$OC(O)Ay, —R$^{10}$OC(O)Het, —CO$_2$R$^{10}$, —R$^{10}$CO$_2$R$^9$, —C(O)NR$^7$Ay, —C(O)NHR$^{10}$Ay, —R$^{10}$C(O)NR$^9$R$^{11}$, —C(S)NR$^9$R$^{11}$, —R$^{10}$C(S)NR$^9$R$^{11}$, —R$^{10}$NHC(NH)NR$^9$R$^{11}$, —C(NH)NR$^7$R$^8$, —C(NH)NR$^7$Ay, —R$^{10}$C(NH)NR$^9$R$^{11}$, —S(O)$_2$NR$^7$R$^8$, —S(O)$_2$NR$^7$Ay, —R$^{10}$SO$_2$NHCOR$^9$, —R$^{10}$SO$_2$NR$^9$R$^{11}$, —R$^{10}$SO$_2$R$^9$, —R$^{10}$OS(O)$_n$R$^9$, —R$^{10}$NHSO$_2$R$^9$, —R$^{10}$NHCOR$^9$, —S(O)$_n$R$^9$, —S(O)$_n$Ay, —S(O)$_n$Het, cyano, azido and nitro, or any subset thereof.

Specific examples of some prefered R$^1$ groups are selected from the group consisting of methyl, ethyl, propyl, isopropyl, butyl, isobutyl, t-butyl, methoxy, ethoxy, propoxy, isopropoxy, butoxy, t-butoxy, thiomethoxy and thioethoxy or any subset thereof.

In one embodiment, compounds of formula (I) are defined where R$^2$ contains an aryl, heterocyclic or heteroaryl moiety (e.g., R$^2$ is selected from the group consisting of —OAy, Ay, —NHR$^{10}$Ay, —S(O)$_n$Ay, —R$^{10}$NR$^7$Ay, Het, —NHHet, —NHR$^{10}$Het, —OHet, and —OR$^{10}$Het, or any subset thereof). In another embodiment, compounds of formula (I) are defined where R$^2$ contains a heterocyclic or heteroaryl moiety (e.g., R$^2$ is selected from the group consisting of Het, —NHHet, —NHR$^{10}$Het, —OHet and —OR$^{10}$Het, or any subset thereof). In yet another embodiment, the compounds of formula (I) are defined where R$^2$ contains no aryl, heterocyclic or heteroaryl moiety (e.g., R$^2$ is selected from the group consisting of H, halo, alkyl, cycloalkyl, alkenyl, cycloalkenyl, —NR$^7$R$^8$, —OR$^7$, —S(O)$_n$R$^9$ and —R$^{10}$NR$^7$R$^8$, or any subset thereof). In another embodiment, R$^2$ contains no heteroaryl or heterocyclic moiety but may contain an aryl moeity (e.g., R$^2$ is selected from the group consisting of H, halo, alkyl, cycloalkyl, alkenyl, cycloalkenyl, —NR⁷R⁸, —OR⁷, Ay, —NHR¹⁰Ay, —OAy, —S(O)$_n$R⁹, —S(O)$_n$Ay, —R¹⁰NR⁷R⁸, and —R¹⁰NR⁷Ay, or any subset thereof).

In one embodiment the compounds of formula (I) are defined wherein $R^2$ is selected from the group consisting of halo, alkyl, cycloalkyl, alkenyl, cycloalkenyl, —NR⁷R⁸, —OR⁷, —OAy, —S(O)$_n$R⁹, —R¹⁰NR⁷R⁸, Ay, —R¹⁰NR⁷Ay, Het, —NHHet, —NHR¹⁰Het, —OHet, and —OR¹⁰Het.

$R^2$ is preferably selected from the group consisting of —NR⁷R⁸, —OR⁷, —S(O)$_n$R⁹, Het, —NHHet and —NHR¹⁰Het, or any subset thereof. More preferably, $R^2$ is selected from the group consisting of —NR⁷R⁸, Het, —NHR¹⁰Het and —NHHet, or any subset thereof. Particularly preferred compounds of formula (I) are defined where $R^2$ is —NR⁷R⁸ or Het.

In one embodiment, when Y is CH, $R^2$ is not H.

Preferably, $R^7$ and $R^8$ are each the same or different and are independently selected from the group consisting of H, alkyl, cycloalkyl, —R¹⁰-cycloalkyl, —R¹⁰OR⁹, —R¹⁰NR⁹R¹¹—C(O)R⁹ and —R¹⁰CO₂R⁹, or any subset thereof. More preferably, $R^7$ and $R^8$ are each the same or different and are independently selected from the group consisting of H, alkyl, cycloalkyl and —R¹⁰-cycloalkyl, or any subset thereof. In one embodiment, $R^7$ and $R^8$ are each the same or different and are independently selected from the group consisting of H, alkyl and cycloalkyl, or any subset thereof.

Preferably $R^9$ and $R^{11}$ are each the same or different and are independently selected from the group consisting of H, alkyl, cycloalkyl and —R¹⁰-cycloalkyl, or any subset thereof. More preferably, $R^9$ and $R^{11}$ are each the same or different and are independently selected from the group consisting of H and alkyl, or any subset thereof.

Preferably $R^{10}$ is alkyl or cycloalkyl; more preferably alkyl.

More particularly, preferred embodiments of the present invention include compounds of formula (I) wherein $R^2$ is selected from the group consisting of —NH₂, —NH-alkyl, —NH-cycloalkyl, —N(alkyl)(alkyl), -Het (e.g., pyrrolidone), —NHHet and —NH-alkyl-Het, or any subset thereof. More preferably, the compounds of formula (I) are defined wherein $R^2$ is selected from the group consisting of —NH-alkyl and —NH-cycloalkyl. Preferred embodiments include those compounds of formula (I) wherein $R^2$ is —NH-propyl, —NH-isopropyl, —NH-cyclopropyl, —NH-butyl, —NH-isobutyl, —NH-cyclobutyl, —NH-cyclopentyl, —NH-cyclohexyl, —NH(CH₂)₂OCH₃, pyrrolidine (e.g., pyrrolidine bonded through N) and morpholine (e.g., morpholine bonded through N), or any subset thereof.

In another embodiment, the compounds of formula (I) include those compounds defined where at least one of $R^3$ and $R^4$ contains an aryl, heterocyclic or heteroaryl moiety (or more preferably a heterocyclic or heteroaryl moiety but exclude aryl moieties). A preferred embodiment includes those compounds of formula (I) where neither $R^3$ nor $R^4$ contain an aryl, heterocyclic or heteroaryl moiety (or more preferably, neither contains a heterocyclic or heteroaryl moiety but may contain an aryl moiety). Based on the guidance given above for $R^1$ and $R^2$, one skilled in the art can readily determine the list of appropriate groups defining $R^3$ and $R^4$ which contain or exclude aryl, heterocyclic or heteroaryl moieties.

$R^3$ is preferably selected from the group consisting of H, halo, alkyl, Ay, —OR⁷, —R¹⁰OR⁷, —NR⁷R⁸, —R¹⁰NR⁷R⁸ and —CO₂R⁷, or any subset thereof. More preferably, $R^3$ is selected from the group consisting of H, halo, alkyl, —OR⁷ and —NR⁷R⁸, or any subset thereof. Most preferably $R^3$ is H or alkyl. In one embodiment $R^3$ is H.

$R^4$ is preferably H, halo, alkyl, Ay, —OR⁷, —R¹⁰OR⁷, —NR⁷R⁸, —R¹⁰NR⁷R⁸ and —CO₂R⁷, or any subset thereof. More preferably, $R^4$ is H, halo, alkyl, —OR⁷ and —NR⁷R⁸, or any subset thereof. Most preferably $R^4$ is H or alkyl. In one embodiment $R^4$ is H.

Preferably q is 0, 1 or 2. In one embodiment, q is 0. In one preferred embodiment, q is 1. In one embodiment, q is 2 and the two $R^5$ groups are bonded to adjacent carbon atoms, and optionally, together with the atoms to which they are bonded, they form a $C_{5-6}$ cycloalkyl or aryl. The phrase "two adjacent $R^5$ groups" refers to two $R^5$ groups, each bonded to adjacent carbon atoms on the phenyl ring. In the embodiment where two adjacent $R^5$ groups together with the atoms to which they are bonded form a cycloalkyl or aryl, q is preferably 2, 3, 4 or 5; more preferably 2.

$R^5$ may be in the ortho, meta or para position.

Another class of compounds of formula (I) includes those compounds defined wherein at least one $R^5$ contains an aryl, heterocyclic or heteroaryl moiety (preferably a heterocyclic or heteroaryl moiety) and two adjacent $R^5$ groups together with the atoms to which they are bonded do not form a $C_{5-6}$ cycloalkyl or aryl. Another class of compounds of formula (I) includes those compounds defined wherein q is 3, 4 or 5, at least one $R^5$ contains an aryl, heterocyclic or heteroaryl moiety (preferably a heterocyclic or heteroaryl moiety) and two adjacent $R^5$ groups together with the atoms to which they are bonded do form $C_{5-6}$ cycloalkyl or aryl. Another class of compounds of formula (I) includes those compounds defined where no $R^5$ contains an aryl, heterocyclic or heteroaryl moiety (or in one embodiment no $R^5$ contains a heterocyclic or heteroaryl moiety) and two adjacent $R^5$ groups together with the atoms to which they are bonded do not form a $C_{5-6}$ cycloalkyl or aryl. Another class of compounds of formula (I) includes those compounds defined wherein q is 2, 3, 4 or 5, no $R^5$ contains an aryl, heterocyclic or heteroaryl moiety (or in one embodiment no $R^5$ contains a heterocyclic or heteroaryl moiety) and two adjacent $R^5$ groups together with the atoms to which they are bonded do form a $C_{5-6}$ cycloalkyl or aryl. Based on the guidance given above for $R^2$, one skilled in the art can readily determine the list of appropriate groups defining $R^5$ which contain or exclude aryl, heterocyclic or heteroaryl moieties.

When two adjacent $R^5$ groups together with the atoms to which they are bonded form a $C_{5-6}$ cycloalkyl or aryl, q is preferably 2, 3, 4 or 5; more preferably 2. In such embodiments, each $R^5$ group may be the same or different and is preferably selected from the group consisting of alkyl, and alkenyl. For example, in one embodiment two adjacent $R^5$ groups are are alkyl and together with the atoms to which they are bonded, they form a cycloalkyl group such as:

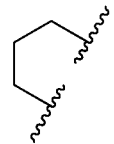

From this example, additional embodiments, including those where two adjacent $R^5$ groups together with the atoms to which they are bonded form an aryl group can be readily ascertained by those skilled in the art.

In one preferred embodiment, two $R^5$ groups together with the atoms to which they are bonded do not form a $C_{5-6}$ cycloalkyl or aryl.

Preferably, each $R^5$ is the same or different and is independently selected from the group consisting of halo, alkyl, alkenyl, —$OR^7$, —$CO_2R^9$, —$NR^7R^8$, —$C(O)NR^7R^8$, Ay, —OAy, —$NR^7$Ay, —$NHR^{10}$Ay, —$C(O)NR^7$Ay, Het, —$S(O)_2NR^7R^8$, cyano, nitro and azido, or any subset thereof. More preferably, each $R^5$ is the same or different and is independently selected from the group consisting of halo, alkyl, —$OR^7$, —$NR^7R^8$, —$C(O)NR^7R^8$, Het, —$S(O)_2NR^7R^8$, cyano and nitro, or any subset thereof. Most preferably, each $R^5$ is the same or different and is independently selected from the group consisting of halo, alkyl, —$OR^7$, —$NR^7R^8$ and cyano, or any subset thereof.

In particular, preferred embodiments of the compounds of formula (I) are defined where $R^5$ is halo (e.g., fluoro or chloro), alkyl (e.g., methyl), O-alkyl (e.g., O-methyl, O-isobutyl, and

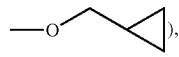

O-allyl, cyano, —NH—$CH_3$, and —$N(CH_3)_2$, or any subset thereof.

In one preferred class of compounds of formula (I), p is 0, 1 or 2. More preferably, p is 0 or 1. In one particular preferred embodiment, p is 1.

$R^6$ may be in the 4, 5 or 6 position. In one embodiment, p is 1 and $R^6$ is in the C-5 position.

One class of compounds of formula (I) includes those compounds defined wherein at least one $R^6$ contains an aryl, heterocyclic or heteroaryl moiety (preferably a heterocyclic or heteroaryl moiety) and two adjacent $R^6$ groups together with the atoms to which they are bonded do not form a $C_{5-6}$cycloalkyl or a 5- or 6-membered heterocyclic group containing 1 or 2 heteroatoms. Another class of compounds of formula (I) includes those compounds defined wherein p is 3, at least one $R^6$ contains an aryl, heterocyclic or heteroaryl moiety (preferably a heterocyclic or heteroaryl moiety) and two adjacent $R^6$ groups together with the atoms to which they are bonded do form a $C_{5-6}$ cycloalkyl or a 5- or 6-membered heterocyclic group containing 1 or 2 heteroatoms. A preferred class of compounds of formula (I) includes those compounds defined where no $R^6$ contains an aryl, heterocyclic or heteroaryl moiety (or in one embodiment no $R^6$ contains a heterocyclic or heteroaryl moeity) and two adjacent $R^6$ groups together with the atoms to which they are bonded do not form a $C_{5-6}$ cycloalkyl or a 5- or 6-membered heterocyclic group containing 1 or 2 heteroatoms. Another class of compounds of formula (I) includes those compounds defined wherein p is 2 or 3, no $R^6$ contains an aryl, heterocyclic or heteroaryl moiety (or in one embodiment no $R^6$ contains a heterocyclic or heteroaryl moiety) and two adjacent $R^6$ groups together with the atoms to which they are bonded do form a $C_{5-6}$ cycloalkyl or a 5- or 6-membered heterocyclic group containing 1 or 2 heteroatoms.

Based on the guidance given above for $R^1$ and $R^2$, one skilled in the art can readily determine the list of appropriate groups defining $R^6$ which contain or exclude aryl, heterocyclic or heteroaryl moeities.

In those embodiments where two adjacent $R^6$ groups together with the atoms to which they are bonded form a $C_{5-6}$ cycloalkyl or a 5- or 6-membered heterocyclic group having 1 or 2 heteroatoms (i.e., a cycloalkyl or heterocyclic ring), each $R^6$ may be the same or different and is preferably selected from the group consisting of alkyl, alkenyl, —$OR^7$, —$NR^7R^8$ and —$S(O)_nR^9$. For example, in one embodiment two adjacent $R^6$ groups are —$OR^7$ and together with the atoms to which they are bonded, they form a heterocyclic group such as:

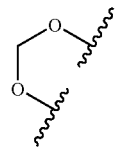

In another embodiment, two adjacent $R^6$ groups are alkyl and together with the atoms to which they are bonded, they form a cycloalkyl group such as:

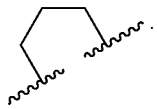

In another embodiment two adjacent $R^6$ groups are defined as —$OR^7$, —$NR^7R^8$ respectively and together with the atoms to which they are bonded, they form a heterocyclic group such as:

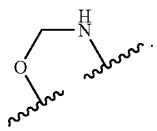

From these examples, additional embodiments can be readily ascertained by those skilled in the art. In one preferred embodiment, two $R^6$ groups together with the atoms to which they are bonded do not form a $C_{5-6}$ cycloalkyl or a 5- or 6-membered heterocyclic group.

Preferably, each $R^6$ is the same or different and is independently selected from the group consisting of halo, alkyl, Ay, Het, —$OR^7$, —OAy, —OHet, —$R^{10}OR^9$, —$R^{10}NR^7R^8$, —$C(O)R^9$, —$CO_2R^9$, —$C(O)NR^7R^8$, —$C(O)NR^7$Ay, —$C(O)NHR^{10}$Het, —$R^{10}C(O)NR^9R^{11}$, —$S(O)_2NR^7R^8$, —$R^{10}SO_2NHCOR^9$, —$S(O)_nR^9$, cyano, azido and nitro, or any subset thereof. More preferably, each $R^6$ is the same or different and is independently selected from the group consisting of halo, alkyl, Het, —$OR^7$, —$C(O)NR^7R^8$—$S(O)_2NR^7R^8$, —$S(O)_nR^9$ and cyano, or any subset thereof. Most preferably, each $R^6$ is the same or different and is independently selected from the group consisting of halo, Het, —$OR^7$ and —$S(O)_nR^9$, or any subset thereof.

In one preferred embodiment, the compounds of formula (I) are defined wherein when Y is —CH and $R^6$ is —$CO_2R^9$, $R^9$ is not H. In another preferred embodiment, the compounds of formula (I) are defined wherein when $R^6$ is —$CONR^7R^8$, neither $R^7$ nor $R^8$ is H.

In another embodiment, $R^6$ is selected from the group consisting of halo, alkyl, alkenyl, alkynyl, cycloalkyl, cycloalkenyl, —$R^{10}$cycloalkyl, Ay, Het, —$R^{10}$Ay, —$R^{10}$Het, —$OR^7$, —OAy, OHet, —$R^{10}OR^9$, —$OR^{10}$Ay, —$OR^{10}$Het, —$R^{10}NR^7R^8$, —$R^{10}NR^7$Ay, —$R^{10}C(O)R^9$, —C(O)R⁹, —C(O)Ay, —C(O)Het, —CO₂R¹⁰, —R¹⁰CO₂R⁹, —C(O)NR⁷Ay, —C(O)NHR¹⁰Het, —R¹⁰C(O)NR⁹R¹¹, —C(S)NR⁹R¹¹, —R¹⁰C(S)NR⁹R¹¹, —R¹⁰NHC(NH)NR⁹R¹¹, —C(NH)NR⁷R⁸, —C(NH)NR⁷Ay, —R¹⁰C(NH)NR⁹R¹¹, —S(O)₂NR⁷R⁸, —S(O)₂NR⁷Ay, —R¹⁰SO₂NHCOR⁹, —R¹⁰SO₂NR⁹R¹¹, —R¹⁰SO₂R⁹, —S(O)ₙR⁹, cyano, azido and nitro, or any subset thereof; or two adjacent R⁶ groups together with the atoms to which they are bonded form a C₅₋₆ cycloalkyl or a 5- or 6-membered heterocyclic group containing 1 or 2 heteroatoms.

In one preferred embodiment, R⁶ is selected from the group consisting of Cl, Br, F, methyl, ethyl, isopropyl, pyrrolidine, morpholine, —OH, —O-alkyl, —CONH₂, —CONH-alkyl, —CON(alkyl)₂, —S-alkyl, —CF₃ and —SO₂NH₂, or any subset thereof. In one preferred embodiment, R⁶ is selected from the group consisting of Cl, Br, F, methyl, ethyl, isopropyl, pyrrolidine, morpholine, —OH, —O-methyl, —O-isopropyl, —CONH₂, —CON(H)CH₃, —CON(CH₃)₂, —S-methyl, —S-ethyl, —S-isopropyl, —CF₃ and —SO₂NH₂, or any subset thereof. In one preferred embodiment, R⁶ is halo, preferably Cl or Br. In one embodiment R⁶ is trifluoromethyl.

It is to be understood that the present invention includes all combinations and subsets of the particular and preferred groups defined hereinabove.

Preferred compounds of formula (I) include but are not limited to:

2-(4-Fluorophenyl)-7-methyl-3-(4-pyrimidinyl)pyrazolo[1,5-a]pyridine;
2-(4-Fluorophenyl)-7-methylthio-3-(4-pyrimidinyl)pyrazolo[1,5-a]pyridine;
2-(4-Fluorophenyl)-7-methylsulfinyl-3-(4-pyrimidinyl)pyrazolo[1,5-a]-pyridine;
7-(2-Fluoroethoxy)-2-(4-fluorophenyl)-3-(4-(2-methylthio)pyrimidinyl)-pyrazolo[1,5-α]pyridine;
N-Butyl-4-[7-(2-fluoroethoxy)-2-(4-fluorophenyl)pyrazolo[1,5-a]pyridin-3-yl]-2-pyrimidinamine;
N-Benzyl-4-[7-(2-fluoroethoxy)-2-(4-fluorophenyl)pyrazolo[1,5-a]pyridin-3-yl]-2-pyrimidinamine;
2-(4-Fluorophenyl)-3-(4-(2-methylthio)pyrimidinyl)-7-(2,2,2-trifluoro-ethoxy)pyrazolo[1,5-a]pyridine;
N-Butyl-4-[2-(4-fluorophenyl)-7-(2,2,2-trifluoroethoxy)pyrazolo[1,5-a]pyridin-3-yl]-2-pyrimidinamine;
N-Benzyl-4-[2-(4-fluorophenyl)-7-(2,2,2-trifluoroethoxy)pyrazolo[1,5-a]-pyridin-3-yl]-2-pyrimidinamine;
N-Cyclopropyl-4-[2-(4-fluorophenyl)-7-(2,2,2-trifluoroethoxy)pyrazolo[1,5-a]pyridin-3-yl]-2-pyrimidinamine;
N-Cyclopentyl-4-[2-(4-fluorophenyl)-7-(2,2,2-trifluoroethoxy)pyrazolo[1,5-a]pyridin-3-yl]-2-pyrimidinamine;
N-Cyclohexyl-4-[2-(4-fluorophenyl)-7-(2,2,2-trifluoroethoxy)pyrazolo[1,5-a]pyridin-3-yl]-2-pyrimidinamine;
3-(4-[2-(4-Fluorophenyl)-7-(2,2,2-trifluoroethoxy)pyrazolo[1,5-a]pyridin-3-yl]-2-pyrimidinylamino)-1-propanol;
2-(4-Fluorophenyl)-3-(4-(2-methyloxy)pyrimidinyl)-7-(2,2,2-trifluoro ethoxy)pyrazolo[1,5-a]pyridine;
2-(4-Fluorophenyl)-3-(4-(2-phenyloxy)pyrimidinyl)-7-(2,2,2-trifluoro ethoxy)pyrazolo[1,5-a]pyridine;
2-(4-Fluorophenyl)-3-(4-(2-(2,2,2-trifluoroethoxy))pyrimidinyl)-7-(2,2,2-trifluoroethoxy)pyrazolo[1,5-α]pyridine;
2-(4-Fluorophenyl)-3-(4-(2-methylsulfinyl)pyrimidinyl)-7-(ethylsulfinyl)pyrazolo[1,5-a]pyridine;
2-(4-Fluorophenyl)-3-(4-(2-methylthio)pyrimidinyl)-7-(ethylthio)pyrazolo[1,5-a]pyridine;
Dimethyl 2-(4-fluorophenyl)-3-(4-(2-cyclopropylamino)pyrimidinyl)-7-pyrazolo[1,5-a ]pyridinylcarboxamide;
7-(2-Fluoroethoxy)-2-(4-fluorophenyl)-3-(4-(2-methylsulfinyl)pyrimidinyl)-pyrazolo[1,5-a]pyridine;
2-(4-Fluorophenyl)-3-(4-(2-methylsulfinyl)pyridinyl)-7-(2,2,2-trifluoroethoxy)-pyrazolol[1,5-a]pyridine;
2-(4-Fluorophenyl)-7-methyl-3-(4-pyridinyl)pyrazolo[1,5-a]pyrid ine;
2-(4-Fluorophenyl)-7-methoxy-3-(4-pyridinyl)pyrazolo[1,5-a]-pyridine;
2-(4-Fluorophenyl)-3-(2-fluoro-4-pyridinyl)-7-methoxy-pyrazolo[1,5-a]pyridine;
N-Butyl-4-[2-(4-fluorophenyl)-7-methoxypyrazolo[1,5-a]pyridin-3-yl]-2-pyridinamine;
N-{4-[5-Chloro-7-(ethylsulfanyl)-2-(4-fluorophenyl)pyrazolo[1,5-a]pyridin-3-yl]-2-pyrimidinyl}-N-cyclopentylamine
Ethyl 3-[2-(cyclopentylamino)-4-pyrimidinyl]-2-(4-fluorophenyl)-7-methylpyrazolo[1,5-a]pyridine-6-carboxylate;
3-[2-(Cyclopentylamino)-4-pyrimidinyl]-2-(4-fluorophenyl)-7-methylpyrazolo[1,5-α]pyridine-6-carboxylic acid;
3-[2-(Cyclopentylamino)-4-pyrimidinyl]-N-cyclopropyl-2-(4-fluorophenyl)-7-methylpyrazolo[1,5-a]pyridine-6-carboxamide;
N-Butyl-4-[7-butyl-2-(4-fluorophenyl)pyrazolo[1,5-a]pyridin-3-yl]2-pyrimidinamine;
N-Butyl-4-[2-(4-fluorophenyl)-7-methylpyrazolo[1,5-a]pyridin-3-yl]-2-pyrimidinamine;
N-Butyl-4-[2-(4-fluorophenyl)-7-octylpyrazolo[1,5-a]pyridin-3-yl]-2-pyrimidinamine;
N-Cyclopropyl-4-[7-ethyl-2-(4-fluorophenyl)pyrazolo[1,5-a]pyridin-3-yl]-2-pyrimidinamine;
4-[7-Butoxy-2-(4-methoxyphenyl)pyrazolo[1,5-a]pyridin-3-yl]-N-cyclopentyl-2-pyrimidinamine;
4-[5-Chloro-2-(3-chlorophenyl)-7-(methylsulfanyl)pyrazolo[1,5-a]pyridin-3-yl]-N -cyclopentyl-2-pyrimidinamine;
N-cyclopentyl-6-[2-(4fluorophenyl)-7-(methylthio)pyrazolo[1,5-a]pyridin-3-yl]pyrimidin-4-amine;
N-Cyclopentyl-4-[2-(4-fluorophenyl)-7-(methylthio)-5-morpholin-4-ylpyrazolo[1,5-α]pyridin-3-yl]pyrimidin-2-amine; and
N-Cyclopentyl-4-[2-(4-fluorophenyl)-7-(isopropylthio)-5-morpholin-4yipyrazolo[1,5-α]pyridin-3-yl]pyrimidin-2-amine;

and pharmaceutically acceptable salts, solvates and physiologically functional derivatives thereof.

It will be appreciated by those skilled in the art that the compounds of the present invention may also be utilized in the form of a pharmaceutically acceptable salt or solvate thereof. The pharmaceutically acceptable salts of the compounds of formula (I) include conventional salts formed from pharmaceutically acceptable inorganic or organic acids or bases as well as quaternary ammonium salts. More specific examples of suitable acid salts include hydrochloric, hydrobromic, sulfuric, phosphoric, nitric, perchloric, fumaric, acetic, propionic, succinic, glycolic, formic, lactic, maleic, tartaric, citric, palmoic, malonic, hydroxymaleic, phenylacetic, glutamic, benzoic, salicylic, fumaric, toluenesulfonic, methanesulfonic, naphthalene-2-sulfonic, benzenesulfonic hydroxynaphthoic, hydroiodic, malic, steroic, tannic and the like. Other acids such as oxalic, while not in themselves pharmaceutically acceptable, may be useful in the preparation of salts useful as intermediates in obtaining the compounds of the invention and their pharmaceutically acceptable salts. More specific examples of suitable basic salts include sodium, lithium, potassium, magnesium, aluminium, calcium, zinc, N,N'-dibenzylethylenediamine, chloroprocaine, choline, diethanolamine, ethylenediamine, N-methylglucamine and procaine salts.

The term "solvate" as used herein refers to a complex of variable stoichiometry formed by a solute (a compound of formula (I)) and a solvent. Solvents, by way of example, include water, methanol, ethanol, or acetic acid.

The term "physiologically functional derivative" as used herein refers to any pharmaceutically acceptable derivative of a compound of the present invention, for example, an ester or an amide of a compound of formula (I), which upon administration to an animal, particularly a mammal, such as a human, is capable of providing (directly or indirectly) a compound of the present ivnention or an active metabolite thereof. See, for example, Burger's Medicinal Chemistry And Drug Discovery, 5th Edition, Vol 1: Principles And Practice.

Processes for preparing pharmaceutically acceptable salts, solvates and physiologically functional derivatives of the compounds of formula (I) are conventional in the art. See, e.g., Burger's Medicinal Chemistry And Drug Discovery 5th Edition, Vol 1: Principles And Practice.

As will be apparent to those skilled in the art, in the processes descibed below for the preparation of compounds of formula (I), certain intermediates, particularly compounds of formula (XI), may be in the form of pharmaceutically acceptable salts, solvates or physiologically functional derivatives of the compound. Those terms as applied to any intermediate employed in the process of preparing compounds of formula (I) have the same meanings as noted above with respect to compounds of formula (I). Processes for preparing pharmaceutically acceptable salts, solvates and physiologically functional derivatives of such intermediates are known in the art and are analogous to the process for preparing pharmaceutically acceptable salts, solvates and physiologically functional derivatives of the compounds of formula (I).

Certain compounds of formula (I) may exist in stereoisomeric forms (e.g. they may contain one or more asymmetric carbon atoms or may exhibit cis-trans isomerism). The individual stereoisomers (enantiomers and diastereomers) and mixtures of these are included within the scope of the present invention. The present invention also covers the individual isomers of the compounds represented by formula (I) as mixtures with isomers thereof in which one or more chiral centers are inverted. Likewise, it is understood that compounds of formula (I) may exist in tautomeric forms other than that shown in the formula and these are also included within the scope of the present invention.

The present invention further provides compounds of formula (I) for use in medical therapy, e.g. in the treatment or prophylaxis, including suppression of recurrence of symptoms, of a viral disease in an animal, e.g. a mammal such as a human. The compounds of formula (I) are especially useful for the treatment or prophylaxis of viral diseases such as herpes viral infections. Herpes viral infections include, for example, herpes simplex virus 1 (HSV-1), herpes simplex virus 2 (HSV-2), cytomegalovirus (CMV), Epstein Barr virus (EBV), Varicella zoster virus (VZV), human herpes virus 6 (HHV-6), human herpes virus 7 (HHV-7), and human herpes virus 8 (HHV-8). Thus, the compounds of the invention are also useful in the treatment or prophylaxis of the symptoms or effects of herpes virus infections.

The compounds of the invention are useful in the treatment or prophylaxis of conditions or diseases associated with herpes virus infections, particularly conditions or diseases associated with latent herpes virus infections in an animal, e.g., a mammal such as a human. By conditions or diseases associated with herpes viral infections is meant a condition or disease, excluding the viral infection per se, which results from the presence of the viral infection, such as chronic fatigue syndrome which is associated with EBV and multiple sclerosis which ahs been associated with herpes viral infections such as EBV and HHV-6. Further examples of such conditions or diseases are described in the background section above.

In addition to those conditions and diseases, the compounds of the present invention may also be used for the treatment or prophylaxis of cardiovascular diseases and conditions associated with herpes virus infections, in particular atherosclerosis, coronary artery disease and restenosis and specifically restenosis following angioplasty (RFA). Restenosis is the narrowing of the blood vessels which can occur after injury to the vessel wall, for example injury caused by balloon angioplasty or other surgical and/or diagnostic techniques, and is characterized by excessive proliferation of smooth muscle cells in the walls of the blood vessel treated. It is thought that in many patients suffering from restenosis following angioplasty, viral infection, particularly by CMV and/or HHV-6 plays a pivotal role in the proliferation of the smooth muscle cells in the coronary vessel. Restenosis can occur following a number of surgical and/or diagnostic techniques, for example, transplant surgery, vein grafting, coronary by-pass grafting and, most commonly following angioplasty.

There is evidence from work done both in vitro and in vivo, indicating that restenosis is a multifactorial process. Several cytokines and growth factors, acting in concert, stimulate the migration and proliferation of vascular smooth muscle cells (SMC) and production of extracellular matrix material, which accumulate to occlude the blood vessel. In addition growth suppressors act to inhibit the proliferation of SMC's and production of extracellular matrix material.

In addition, compounds of formula (I) may be useful in the treatment or prophylaxis of hepatitis B or hepatitis C viruses, human papilloma virus (HPV) and HIV.

The present invention provides a method for the treatment or prophylaxis of a viral infection in an animal such as a mammal (e.g., a human), particularly a herpes viral infection, which method comprises administering to the animal a therapeutically effective amount of the compound of formula (I).

As used herein, the term "prophylaxis" refers to the complete prevention of infection, the prevention of occurrence of symptoms in an infected subject, the prevention of recurrence of symptoms in an infected subject, or a decrease in severity or frequency of symptoms of viral infection, condition or disease in the subject.

As used herein, the term "treatment" refers to the partial or total elimination of symptoms or decrease in severity of symptoms of viral infection, condition or disease in the subject, or the elimination or decrease of viral presence in the subject.

As used herein, the term "therapeutically effective amount" means an amount of a compound of formula (I) which is sufficient, in the subject to which it is administered, to treat or prevent the stated disease, condition or infection. For example, a therapeutically effective amount of a compound of formula (I) for the treatment of a herpes virus infection is an amount sufficient to treat the herpes viral infection in the subject.

The present invention also provides a method for the treatment or prophylaxis of conditions or diseases associated with herpes viral infections in an animal such as a mammal (e.g., a human), which comprises administering to the animal a therapeutically effective amount of the compound of formula (I). In one embodiment, the present invention provides a method for the treatment or prophylaxis of chronic fatigue syndrome and multiple sclerosis in an animal such as a mammal (e.g., a human), which comprises administering to the animal a therapeutically effective amount of a compound of formula (I). The foregoing method is particularly useful for the treatment or prophylaxis of chronic fatigue syndrome and multiple sclerosis associated with latent infection with a herpes virus.

In another embodiment, the present invention provides a method for the treatment or prophylaxis of a cardiovascular condition such as atherosclerosis, coronary artery disease or restenosis (particularly restenosis followign surgery such as angioplasty), which comprises administering to the animal a therapeutically effective antiviral amount of the compound of formula (I).

The present invention further provides a method for the treatment or prophylaxis of hepatitis B or hepatitis C viruses in an animal such as a mammal (e.g., a human), which comprises administering to the animal a therapeutically effective amount of the compound of formula (I).

The present invention further provides a method for the treatment or prophylaxis of human papilloma virus in an animal such as a mammal (e.g., a human), which comprises administering to the animal a therapeutically effective amount of the compound of formula (I).

The present invention further provides a method for the treatment or prophylaxis of HIV in an animal such as a mammal (e.g., a human), which comprises administering to the animal a therapeutically effective amount of the compound of formula (I).

The present invention also provides the use of the compound of formula (I) in the preparation of a medicament for the treatment or prophylaxis of a viral infection in an animal such as a mammal (e.g., a human), particularly a herpes viral infection; the use of the comound of formula (I) in the preparation of a medicament for the treatment of conditions or disease associated with a herpes viral infection; and the use of the compound of formula (I) in the preparation of a medicament for the treatment or prophylaxis of hepatitis B or hepatitis C viruses, human papilloma virus and HIV. In particular, the present invention also provides the use of a compound of formula (I) in the preparation of a medicament for the treatment or prophylaxis of chronic fatigue syndrome or multiple sclerosis. In one embodiment, the present invention provides the use of a compound of formula (I) in the preparation of a medicament for the treatment or prophylaxis of cardiovascular disease, such as restenosis and atherosclerosis.

The compounds of formula (I) are conveniently administered in the form of pharmaceutical compositions. Such compositions may conveniently be presented for use in conventional manner in admixture with one or more physiologically acceptable carriers or diluents.

While it is possible that compounds of the present invention may be therapeutically administered as the raw chemical, it is preferable to present the active ingredient as a pharmaceutical formulation or composition. The pharmaceutical composition may include one or more pharmaceutically acceptable carriers or diluents together with the compound of formula (I). The carrier(s) or diluent(s) must be "acceptable" in the sense of being compatible with the other ingredients of the formulation and not deleterious to the recipient thereof.

Accordingly, the present invention further provides for a pharmaceutical formulation or composition comprising a compound of formula (I). In one embodiment, the pharmaceutical formulation further comprises one or more pharmaceutically acceptable carriers or dilents and, optionally, other therapeutic and/or prophylactic ingredients.

The formulations include those suitable for oral, parenteral (including subcutaneous e.g. by injection or by depot tablet, intradermal, intrathecal, intramuscular e.g. by depot and intravenous), rectal and topical (including dermal, buccal and sublingual) administration although the most suitable route may depend upon for example the condition, age, and disorder of the recipient as well as the viral infection or disease being treated. The formulations may conveniently be presented in unit dosage form and may be prepared by any of the methods well known in the art of pharmacy. All methods include the step of bringing into association the compound(s) ("active ingredient") with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation. Formulations suitable for oral administration may be presented as discrete units such as capsules, cachets or tablets (e.g. chewable tablets in particular for paediatric administration) each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste. A tablet may be made by compression or moulding, optionally with one or more accessory ingredients. Compressed tablets may be prepared by compressing in a suitable machine the active ingredient in a free-flowing form such as a powder or granules, optionally mixed with other conventional excipients such as binding agents, (for example, syrup, acacia, gelatin, sorbitol, tragacanth, mucilage of starch or polyvinylpyrrolidone), fillers (for example, lactose, sugar, microcrystalline cellulose, maize-starch, calcium phosphate or sorbitol), lubricants (for example, magnesium stearate, stearic acid, talc, polyethylene glycol or silica), disintegrants (for example, potato starch or sodium starch glycollate) or wetting agents, such as sodium lauryl sulfate. Moulded tablets may be made by moulding in a suitable machine a mixture of the powdered compound moistened with an inert liquid diluent. The tablets may optionally be coated or scored and may be formulated so as to provide slow or controlled release of the active ingredient therein. The tablets may be coated according to methods well-known in the art.

Alternatively, the compounds of the present invention may be incorporated into oral liquid preparations such as aqueous or oily suspensions, solutions, emulsions, syrups or elixirs, for example. Moreover, formulations containing these compounds may be presented as a dry product for constitution with water or other suitable vehicle before use. Such liquid preparations may contain conventional additives such as suspending agents such as sorbitol syrup, methyl cellulose, glucose/sugar syrup, gelatin, hydroxyethylcellulose, carboxymethyl cellulose, aluminum stearate gel or hydrogenated edible fats; emulsifying agents such as lecithin, sorbitan mono-oleate or acacia; non-aqueous vehicles (which may include edible oils) such as almond oil, fractionated coconut oil, oily esters, propylene glycol or ethyl alcohol; and preservatives such as methyl or propyl p-hydroxybenzoates or sorbic acid. Such preparations may also be formulated as suppositories, e.g., containing conventional suppository bases such as cocoa butter or other glycerides.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations may be presented in unit-dose or multi-dose containers, for example sealed ampoules and vials, and may be stored in a freeze-dried (lyophilised) condition requiring only the addition of a sterile liquid carrier, for example, water-for-injection, immediately prior to use. Extemporaneous injection solutions and suspensions may be prepared from sterile powders, granules and tablets of the kind previously described. Formulations for rectal administration may be presented as a suppository with the usual carriers such as cocoa butter, hard fat or polyethylene glycol.

Formulations for topical administration in the mouth, for example buccally or sublingually, include lozenges comprising the active ingredient in a flavoured base such as sucrose and acacia or tragacanth, and pastilles comprising the active ingredient in a base such as gelatin and glycerin or sucrose and acacia.

The compounds may also be formulated as depot preparations. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

In addition to the ingredients particularly mentioned above, the formulations may include other agents conventional in the art having regard to the type of formulation in question, for example those suitable for oral administration may include flavouring agents.

It will be appreciated that the amount of a compound of the invention required for use in treatment will vary with the nature of the condition being treated and the age and the condition of the patient and will be ultimately at the discretion of the attendant physician or veterinarian. In general, however, doses employed for adult human treatment will typically be in the range of 0.02–5000 mg per day, preferably 100–1500 mg per day. The desired dose may conveniently be presented in a single dose or as divided doses administered at appropriate intervals, for example as two, three, four or more sub-doses per day. The formulations according to the invention may contain between 0.1–99% of the active ingredient, conveniently from 30–95% for tablets and capsules and 3–50% for liquid preparations.

The compound of formula (I) for use in the instant invention may be used in combination with other therapeutic agents for example, non-nucleotide reverse transcriptase inhibitors, nucleoside reverse transcriptase inhibitors, protease inhibitors and/or other antiviral agents. The invention thus provides in a further aspect the use of a combination comprising a compound of formula (I) with a further therapeutic agent in the treatment of viral infections. Particular antiviral agents which may be combined with the compounds of the present invention include aciclovir, valaciclovir, fameyclovir, ganciclovir, docosanol, miribavir, amprenavir, lamivudine, zidovudine, and abacavir. Preferred antiviral agents for combining with the compounds of the present invention include aciclovir and valaciclovir. Thus the present invention provides in a further aspect, a combination comprising a compound of formula (I) and an antiviral agent selected from the group consisting of aciclovir or valaciclovir; the use of such combination in the treatment of viral infections and the preparation of a medicament for the treatment of viral infections, and a method of treating viral infections comprising administering a compound of formula (I) and an antiviral agent selected from the group consisting of acyclovir and valacyclovir.

When the compounds of formula (I) are used in combination with other therapeutic agents, the compounds may be administered either sequentially or simultaneously by any convenient route.

The combinations referred to above may conveniently be presented for use in the form of a pharmaceutical formulation and thus pharmaceutical formulations comprising a combination as defined above optionally together with a pharmaceutically acceptable carrier or diluent comprise a further aspect of the invention. The individual components of such combinations may be administered either sequentially or simultaneously in separate or combined pharmaceutical formulations.

When combined in the same formulation it will be appreciated that the two compounds must be stable and compatible with each other and the other components of the formulation and may be formulated for administration. When formulated separately they may be provided in any convenient formulation, in such a manner as are known for such compounds in the art.

When a compound of formula (I) is used in combination with a second therapeutic agent active against the viral infection, the dose of each compound may differ from that when the compound is used alone. Appropriate doses will be readily appreciated by those skilled in the art.

Compounds of formula (I) are prepared using the methods described below. The following methods and schemes describe processes for preparing compounds of formula (XI) and pharmaceutically acceptable salts, solvates and physiologically functional derivatives thereof. It will be appreciated by those skilled in the art that the compounds of formula (XI) encompass all compounds of formula (I) and are in fact the same as the compounds of formula (I) when compounds of formula (XI) are defined wherein $R^{1a}=R^1$. When the compounds of formula (XI) are defined wherein $R^{1a}$ is H or halo, the compounds of formula (XI) or pharmaceutically acceptable salts, solvates and physiologically functional derivatives thereof may be converted into compounds of formula (I) using methods described below.

Compounds of formula (XI) wherein Y is N; $R^2$ is selected from the group consisting of H, alkyl, cycloalkyl, alkenyl, cycloalkenyl, —$NR^7R^8$, Ay, —$NHR^{10}$Ay, —$OR^7$, —OAy, —$S(O)_nR^9$, —$S(O)_n$Ay, —$R^{10}NR^7R^8$, —$R^{10}NR^7$Ay, Het, —NHHet, —$NHR^{10}$Het, —OHet, and —$OR^{10}$Het; $R^3$ is H and $R^4$ is H, may be conveniently prepared by a general process outlined in Scheme 1 below.

Scheme 1

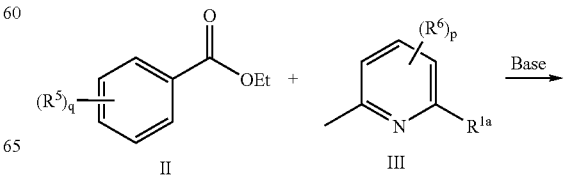

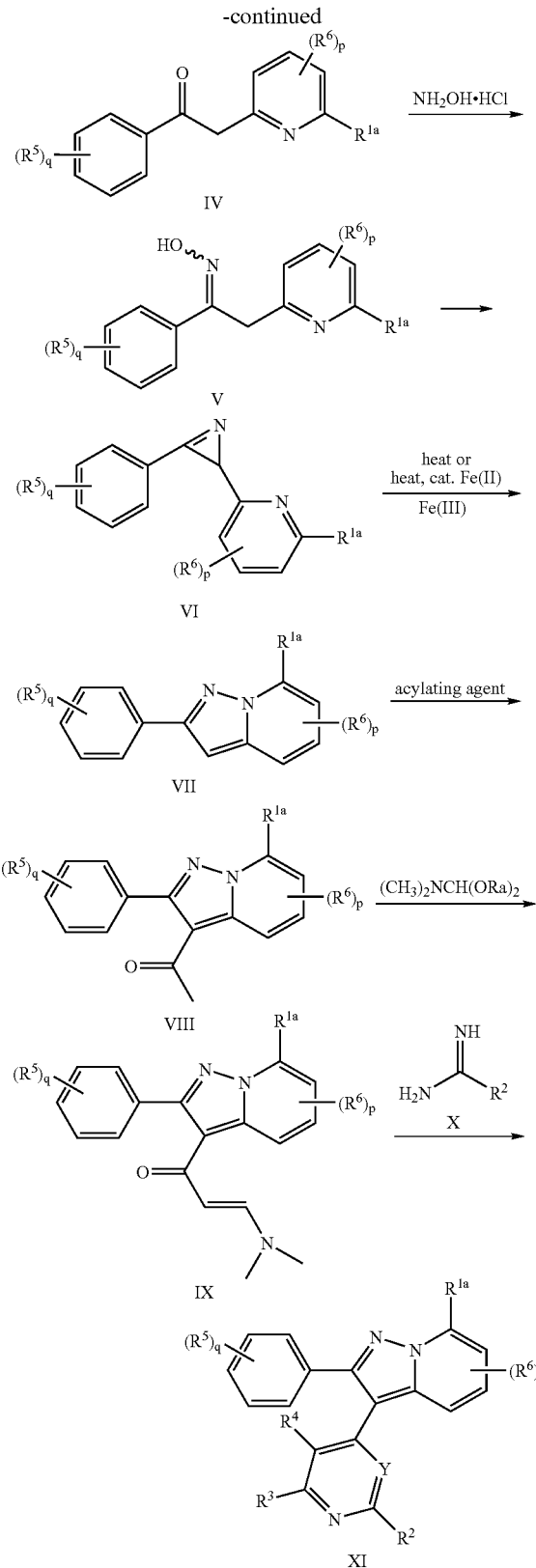

wherein:

$R^{1a}$ is selected from the group consisting of H, halo, alkyl, alkenyl, alkynyl, cycloalkyl, cycloalkenyl, —$R^{10}$cycloalkyl, —$R^{10}$Ay, —$R^{10}$Het, —$OR^7$, —OAy, —OHet, —$OR^{10}$Ay, —$OR^{10}$Het, —$R^{10}OR^9$, —$R^{10}NR^7R^8$, —$R^{10}NR^7$Ay, —$R^{10}C(O)R^9$, —$C(O)R^9$, —C(O)Ay, —C(O)Het, —$R^{10}OC(O)R^9$, —$R^{10}OC(O)$Ay, —$R^{10}OC(O)$Het, —$CO_2R^9$, —$R^{10}CO_2R^9$, —C(O)$NR^7R^8$, —C(O)$NR^7$Ay, —C(O)$NHR^{10}$Ay, —$R^{10}C(O)NR^9R^{11}$, —$C(S)NR^9R^{11}$, —$R^{10}C(S)NR^9R^{11}$, —$R^{10}NHC(NH)NR^9R^{11}$, —$C(NH)NR^7R^8$, —C(NH)$NR^7$Ay, —$R^{10}C(NH)NR^9R^{11}$, —$S(O)_2NR^7R^8$, —$S(O)_2NR^7$Ay, —$R^{10}SO_2NHCOR^9$, —$R^{10}SO_2NR^9R^{11}$, —$R^{10}SO_2R^9$, —$R^{10}OS(O)_nR^9$, —$R^{10}NHSO_2R^9$, —$R^{10}NHCOR^9$, —$S(O)_nR^9$, —$S(O)_n$Ay, —$S(O)_n$Het, cyano, azido and nitro;

each $R^7$ and $R^8$ are the same or different and are independently selected from the group consisting of H, alkyl, cycloalkyl, alkenyl, cycloalkenyl, —$R^{10}$cycloalkyl, —$OR^9$, —$R^{10}OR^9$, —$R^{10}NR^9R^{11}$, —$R^{10}C(O)R^9$, —$C(O)R^9$, —$CO_2R^9$, —$R^{10}CO_2R^9$, —$C(O)NR^9R^{11}$, —$R^{10}C(O)NR^9R^{11}$, —$C(S)NR^9R^{11}$, —$R^{10}C(S)NR^9R^{11}$, —$R^{10}NHC(NH)NR^9R^{11}$, —$R^{10}C(NH)NR^9R^{11}$, —$C(NH)NR^9R^{11}$, —$SO_2NR^9R^{11}$, —$R^{10}SO_2NR^9R^{11}$, —$R^{10}NHSO_2R^9$, —$SO_2R^{10}$, —$R^{10}SO_2R^{10}$, —$R^{10}NHCOR^9$ and —$R^{10}SO_2NHCOR^9$;

each $R^9$ and $R^{11}$ are the same or different and are independently selected from the group consisting of H, alkyl, cycloalkyl, —$R^{10}$cycloalkyl, —$R^{10}$OH, —$R^{10}(OR^{10})$w where w is 1–10, and —$R^{10}NR^{10}R^{10}$;

each $R^{10}$ is the same or different and is independently selected from the group consisting of alkyl, cycloalkyl, alkenyl, cycloalkenyl and alkynyl;

Ay is an aryl;

Het is a 5- or 6-membered heterocyclic or heteroaryl group;

n is 0, 1 or 2;

$R^2$ is selected from the group consisting of H, alkyl, cycloalkyl, alkenyl, cycloalkenyl, —$NR^7R^8$, Ay, —$NHR^{10}$Ay, —$OR^7$, —OAy, —$S(O)_nR^9$, —$S(O)_n$Ay, —$R^{10}NR^7R^8$, —$R^{10}NR^7$Ay, Het, —NHHet, —$NHR^{10}$Het, —OHet and —$OR^{10}$Het;

Y is N;

$R^3$ and $R^4$ are both H;

q is 0, 1, 2, 3, 4 or 5;

each $R^5$ is the same or different and is independently selected from the group consisting of halo, alkyl, alkenyl, alkynyl, cycloalkyl, cycloalkenyl, —$R^{10}$cycloalkyl, Ay, —$NHR^{10}$Ay, —$NR^7$Ay, Het, —NHHet, —$NHR^{10}$Het, —$OR^7$, —OAy, —OHet, —$R^{10}OR^9$, —$NR^7R^8$, —$R^{10}NR^7R^8$, —$R^{10}NR^7$Ay, —$R^{10}C(O)R^9$, —$C(O)R^9$, —C(O)Ay, —C(O)Het, —$CO_2R^9$, —$R^{10}CO_2R^9$, —C(O)$NR^7R^8$, —C(O)$NR^7$Ay, —C(O)$NHR^{10}$Het, —$R^{10}C(O)NR^9R^{11}$, —$C(S)NR^9R^{11}$, —$R^{10}C(S)NR^9R^{11}$, —$R^{10}NHC(NH)NR^9R^{11}$, —$C(NH)NR^7R^8$, —C(NH)$NR^7$Ay, —$R^{10}C(NH)NR^9R^{11}$, —$S(O)_2NR^7R^8$, —$S(O)_2NR^7$Ay, —$R^{10}SO_2NHCOR^9$, —$R^{10}SO_2NR^9R^{11}$, —$R^{10}SO_2R^9$, —$S(O)_nR^9$, cyano, azido and nitro; or two adjacent $R^5$ groups together with the atoms to which they are bonded form a $C_{5-6}$ cycloalkyl or aryl;

p is 0, 1, 2 or 3;

each $R^6$ is the same or different and is independently selected from the group consisting of halo, alkyl, alkenyl, alkynyl, cycloalkyl, cycloalkenyl, —$R^{10}$cycloalkyl, Ay, Het, —$R^{10}$Ay, —$R^{10}$Het, —$OR^7$, —OAy, —OHet, —$R^{10}R^9$, —$OR^{10}$Ay, —$OR^{10}$Het, —$R^{10}NR^7R^8$, —$R^{10}NR^7$Ay, —$R^{10}C(O)R^9$, —C(O)$R^9$, —C(O)Ay, —C(O)Het, —$CO_2R^9$, —$R^{10}CO_2R^9$, —C(O)$NR^7R^8$, —C(O)$NR^7$Ay, —C(O)$NHR^{10}$Het, —$R^{10}C(O)NR^9R^{11}$, —$C(S)NR^9R^{11}$, —R¹⁰C(S)NR⁹R¹¹, —R¹⁰NHC(NH)NR⁹R¹¹, —C(NH)
NR⁷R⁸, —C(NH)NR⁷Ay, —R¹⁰C(NH)NR⁹R¹¹, —S(O)₂
NR⁷R⁸, —S(O)₂NR⁷Ay, —R¹⁰SO₂NHCOR⁹,
—R¹⁰SO₂NR⁹R¹¹, —R¹⁰SO₂R⁹, —S(O)ₙR⁹, cyano,
azido and nitro; or
two adjacent R⁶ groups together with the atoms to which
they are bonded form a $C_{5-6}$ cycloalkyl or a 5- or
6-membered heterocyclic group containing 1 or 2 heteroatoms; and Ra is alkyl or cycloalkyl.

Generally, the process for preparing the compounds of formula (I) wherein Y is N; R² is selected from the group consisting of H, alkyl, cycloalkyl, alkenyl, cycloalkenyl, —NR⁷R⁸, Ay, —NHR¹⁰Ay, —OR⁷, —OAy, —S(O)ₙR⁹, —S(O)ₙAy, —R¹⁰NR⁷R⁸, —R¹⁰NR⁷Ay, Het, —NHHet, —NHR¹⁰Het, —OHet, and —OR¹⁰Het; R³ is H and R⁴ is H, (all formulas and all other variables having been defined above in connection with Scheme 1) comprises the steps of:

(a) reacting a 2-picoline compound of formula (III) with a benzoylating agent of formula (II) to prepare the compound of formula (IV);
(b) reacting the compound of formula (IV) with a hydroxylamine source to prepare a compound of formula (V);
(c) reacting the compound of formula (V) with an acylating or sulfonylating agent to prepare a compound of formula (VI);
(d) rearranging the compound of formula (VI) to prepare a compound of formula (VII);
(e) acylating the compound of formula (VII) to prepare a compound of formula (VIII);
(f) reacting the compound of formula (VIII) with a dimethylformamide dialkyl acetal of formula $(CH_3)_2NCH(ORa)_2$ to prepare a compound of formula (IX);
(g) reacting the compound of formula (IX) with a compound of formula (X) to prepare a compound of formula (XI); and
(h) when $R^{1a}$ is H or halo, converting the compound of formula (XI) to a compound of formula (I).

When the compounds of formula (XI) are defined where $R^{1a}$ is H or halo, the process for preparing compounds of formula (I) comprises the additional step (h) of converting the compounds of formula (XI) to compounds of formula (I). Such conversion can be achieved using the methods described below or other suitable methods conventional in the art for this type of transformation.

More specifically, compounds of formula (I) wherein Y is N; R² is selected from the group consisting of H, alkyl, cycloalkyl, alkenyl, cycloalkenyl, —NR⁷R⁸, Ay, —NHR¹⁰Ay, —OR⁷, —OAy, —S(O)ₙR⁹, —S(O)ₙAy, —R¹⁰NR⁷R⁸, —R¹⁰NR⁷Ay, Het, —NHHet, —NHR¹⁰Het, —OHet, and —OR¹⁰Het; R¹³ is H and R⁴ is H, can be prepared by reacting a compound of formula (IX) with a compound of formula (X) to prepare a compound of formula (XI), and when $R^{1a}$ is H or halo, converting to a compound of formula (I).

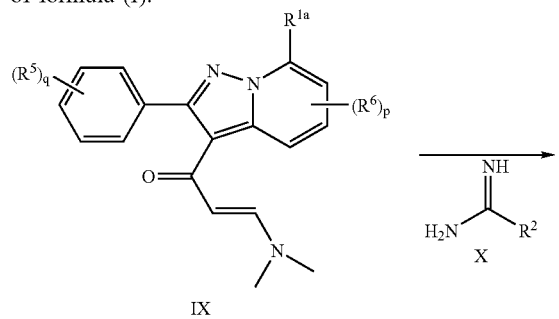

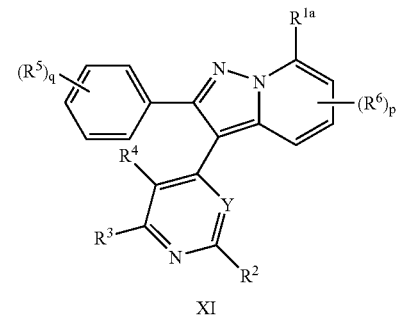

wherein all variables are as defined above in connection with Scheme 1.

This method can be readily carried out by mixing a compound of formula (IX) with a compound of formula (X) in a suitable solvent, optionally in the presence of a base (preferably when the amidine is in a salt form), and heating the reaction to 50–150° C. Typical solvents include lower alcohols such as methanol, ethanol, isopropanol, dimethylformamide, and the like. The base is typically a sodium alkoxide, potassium carbonate, or an amine base such as triethylamine. In one embodiment, the solvent is dimethylformamide and the base is potassium carbonate, or an amine base such as triethylamine.

Compounds of the formula (VIII) may be conveniently prepared by reacting a compound of formula (VII) with a dimethylformamide dialkyl acetal of formula $(CH_3)_2NCH(ORa)_2$.

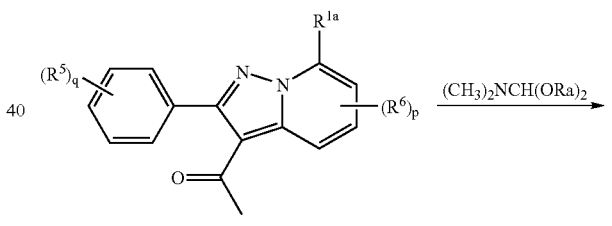

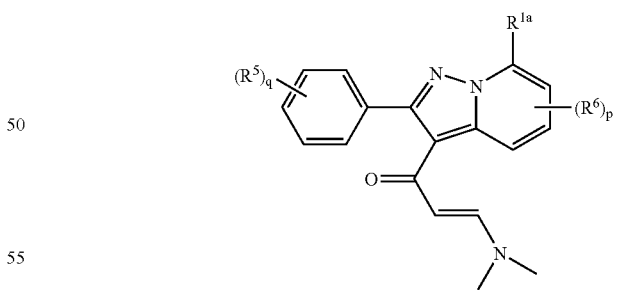

wherein all variables are as defined above in connection with Scheme 1.

Typical dimethylformamide dialkylacetal compounds for use in this method include but are not limited to dimethylformamide dimethylacetal and dimethylformamide di-tert-butylacetal. The reaction is carried out by mixing a compound of formula (VIII) with the dimethylformamide dialkyl acetal, optionally with heating.

Compounds of the formula (VIII) may be conveniently prepared from compounds of the formula (VII) using an acylation procedure.

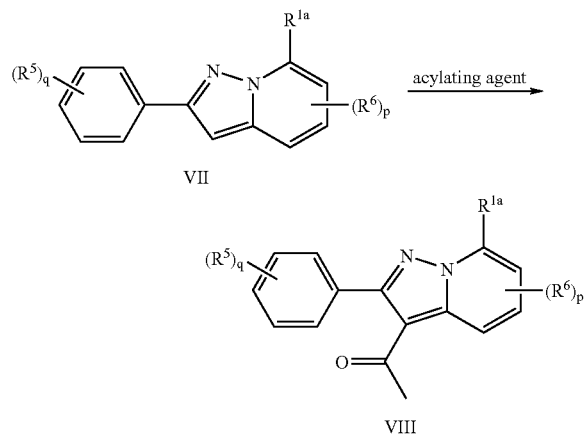

wherein all variables are as defined above in connection with Scheme 1.

Typically the acylation is carried out by treating the compounds of formula (VII) with an acylating agent, optionally in the presence of an acid or Lewis acid catalyst in an inert solvent with optional heating. Typical acylating agents will be readily determined by those skilled in the art. One preferred acylating agent is acetic anhydride. Lewis acid catalysts are also known to those skilled in the art. One preferred Lewis acid catalyst for use in this reaction is boron trifluoride diethyl etherate. A suitable solvent is toluene.

Compounds of formula (VII) are conveniently prepared by rearranging an azirine compound of formula (VI).

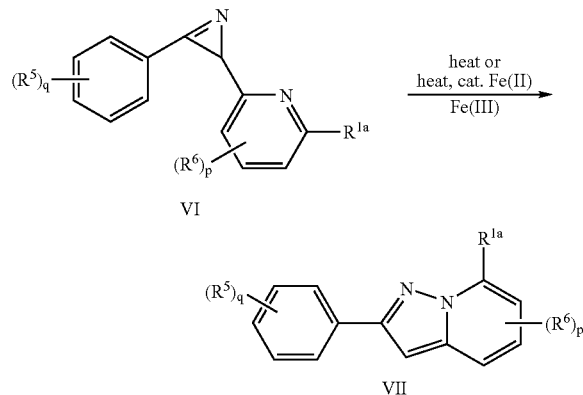

wherein all variables are as defined above in connection with Scheme 1.

The rearrangement of the azirines of formula (VI) can be accomplished by heating a solution of the azirine of formula (VI) in a suitable solvent at a temperature of about 160–200° C. Suitable inert solvents include, but are not limited to, 1-methyl-2-pyrrolidinone, and 1,2,4-trichlorobenzene. A more preferred method for rearrangement of the azirine of formula (VI) to compounds of formula (VII) involves reacting the compound of formula (VI) with ferrous chloride ($FeCl_2$) or ferric chloride ($FeCl_3$). This reaction is typically done in an inert solvent with heating. A preferred solvent for this reaction is 1,2-dimethoxyethane and the like.

Typically the azirines of formula (VI) are prepared from oxime compounds of formula (V) by treatment with acylating or sulfonylating agents in the presence of a base.

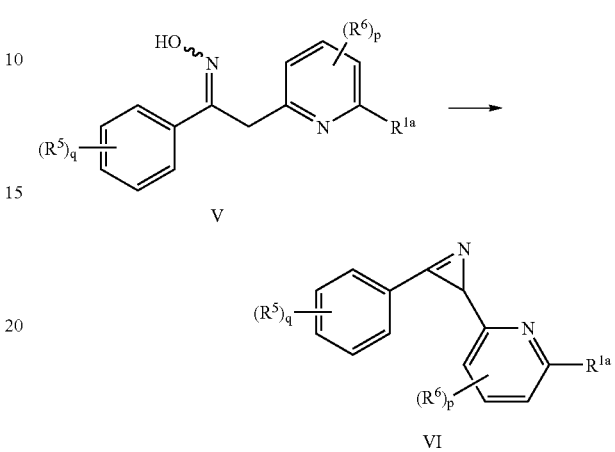

wherein all variables are as defined above in connection with Scheme 1.

Typical acylating or sulfonylating agents include but are not limited to, acetic anhydride, trifluoroacetic anhydride, methanesulfonyl chloride, toluenesulfonyl chloride and the like. Typical bases include, but are not limited to, triethylamine, diisopropylethylamine, pyridine, and the like. The reaction may be carried out in an inert solvent such as for example, chloroform, dichloromethane, toluene or the like.

The oxime compounds of formula (V) are readily prepared by treating ketone compounds of formula (IV) with a hydroxylamine source, in a suitable solvent, and optionally with a base.

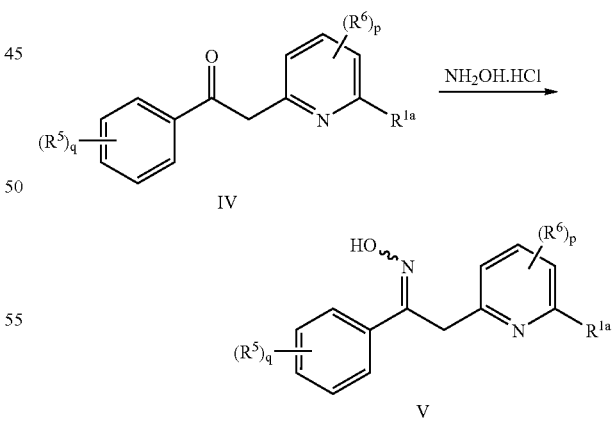

wherein all variables are as defined above in connection with Scheme 1.

Preferably the hydroxylamine is hydroxylamine hydrochloride and the base is an aqueous solution of sodium hydroxide. Suitable solvents include lower alcohols such as methanol, ethanol and isopropanol.

The ketone compounds of formula (IV) can be prepared by treatment of a picoline compound of formula (III) with a benzoylating agent of formula (II) in the presence of a base.

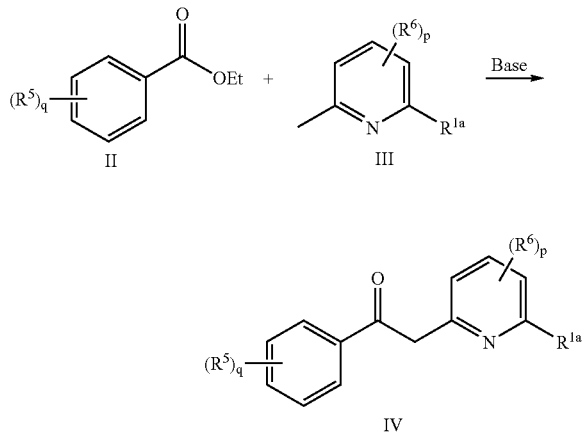

wherein all variables are as defined above in connection with Scheme 1.

The benzoylating agents of formula (II) and the picoline compounds of formula (III) are commercially available or may be prepared using conventional methods known to those skilled in the art. Preferred benzoylating agents of formula (II) include, but are not limited to, benzoyl esters. An example of a suitable base is lithium bis(trimethylsilyl) amide in an inert solvent such as tetrahydrofuran.

An alternative synthesis for compounds of formula (VII) involves treating a ketone of formula (IV) with an aminating agent in a suitable solvent and optionally heating the reaction. The aminating agent is, preferably, O-(mesitylsulfonyl) hydroxylamine and preferred solvents include chloroform, dichloromethane and the like.

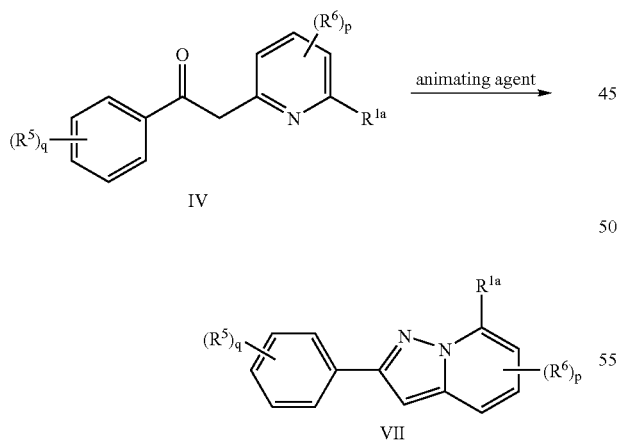

wherein all variables are as defined above in connection with Scheme 1.

Ketones such as the compounds of formula (IV) can be readily prepared using procedures described in the literature (Cassity, R. P.; Taylor, L T.; Wolfe, J. F. *J.Org. Chem.* 1978, 2286) and in concert with the details described above in Scheme 1.

Another approach to the synthesis of compounds of formula (VIII) involves the conversion of ketones of formula (IV) to oximes such as (V) followed by treatment of the oximes with an aminating agent.

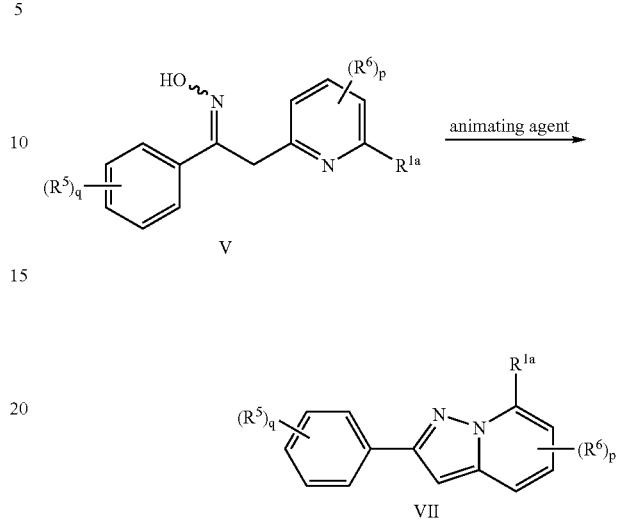

wherein all variables are as defined above in connection with Scheme 1. This reaction may be conducted using essentially the reaction conditions employed for the foregoing conversion of the ketone to the compounds of formula (VII).

Preparation of the compounds of formula (V) is described above.

Another alternative synthesis for the compounds of formula (VII) involves the decarboxylation of a compound of formula (XXIII).

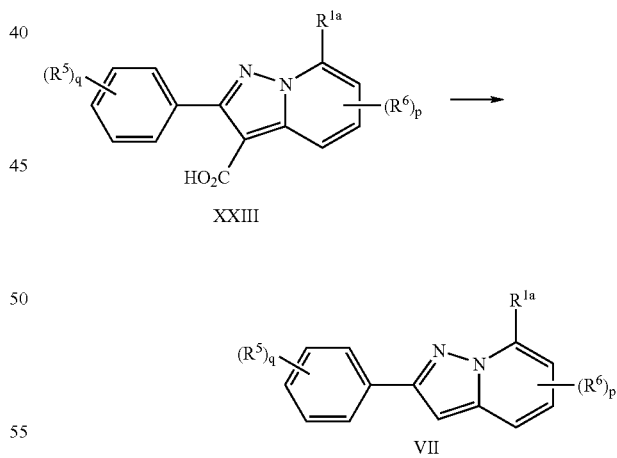

wherein all variables are as described above in connection with Scheme 1.

The decarboxylation may be carried out by any one of a variety of methods described in the literature for similar decarboxylations. For example: heating a solution of a compound of formula (XXIII) in an inert solvent, or conversion to a 'Barton ester' followed by treatment with a radical reductant, for example tributyltin hydride (Crich, D. *Aldrichimica Acta*, 1987, 20, 35).

Compounds of formula (XXIII) can be prepared by simple hydrolysis of lower alkyl esters of formula (XXIV).

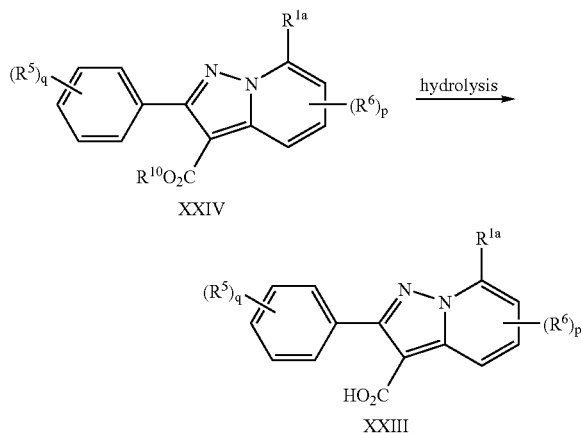

wherein all variables are as defined above in connection with Scheme 1.

The ester compounds formula (XXIV) can be conveniently hydrolyzed to their corresponding caboxylic acids (i.e., compounds of formula (XXIII) by standard hydrolysis conditions employed to effect similar hydrolysis reactions (Larock, Comprehensive Organic Transformations, 1989, 981). For example, treatment of a solution of a compound of formula (XXIV) in a lower alcohol, for example methanol, with sodium hydroxide followed by heating the mixture for an appropriate time gives the compound of formula (XXV).

Esters such as compounds of formula (XXIV) may be prepared by a [3+2] dipolar cycloaddition reaction between compounds of formula (XXV) and acetylene compounds of formula (XXVI). See, Hardy, C. R. *Adv. Het. Chem.* 1984, 36, 343.

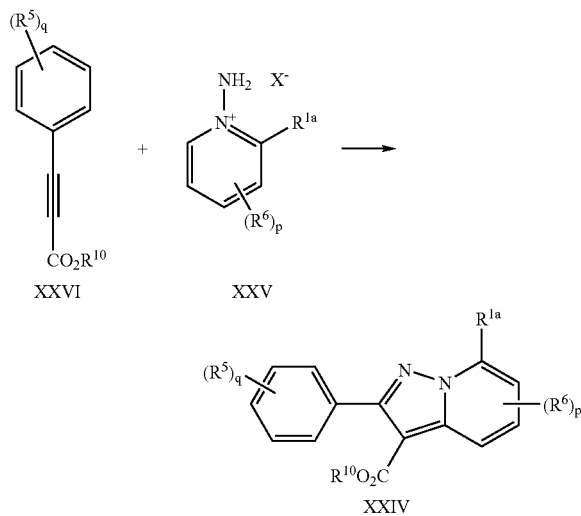

wherein $X^+$ is a halide ion and all other variables are as defined above in connection with Scheme 1.

Conveniently the reaction may be carried out by mixing the compound of formula (XXV) and the compound of formula (XXVI) in equal molar amounts, in an inert solvent, and adding a suitable base. The mixture is then stirred at between 20–100° C. until the reaction is judged complete by the disappearance of one of the reactants. Preferred solvents include but are not limited to acetonitrile, dioxane, tetrahydrofuran, dimethylformamide and the like. Preferred bases include non-nucleophilic amines such as 1,8-diazabicyclo[5.4.0]undec-7-ene, 1,5-diazabicyclo[4.3.0]non-5-ene, 1,4-diazabicyclo[2.2.2]octane and the like.

Compounds of formula (XXV) are aminated pyridine derivatives and are either commercially available or can be conveniently prepared by reacting a suitable pyridine with an aminating reagent such as O-(mesitylsulfonyl)hydroxylamine, O-(diphenylphosphinyl)hydroxylamine and the like.

Compounds of formula (XXVI) are either known compounds or compounds which can be prepared using methods described in the literature. Preferred methods include the reaction of acetylenes such as those of formula (XXVII) with a suitable base to generate an acetylenic anion and subsequent reaction of the anion with an alkoxycarbonylating agent.

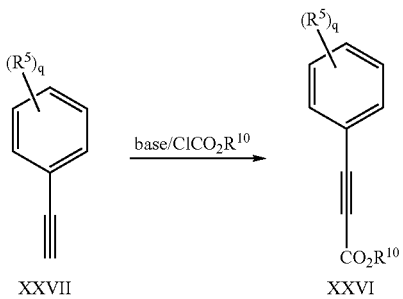

Preferably the compound of formula (XXVII) is dissolved in an inert solvent, such as tetrahydrofuran, and the solution is cooled to about −75° C. A non-nuclephilic base is added in sufficient quantity to effect deprotonation of the compound of formula (XXVII). The preferred bases include, but are not limited to, n-butyllithium, lithium diisopropylamide, sodium bis(trimethylsilyl)amide and the like. To the reaction mixture is then added a reagent capable of reacting with an anion to introduce an alkoxycarbonyl group. Preferred reagents include, but are not limited to, methyl chloroformate, ethyl chloroformate, benzyl chloroformate and the like.

Compounds of formula (XXVII) are either known compounds or can be prepared by literature methods such as those described in, for example, Negishi, E *J. Org. Chem.* 1997, 62, 8957.

In a further embodiment of the present invention, compounds of formula (XI) wherein Y is N; $R^2$ is selected from the group consisting of H, alkyl, cycloalkyl, alkenyl, cycloalkenyl, $—NR^7R^8$, Ay, $—NHR^{10}Ay$, $—OR^7$, $—OAy$, $—S(O)_nR^9$, $—S(O)_nAy$, $—R^{10}NR^7R^8$, $—R^{10}NR^7Ay$, Het, $—NHHet$, $—NHR^{10}Het$, $—OHet$, and $—OR^{10}Het$; $R^3$ is selected from the group consisting of H, alkyl, cycloalkyl, alkenyl, Ay, $—R^{10}OR^7$, $—R^{10}OAy$, $—NR^7R^8$ where $R^7$ and $R^8$ are not H, $—NR^7Ay$ where $R^7$ is not H, $—R^{10}NR^7R^8$, $—R^{10}NR^7Ay$, $—C(O)R^7$, $—C(O)Ay$, $—CO_2R^7$, $—CO_2Ay$, $—SO^2NHR^9$ and Het; and $R^4$ is H, and pharmacuetically acceptable salts, solvates and physiologically functional derivatives thereof, may be conveniently prepared by the process outlined in Scheme 2 below.

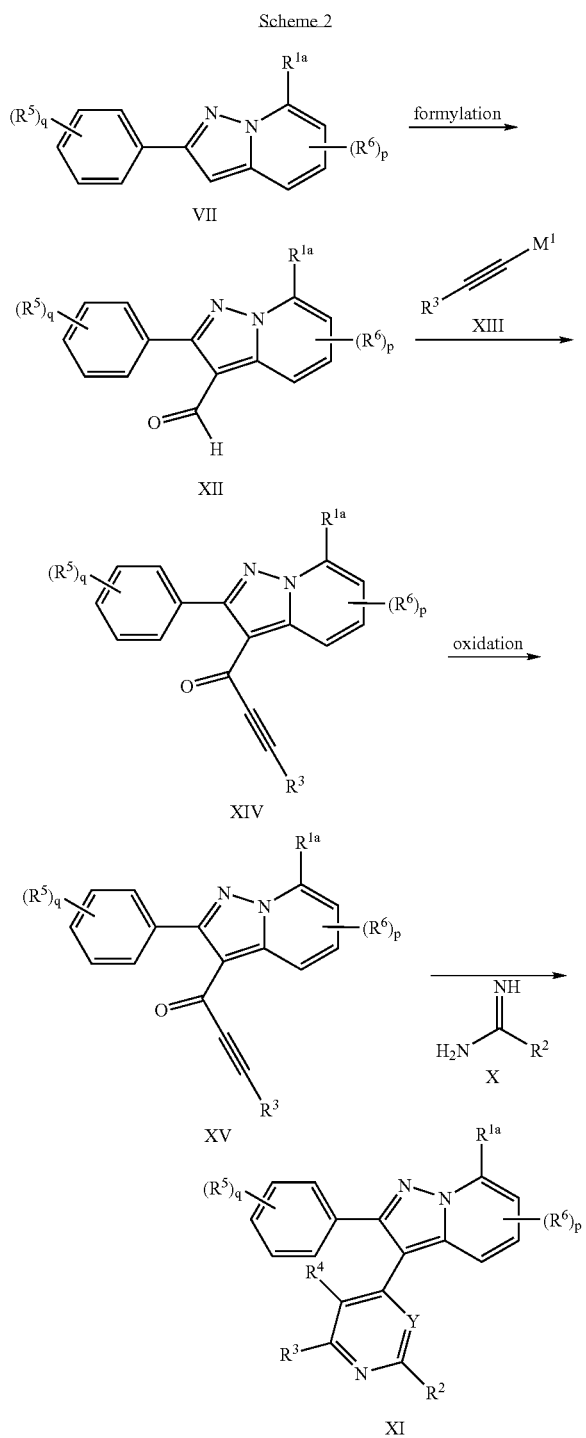

Scheme 2 wherein:
$R^{1a}$ is selected from the group consisting of H, halo, alkyl, alkenyl, alkynyl, cycloalkyl, cycloalkenyl, —$R^{10}$cycloalkyl, —$R^{10}$Ay, —$R^{10}$Het, —$OR^7$, —OAy, —OHet, —$OR^{10}$Ay, —$OR^{10}$Het, —$OR^9$, —$R^{10}NR^7R^8$, —$R^{10}NR^7$Ay, —$R^{10}C(O)R^9$, —$C(O)R^9$, —C(O)Ay, —C(O)Het, —$R^{10}OC(O)R^9$, —$R^{10}OC(O)$Ay, —$R^{10}OC(O)$Het, —$CO_2R^9$, —$R^{10}CO_2R^9$, —C(O)$NR^7R^8$, —C(O)$NR^7$Ay, —C(O)$NHR^{10}$Ay, —$R^{10}C(O)NR^9R^{11}$, —C(S)$NR^9R^{11}$, —$R^{10}C(S)NR^9R^{11}$, —$R^{10}$NHC(NH)$NR^9R^{11}$, —C(NH)$NR^7R^8$, —C(NH)$NR^7$Ay, —$R^{10}$C(NH)$NR^9R^{11}$, —$S(O)_2NR^7R^8$, —$S(O)_2NR^7$Ay, —$R^{10}SO_2NHCOR^9$, —$R^{10}SO_2NR^9R^{11}$, —$R^{10}SO_2R^9$, —$R^{10}OS(O)_nR^9$, —$R^{10}NHSO_2R^9$, —$R^{10}NHCOR^9$, —$S(O)_nR^9$, —$S(O)_n$Ay, —$S(O)_n$Het, cyano, azido and nitro;

each $R^7$ and $R^8$ are the same or different and are independently selected from the group consisting of H, alkyl, cycloalkyl, alkenyl, cycloalkenyl, —$R^{10}$cycloalkyl, —$OR^9$, —$R^{10}OR^9$, —$R^{10}NR^9R^{11}$, —$R^{10}C(O)R^9$, —$C(O)R^9$, —$CO_2R^9$, —$R^{10}CO_2R^9$, —C(O)$NR^9R^{11}$, —$R^{10}C(O)NR^9R^{11}$, —C(S)$NR^9R^{11}$, —$R^{10}C(S)NR^9R^{11}$, —$R^{10}$NHC(NH)$NR^9R^{11}$, —$R^{10}$C(NH)$NR^9R^{11}$, —C(NH)$NR^9R^{11}$, —$SO_2NR^9R^{11}$, —$R^{10}SO_2NR^9R^{11}$, —$R^{10}NHSO_2R^9$, —$SO_2R^{10}$, —$R^{10}SO_2R^{10}$, —$R^{10}NHCOR^9$ and —$R^{10}SO_2NHCOR^9$;

each $R^9$ and $R^{11}$ are the same or different and are independently selected from the group consisting of H, alkyl, cycloalkyl, —$R^{10}$cycloalkyl, —$R^{10}OH$, —$R^{10}(OR^{10})_w$ where w is 1–10, and —$R^{10}NR^{10}R^{10}$;

each $R^{10}$ is the same or different and is independently selected from the group consisting of alkyl, cycloalkyl, alkenyl, cycloalkenyl and alkynyl;

Ay is an aryl;

Het is a 5- or 6-membered heterocyclic or heteroaryl group;

n is 1 or 2;

$R^2$ is selected from the group consisting of H, alkyl, cycloalkyl, alkenyl, cycloalkenyl, —$NR^7R^8$, Ay, —$NHR^{10}$Ay, —$OR^7$, —OAy, —$S(O)_nR^9$, —$S(O)_n$Ay, —$R^{10}NR^7R^8$, —$R^{10}NR^7$Ay, Het, —NHHet, —$NHR^{10}$Het, —OHet and —$OR^{10}$Het;

Y is N;

$R^3$ is selected from the group consisting of H, alkyl, cycloalkyl, alkenyl, Ay, —$R^{10}OR^7$, —$R^{10}$OAy, —$NR^7R^8$ where $R^7$ and $R^8$ are not H, —$NR^7$Ay where $R^7$ is not H, —$R^{10}NR^7R^8$, —$R^{10}NR^7$Ay, —$C(O)R^7$, $C(O)$Ay, —$CO_2R^7$, —$CO_2$Ay, —$SO_2NHR^9$ and Het;

$R^4$ is H;

q is 0, 1, 2, 3, 4 or 5;

each $R^5$ is the same or different and is independently selected from the group consisting of halo, alkyl, alkenyl, alkynyl, cycloalkyl, cycloalkenyl, —$R^{10}$cycloalkyl, Ay, —$NHR^{10}$Ay, —$NR^7$Ay, Het, —NHHet, —$NHR^{10}$Het, —$OR^7$, —OAy, —OHet, —$R^{10}OR^9$, —$NR^7R^8$, —$R^{10}NR^7R^8$, —$R^{10}NR^7$Ay, —$R^{10}C(O)R^9$, —$C(O)R^9$, —C(O)Ay, —C(O)Het, —$CO_2R^9$, —$R^{10}CO_2R^9$, —C(O)$NR^7R^8$, —C(O)$NR^7$Ay, —C(O)$NHR^{10}$Het, —$R^{10}C(O)NR^9R^{11}$, —C(S)$NR^9R^{11}$, —$R^{10}C(S)NR^9R^{11}$, —$R^{10}$NHC(NH)$NR^9R^{11}$, —C(NH)$NR^7R^8$, —C(NH)$NR^7$Ay, —$R^{10}$C(NH)$NR^9R^{11}$, —$S(O)_2NR^7R^8$, —$S(O)_2NR^7$Ay, —$R^{10}SO_2NHCOR^9$, —$R^{10}SO_2NR^9R^{11}$, —$R^{10}SO_2R^9$, —$S(O)_nR^9$, cyano, azido and nitro; or two adjacent $R^5$ groups together with the atoms to which they are bonded form a $C_{5-6}$ cycloalkyl or aryl;

p is 0, 1, 2 or 3; each $R^6$ is the same or different and is independently selected from the group consisting of halo, alkyl, alkenyl, alkynyl, cycloalkyl, cycloalkenyl, —$R^{10}$cycloalkyl, Ay, Het, —$R^{10}$Ay, —$R^{10}$Het, —$OR^7$, —OAy, —OHet, —$R^{10}OR^9$, —$OR^{10}$Ay, —$OR^{10}$Het, —$R^{10}NR^7R^8$, —$R^{10}NR^7$Ay, —$R^{10}C(O)R^9$, —$C(O)R^9$, —C(O)Ay, —C(O)Het, —$CO_2R^9$, —$R^{10}CO_2R^9$, —C(O)$NR^7R^8$, —C(O)$NR^7$Ay, —C(O)$NHR^{10}$Het, —$R^{10}C(O)NR^9R^{11}$, —C(S)$NR^9R^{11}$, —$R^{10}C(S)NR^9R^{11}$, —$R^{10}$NHC(NH)$NR^9R^{11}$, —C(NH)$NR^7R^8$, —C(NH)$NR^7$Ay, —$R^{10}$C(NH)$NR^9R^{11}$, —$S(O)_2NR^7R^8$, —$S(O)_2NR^7$Ay, —R[10]SO$_2$NHCOR[9], —R[10]SO$_2$NR[9]R[11], —R[10]SO$_2$R[9], —S(O)$_n$R[9], cyano, azido and nitro; or two adjacent R[6] groups together with the atoms to which they are bonded form a C[5-6] cycloalkyl or a 5- or 6-membered heterocyclic group containing 1 or 2 heteroatoms; and M[1] is Li, Mg-halide or cerium-halide, wherein halide is halo.

Generally, the process for preparing compounds of formula (I) wherein Y is N; R[2] is selected from the group consisting of H, alkyl, cycloalkyl, alkenyl, cycloalkenyl, —NR[7]R[8], Ay, —NHR[10]Ay, —OR[7], —OAy, —S(O)$_n$R[9], —S(O)$_n$Ay, —R[10]NR[7]R[8], —R[10]NR[7]Ay, Het, —NHHet, —NHR[10]Het, —OHet, and —OR[10]Het; R[3] is selected from the group consisting of H, alkyl, cycloalkyl, alkenyl, Ay, —R[10]OR[7], —R[10]OAy, —NR[7]R[8] where R[7] and R[8] are not H, —NR[7]Ay where R[7] is not H, —R[10]NR[7]R[8], —R[10]NR[7]Ay, —C(O)R[7], —C(O)Ay, —CO$_2$R[7], —CO$_2$Ay, —SO$_2$NHR[9] and Het; and R[4] is H, (all other variables having been defined above in connection with Scheme 2), comprises the following steps:

(a) formylating the compound of formula (VII) to prepare a compound of formula (XII);
(b) reacting the compound of formula (XII) with a compound of formula (XIII) to prepare a compound of formula (XIV);
(c) oxidizing the compound of formula (XI) to prepare a compound of formula (XV);
(d) reacting the compound of formula (XV) with a compound of formula (X) to prepare the compound of formula (XI); and
(e) when R[1a] is H or halo, converting the compound of formula (XI) to a compound of formula (I).

When the compounds of formula (XI) are defined where R[1a] is H or halo, the process for preparing compounds of formula (I) comprises the additional step (e) of converting the compounds of formula (XI) to compounds of formula (I). Such conversion can be achieved using the methods described below or other suitable methods conventional in the art for this type of transformation.

More specifically, compounds of formula (I) wherein Y is N; R[2] is selected from the group consisting of H, alkyl, cycloalkyl, alkenyl, cycloalkenyl, —NR[7]R[6], Ay, —NHR[10]Ay, —OR[7], —OAy, —S(O)$_n$R[9], —S(O)$_n$Ay, —R[10]NR[7]R[8], —R[10]NR[7]Ay, Het, —NHHet, —NHR[10]Het, —OHet, and —OR[10]Het; R[3] is selected from the group consisting of H, alkyl, cycloalkyl, alkenyl, Ay, —R[10]R[7], —R[10]OAy, —NR[7]R[8] where R[7] and R[8] are not H, —NR[7]Ay where R[7] is not H, —R[10]NR[7]R[8], —R[10]NR[7]Ay, —C(O)R[7], —C(O)Ay, —CO$_2$R[7], —CO$_2$Ay, —SO$_2$NHR[9] and Het; and R[4] is H, may be prepared by reacting a compound of formula (XV) with a compound of formula (X) to prepare a compound of formula (XI), and when R[1a] is H or halo, converting to a compound of formula (I).

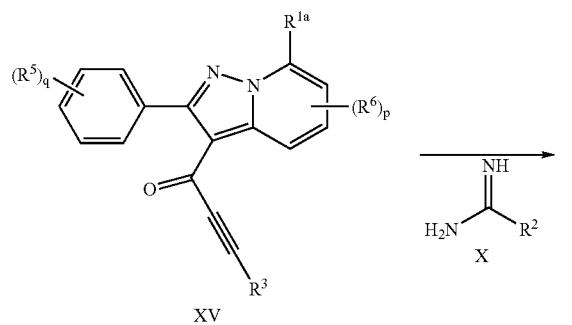

XV

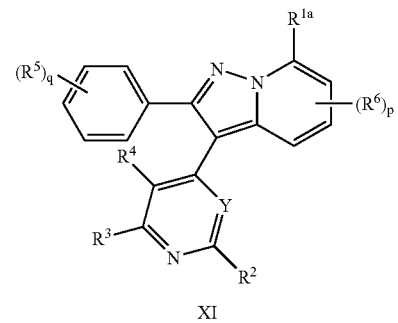

XI wherein all variables are as defined above in connection with Scheme 2.

This method can be readily carried out by mixing a compound of formula (XV) with a compound of formula (X) in a suitable solvent, optionally in the presence of a base. The reaction may be heated to 50–150° C. or performed at ambient temperature. Typical solvents include but are not limited to lower alcohols such as methanol, ethanol, isopropanol and the like. Typical bases include for example, sodium alkoxide, potassium carbonate, or an amine base such as triethylamine. In another embodiment, the solvent is N,N-dimethylformamide and the base is potassium carbonate, or an amine base such as triethylamine.

Compounds of formula (XV) may be conveniently prepared by oxidation of a compound of formula (XI).

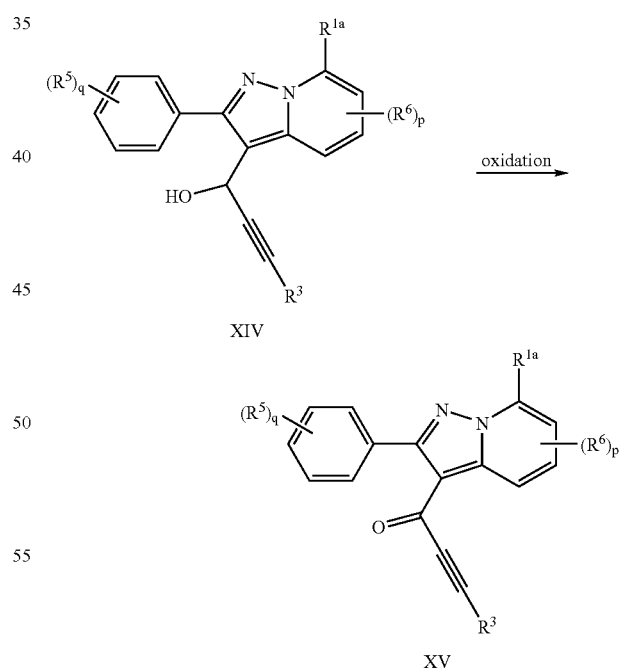

wherein all variables are as defined above in connection with Scheme 2. Preferred oxidizing agents include but are not limited to, manganese dioxide, and the like, in an inert solvent. Suitable inert solvents include but are not limited to, dichloromethane, chloroform, N,N-dimethylformamide, ether, and the like.

Compounds of formula (XI) may be conveniently prepared by reacting a compound of formula (XII) with a compound of formula (XIII).

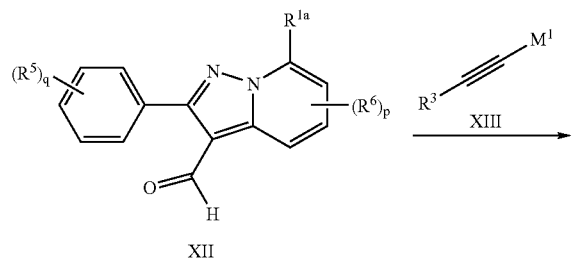

wherein all variables are as defined above in connection with Scheme 2.

Preferred metals ($M^1$) in the compounds of formula (XIII) include but are not limited to, lithium, magnesium(II) halides, cerium(III) halides, and the like. Compounds of formula (XIII) may be purchased from commercial sources or prepared by methods known to one skilled in the art.

Compounds of formula (XII) may be conveniently prepared from compounds of formula (VII) by a formylation procedure.

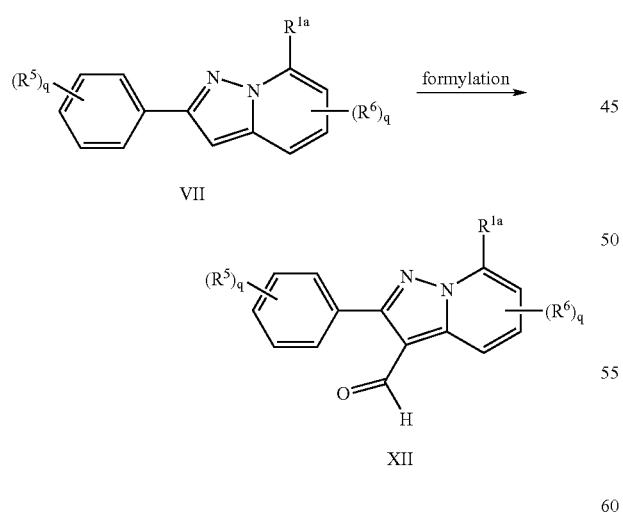

wherein all variables are as defined above in connection with Scheme 2.

Typically the formylation is carried out via the Vilsmeier-Haack reaction. The Vilsmeier-Haack reagents can be purchased from commercial sources or prepared in situ. Preferable conditions include, but are not limited to treating compounds of formula (VI) with a premixed solution of phosphorous oxychloride in N,N-dimethylformamide optionally with heating the reaction to 50–150° C.

The compounds of formula (VII) are prepared according to the process described above in connection with Scheme 1.

Further compounds of formula (XI) wherein Y is N and $R^2$ is selected from the group consisting of H, alkyl, cycloalkyl, alkenyl, cycloalkenyl, —$NR^7R^8$, Ay, —$NHR^{10}$Ay, —$OR^7$, —OAy, —$S(O)_nR^9$, —$S(O)_n$Ay, —$R^{10}NR^7R^8$, —$R^{10}NR^7$Ay, Het, —NHHet, —$NHR^{10}$Het, —OHet and —$OR^{10}$Het, may be conveniently prepared by the process outlined in Scheme 3 below.

Scheme 3

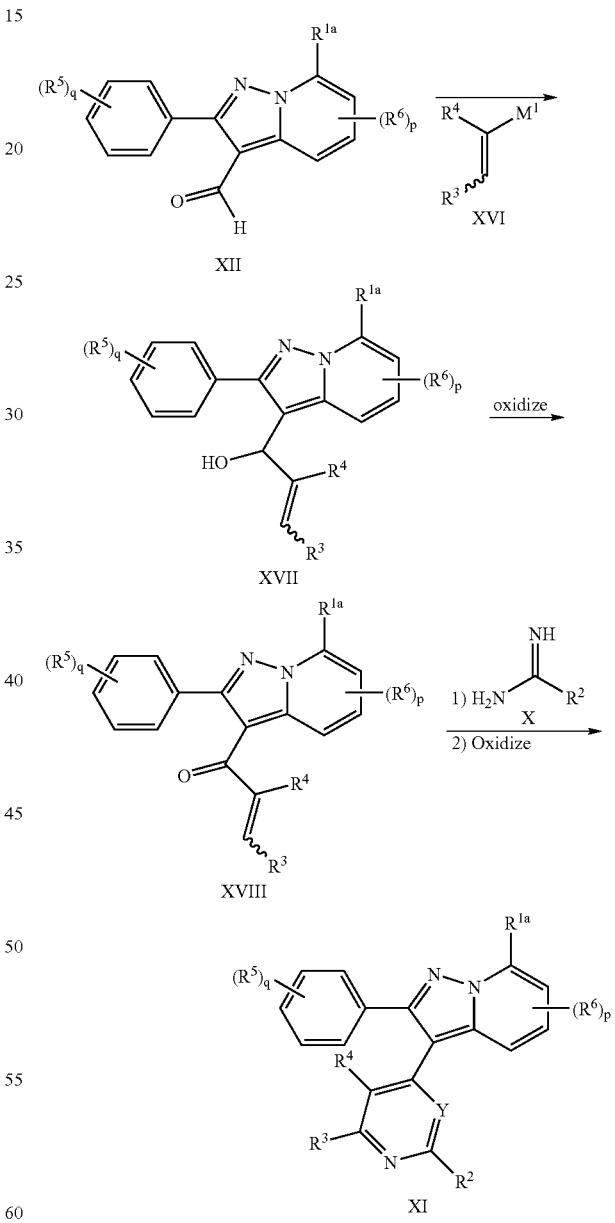

wherein:
$R^{1a}$ is selected from the group consisting of H, halo, alkyl, alkenyl, alkynyl, cycloalkyl, cycloalkenyl, —$R^{10}$cycloalkyl, —$R^{10}$Ay, —$R^{10}$Het, —$OR^7$, —OAy, —OHet, —$OR^{10}$Ay, —$OR^{10}$Het, —$R^{10}R^9$, —$R^{10}NR^7R^8$, —R$^{10}$NR$^7$Ay, —R$^{10}$C(O)R$^9$, —C(O)R$^9$, —C(O)Ay, —C(O)Het, —R$^{10}$OC(O)R$^9$, —R$^{10}$C(O)Ay, —R$^{10}$OC(O)Het, —CO$_2$R$^9$, —R$^{10}$CO$_2$R$^9$, —C(O)NR$^7$R$^8$, —C(O)NR$^7$Ay, —C(O)NHR$^{10}$Ay, —R$^{10}$C(O)NR$^9$R$^{11}$, —C(S)NR$^9$R$^{11}$, —R$^{10}$C(S)NR$^9$R$^{11}$, —R$^{10}$NHC(NH)NR$^9$R$^{11}$, —C(NH)NR$^7$R$^8$, —C(NH)NR$^7$Ay, —R$^{10}$C(NH)NR$^9$R$^{11}$, —S(O)$_2$NR$^7$R$^8$, —S(O)$_2$NR$^7$Ay, —R$^{10}$SO$_2$NHCOR$^9$, —R$^{10}$SO$_2$NR$^9$R$^{11}$, —R$^{10}$SO$_2$R$^9$, —R$^{10}$OS(O)$_n$R$^9$, —R$^{10}$NHSO$_2$R$^9$, —R$^{10}$NHCOR$^9$, —S(O)$_n$R$^9$, —S(O)$_n$Ay, —S(O)$_n$Het, cyano, azido and nitro;

each R$^7$ and R$^8$ are the same or different and are independently selected from the group consisting of H, alkyl, cycloalkyl, alkenyl, cycloalkenyl, —R$^{10}$cycloalkyl, —OR$^9$, —R$^{10}$OR$^9$, —R$^{10}$NR$^9$R$^{11}$, —R$^{10}$C(O)R$^9$, —C(O)R$^9$, —CO$_2$R$^9$, —R$^{10}$CO$_2$R$^9$, —C(O)NR$^9$R$^{11}$, —R$^{10}$C(O)NR$^9$R$^{11}$, —C(S)NR$^9$R$^{11}$, —R$^{10}$C(S)NR$^9$R$^{11}$, —R$^{10}$NHC(NH)NR$^9$R$^{11}$, —R$^{10}$C(NH)NR$^9$R$^{11}$, —C(NH)NR$^9$R$^{11}$, —SO$_2$NR$^9$R$^{11}$, —R$^{10}$SO$_2$NR$^9$R$^{11}$, —R$^{10}$NHSO$_2$R$^9$, —SO$_2$R$^{10}$, —R$^{10}$SO$_2$R$^{10}$, —R$^{10}$NHCOR$^9$ and —R$^{10}$SO$_2$NHCOR$^9$;

each R$^9$ and R$^{11}$ are the same or different and are independently selected from the group consisting of H, alkyl, cycloalkyl, —R$^{10}$cycloalkyl, —R$^{10}$OH, —R$^{10}$(OR$^{10}$)w where w is 1–10, and —R$^{10}$NR$^{10}$R$^{10}$;

each R$^{10}$ is the same or different and is independently selected from the group consisting of alkyl, cycloalkyl, alkenyl, cycloalkenyl and alkynyl;

Ay is an aryl;

Het is a 5- or 6-membered heterocyclic or heteroaryl group;

n is 0, 1 or 2;

R$^2$ is selected from the group consisting of H, alkyl, cycloalkyl, alkenyl, cycloalkenyl, —NR$^7$R$^8$, Ay, —NHR$^{10}$Ay, —OR$^7$, —OAy, —S(O)$_n$R$^9$, —S(O)$_n$Ay, —R$^{10}$NR$^7$R$^8$, —R$^{10}$NR$^7$Ay, Het, —NHHet, —NHR$^{10}$Het, —OHet and —OR$^{10}$Het;

Y is N;

R$^3$ and R$^4$ are the same or different and are each independently selected from the group consisting of H, halo, alkyl, cycloalkyl, alkenyl, Ay, —OR$^7$, —OAy, —R$^{10}$OR$^7$, —R$^{10}$OAy, —NR$^7$R$^8$, —NR$^7$Ay, —R$^{10}$NR$^7$R$^8$, —R$^{10}$NR$^7$Ay, —C(O)R$^7$, C(O)Ay, —CO$_2$R$^7$, —CO$_2$AY, —SO$_2$NHR$^9$, Het, —NHHet and —NHR$^{10}$Het;

q is 0, 1, 2, 3, 4 or 5;

each R$^5$ is the same or different and is independently selected from the group consisting of halo, alkyl, alkenyl, alkynyl, cycloalkyl, cycloalkenyl, —R$^{10}$cycloalkyl, Ay, —NHR$^{10}$Ay, —NR$^7$Ay, Het, —NHHet, —NHR$^{10}$Het, —OR$^7$, —OAy, —OHet, —R$^{10}$OR$^9$, —NR$^7$R$^8$, —R$^{10}$NR$^7$R$^8$, —R$^{10}$NR$^7$Ay, —R$^{10}$C(O)R$^9$, —C(O)R$^9$, —C(O)Ay, —C(O)Het, —CO$_2$R$^9$, —R$^{10}$CO$_2$R$^9$, —C(O)NR$^7$R$^8$, —C(O)NR$^7$Ay, —C(O)NHR$^{10}$Het, —R$^{10}$C(O)NR$^9$R$^{11}$, —C(S)NR$^9$R$^{11}$, —R$^{10}$C(S)NR$^9$R$^{11}$, —R$^{10}$NHC(NH)NR$^9$R$^{11}$, —C(NH)NR$^7$R$^8$, —C(NH)NR$^7$Ay, —R$^{10}$C(NH)NR$^9$R$^{11}$, —S(O)$_2$NR$^7$R$_8$, —S(O)$_2$NR$^7$Ay, —R$^{10}$SO$_2$NHCOR$^9$, —R$^{10}$SO$_2$NR$^9$R$^{11}$, —R$^{10}$SO$_2$R$^9$, —S(O)$_n$R$^9$, cyano, azido and nitro; or two adjacent R$^5$ groups together with the atoms to which they are bonded form a C$_{5-6}$ cycloalkyl or aryl;

p is 0, 1, 2 or 3;

each R$^6$ is the same or different and is independently selected from the group consisting of halo, alkyl, alkenyl, alkynyl, cycloalkyl, cycloalkenyl, —R$^{10}$cycloalkyl, Ay, Het, —R$^{10}$Ay, —R$^{10}$Het, —OR$^7$, —OAy, —OHet, —R$^{10}$OR$^9$, —OR$^{10}$Ay, —OR$^{10}$Het, —NR$^7$R$^8$, —NR$^7$Ay, —R$^{10}$C(O)R$^9$, —C(O)R$^9$, —C(O)Ay, —C(O)Het, —CO$_2$R$^9$, —R$^{10}$CO$_2$R$^9$, —C(O)NR$^7$R$^8$, —C(O)NR$^7$Ay, —C(O)NHR$^{10}$Het, —R$^{10}$C(O)NR$^9$R$^{11}$, —C(S)NR$^9$R$^{11}$, —R$^{10}$C(S)NR$^9$R$^{11}$, —R$^{10}$NHC(NH)NR$^9$R$^{11}$, —C(NH)NR$^7$R$^8$, —C(NH)NR$^7$Ay, —R$^{10}$C(NH)NR$^9$R$^{11}$, —S(O)$_2$NR$^7$R$^8$, —S(O)$_2$NR$^7$Ay, —R$^{10}$SO$_2$NHCOR$^9$, —R$^{10}$SO$_2$NR$^9$R$^{11}$, —R$^{10}$SO$_2$R$^9$, —S(O)$_n$R$^9$, cyano, azido and nitro; or two adjacent R$^6$ groups together with the atoms to which they are bonded form a C$_{5-6}$ cycloalkyl or a 5- or 6-membered heterocyclic group containing 1 or 2 heteroatoms; and M$^1$ is Li, Mg-halide or cerium-halide, wherein halide is halo.

Generally, the process for preparing compounds of formula (I) wherein Y is N and R$^2$ is selected from the group consisting of H, alkyl, cycloalkyl, alkenyl, cycloalkenyl, —NR$^7$R$^8$, Ay, —NHR$^{10}$Ay, —OR$^7$, —OAy, —S(O)$_n$R$^9$, —S(O)Ay, —R$^{10}$NR$^7$R$^9$, —R$^{10}$NR$^7$Ay, Het, —NHHet, —NHR$^{10}$Het, —OHet, and —OR$^{10}$Het, (all formulas and all other variables having been defined above in connection with Scheme 3), comprises the following steps:

(a) formylating the compound of formula (VII) to prepare a compound of formula (XI);

(b) reacting the compound of formula (XII) with a compound of formula (XVI) to prepare a compound of formula (XVII);

(c) oxidizing the compound of formula (XVIII) to prepare a compound of formula (d) reacting the compound of formula (XVIII) with a compound of formula (X) followed by oxidative aromatization to prepare a compound of formula (XI); and (e) when R$^{1a}$ is H or halo, converting the compound of formula (XI) to a compound of formula (I).

When the compounds of formula (XI) are defined where R$^{1a}$ is H or halo, the process for preparing compounds of formula (I) comprises the additional step (e) of converting the compounds of formula (XI) to compounds of formula (I). Such conversion can be achieved using the methods described below or other suitable methods conventional in the art for this type of transformation.

More specifically, compounds of formula (I) wherein Y is N and R$^2$ is selected from the group consisting of H, alkyl, cycloalkyl, alkenyl, cycloalkenyl, —NR$^7$R$^8$, Ay, —NHR$^{10}$Ay, —OR$^7$, —OAy, —S(O)$_n$R$^9$, —S(O)$_n$Ay, —R$^{10}$NR$^7$R$^8$, —R$^{10}$NR$^7$Ay, Het, —NHHet, —NHR$^{10}$Het, —OHet, and —OR$^{10}$Het, can be prepared by reacting a compound of formula (XVIII) with a compound of formula (X) followed by oxidative aromatization to prepare a compound of formula (XI) and when R$^{1a}$ is H or halo, converting to a compound of formula (I).

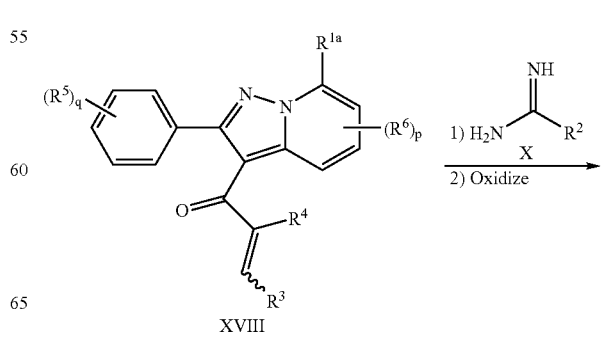

XVIII

-continued

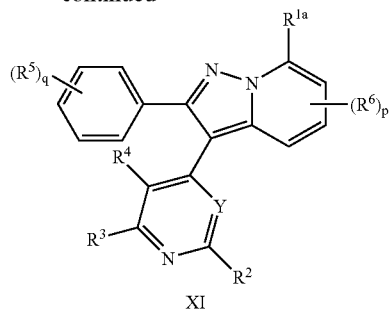

XI wherein all variables are as defined above in connection with Scheme 3.

The condensation is conveniently carried out by treating the compound of formula (XVIII) with a compound of formula (X) in an inert solvent, optionally in the presence of a base. The reaction may be heated to 50–15° C. or performed at ambient temperature. Suitable inert solvents include lower alcohols such as, for example, methanol, ethanol, isopropanol and the like. The base is typically sodium alkoxide, potassium carbonate, or an amine base such as triethylamine. In another embodiment, the solvent is N,N-dimethylformamide and the base is potassium carbonate, or an amine base such as triethylamine. The reaction produces a dihydropyrimidine intermediate.

Preferably in the same reaction vessel, the dihydropyrimidine intermediate may be oxidized to a compound of formula (XI) by the addition of an oxidizing agent. The reaction may be heated to 50–150° C. or performed at ambient temperature. Preferably, the oxidizing agent is oxygen ($O_2$), palladium on carbon, 2,3-dichloro-5,6 dicyano-1,4-benzoquinone, or the like.

Compounds of formula (XVIII) may be conveniently prepared by oxidation of compounds of formula (XVII).

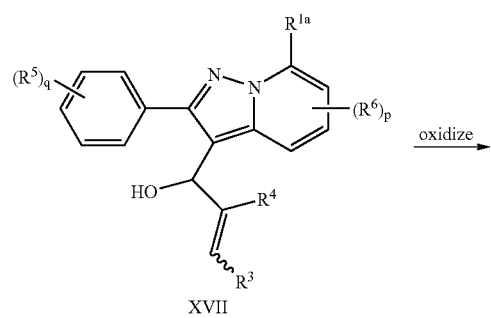

XVII

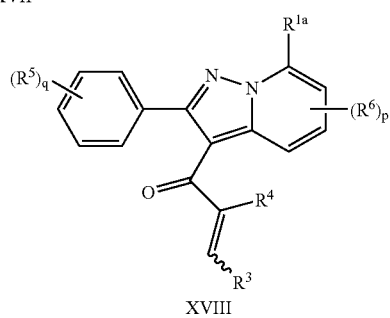

XVIII wherein all variables are as defined above in connection with Scheme 3.

Preferred oxidizing agents for the oxidation of compounds of formula (XIII) include but are not limited to manganese dioxide, and the like. The oxidation is typically carried out in an inert solvent such as for example, dichloromethane, chloroform, N,N-dimethylformamide, ether, and the like.

Compounds of formula (XVII) may be conveniently prepared by reacting a compound of formula (XII) with a compound of formula (XVI).

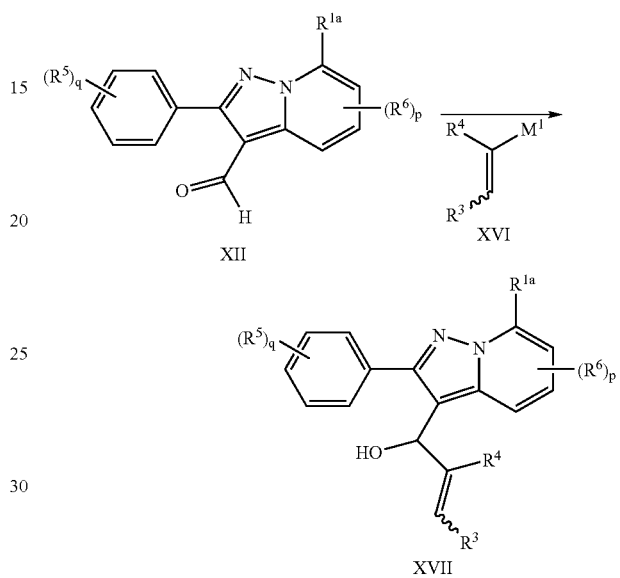

wherein $M^1$ is a metal such as for example, lithium, magnesium(II) halides, cerium(III) halides, and the like and all other variables are as defined above in connection with Scheme 3. Compounds of formula (XVI) may be purchased from commercial sources or prepared by methods known to one skilled in the art. The compounds of formula (XII) may be prepared using the methods described above in connection with Scheme 2.

Compounds of formula (XI) wherein Y is CH or N, and pharmacuetically acceptable salts, solvates and physiologically functional derivatives thereof, may be conveniently prepared by the process outlined in Scheme 4 below.

Scheme 4

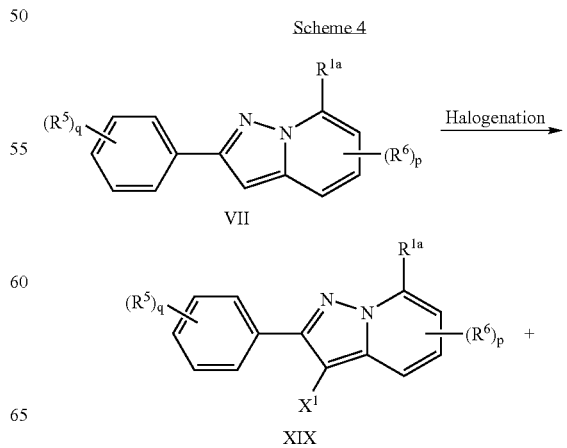

-continued

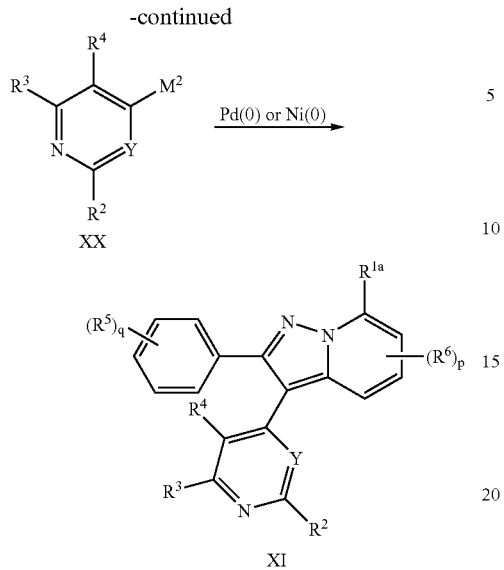

$$\xrightarrow{Pd(0) \text{ or } Ni(0)}$$

XX

XI wherein:

$X^1$ is halo, preferably bromo or iodo;

$R^{1a}$ is selected from the group consisting of H, halo, alkyl, alkenyl, alkynyl, cycloalkyl, cycloalkenyl, —$R^{10}$cycloalkyl, —$R^{10}$Ay, —$R^{10}$Het, —$OR^7$, —OAy, —OHet, —$OR^{10}$Ay, —$OR^{10}$Het, —$R^{10}R^9$, —$R^{10}NR^7R^8$, —$R^{10}NR^7$Ay, —$R^{10}C(O)R^9$, —$C(O)R^9$, —$C(O)$Ay, —$C(O)$Het, —$R^{10}OC(O)R^9$, —$R^{10}OC(O)$Ay, —$R^{10}OC(O)$Het, —$CO_2R^9$, —$R^{10}CO_2R^9$, —$C(O)NR^7R^8$, —$C(O)NR^7$Ay, —$C(O)NHR^{10}$Ay, —$R^{10}C(O)NR^9R^{11}$, —$C(S)NR^9R^{11}$, —$R^{10}C(S)NR^9R^{11}$, —$R^{10}NHC(NH)NR^9R^{11}$, —$C(NH)NR^7R^8$, —$C(NH)NR^7$Ay, —$R^{10}C(NH)NR^9R^{11}$, —$S(O)_2NR^7R^8$, —$S(O)_2NR^7$Ay, —$R^{10}SO_2NHCOR^9$, —$R^{10}SO_2NR^9R^{11}$, —$R^{10}SO_2R^9$, —$R^{10}S(O)_nR^9$, —$R^{10}NHSO_2R^9$, —$R^{10}NHCOR^9$, —$S(O)_nR^9$, —$S(O)_n$Ay, —$S(O)_n$Het, cyano, azido and nitro;

each $R^7$ and $R^8$ are the same or different and are independently selected from the group consisting of H, alkyl, cycloalkyl, alkenyl, cycloalkenyl, —$R^{10}$cycloalkyl, —$OR^9$; —$R^{10}R^9$, —$R^{10}NR^9R^{11}$, —$R^{10}C(O)R^9$, —$C(O)R^9$, —$CO_2R^9$, —$R^{10}CO_2R^9$, —$C(O)NR^9R^{11}$, —$R^{10}C(O)NR^9R^{11}$, —$C(S)NR^9R^{11}$, —$R^{10}C(S)NR^9R^{11}$, —$R^{10}NHC(NH)NR^9R^{11}$, —$R^{10}C(NH)NR^9R^{11}$, —$C(NH)NR^9R^{11}$, —$SO_2NR^9R^{11}$, —$R^{10}SO_2NR^9R^{11}$, —$R^{10}NHSO_2R^9$, —$SO_2R^{10}$, —$R^{10}SO_2R^{10}$, —$R^{10}NHCOR^9$ and —$R^{10}SO_2NHCOR^9$;

each $R^9$ and $R^{11}$ are the same or different and are independently selected from the group consisting of H, alkyl, cycloalkyl, —$R^{10}$cycloalkyl, —$R^{10}$OH, —$R^{10}$(OR^{10})w where w is 1–10, and —$R^{10}NR^{10}R^{10}$;

each $R^{10}$ is the same or different and is independently selected from the group consisting of alkyl, cycloalkyl, alkenyl, cycloalkenyl and alkynyl;

Ay is an aryl;

Het is a 5- or 6-membered heterocyclic or heteroaryl group;

n is 0, 1 or 2;

$R^2$ is selected from the group consisting of H, halo, alkyl, cycloalkyl, alkenyl, cycloalkenyl, —$NR^7R^8$, Ay, —$NHR^{10}$Ay, —$OR^7$, —OAy, —$S(O)_nR^9$, —$S(O)_n$Ay, —$R^{10}NR^7R^8$, —$R^{10}NR^7$Ay, Het, —NHHet, —$NHR^{10}$Het, —OHet and —$OR^{10}$Het;

Y is N or CH;

$R^3$ and $R^4$ are the same or different and are each independently selected from the group consisting of H, halo, alkyl, cycloalkyl, alkenyl, Ay, —$OR^7$, —OAy, —$R^{10}OR^7$, —$R^{10}$OAy, —$NR^7R^8$, —$NR^7$Ay, —$R^{10}NR^8$, —$R^{10}NR^7$Ay, —$C(O)R^7$, $C(O)$Ay, —$CO_2R^7$, —$CO_2$Ay, —$SO_2NHR^9$, Het, —NHHet and —$NHR^{10}$Het;

q is 0, 1, 2, 3, 4 or 5;

each $R^5$ is the same or different and is independently selected from the group consisting of halo, alkyl, alkenyl, alkynyl, cycloalkyl, cycloalkenyl, —$R^{10}$cycloalkyl, Ay, —$NHR^{10}$Ay, —$NR^7$Ay, Het, —NHHet, —$NHR^{10}$Het, —$OR^7$, —OAy, —OHet, —$R^{10}OR^9$, —$NR^7R^8$, —$R^{10}NR^7R^8$, —$R^{10}NR^7$Ay, —$R^{10}C(O)R^9$, —$C(O)R^9$, —$C(O)$Ay, —$C(O)$Het, —$CO_2R^9$, —$R^{10}CO_2R^9$, —$C(O)NR^7R^8$, —$C(O)NR^7$Ay, —$C(O)NHR^{10}$Het, —$R^{10}C(O)NR^9R^{11}$, —$C(S)NR^9R^{11}$, —$R^{10}C(S)NR^9R^{11}$, —$R^{10}NHC(NH)NR^9R^{11}$, —$C(NH)NR^7R^8$, —$C(NH)NR^7$Ay, —$R^{10}C(NH)NR^9R^{11}$, —$S(O)_2NR^7R^8$, —$S(O)_2NR^7$Ay, —$R^{10}SO_2NHCOR^9$, —$R^{11}SO_2NR^9R^{11}$, —$R^{10}SO_2R^9$, —$S(O)_nR^9$, cyano, azido and nitro; or two adjacent $R^5$ groups together with the atoms to which they are bonded form a $C_{5-6}$ cycloalkyl or aryl;

p is 0, 1, 2 or 3;

each $R^6$ is the same or different and is independently selected from the group consisting of halo, alkyl, alkenyl, alkynyl, cycloalkyl, cycloalkenyl, —$R^{10}$cycloalkyl, Ay, Het, —$R^{10}$Ay, —$R^{10}$Het, —$OR^7$, —OAy, —OHet, —$R^{10}OR^9$, —$OR^{10}$Ay, —$OR^{10}$Het, —$R^{10}NR^7R^8$, —$R^{10}NR^7$Ay, —$R^{10}C(O)R^9$, —$C(O)R^9$, —$C(O)$Ay, —$C(O)$Het, —$CO_2R^9$, —$R^{10}CO_2R^9$, —$C(O)NR^7R^8$, —$C(O)NR^7$Ay, —$C(O)NHR^{10}$Het, —$R^{10}C(O)NR^9R^{11}$, —$C(S)NR^9R^{11}$, —$R^{10}C(S)NR^9R^{11}$, —$R^{10}NHC(NH)NR^9R^{11}$, —$C(NH)NR^7R^8$, —$C(NH)NR^7$Ay. —$R^{10}C(NH)NR^9R^{11}$, —$S(O)_2NR^7R^8$, —$S(O)_2NR^7$Ay, —$R^{10}SO_2NHCOR^9$, —$R^{10}SO_2NR^9R^{11}$, —$R^{10}SO_2R^9$, —$S(O)_nR^9$, cyano, azido and nitro; or two adjacent $R^6$ groups together with the atoms to which they are bonded form a $C_{5-6}$ cycloalkyl or a 5- or 6-membered heterocyclic group containing 1 or 2 heteroatoms; and $M^2$ is —$B(OH)_2$, —$B(ORa)_2$, —$B(Ra)_2$, —$Sn(Ra)_3$, Zn-halide, ZnRa, Mg-halide where Ra is alkyl or cycloalkyl and halide is halo.

Generally, the process for preparing compounds of formula (I) (all formulas and variables having been defined above in connection with Scheme 4), comprises the following steps:

(a) halogenating a compound of formula (VII) to prepare a compound of formula (XIX);

(b) reacting a compound of formula (XIX) with a compound of formula (XX) to prepare a compound of formula (XI); and (c) when $R^{1a}$ is H or halo, converting the compound of formula (XI) to a compound of formula (I).

When the compounds of formula (XI) are defined where $R^{1a}$ is H or halo, the process for preparing compounds of formula (I) comprises the additional step (c) of converting the compounds of formula (XI) to a compound of formula (I). Such conversion can be achieved using the methods described below or other suitable methods conventional in the art for this type of transformation.

More specifically, compounds of formula (XI) can be prepared by reacting a compound of formula (XIX) with a compound of formula (XX).

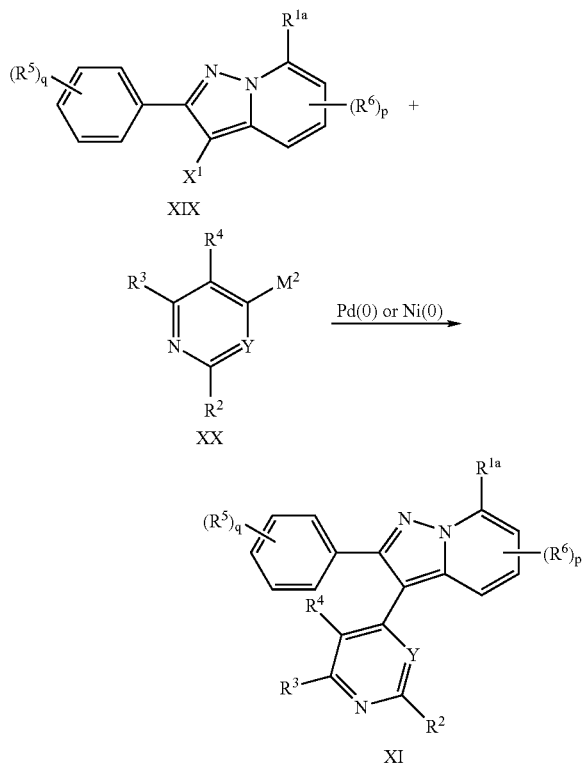

wherein all variables are as defined above in connection with Scheme 4.

The reaction may be carried out in an inert solvent, in the presence of a palladium (0) or nickel (0) catalyst. The reaction may optionally be heated to about 50–150° C. Preferably the reaction is performed by reacting equimolar amounts of a compound of formula (XIX) with a Het-metal compound of formula (XX), but the reaction may also be performed in the presence of an excess of compound of the formula (XX). The palladium or nickel catalyst is preferably present in 1–10 mol % compared to the compound of formula (XIX). Examples of suitable palladium catalysts include but are not limited to, tetrakis(triphenylphosphine) palladium (0), dichlorobis(triphenyl-phosphine)palladium (II), tris(dibenzylideneacetone)dipalladium (0), and bis (diphenylphosphinoferrocene)palladium (II) dichloride. Suitable solvents include but are not limited to, N,N-dimethylformamide, toluene, tetrahydrofuran, dioxane, and 1-methyl-2-pyrrolidinone. When the Het-metal compound of formula (XX) is a boronic acid or ester or a borinate the reaction is more conveniently carried out by adding a base in a proportion equivalent to, or greater than, that of the compound of formula (XX). Het-metal compounds of formula (XX) may be obtained from commercial sources or prepared either as discreet isolated compounds or generated in situ using methods known to one skilled in the art (Suzuki, A. *J. Organomet Chem.* 1999, 576, 147; Stille, J. *Angew. Chem. Int Ed. Engl.* 1986, 25, 508; Snieckus, V. *J.Org. Chem.* 1995, 60, 292.)

Compounds of formula (XIX) can be prepared from compounds of formula (VII) by a halogenation procedure.

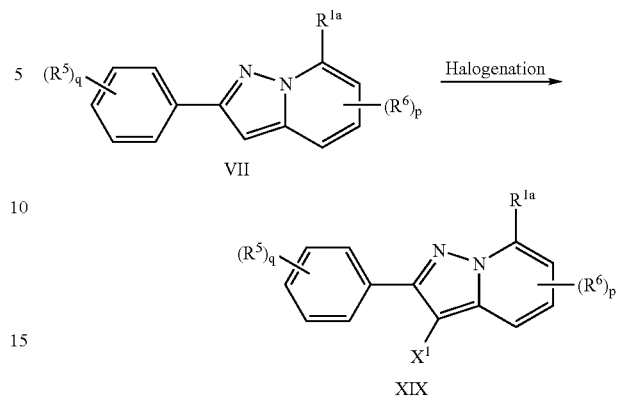

wherein all variables are as defined above in connection with Scheme 4.

Typically, the halogenation reaction is carried out by subjecting the compounds of formula (VII) to a halogenating agent in a suitable solvent. Suitable halogenating agents include but are not limited to, N-bromosuccinimide, trialkylammonium tribromides, bromine, N-chlorosuccinimide, N-iodosuccinimide, iodine monochloride, and the like. Suitable solvents include, for example, N,N-dimethylformamide, tetrahydrofuran, dioxane, 1-methyl-2-pyrrolidinone, carbon tetrachloride, toluene, dichloromethane, diethyl ether, and the like.

The compounds of formula (VII) can be prepared using methods described above in connection with Scheme 1.

Alternatively, compounds of formula (XIX) wherein $X^1$ is bromo may be conveniently prepared from compounds of Formula (XXIII) by a bromination/decarboxylation sequence as shown below.

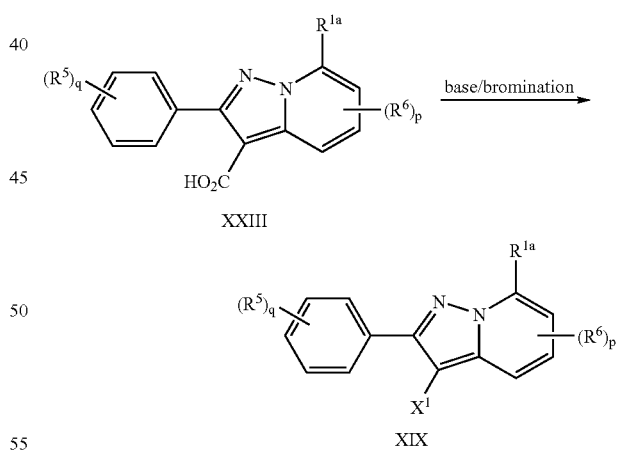

wherein all variables are as defined above in connection with Scheme 4.

The compound of formula (XXIII), dissolved in a suitable solvent, is treated with a base followed by a brominating agent and the mixture is stirred at or about 25° C. until the reaction is judged complete by the disappearance of the compound of formula (XXIII). Suitable solvents include, but are not limited to, dimethylformamide, dimethylacetamide, dioxane and the like. The base is preferably sodium hydrogen carbonate and the brominating agent can be, for example, N-bromosuccinimide.

The compounds of formula (XXIII) are prepared according to the methods described above in connection with Scheme 1.

According to another process of the present invention, compounds of formula (XI) may be conveniently prepared by a process which involves reacting a ketone of formula (XXI) with an N-aminopyridine derivative of formula (XXII) in the presence of an acid or a base. Typically the acid is p-toluenesulfonic acid and the base can be potassium carbonate, sodium hydroxide, cesium carbonate, lithium hydroxide, triethylamine, potassium tert-butoxide.

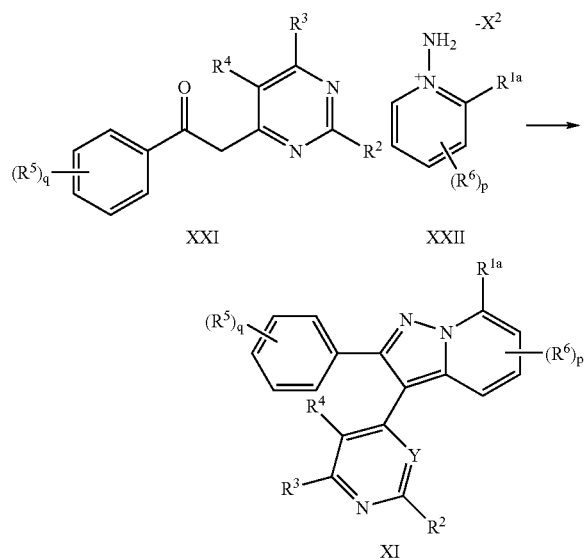

wherein $X^2$ is I, mesitylsulfonyl and all other variables are as defined above in connection with Scheme 4.

In the compounds of formula (XI), when $R^{1a}$ is other than H or halo (i.e., $R^{1a}=R^1$) the forgoing synthesis provide the compounds of formula (I) directly. In the embodiment where compounds of formula (XI) are defined where $R^{1a}$ is H or halo, the compounds of formula (XI) may be converted to compounds of formula (I). For example, compounds of formula (XI-A) (i.e., compounds of formula (XI) wherein $R^{1a}$ is H) may be converted to compounds of formula (XI-B) (i.e., compounds of formula (XI) wherein $R^{1a}$ is halo or $R^1$) by a deprotonation/electrophile quench protocol. For example, the process may be carried out by reacting a compound of formula (XI-A) with a base, such as n-butyllithium, followed by reacting with an electrophilic agent to give compounds of formula (XI-B) wherein E is halo or $R^1$, or compounds of formula (I).

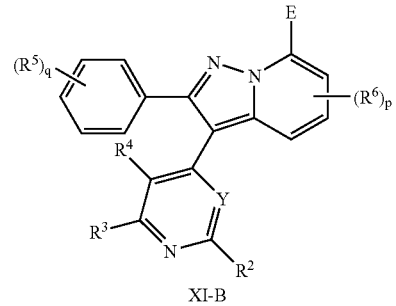

wherein E is halo or $R^1$ and all other variables are as defined above in connection with any of the processes described above.

Electrophiles which may be used in this process include, but are not limited to: alkyl halides (E=methyl, benzyl etc.); N-bromosuccinimide (E=bromine); N-chlorosuccinimide (E=chlorine); carbon tetrachloride (E=chlorine); N-iodosuccinimide (E=iodine); aldehydes (E=CH(OH)$R^{10}$); dimethylformamide (E=CHO); dimethyl disulfide (E=SMe); carbon dioxide (E=CO$_2$H); dimethylcarbamoyl chloride (E=C(O)NMe$_2$) and the like. As will be apparent, when using the above reagents if the electrophile is a halide the C-7 substituent is defined as a compound of formula (XI) which is useful as an intermediate en route to a compound of formula (I). The conversion of compounds of formula (XI) wherein $R^{1a}$ is halo to compounds of formula (I) can be achieved using the methods described below or other methods conventional in the art for this type of transformation.

Each of the foregoing processes may further comprise the step of converting the compounds of formula (XI) or (I) to a pharmaceutically acceptable salt, solvate, or physiologically functional derivative thereof, using techniques well known to those skilled in the art.

As will be apparent to those skilled in the art, the compounds of formula (I) may be converted to other compounds of formula (I) using techniques well known in the art. For example, one method of converting compounds of formula (I) to other compounds of formula (I) comprises a) oxidizing the compound of formula (I-A) to prepare a compound of formula (I-B) and then b) optionally reacting a compound of formula (I-B) with an oxygen or amine nucleophile of formula $R^2$, wherein $R^2$ is selected from the group consisting of —NR$^7$R$^8$, —NHR$^{10}$Ay, —OR$^7$, —OAy, Het bonded through N, —NHHet, NHR$^{10}$Het, OHet and —OR$^{10}$Het to produce a compound of formula (I) wherein $R^2$ is selected from the group consisting of —NR$^7$R$^8$, —NHR$^{10}$Ay, —OR$^7$, —OAy, Het bonded through N, —NH-Het, NHR$^{10}$Het, OHet and —OR$^{10}$Het.

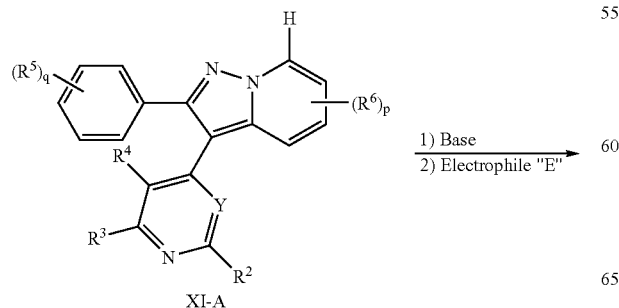

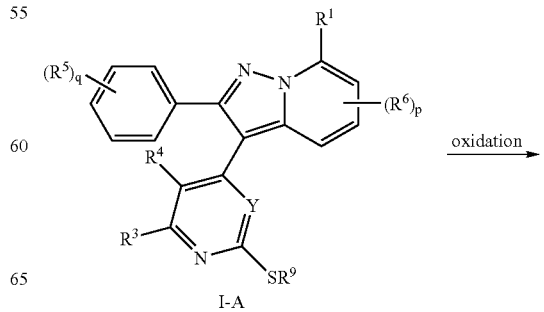

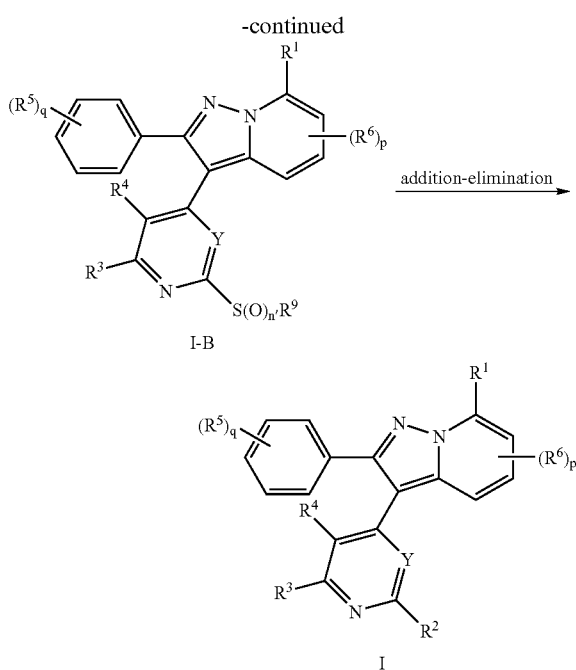

I-B

I wherein:

n' is 1 or 2;

R² is selected from the group consisting of H, halo, alkyl, cycloalkyl, alkenyl, cycloalkenyl, —NR⁷R⁸, —NHR¹⁰Ay, —OR⁷, —OAy, Het bonded through N, —NHHet, —NHR¹⁰Het, —OHet, and —OR¹⁰Het; and all other variables are as defined in connection with any of the processes described above.

More specifically, compounds of formula (I) can be prepared by reacting a compound of formula (I-B) (i.e., compounds of formula I wherein R² is S(O)$_{n'}$R⁹ where n' is 1 or 2) with an oxygen or amine nucleophile of formula R², wherein R² is —NR⁷R⁸, —NHR¹⁰Ay, —OR⁷, —OAy, Het bonded through N, —NHHet, —NHR¹⁰Het, —OHet and —OR¹⁰Het. The reaction may be carried out neat or in a suitable solvent and may be heated to 50–150° C. Typically the solvent is a lower alcohol such as methanol, ethanol, isopropanol and the like or solvent such as N,N-dimethylformamide or tetrahydrofuran, and the like. Optionally a base may be used to facilitate the reaction. Typically the base can be potassium carbonate, or an amine base such as triethylamine.

Compounds of formula (I-B) may be conveniently prepared by reacting a compound of formula (I-A) (i.e., compounds of formula I wherein R² is —S(O)$_n$R⁹ where n is 0) with an oxidizing agent in an inert solvent, optionally in the presence of a base. Typically the oxidizing agent is a peracid such as m-chloroperbenzoic acid or the like, optionally with a base such as sodium bicarbonate. Careful monitoring of the stoichiometry between the oxidizing agent and the substrate allows the product distribution between sulfoxide (n=1), and sulfone (n=2) to be controlled. Suitable solvents include but are not limited to, dichloromethane, chloroform and the like.

Compounds of formula (I-A) are prepared by methods described above wherein R² is —SR⁹ from the reaction of compounds selected from the group consisting of compounds of formula (IX), compounds of formula (XV) and compounds of formula (XVII) with a compound of formula (X-A) (i.e., the compound of formula (X) wherein R² is —SR⁹). The requisite compound of formula (X-A) can be obtained from commercial sources or prepared by methods known to one skilled in the art.

As will be apparent to one skilled in the art, the foregoing conversion method is applicable to compounds of formula (XI) (e.g. compounds where R¹ᵃ is H or halo) wherein R² is —SR⁹ to form other compounds of the formula (IX) wherein R² is —NR⁷R⁸, —OR⁷, —OAy, Het linked through N, —NHHet, —NHR¹⁰Het, —OHet and —OR¹⁰Het. Such compounds of formula (XI) may be further converted to compounds of formula (I) using methods described above.

Another particularly useful method for converting compounds of formula (I) to other compounds of formula (I) comprises reacting a compound of formula (I-C) (i.e., a compound of formula (I) wherein R² is fluoro) with an amine such as for example, an amine of formula H—NR⁷R⁸, H—NHR¹⁰Ay, H—NHHet, or H—NHR¹⁰Het, or a heterocyclic or heteroaryl group (Het), and optionally heating the mixture to 50–150° C. to prepare a compound of formula (I-D) (i.e., a compound of formula (I) wherein R² is an amine or substituted amine).

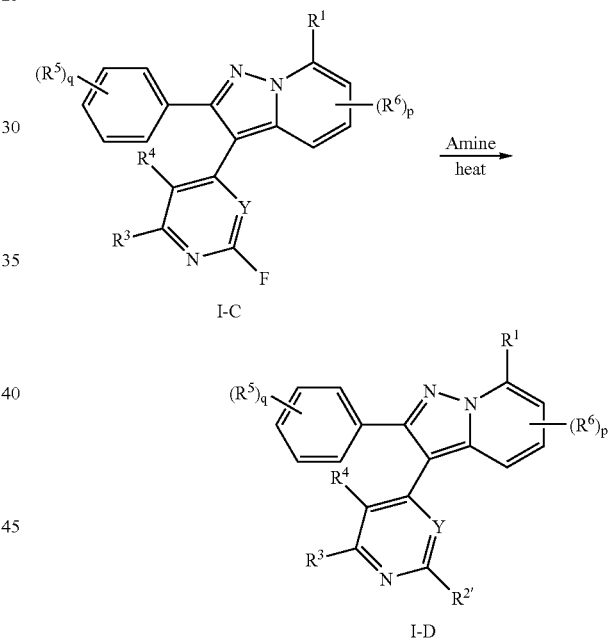

wherein R²' is selected from the group consisting of —NR⁷R⁸, —NHR¹⁰Ay, Het, —NHHet and —NHR¹⁰Het, and all other varaibles are as defined in connection with any of the processes described above.

This procedure may be carried out by mixing a compound of formula (I-C) in the amine neat, or in a suitable solvent with an excess of amine to produce a compound of formula (I-D). Typically the solvent is a lower alcohol such as methanol, ethanol, isopropanol and the like. Other suitable solvents may include N,N-dimethylformamide, 1-methyl-2-pyrrolidine and the like.

As will be apparent to one skilled in the art, this method for replacement of R²=fluoro with an amine in compounds of formula (I) to form other compounds of formula (I) is applicable to analagous sequences for compounds of formula (XI) (e.g. compounds where R¹ᵃ is H or halo). The newly formed compounds of formula (XI) can be ultimately converted to compounds of formula (I) using methods described herein.

As a further example of conversion of compounds of the formula (XI) to compounds of the formula (I), the compounds of formula (XI-C), wherein $R^6$=6-trifluoromethyl, can be prepared using the techniques described above in Schemes 1, 2 and 3 and converted to compounds of the formula (XI-E).

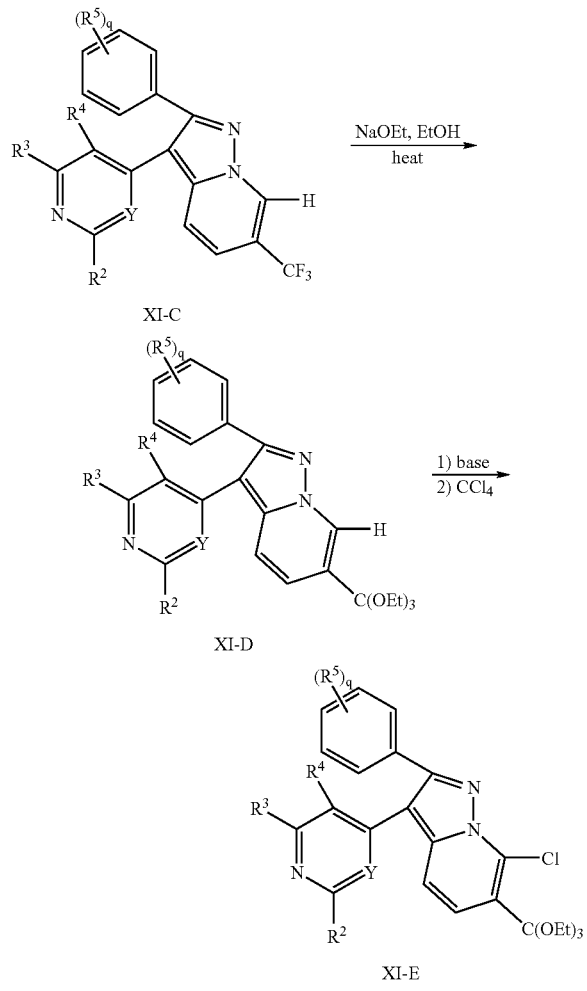

wherein all variables are as defined in connection with any of the processes described above.

Compounds of formula (XI-C) can be converted to compounds of formula (XI-D) by treatment with a metal alkoxide in an alcohol solvent. Suitable conditions include the use of sodium ethoxide as the alkoxide, and ethanol as a solvent. The reaction may be heated to 60° C.

A halogenation procedure can be facilitated by treatment of a compound of formula (XI-D) with a base followed by reaction with a halogenating agent to provide a compound of formula (XI-E). It will be apparent to one skilled in the art that these compounds of the formula (XI-E) can be converted to compounds of the formula (I) using any of numerous methods described herein.

The compounds of formula (XI-C) can be obtained using the procedures described above in connection with Schemes 1, 2 or 3. In one particularly useful embodiment, the compounds of formula (XI-C) are prepared using the procedures described in connection with any of Schemes 1, 2 or 3, with the exception that the first step, i.e., the preparation of compounds of formula (IV), involves the condensation of 2-chloro-5-trifluoromethylpyridine with the acetophenone of formula (XXX)

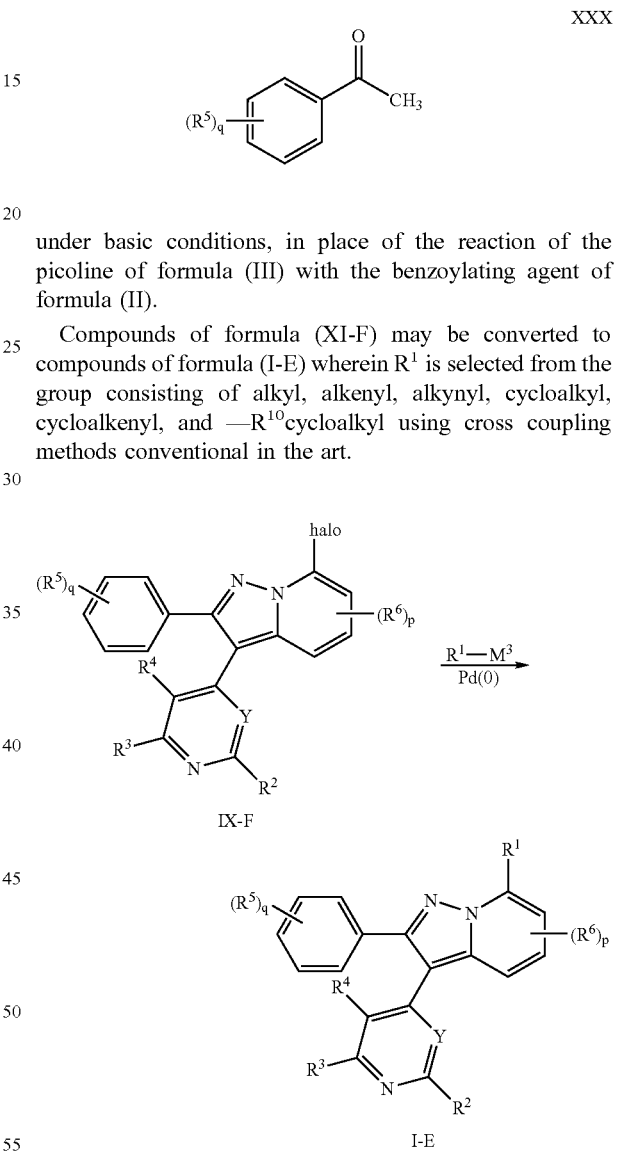

under basic conditions, in place of the reaction of the picoline of formula (III) with the benzoylating agent of formula (II).

Compounds of formula (XI-F) may be converted to compounds of formula (I-E) wherein $R^1$ is selected from the group consisting of alkyl, alkenyl, alkynyl, cycloalkyl, cycloalkenyl, and —$R^{10}$cycloalkyl using cross coupling methods conventional in the art.

wherein:

$R^1$ is selected from the group consisting of alkyl, alkenyl, alkynyl, cycloalkyl, cycloalkenyl, and —$R^{10}$cycloalkyl;

$M^3$ is $B(OH)_2$, $B(ORa)_2$, $B(Ra)_2$, $Sn(Ra)_3$, Zn-halide; Zn—Ra or Mg-halide, wherein Ra is alkyl or cycloalkyl and halide is halo; and all other variables are as defined in connection with any of the processes described above.

The process comprises coupling the compound of formula (XI-F) with a transmetalation partner of the formula $R^1$-$M^3$. This process can be readily carried out by mixing a compound of formula (XI-F) with a transmetalation species of formula $R^1$-$M^3$ in the presence of a catalytic amount of a palladium (0) source. The reactions are typically performed in an inert solvent optionally with heating to 50 to 150° C. Examples of suitable palladium catalysts include but are not limited to, tetrakis(triphenylphosphine)palladium (0), dichlorobis(triphenylphosphine)-palladium(II), tris(dibenzylideneacetone)dipalladium (0), and bis(diphenylphosphino-ferrocene)palladium (II) dichloride. Suitable solvents include but are not limited to, N,N-dimethylformamide, toluene, tetrahydrofuran, dioxane, and 1-methyl-2-pyrrolidinone. Transmetalation species of the formula $R^1$-$M^3$ are available from commercial sources or can be prepared by methods known to one skilled in the art.

Compounds of formula (XI-F) may be converted to compounds wherein $R^1$ is —$OR^7$ or —OAy as summarized below.

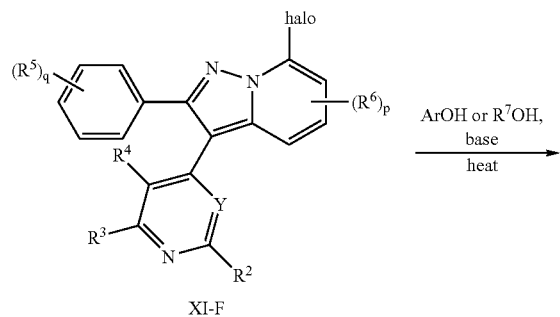

XI-F

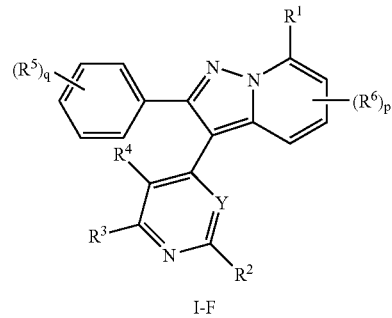

I-F wherein $R^1$ is —$OR^7$ or —OAy and all other variables are as defined in connection with any of the processes described above.

This transformation is most conveniently carried out by mixing the compound of formula (XI-F) (preferably where halo is chloro) with an excess of the alcohol optionally in the presence of an inert solvent, and heating the mixture to about 100–150° C.

As a further example of converting compounds of formula (I) into other compounds of formula (I), compounds of formula (I-G) (i.e., compounds of formula (I) wherein q is 1 or more and at least one $R^5$ is O-methyl) may be converted to compounds of formula (I-H) (i.e., compounds of formula (I) wherein q is 1 or more and at least one $R^5$ is —OH) using conventional demethylation techniques. Additionally, compounds of formula (I-H) may optionally be converted to compounds of formula (I-J) (i.e., compounds of formula (I) wherein q is 1 or more and at least one $R^5$ is —$OR^{10}$). For example, the foregoing conversions are represented schematically as follows:

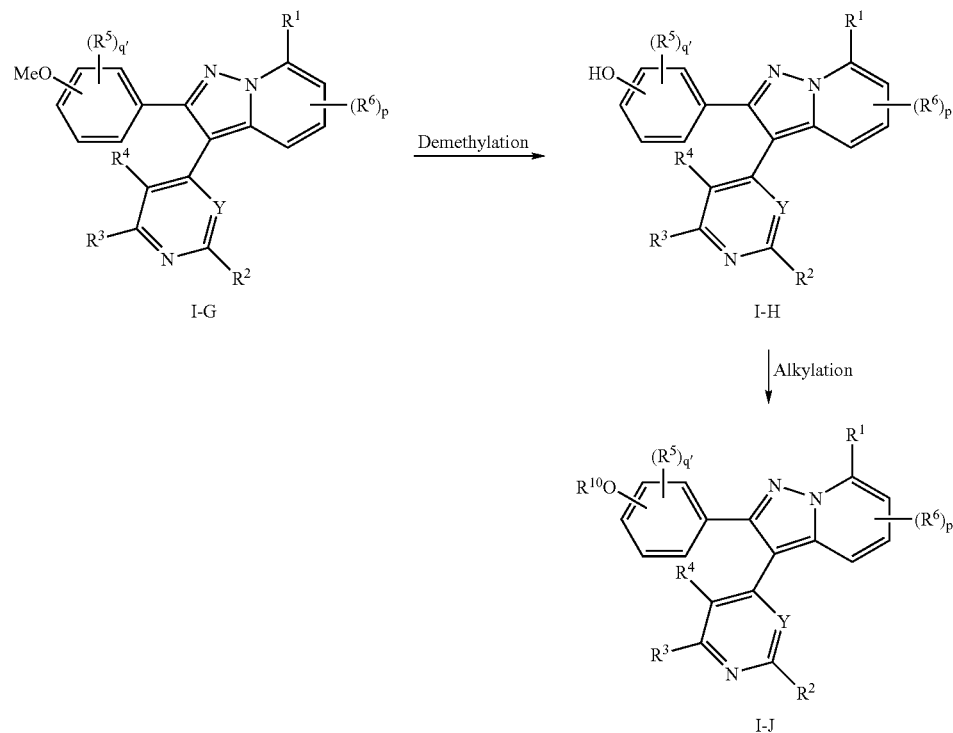

wherein q' is 0, 1, 2, 3 or 4, and all other variables are as defined in connection with any of the processes described above.

The demethylation reaction may be carried out by treating a compound of formula (I-G) in a suitable solvent with a Lewis acid at a temperature of −78° C. to room temperature, to produce a compound of formula (I-H). Typically the solvent is an inert solvent such as dichloromethane, chloroform, acetonitrile, toluene and the like. The Lewis acid may be boron tribromide, trimethylsilyl iodide and the like.

Optionally, the compounds of formula (I-H) may be further converted to compounds of formula (I-J) by an alkylation reaction. The alkylation reaction may be carried out by treating a compound of formula (I-H) in suitable solvent with an alkyl halide of formula $R^{10}$-Halo where $R^{10}$ is as defined above, to form a compound of formula (I-J). The reaction is preferably carried out in the presence of a base and with optionally heating to 50–200° C. The reaction may be carried out in solvents such as N,N-dimethylformamide, dimethylsulfoxide and the like. Typically the base is potassium carbonate, cesium carbonate, sodium hydride or the like. Additionally, as will be apparent to those skilled in the art, the alkylation reaction can be carried out under Mitsunobu conditions.

In yet another example, compounds of formula (I-K) (i.e., compounds of formula (I) wherein q is 1 or more and at least one $R^5$ is halo) or compound of formula (I-M) (i.e. compounds of formula (I) wherein q is 1 or more and at least one $R^5$ is nitro) can be converted to compounds of formula (I-L) (i.e., compounds of formula (I) wherein q is 1 or more and at least one $R^5$ is $NH_2$). Optionally, compounds of formula (I-L) may then be converted to compounds of formula (I-N) (i.e., compounds of formula (I) wherein q is 1 or more and at least one $R^5$ is —$NR^7R^8$ where $R^7$ and $R^8$ are not both H). For example, the foregoing conversions are represented schematically as follows:

a palladium (0) source, a base and a suitable ligand, followed by hydrolysis to give a compound of formula (I-L). See J. Wolfe, et al., *Tetrahedron Letters* 38:6367–6370 (1997). Typically the imine is benzophenoneimine, the palladium (0) source is tris(dibenzylideneacetone)dipalladium(0), the base is sodium tert-butoxide and the ligand is racemic-2,2'-bis(diphenylphosphino)-1,1'-binaphthyl. Suitable solvents include N,N-dimethylformamide and the like.

Compounds of formula (I-L) can also be obtained from compounds of formula (I-M) by reduction. The reduction can conveniently be carried out by using zinc, tin or iron and acid, by using tin(II)chloride, or by using palladium or platinum catalysts under hydrogen atmosphere in a suitable solvent as obvious to one skilled in the art of organic synthesis.

Reaction of a compound of formula (I-L) with compound of formula $R^7$-halogen in a suitable solvent in the presence of base, optionally with heating may be used to prepare compounds of formula (I-N). Typically the base is triethylamine or pyridine and the solvent is N,N-dimethylformamide and the like.

Additional compounds of formula (I-N) can be obtained by reductive amination of compounds of formula (I-L) with ketones or aldehydes. See, A. Abdel-Magid, et al., *J. Org. Chem.* 61:3849–3862 (1996). Typically a compound of formula (I-L) is treated with an aldehyde or a ketone in the presence of an acid, such as acetic acid, and a reducing agent, such as sodium triacetoxyborohydride and the like, in an inert solvent such as dichloroethane and the like.

Other transformations well known to those skilled in the art for use with anilines may be used to convert compounds of formula (I-L) to compounds of formula (I-N).

Based upon this disclosure and the examples contained herein one skilled in the art can readily convert compounds of formula (I) or a pharmaceutically acceptable salt, solvate or physiologically functional derivative thereof into other

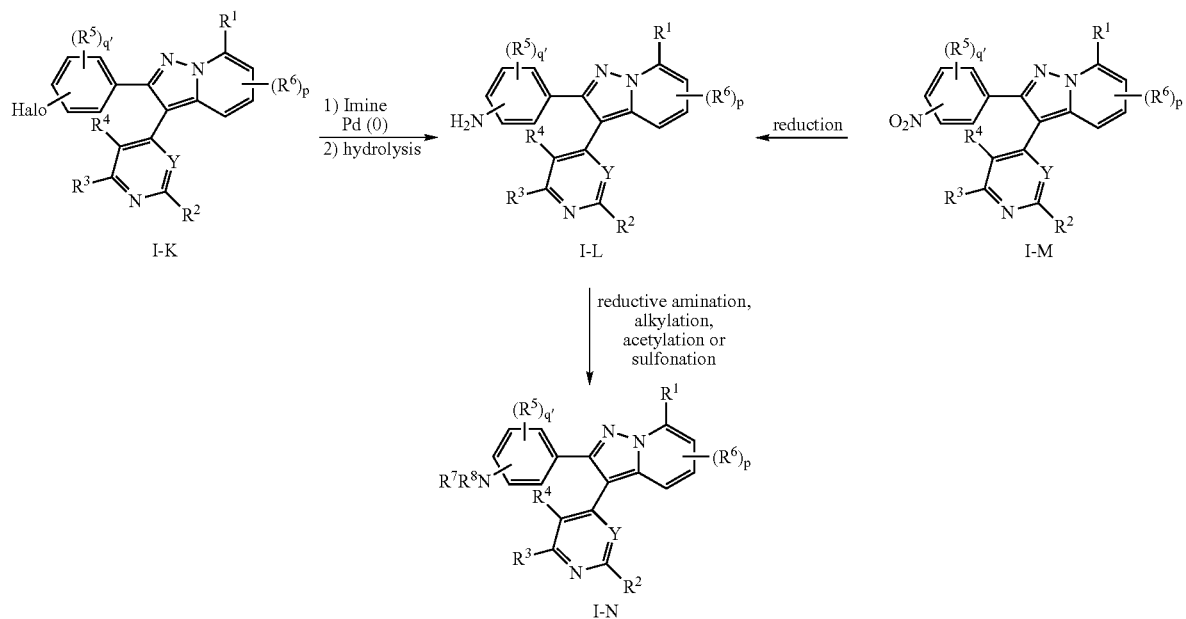

wherein q' is 1, 2, 3 or 4 and all other variables are as defined in connection with any of the processes described above.

The process of converting compounds of formula (I-K) to compounds of formula (I-L) is carried out by reacting a compound of formula (I-K) with an imine in the presence of compounds of formula (I), or a pharmaceutically acceptable salt, solvate or physiologically functional derivative thereof.

The present invention also provides radiolabeled compounds of formula (I) and biotinylated compounds of formula (I). Radiolabeled compounds of formula (I) and biotinylated compounds of formula (I) can be prepared using conventional techniques. For example, radiolabeled compounds of formula (I) can be prepared by reacting the compound of formula (I) with tritium gas in the presence of an appropriate catalyst to produce radiolabeled compounds of formula (I).

In one preferred embodiment, the compounds of formula (I) are tritiated.

The radiolabeled compounds of formula (I) and the biotinylated compounds of formula (I) are useful in assays for the identification of compounds for the treatment or prophylaxis of viral infections such as herpes viral infections. Accordingly, the present invention provides an assay method for identifying compounds which have activity for the treatment or prophylaxis of viral infections such as herpes viral infections, which method comprises the step of specifically binding the radiolabeled compound of formula (I) or the biotinylated compound of formula (I) to the target protein. More specifically, suitable assay methods will include competition binding assays. The radiolabeled compounds of formula (I) and the biotinylated compounds of formula (I) can be employed in assays according to the methods conventional in the art.

The following examples are illustrative embodiments of the invention, not limiting the scope of the invention in any way. Reagents are commercially available or are prepared according to procedures in the literature. Example numbers refer to those compounds listed in the tables above. $^1$H and $^{13}$C NMR spectra were obtained on Varian Unity Plus NMR spectrophotometers at 300 or 400 MHz, and 75 or 100 MHz respectively. $^{19}$F NMR were recorded at 282 MHz. Mass spectra were obtained on Micromass Platform, or ZMD mass spectrometers from Micromass Ltd. Altrincham, UK, using either Atmospheric Chemical Ionization (APCI) or Electrospray Ionization (ESI). Analytical thin layer chromatography was used to verify the purity of some intermediates which could not be isolated or which were too unstable for full characterization, and to follow the progress of reactions. Unless otherwise stated, this was done using silica gel (Merck Silica Gel 60 F254). Unless otherwise stated, column chromatography for the purification of some compounds, used Merck Silica gel 60 (230–400 mesh), and the stated solvent system under pressure. All compounds were characterized as their free-base form unless otherwise stated. On occasion the corresponding hydrochloride salts were formed to generate solids where noted.

EXAMPLE 1

2-(4-Fluorophenyl)-3-(4-pyrimidinyl)-pyrazolo[1,5-a]pyridine

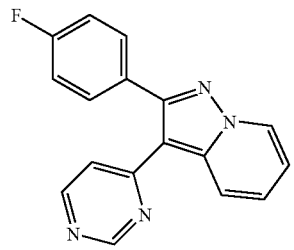

a) 1-(4-Fluorophenyl)-2-(4-pyrimidinyl)-ethanone.

To a stirred solution of 4-methylpyrimidine (20.64 g, 0.22 mol) and ethyl 4-fluorobenzoate (36.9 g, 0.22 mol) in dry tetrahydrofuran (100 mL) at 0° C. under nitrogen was added lithium bis(trimethylsilyl)amide (1M in tetrahydrofuran, 440 mL, 0.44 mol) over a 2 hour period. A white precipitate deposited during the addition and this suspension was stirred at room temperature overnight The reaction was diluted with 100 mL of water and filtered. The filtrate was washed with water three times and dried. The solution was diluted with ethyl acetate (100 mL) and the organic phase separated. The aqueous phase was further extracted with ethyl acetate (100 mL). Organic phases were dried over magnesium sulfate and concentrated and combined with the filtrate to give a combined yield of 47 g (98%) of product. $^1$H NMR (CDCl$_3$) exists as a 2:1 mixture of enol:keto tautomers: δ enol form: 5.95 (s, 1H), 6.92 (dd, J=1.2, 5.7 Hz, 1H), 7.06–7.14 (m, 2H), 7.83 (dd, J=5.4, 8.7 Hz, 2H), 8.40 (d, J=5.7 Hz, 1H), 8.8 (s, 1H); keto form: 4.42 (s, 2H), 7.12–7.18 (m, 2H), 7.34 (d, J=4.2 Hz, 1H), 8.06 (dd, J=5.3, 8.8 Hz, 2H), 8.67 (d, J=5.1 Hz, 1H), 9.16 (s, 1H); APESI–MS m/z 215 (M–1)$^-$.

b) A solution of 1-(4-fluorophenyl)-2-(4-pyrimidinyl)-ethanone (21.6 g, 0.1 mol), 1-aminopyridinium iodide (22.2 g, 0.1 mol) and potassium carbonate (41.4 g, 0.3 mol) in a mixture of water (300 mL) and isopropanol (300 mL) was heated and stirred at 100° C. for 16 hours. The isopropanol was removed under vacuum and the resulting aqueous phase extracted with dichloromethane (5×200 mL). The dichloromethane extracts were combined and the solvent evaporated under reduced pressure to leave a red solid which was purified by silica gel chromatography eluting with a hexane:ethyl acetate to give the title compound as a yellow solid, 9.16 g (32%). $^1$H NMR (DMSO-d$_6$): δ 7.07 (d, J=5.4 Hz, 1H), 7.14 (t, J=6.8 Hz, 1H), 7.32 (t, J=8.7 Hz, 2H), 7.53 (t, J=7.8 Hz, 1H), 7.60 (dd, J=5.7, 8.7 Hz, 2H), 8.40 (d, J=8.9 Hz, 1H), 8.54 (d, J=5.3 Hz, 1H), 8.83 (d, J=7.1 Hz, 1H), 9.16 (s, 1H), APESI+MS m/z 291 (M+1).

EXAMPLE 2

2-(4-Fluorophenyl)-3-(4-(2-methylthio)pyrimidinyl)-pyrazolo[1,5-a]pyridine

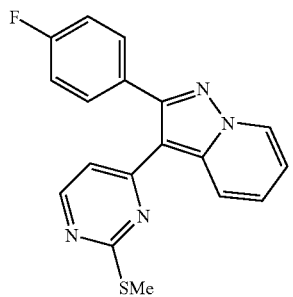

a) 1-(4-Fluorophenyl)-2-(4-(2-methylthio)pyrimidinyl)ethanone.

To a stirred solution of 2-methylthio-4-methylpyrimidine (66 g, 0.47 mol) and ethyl 4-fluorobenzoate (79 g, 0.47 mol) in dry tetrahydrofuran (400 mL) at 0° C. under nitrogen was added lithium bis(trimethylsilyl)amide (1N in tetrahydrofuran, 940 mL, 0.94 mol) over a 2 hour period. The solution was stirred at ice bath temperature for 18 hours. The solution was poured into 2 L of ice cold 0.5 N hydrochloric acid. A precipitate formed which was filtered off and air dried. Second and third crops of solids were obtained as the precipitate was washed with water. The combined precipitates were recrystalized from acetone and water to give product as a yellow solid: 117 g (95%). ¹H NMR (CDCl₃): δ (all in enol form): 3.0 (s, 3H), 6.29 (s, 1H), 7.01 (d, J=5.7 Hz, 1H), 7.48 (t, J=8.7 Hz, 2H), 8.20 (dd, J=5.4, 8.8 Hz, 2H), 8.68 (d, J=5.7 Hz, 1H); APESI–MS m/z 261 (M–1)⁻.

b) A solution of 1-(4-fluorophenyl)-2-(4-(2-methylthio)pyrimidinyl)ethanone (13.0 g, 50 mmol) in isopropanol (300 mL) was warmed to reflux. A solution of 1-aminopyridinium iodide (14 g, 63 mmol) in water (300 mL) was treated with 2N sodium hydroxide (31.5 mL). This solution was added to the ketone over a period of two hours while the mixture was heated at reflux. After an additional seven hours, the isopropanol was partially evaporated under reduced pressure and the resulting solution was extracted with dichloromethane (2×300 mL). The dichloromethane extracts were combined, dried (magnesium sulfate), filtered and the solvent evaporated under reduced pressure to leave a red solid which was purified by silica gel chromatography with dichloromethane to give the title compound as a yellow solid, 4.5 g (26%). ¹H NMR (DMSO-d₆): δ 2.5 (s, 3H), 6.80 (d, J=5.3 Hz, 1H), 7.18 (t, J=6.9 Hz, 1H), 7.36 (t, J=8.8 Hz, 2H), 7.59 (t, J=7.9 Hz, 1H), 7.60 (dd, J=5.7, 8.7 Hz, 2H), 8.38 (d, J=9.1 Hz, 1H), 8.40 (d, J=5.3 Hz, 1H), 8.88 (d, J=7.0 Hz, 1H), APESI+MS m/z 337 (M+1).

EXAMPLE 3

2-(4-Fluorophenyl)-3-(4-(2-methylsulfinyl)pyrimidinyl)-pyrazolo[1,5-a]pyridine

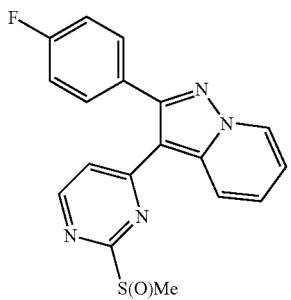

To a stirred solution of 2-(4-fluorophenyl)-3-(4-(2-methylthio)pyrimidinyl)-pyrazolo[1,5-a]pyridine (0.285 g, 0.85 mmol) in dichloromethane (10 mL) was added, dropwise, a solution of (0.257 g, 0.85–1.23 mmol) of 57–86% m-chloroperoxybenzoic acid in dichloromethane (5 mL). After 10 minutes, the solution was quenched by the addition of aqueous potassium carbonate (20 mL), and the organic phase was separated. The aqueous phase was further extracted with dichloromethane (2×20 mL) and the dichloromethane phases dried over magnesium sulfate filtered and concentrated to give a crude white solid. Chromatography on silica gel eluting with a hexane/Ethyl acetate gradient (0–100% ethyl acetate) gave the title compound as a white solid, 0.213 g (60: ¹H NMR (CDCl₃): δ 3.05 (s, 3H), 7.07–7.11 (m, 2H), 7.25 (d, J=8.5 Hz, 2H), 7.55 (t, J=7.8 Hz, 1H), 7.64 (dd, J=5.5, 6.9 Hz, 2H), 8.52 (d, J=5.1 Hz, 1H), 8.59 (d, J=6.9 Hz, 1H), 8.84 (d, J=9.0 Hz, 1H); APESI+MS m/z 353 (M+1)⁻.

EXAMPLE 4

N-Butyl-4-[2-(4-fluorophenyl)pyrazolo[1,5-a]pyridin-3-yl]-2-pyrimidinamine

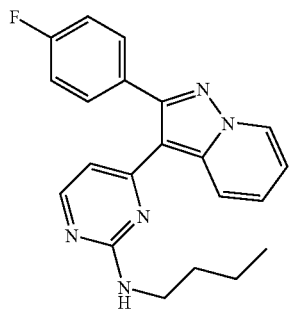

A solution of 2-(4-fluorophenyl)-3-(4-(2-methylsulfinyl)pyrimidinyl)-pyrazolo[1,5-a]pyridine (Example 3, 0.03 g 0.085 mmol) in n-butylamine (0.5 mL) was heated to reflux for 0.25 hours. On cooling a white solid deposits, which was collected by filtration, washed with hexane and dried under vacuum to give the title compound as a white solid, 0.029 g (94%). ¹H NMR (DMSO-d₆): δ 0.87 (t, J=7.4 Hz, 3H), 1.31 (sextet, J=7.4 Hz, 2H), 1.49(quintet, J=7.2 Hz, 2H), 3.25 (q, J=6.6 Hz, 2H), 6.4 (bs, 1H), 7.06 (t, J=6.8 Hz, 1H), 7.13 (bs, 1H), 7.29 (t, J=8.8 Hz, 2H), 7.43 (t, J=7.8 Hz, 1H), 7.59 (dd, J=5.7, 8.5 Hz, 2H), 8.01 (d, J=5.3 Hz, 1H), 8.40 (bs, 1H), 8.76 (d, J=6.9 Hz, 1H); APESI+MS m/z 362 (M+1)⁻.

EXAMPLE 5

2-(4-Fluorophenyl)-7-methyl-3-(4-pyrimidinyl)pyrazolo[1,5-a]pyridine

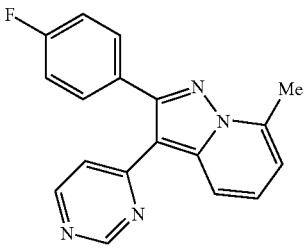

A solution of 2-(4-fluorophenyl)-3-(4-pyrimidinyl)-pyrazolo[1,5-a]pyridine (Example 1, 0.2 g, 0.69 mmol) in dry tetrahydrofuran (5 mL) was cooled to –78° C. under nitrogen and lithium diisopropylamide (0.45 mL of a 2M solution in heptane/tetrahydrofuran/ethylbenzene, 0.9 mmol) was added dropwise. The reaction mixture was stirred for about 10 minutes and methyl iodide (0.2 mL, 4 mmol) was added. The solution was allowed to warm to room temperature and stirred for a further 1.5 hours. The reaction mixture was diluted with diethyl ether (20 mL), water (20 mL) added, and the organic phase separated. The aqueous phase was further extracted with ether (20 mL) and the combined ether phases were dried over anhydrous magnesium sulfate, filtered and the solvents evaporated to give a yellow solid. Chromatography on silica gel eluting with 9:1 hexane/ethyl acetate gave the title compound, 0.080 g (38%). ¹H NMR (DMSO-d$_6$): δ 2.72 (s, 3H), 7.05 (d, J=6.3 Hz, 2H), 7.32 (t, J=8.8 Hz, 2H), 7.46 (dd, J=7.0, 8.6 Hz, 1H), 7.61 (dd, J=5.5, 8.6 Hz, 2H), 8.32 (d, J=9.0 Hz, 1H), 8.52 (d, J=5.5 Hz, 1H), 9.15 (s, 1H); APESI+MS m/z 305 (M+1)⁻.

EXAMPLE 6

2-(4-Fluorophenyl)-7-methylthio-3-(4-pyrimidinyl)pyrazolo[1,5-a]pyridine

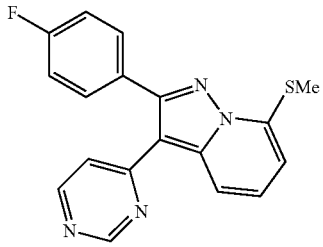

In a similar manner as described in Example 5, using dimethyl disulfide in place of methyl iodide, was obtained the title compound, (72%). ¹H NMR (DMSO-d$_6$): δ 2.46 (s, 3H), 7.01 (d, J=7.3 Hz, 1H), 7.06 (d, J=4.7 Hz, 1H), 7.33 (t, J=8.8 Hz, 2H), 7.53 (t, J=8.2 Hz, 1H), 7.61 (dd, J=5.5, 8.4 Hz, 2H), 8.22 (d, J=8.8 Hz, 1H), 8.53 (d, J=5.5 Hz, 1H), 9.15 (s, 1H); APCI+MS m/z 336 (M)⁻.

EXAMPLE 7

2-(4-Fluorophenyl)-7-methylsulfinyl-3-(4-pyrimidinyl)pyrazolo[1,5-a]-pyridine

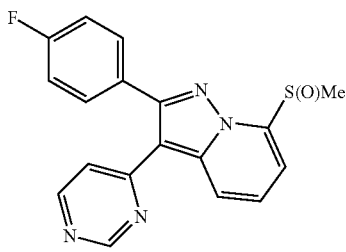

To a stirred solution of 2-(4-fluorophenyl)-7-methylthio-3-(4-pyrimidinyl)pyrazolo[1,5-a]pyridine (Example 6, 0.246 g, 0.73 mmol) in chloroform (20 mL) was added, dropwise, a solution of of m-chloroperbenzoic acid (57–86%, 0.221 g, 0.73–1.1 mmol) in chloroform (10 mL). After 1 hour, the reaction was quenched by the addition of aqueous potassium carbonate (20 mL), and the organic phase was separated. The aqueous phase was further extracted with chloroform (2×20 mL) and the combined chloroform phases were dried over anhydrous magnesium sulfate. The drying agent was removed by filtration and the solvent was evaporated to give a light brown solid. Chromatography on silica gel eluting with a hexane/ethyl acetate gradient (0–30% ethyl acetate) gave the title compound as the major product, 0.170 g (66%). ¹H NMR (DMSO-d$_6$): δ 3.11 (s, 3H), 7.13 (d, J=5.4 Hz, 1H), 7.33 (t, J=8.8 Hz, 2H), 7.50 (d, J=7.0 Hz, 1H), 7.63 (dd, J=5.7, 8.6 Hz, 2H), 7.76 (dd, J=7.4, 8.1 Hz, 1H), 8.50 (d, J=8.8 Hz, 1H), 8.60 (d, J=5.5 Hz, 1H), 9.20 (s, 1H); APESI+MS m/z 353 (M+1)⁻.

EXAMPLE 8

7-(2-Fluoroethoxy)-2-(4-fluorophenyl)-3-(4-(2-methylthio)pyrimidinyl)-pyrazolo[1,5-a]pyridine

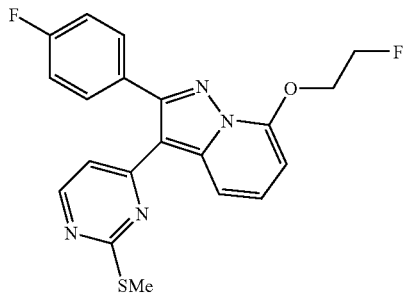

a) 7-(2-Fluoroethoxy)-2-(4-fluorophenyl)-3-(4-(2-methylthio)pyrimidinyl)-pyrazolo[1,5-a]pyridine.

To a stirred solution of 2-fluoroethanol (0.128 g, 2 mmol) in tetrahydrofuran (5 mL), under nitrogen, was added potassium tert-butoxide (1M in tert-BuOH. 2.0 mL, 2 mmol) and the resulting solution stirred for 5 minutes. A solution of 7-chloro-2-(4-fluorophenyl)-3-(4-(2-methylthio)pyrimidinyl)pyrazolo[1,5-a]pyridine (0.15 g, 0.4 mmol) in dichloromethane (0.5 mL) was then added dropwise and the reaction stirred for 16 hours. Dichloromethane (20 mL) and water (20 mL) were added and the aqueous phase was separated. The aqueous phase was further extracted with dichloromethane (2×20 mL) and the combined organic phases were dried over anhydrous magnesium sulfate and the solvents evaporated to give a brown solid. Purification on silica gel using 4:1 hexane/ethyl acetate as eluent gave the title compound, 0.111 g (70%). ¹H NMR (CDCl$_3$): δ 2.59 (s, 3H), 4.60 (t, J=4.1 Hz, 1H), 4.67 (t, J=4.1 Hz, 1H), 4.87 (t, J=4.1 Hz, 1H), 4.98 (t, J=4.1 Hz, 1H), 6.37 (d, J=7.3 Hz, 1H), 6.64 (d, J=5.3 Hz, 1H), 7.13 (t, J=8.6 Hz, 2H), 7.37 (t, J=8.2 Hz, 1H), 7.58 (dd, J=5.3, 8.6 Hz, 2H), 8.15 (d, J=8.8 Hz, 1H), 8.21 (d, J=5.5 Hz, 1H); APESI+MS m/z 399 (M+1)⁻.

b) 7-Chloro-2-(4-fluorophenyl)-3-(4-(2-methylthio)pyrimidinyl)pyrazolo[1,5-a]pyridine.

A solution of 2-(4-fluorophenyl)-3-(4-(2-methylthio)pyrimidinyl)-pyrazolo[1,5-a]pyridine (Example 2, 1.0 g, 3.0 mmol) in tetrahydrofuran (20 mL) was cooled to under nitrogen, lithium diisopropylamide (2M solution in heptane/tetrahydrofuran/ethylbenzene, 3.0 mL, 6.0 mmol) was added dropwise. The solution was stirred for 5 minutes then a solution of toluenesulfonyl chloride (1.2 g, 6.3 mmol) in tetrahydrofuran (5 mL) was added dropwise and the reaction mixture was stirred for 1 hour at −78° C. and then allowed to warm to room temperature. Ethyl acetate (30 mL) and water (20 mL) were added and the organic phase was separated. The aqueous phase was extracted with Ethyl acetate (3×20 mL) and the combined ethyl acetate phases were dried over magnesium sulfate filtered and the solvent was evaporated to give a brown oil. Purification on silica gel using 1:1 hexane/dichloromethane as eluent gave 7-chloro-2-(4-fluorophenyl)-3-(4-(2-methylthio)pyrimidinyl)pyrazolo[1,5-a]pyridine, 0.316 g (28%). ¹H NMR (CDCl$_3$): δ 2.65 (s, 3H), 6.73 (d, J=5.4 Hz, 1H), 7.12–7.25 (m, 3H), 7.39 (dd, J=7.4, 8.9 Hz, 1H), 7.62–7.69 (m, 2H), 8.30 (d, J=5.2 Hz, 1H), 8.50 (d, J=8.1 Hz, 1H); APEI+MS m/z 371/373 (M+1)⁻.

EXAMPLE 9

N-Butyl-4-[7-(2-fluoroethoxy)-2-(4-fluorophenyl)pyrazolo[1,5-a]pyridin-3-yl]-2-pyrimidinamine

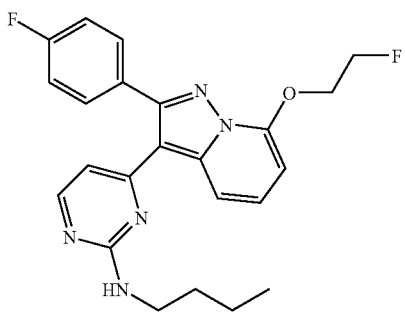

In a similar manner as described in Example 4, from 7-(2-fluoroethoxy)-2-(4-fluorophenyl)-3-(4-(2-methylsulfinyl)pyrimidinyl)pyrazolo[1,5-a]pyridine (Example 24) and n-butylamine was obtained the title compound, (68%). $^1$H NMR (CDCl$_3$): δ 0.96 (t, J=7.3 Hz, 3H), 1.44 (sextet, J=7.5 Hz, 2H), 1.62 (quintet, J=7.5 Hz, 2H), 3.45 (q, J=6.5 Hz, 2H), 4.59 (t, J=4.1 Hz, 1H), 4.66 (t, J=4.1 Hz, 1H), 4.86 (t, J=4.1 Hz, 1H), 4.98 (t, J=4.1 Hz, 1H), 5.4 (bs, 1H), 6.26 (d, J=5.3 Hz, 1H), 6.32 (d, J=7.3 Hz, 1H), 7.11 (t, J=8.7 Hz, 2H), 7.30 (t, J=7.8 Hz, 1H), 7.60 (dd, J=5.4, 8.6 Hz, 2H), 8.01 (d, J=5.1 Hz, 1H), 8.09 (d, J=9.0 Hz, 1H); APESI+MS m/z 424 (M+1)$^-$.

EXAMPLE 10

N-Benzyl-4-[7-(2-fluoroethoxy)-2-(4-fluorophenyl)pyrazolo[1,5-a]pyridin-3-yl]-2-pyrimidinamine

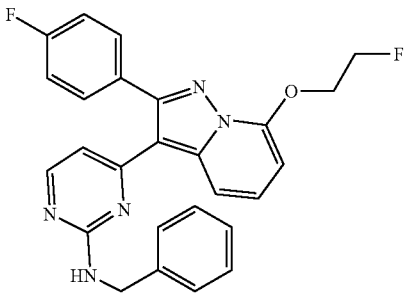

In a similar manner as described in Example 4, from 7-(2-fluoroethoxy)-2-(4-fluorophenyl)-3-(4-(2-methylsulfinyl)pyrimidinyl)pyrazolo[1,5-a]pyridine (Example 24) and benzylamine was obtained the title compound, (73%). $^1$H NMR (CDCl$_3$): δ 4.56 (t, J=4.1 Hz, 1H), 4.64 (t, J=4.1 Hz, 1H), 4.72 (d, J=5.7 Hz, 2H), 4.85 (t, J=4.1 Hz, 1H), 4.96 (t, J=4.1 Hz, 1H), 5.7 (bs, 1H), 6.28–6.31 (m, 2H), 7.08–7.16 (m, 3H), 7.26–7.30 (m, 1H), 7.34 (d, J=7.9 Hz, 2H), 7.39 (t, J=6.5 Hz, 2H), 7.60 (dd, J=5.5, 8.6 Hz, 2H), 7.75 (bs, 1H), 8.01 (d, J=5.1 Hz, 1H); APESI+MS m/z 458 (M+1)$^-$.

EXAMPLE 11

2-(4-Fluorophenyl)-3-(4-(2-methylthio)pyrimidinyl)-7-(2,2,2-trifluoro-ethoxy)pyrazolo[1,5-a]pyridine

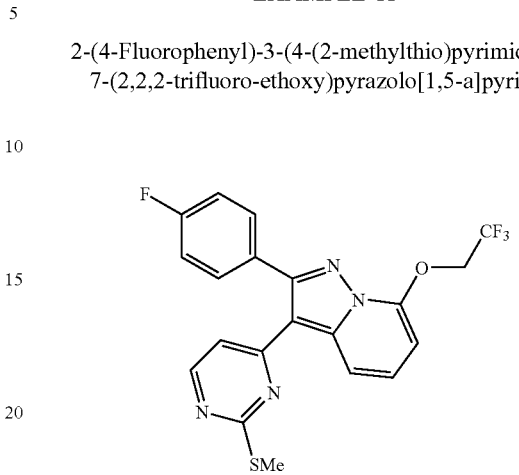

a) 2-(4-Fluorophenyl)-3-(4-(2-methylthio)pyrimidinyl)-7-(2,2,2-trifluoro-ethoxy)pyrazolo[1,5-a]pyridine.

A solution of 7-chloro-2-(4-fluorophenyl)-3-(4-(2-methylthio)-pyrimidinyl)pyrazolo[1,5-a]pyridine (1.6 g, 4.3 mmol) in dichloromethane (100 mL), was cooled in an ice bath. To this solution was added a solution of 2,2,2-trifluoroethanol (1.6 mL, 22 mmol) and potassium tert-butoxide (22 mL of a 1M solution in tert-butanol) in tetrahydrofuran (50 mL). The reaction mixture was subsequently warmed to 60° C. for 18 h, then poured into cold water and neutralized with 1 N HCl. The phases were separated, and the organics were washed with water (2×50 mL), dried (magnesium sulfate), filtered, and evaporated under reduced pressure. The residue was purified by silica gel chromatography with ethyl acetate:hexane (1:2) to give the title compound as a yellow solid, 1.6 g (86%): $^1$H NMR (CDCl$_3$): δ 2.65 (s, 3H), 4.86 (q, J=8.0 Hz, 2H), 6.56 (d, J=7.4 Hz, 1H), 6.73 (d, J=5.4 Hz, 1H), 7.20 (t, J=8.6 Hz, 2H), 7.42 (t, J=8.3 Hz, 1H), 7.65 (dd, J=5.5 Hz, 8.8 Hz, 2H), 8.28 (d, J=8.9 Hz, 1H), 8.29 (d, J=5.2 Hz, 1H); APESI+MS m/z 435 (M+1).

b) 7-Chloro-2-(4-fluorophenyl)-3-(4-(2-methylthio)pyrimidinyl)pyrazolo[1,5-a]-pyridine.

2-(4-Fluorophenyl)-3-(4-(2-methylthio)pyrimidinyl)pyrazolo[1,5-a]pyridine (17 g, 50 mmol) (see Example 2) was dissolved in tetrahydrofuran and cooled to −78° C. in a dry ice/acetone bath. Lithium diisopropylamide (2M solution in tetrahydrofuran, 76 mL, 0.152 mol) was added. After 20 min, carbon tetrachloride (88 mL, 910 mmol) was added. After 2 h, the solution was quenched with saturated brine (50 mL), and layers separated. The organics were washed with saturated brine (100 mL), dried (magnesium sulfate), filtered and concentrated. The residue was purified by silica gel chromatography with dichloromethane to give the title compound as a yellow solid, 15 g (80%). $^1$H NMR (CDCl$_3$): δ 2.67 (s, 3H), 4.86 (q, J=8.0 Hz, 2H), 6.57 (d, J=7.4 Hz, 1H), 6.75 (d, J=5.4 Hz, 1H), 7.21 (t, J=8.6 Hz, 2H), 7.45 (t, J=8.2 Hz, 1H), 7.65 (dd, J=5.4 Hz, 8.7 Hz, 2H), 8.28 (apparent d, J=8.1 Hz, 2H); APESI+MS m/z 371 (M+1).

EXAMPLE 12

N-Butyl-4-[2-(4fluorophenyl)-7-(2,2,2-trifluoroethoxy)pyrazolo[1,5-a]pyridin-3-yl]-2-pyrimidinamine

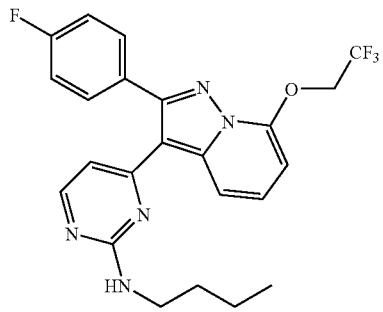

In a similar manner as descibed in Example 4, from 2-(4-fluorophenyl)-3-(4-(2-methylsulfinyl)pyrimidinyl)-7-(2,2,2-trifluoroethoxy)pyrazolo[1,5-a]pyridine (Example 25) and n-butylamine was obtained the title compound as a white solid, (31%). $^1$H NMR (CDCl$_3$): δ 1.02 (t, J=7.3 Hz, 3H), 1.51 (sextet, J=7.5 Hz, 2H), 1.72 (quintet, J=7.5 Hz, 2H), 3.51 (q, J=7.0 Hz, 2H), 4.86 (q, J=8.1 Hz, 2H), 5.2 (bs, 1H), 6.35 (d, J=5.3 Hz, 1H), 6.52 (d, J=7.2 Hz, 1H), 7.17 (t, J=8.7 Hz, 2H), 7.35 (dd, J=7.6, 8.8 Hz, 2H), 7.68 (dd, J=5.4, 8.6 Hz, 2H), 8.10 (d, J=5.3 Hz, 1H), 8.21 (d, J=8.9 Hz, 1H); APESI+MS m/z 460 (M+1)$^-$.

EXAMPLE 13

N-Benzyl-4-[2-(4-fluorophenyl)-7-(2,2,2-trifluoroethoxy)pyrazolo[1,5-a]-pyridin-3-yl]-2-pyrimidinamine

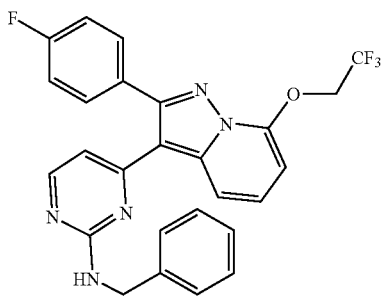

In a similar manner as described in Example 4, from 2-(4-fluorophenyl)-3-(4-(2-methylsulfinyl)pyrimidinyl)-7-(2,2,2-trifluoroethoxy)pyrazolo[1,5-a]pyridine (Example 25, 0.034 g, 0.076 mmol) and benzylamine was obtained the title compound, 0.03 g (80%). $^1$H NMR (CDCl$_3$): δ 4.65 (d, J=5.8 Hz, 2H), 4.72 (dd, J=8.1, 16.3 Hz, 2H), 5.6 (bs, 1H), 6.27 (d, J=5.3 Hz, 1H), 6.36 (d, J=7.3 Hz, 1H), 7.07 (t, J=8.6 Hz, 3H), 7.23–7.29 (m, 1H), 7.29–7.35 (m, 4H), 7.56 (dd, J=5.7, 8.5 Hz, 2H), 7.7 (bs, 1H), 8.00 (d, J=5.3 Hz, 1H); APESI+MS m/z 494 (M+1)$^-$.

EXAMPLE 14

N-Cyclopropyl-4-[2-(4-fluorophenyl)-7-(2,2,2-trifluoroethoxy)pyrazolo[1,5-a]pyridin-3-yl]-2-pyrimidinamine

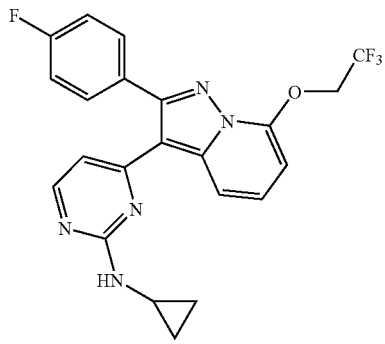

2-(4-Fluorophenyl)-3-(4-(2-methylsulfinyl)pyrimidinyl)-7-(2,2,2-trifluoroethoxy)-pyrazolo[1,5-a]pyridine (Example 25, 1.4 g 3.1 mmol) was dissolved in dichloromethane (50 mL) and treated with cyclopropylamine (10 mL, 61 mmol). The solution was heated at reflux for six days, cooled to room temperature and then diluted with dichloromethane. The solution was washed with saturated sodium bicarbonate (25 mL) and water (25 mL), dried (magnesium sulfate), filtered and the solvent evaporated under reduced pressure. The residue was purified by silica gel chromatography with ethyl acetate:hexane (1:1) as eluent to give the title compound as a white solid, 1.1 g (80%): $^1$H NMR (acetone-d$_6$): δ 0.47 (br. s, 2H), 0.66 (br. s, 2H), 2.70 (m, 1H), 5.02 (q, J=8.2 Hz, 2H), 6.22 (d, J=5.2 Hz, 1H), 6.41 (br. s, 1H), 6.62 (d, J=7.2 Hz, 1H), 7.15 (t, J=8.5 Hz, 2H), 7.33 (t, J=8.1 Hz, 1H), 7.60 (m, 2H), 7.94 (d, J=5.1 Hz, 1H), 8.34 (br. s, 1H); APESI+MS m/z 444 (M+1).

EXAMPLE 15

N-Cyclopentyl-4-[2-(4-fluorophenyl)-7-(2,2,2-trifluoroethoxy)pyrazolo[1,5-a]pyridin-3-yl]-2-pyrimidinamine

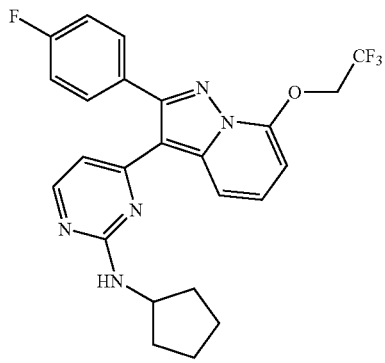

2-(4-Fluorophenyl)-3-(4-(2-methylsulfinyl)pyrimidinyl)-7-(2,2,2-trifluoroethoxy)pyrazolo[1,5-a]pyridine (Example 25, 0.05 g, 0.11 mmol) was dissolved in cyclopentylamine (1 mL) and heated at 60° C. for 18 hours. The reaction mixture was diluted with ethyl acetate (40 mL) and extracted with water (2×10 mL). The organic layer was dried (magnesium sulfate), filtered and the solvent was evaporated under reduced pressure. The residue was purified on a silica gel preparative chromatography plate (2 mm) with ethyl acetate:hexanes (1:2) as eluent to give the title compound, 0.008 g (15%). $^1$H NMR (acetone-d$_6$): δ 1.60 (m, 4H), 1.75 (m, 2H), 2.04 (m, 2H), 4.32 (m, 1H), 5.13 (q, J=8.4 Hz, 2H), 6.23 (br. s, 1H), 6.30 (d, J=4.7 Hz, 1H), 6.73 (d, J=7.5 Hz, 1H), 7.25 (t, J=8.7 Hz, 2H), 7.43 (t, J=8.1 Hz, 1H), 7.70 (dd, J=5.5 Hz, 8.8Hz, 2H), 8.04 (d, J=5.1 Hz, 1H), 8.24 (d, J=9 Hz, 1H); APESI+MS m/z 472 (M+1).

EXAMPLE 16

N-Cyclohexyl-4-[2-(4-fluorophenyl)-7-(2,2,2-trifluoroethoxy)pyrazolo[1,5-a]pyridin-3-yl]-2-pyrimidinamine

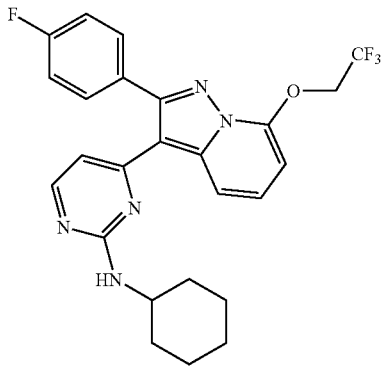

In a similar manner as described in Example 15 from 2-(4-fluorophenyl)-7-(2,2,2-trifluoroethoxy)-3-(4-(2-methylsulfinyl)pyrimidinyl)pyrazolo[1,5-a]pyridine (Example 25) was obtained the title compound, (49%). $^1$H NMR (acetone-d$_6$): δ1.3 (m, 5H), 1.60 (m, 1H), 1.80 (m, 2H), 2.00 (m, 2H), 3.80 (m, 1H), 5.13 (q, J=8.4 Hz, 2H), 6.12 (br s, 1H), 6.30 (br s, 1H), 6.73 (d, J=7.5 Hz, 1H), 7.25 (t, J=8.7 Hz, 2H), 7.43 (t, J=8.1 Hz, 1H), 7.69 (dd, J=5.5 Hz, 8.6 Hz, 2H), 8.04 (d, J=5.1 Hz, 1H), 8.22 (d, J=8.9 Hz, 1H); APESI+MS m/z 485 (M+1).

EXAMPLE 17

3-(4-[2-(4-Fluorophenyl)-7-(2,2,2-trifluoroethoxy)pyrazolo[1,5-a]pyridin-3-yl]-2-pyrimidinylamino)-1-propanol

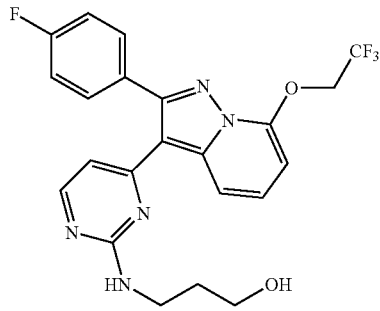

In a similar manner as described in Example 15. From 2-(4-fluorophenyl)-7-(2,2,2-trifluoroethoxy)-3-(4-(2-methylsulfinyl)pyrimidinyl)pyrazolo[1,5-a]pyridine (Example 25) was obtained the title compound, (38%). $^1$H NMR (acetone-d$_6$): δ 1.69 (m, 2H), 3.44 (apparent q, J=6.4 Hz, 2H), 3.53 (br s, 2H), 3.75 (br. s, 1H), 5.01 (q, J=8.4 Hz, 2H), 6.19 (d, J=5.2 Hz, 1H), 6.32 (br.s, 1H), 6.62 (d, J=7.5 Hz, 1H), 7.14 (t, J=8.9 Hz, 2H), 7.32 (t, J=8.2 Hz, 1H), 7.59 (dd, J=5.6 Hz, 8.6 Hz, 2H), 7.93 (d, J=5.2 Hz, 1H), 8.14 (d, J=8.9 Hz, 1H); APESI+MS m/z 462 (M+1).

EXAMPLE 18

2-(4-Fluorophenyl)-3-(4-(2-methyloxy)pyrimidinyl)-7-(2,2,2-trifluoroethoxy)pyrazolo[1,5-a]pyridine

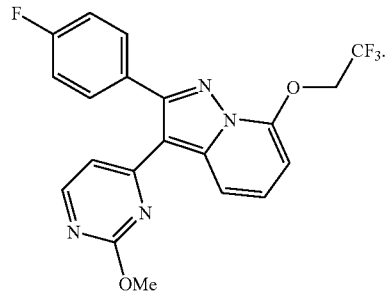

2-(4-Fluorophenyl)-7-(2,2,2-trifluoroethoxy)-3-(4-(2-methylsulfinyl)pyrimidinyl) pyrazolo[1,5-a]pyridine (Example 25) (0.05 g, 0.11 mmol) was dissolved in 2 N ammonia in methanol (20 mL) and the mixture was heated at 80° C. for 18 hours. The reaction mixture was diluted with ethyl acetate (40 mL) and extracted with water (2×10 mL). The organic layer was dried (magnesium sulfate), filtered and evaporated under reduced pressure. The residue was purified on a silica gel preparative chromatography plate (2 mm) with ethyl acetate:hexane (1:2) as eluent to give the title compound, 0.034 g (73%). $^1$H NMR (CDCl$_3$) δ 4.12 (s, 3H), 4.86 (q, J=8.0 Hz, 2H), 6.56 (d, J=7.4 Hz, 1H), 6.71 (d, J=5.2 Hz, 1H), 7.21 (t, J=8.5 Hz, 2H), 7.42 (t, J=8.2 Hz, 1H), 7.65 (dd, J=5.4 Hz, 7.7 Hz, 2H), 8.30 (d, J=5.2 Hz, 1H), 8.35 (d, J=8.9 Hz, 1H); APESI+MS m/z 419 (M+1).

EXAMPLE 19

2-(4-Fluorophenyl)-3-(4-(2-phenyloxy)pyrimidinyl)-7-(2,2,2-trifluoroethoxy)pyrazolo[1,5-a]pyridine

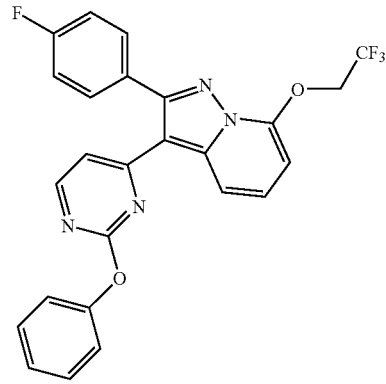

2-(4-Fluorophenyl)-7-(2,2,2-trifluoroethoxy)-3-(4-(2-methylsulfinyl)pyrimidinyl)pyrazolo[1,5-a]pyridine (Example 25) (0.05 g, 0.11 mmol) was dissolved in dichloromethane (3 mL) and treated with a solution of phenol (0.1 mL, 1.1 mmol) and potassium tert-butoxide (1.2 mL of a 1 N in tert-butyl alcohol) in tetrahydrofuran (3 mL). After 30 min at ambient temperature, the reaction was quenched with water and diluted with ethyl acetate (40 mL) and extracted with water (2×10 mL). The organic layer was dried (magnesium sulfate), filtered and evaporated under reduced pressure. The residue was purified on a silica gel preparative chromatography plate (2 mm) with ethyl acetate:hexane (1:2) as eluent to give the title compound, 0.032 g (61%). $^1$H NMR (CDCl$_3$): δ 4.81 (q, J=8.0 Hz, 2H), 6.49 (d, J=7.4 Hz, 1H), 6.74 (d, J=5.4 Hz, 1H), 7.17 (t, J=7.7 Hz, 1H), 7.23 (t, J=8.6 Hz, 2H), 7.32 (d, J=7.7 Hz, 2H), 7.36 (t, J=7.4 Hz, 1H), 7.53 (t, J=7.7 Hz, 2H), 7.63 (dd, J=5.4 Hz, 8.6 Hz, 2H), 7.76 (d, J=8.8 Hz, 1H), 8.31 (d, J=5.4 Hz, 1H); APESI+MS m/z 481 (M+1).

EXAMPLE 20

2-(4-Fluorophenyl)-3-(4-(2-(2,2,2-trifluoroethoxy))pyrimidinyl)-7-(2,2,2-trifluoroethoxy)pyrazolo[1,5-a]pyridine

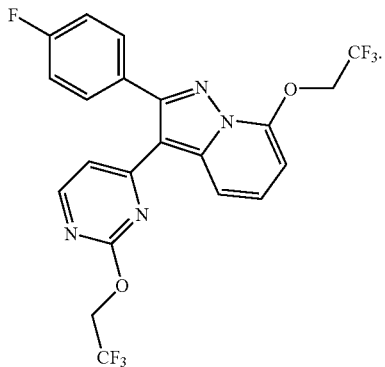

In a similar manner as described in Example 8, from 2-(4-fluorophenyl)-3-(4-(2-methylsulfinyl)pyrimidinyl)-7-(ethylsulfinyl)pyrazolo[1,5-a]pyridine (Example 21) and 2,2,2-trifluoroethanol was obtained the title compound, (10%). $^1$H NMR (CDCl$_3$): δ 4.78–4.85 (m, 4H), 6.52 (d, J=7.3 Hz, 1H), 6.75 (d, J=5.3 Hz, 1H), 7.16 (t, J=8.6 Hz, 2H), 7.41 (t, J=8.2 Hz, 1H), 7.58 (dd, J=5.3, 8.6 Hz, 2H), 8.22 (d, J=8.8 Hz, 1H), 8.25 (d, J=5.3 Hz, 1H); APESI+MS m/z 487 (M+1)$^-$.

EXAMPLE 21

2-(4-Fluorophenyl)-3-(4-(2-methylsulfinyl)pyrimidinyl)-7-(ethylsulfinyl)-pyrazolo[1,5-a]pyridine

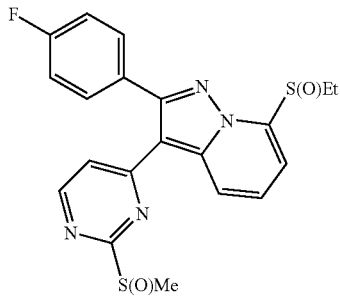

In a similar manner as described in Example 7, from 2-(4-fluorophenyl)-3-(4-(2-methylthio)pyrimidinyl)-7-(ethylthio)pyrazolo[1,5-a]pyridine was obtained the title compound. $^1$H NMR (CDCl$_3$): δ 1.25 (t, J=7.5 Hz, 3H), 3.00 (s, 3H), 3.33–3.45 (m, 2H), 7.05 (d, J=5.5 Hz, 1H), 7.20 (t, J=8.6 Hz, 2H), 7.54–7.59 (m, 3H), 7.67 (dd, J=7.3, 8.8 Hz, 1H), 8.52 (d, J=5.5 Hz, 1H), 8.25 (t, J=8.4 Hz, 1H); APESI+MS m/z 429 (M+1)$^-$.

EXAMPLE 22

2-(4-Fluorophenyl)-3-(4-(2-methylthio)pyrimidinyl)-7-(ethylthio)-pyrazolo[1,5-a]pyridine

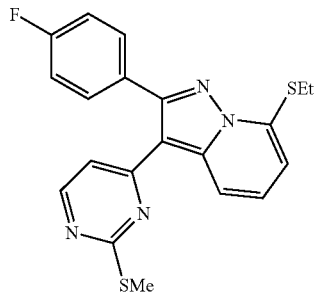

In a similar manner as described in Example 8, from 2-(4-fluorophenyl)-3-(4-(2-methylthio)pyrimidinyl)-pyrazolo[1,5-a]pyridine and diethyl disulfide in place of toluenesulfonyl chloride was obtained 2-(4-fluorophenyl)-3-(4-(2-methylthio)pyrimidinyl)-7-(ethylthio)pyrazolo[1,5-a]pyridine. $^1$H NMR (CDCl$_3$): δ 1.46 (t, J=7.4 Hz, 3H), 2.60 (s, 3H), 3.16 (q, J=7.4 Hz, 2H), 6.67 (d, J=5.5 Hz, 1H), 6.81 (d, J=7.3 Hz, 1H), 7.13 (t, J=8.6 Hz, 2H), 7.35 (t, J=8.1 Hz, 1H), 7.59 (dd, J=5.5, 8.6 Hz, 2H), 8.22 (d, J=5.5 Hz, 1H), 8.28 (d, J=9.0 Hz, 1H).

EXAMPLE 23

Dimethyl 2-(4-fluorophenyl)-3-(4-(2-cyclopropylamino)pyrimidinyl)-7-pyrazolo[1,5-a]pyridinylcarboxamide

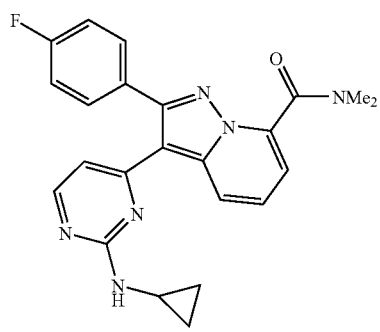

To a stirred solution of 2-(4-fluorophenyl)-7-pyrazolo[1,5-a]pyridine (5.38 g, 25 mmol) in dry tetrahydrofuran (100 mL) at −78° C. was added n-butyl lithium (2.5 M in hexanes. 12.2 mL, 30 mmol) and the mixture was stirred for 20 min. Dimethyl carbamoyl chloride (7.0 mL, 76 mmol) was added in one portion and the mixture was allowed to warm to room temperature. Diethyl ether was added followed by saturated aqueous sodium bicarbonate solution. The organic phase was separated and dried using anhydrous sodium sulfate.

The drying agent was removed by filtration and the solvent was evaporated under reduced pressure. The residue was purified by silica gel chromatography to give dimethyl 2-(4-fluorophenyl)-7-pyrazolo[1,5-a]pyridinylcarboxamide as a light green solid, 6.07 g (85%). In a similar manner as described in Example 34 from dimethyl 2-(4-fluorophenyl)-7-pyrazolo[1,5-a]pyridinylcarboxamide was obtained the title compound. $^1$H NMR (DMSO-$d_6$): δ 8.71 (d, 1H, J=8.1 Hz), 8.11 (d, 1H, J=5.1 Hz), 7.65 (m, 2H), 7.57 (dd, 1H, J=7.2, 8.7 Hz), 7.44 (d, 1H, J=2.7 Hz), 7.37 (m, 2H), 7.18 (d, 1H, J=6.3 Hz), 6.26 (d, 1H, J=5.1 Hz), 3.11 (s, 3H), 2.84 (s, 3H), 2.65 (m, 1H), 0.74 (m, 2H), 0.55 (m, 2H). MS (ES+ve): 417 (87%, M$^+$).

EXAMPLE 24

7-(2-Fluoroethoxy)-2-(4-fluorophenyl)-3-(4-(2-methylsulfinyl)-pyrimidinyl)-pyrazolo[1,5-a]pyridine

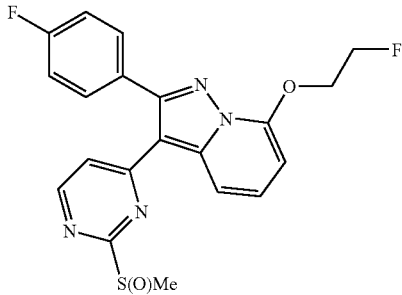

In a similar manner as described in Example 7, from 7-(2-fluoroethoxy)-2-(4-fluorophenyl)-3-(4-(2-methylthio)pyrimidinyl)pyrazolo[1,5-a]pyridine was obtained 7-(2-fluoroethoxy)-2-(4-fluorophenyl)-3-(4-(2-methylsulfinyl)pyrimidinyl)pyrazolo[1,5-a]pyridine. $^1$H NMR (CDCl$_3$): δ 3.04 (s, 3H), 4.65 (t, J=4.0 Hz, 1H), 4.75 (t, J=4.0 Hz, 1H), 4.91 (t, J=4.1 Hz, 1H), 5.06 (t, J=4.1 Hz, 1H), 6.50 (d, J=7.5 Hz, 1H), 7.02 (d, J=5.5 Hz, 1H), 7.24 (t, J=8.6 Hz, 2H), 7.54 (t, J=8.3 Hz, 1H), 7.62–7.67 (m, 2H), 8.48–8.53 (m, 2H).

EXAMPLE 25

2-(4-Fluorophenyl)-3-(4-(2-methylsulfinyl)pyrimidinyl)-7-(2,2,2-trifluoroethoxy)-pyrazolo[1,5-a]pyridine

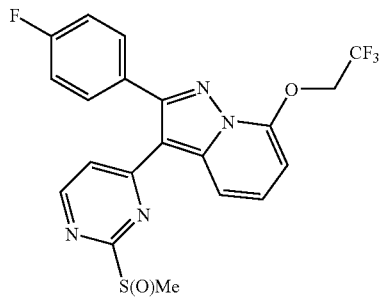

In a similar manner as described in Example 7, from 2-(4-fluorophenyl)-3-(4-(2-methylthio)pyrimidinyl)-7-(2,2,2-trifluoroethoxy)pyrazolo[1,5-a]pyridine and m-chloroperbenzoic acid was obtained 2-(4-fluorophenyl)-3-(4-(2-methylsulfinyl)-pyrimidinyl)-7-(2,2,2-trifluoroethoxy) pyrazolo[1,5-a]pyridine. $^1$H NMR (CDCl$_3$): δ 3.03 (s, 3H), 4.85 (q, J=8.0 Hz, 2H), 6.60 (d, J=7.3 Hz, 1H), 7.05 (d, J=5.3 Hz, 1H), 7.24 (t, J=7.6 Hz, 2H), 7.52 (t, J=8.2 Hz, 2H), 7.60–7.68 (m, 2H), 8.51 (d, J=5.5 Hz, 1H), 8.57 (d, J=8.8 Hz, 1H).

EXAMPLE 26

2-(4Fluorophenyl)-3-(4-pyridyl)-pyrazolo[1,5-a] pyridine

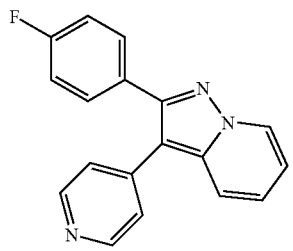

a) 2-(4-Fluorophenyl)-3-(4-pyridyl)-pyrazolo[1,5-a]pyridine.

To a solution of 2-(4-fluorophenyl)-3-bromopyrazolo[1,5-a]pyridine (0.2 g, 0.68 mmol) and 4-(tributylstannyl)pyridine (0.38 g, 1 mmol) in dry toluene (10 mL) was added tetrakis(triphenylphosphine)palladium (0) (0.03 g, 0.03 mmol) and the mixture was heated at reflux temperature under a nitrogen atmosphere for about 48 hours. The mixture was cooled to room temperature and diluted with diethyl ether (40 mL). The mixture was poured into a 10% aqueous solution of potassium fluoride (20 mL) and the mixture was stirred for 1 hour. The biphasic mixture was filtered through a pad (1 cm) of diatomaceous earth and the Organic phase was separated. The aqueous phase was extracted with diethyl ether (10 mL) and the combined organic phases are washed with brine, dried over anhydrous magnesium sulfate, filtered and the solvent evaporated under reduced pressure. The residue was purified using silica gel chromatography with 20% ethyl acetate in hexanes, followed by 50% ethyl acetate in hexanes, as eluent to give the title compound as an off white solid, 0.16 g (80%). $^1$H NMR (CDCl$_3$) δ 8.58 (br s, 2H), 8.50 (d, 1H, J=7.2 Hz), 7.63 (d, 1H, 9 Hz), 7.52 (m, 2H), 7.27–7.20 (m, 3H), 7.06 (t, 2H, 8.7 Hz), 6.86 dt, 1H, J=7, 1 Hz). MS (+ve ion electrospray) 290 (100), (MH$^+$).

b) 2-(4Fluorophenyl)-3-bromopyrazolo[1,5-a]pyridine.

To a solution of 2-(4fluorophenyl)-pyrazolo[1,5-a]pyridine-3-carboxylic acid (0.96 g, 3.75 mmol) in dry N,N-dimethylformamide (10 mL) was added sodium bicarbonate (0.95 g, 11.3 mmol) followed by N-bromosuccinimide (0.667 g, 3.75 mmol) and the mixture was stirred at room temperature under a nitrogen atmosphere for about 90 minutes. The mixture was poured into water (300 mL) and the resulting solid was collected by filtration and washed with water. The solid was dissolved in 10:1 chloroform:methanol (10 mL) and filtered through a pad (0.5 cm) of silica gel using 10:1 chloroform:methanol as eluent. The filtrate was evaporated to leave the title compound as a tan solid, 0.87 g (80%). $^1$H NMR (d6 DMSO) δ 8.7 (d, 1H, J=6.9 Hz), 8.02 (dd, 2H, J=8.7, 5.7 Hz), 7.61 (d, 1H, J=8.4 Hz), 7.40 (t, 1H, J=6 Hz), 7.38 (t, 2H, J=9 Hz), 7.04 (t, 1H, J=6.9 Hz). MS (+ve ion electrospray) 293 (100), (MH$^+$).

c) 2-(4-Fluorophenyl)-pyrazolo[1,5-a]pyridine-3-carboxylic acid.

A solution of methyl 2-(4-fluorophenyl)-pyrazolo[1,5-a]pyridine-3-carboxylate (5.0 g, 18.5 mmol) in 2N aqueous sodium hydroxide (50 ml) and methanol (30 mL) was heated at reflux for about 3 hours. The mixture was filtered and the filtrate was washed with diethyl ether (20 mL) and then concentrated under reduced pressure to about half the original volume. Concentrated hydrochloric acid was added to adjust the pH to about 2 and the resulting solid was collected by filtration and washed with water and dried under vacuum to give the title compound as a white solid, 4.8 g (ca. 100%). $^1$H NMR (d6 DMSO) δ 12.43 (br s, 1h), 8.84 (d, 1H, J=6.9 Hz), 8.14 (d, 1H, J=9 Hz), 7.82 (m, 2H), 7.57 (t, 1H, J=8.1 Hz), 7.28 (t, 2H, J=9 Hz), 7.15 (td, 1H, J=6.9, 1.2 Hz). MS (+ve ion electrospray) 257 (100), (MH$^+$).

d) Methyl 2-(4-fluorophenyl)-pyrazolo[1,5-a]pyridine-3-carboxylate.

A stirred solution of methyl 3-(4-fluorophenyl)propiolate (8.02 g, 45 mmol) and 1-aminopyridinium iodide (10 g, 45 mmol) in dry acetonitrile (150 mL) was cooled to about 0° C. A solution of 1,8-diazabicycloundec-7-ene (13.7 g, 90 mmol) in dry acetonitrile (50 mL) was added dropwise over 1 hour. The mixture was allowed to stir at room temperature for about 18 h. The reaction mixture was cooled in an ice bath for about 30 minutes and the precipitate was collected by filtration and washed with cold acetonitrile (10 mL). The solid was dried under reduced pressure to give the title compound as a white solid, 8.48 g (70%). $^1$H NMR (CDCl3) δ 8.50 (d, 1H, J=8.4 Hz), 8.18 (d, 1H, J=8.8 Hz), 7.78 (m, 2H), 7.42 (t, 1H, J=8.4 Hz), 7.13 (t, 2H, J=8.8 Hz), 6.97 (td, 1H, J=6.8, 1 Hz).). MS (+ve ion electrospray) 271 (100), (MH$^+$).

e) Methyl 3-(4fluorophenyl)propiolate.

A solution of 1-(4-fluorophenyl)-2-trimethylsilylacetylene (64 g, 0.33 mol) in dry diethyl ether (400 mL) was cooled to 0° C. under a nitrogen atmosphere. To this solution was added, dropwise over 45 minutes, a solution of tetrabutylammonium fluoride (1M in tetrahydrofuran, 330 mL, 0.33 mol) via a dropping funnel maintaining the internal temperature below 2° C. The mixture was allowed to warm to room temperature over about 1 hour. Diethyl ether (300 mL) was added to the mixture and the organic solution was washed with water, saturated brine and then dried over anhydrous magnesium sulfate. The magnesium sulfate was removed by filtration and the filtrate was cooled to about −78° C. n-Butyl lithium (1.6M in hexanes, 450 mL, 0.72 mol) was added dropwise via a dropping funnel over about 1 hour while the temperature was maintained below −66° C. After complete addition the mixture was stirred at −78° C. for about 1 hour and then a precooled solution of methyl chloroformate (110 mL, 1.4 mol) in dry diethyl ether (200 mL) was added in a continuous stream as fast as possible. The mixture was allowed to cool to −78° C. and the allowed to warm to room temperature over 1.5 h. The organic reaction mixture was washed with water and saturated brine and then dried over anhydrous magnesium sulfate. The solvents are remove under reduced pressure and the residue dried under reduced pressure to give the title compound as a brown solid, 36.5 g (61%). $^1$H NMR (CDCl3) δ 7.58 (dd, 2H, J=9, 5.4 Hz), 7.07 (t, 2H, J=8.5 Hz), 3.84 (s, 3H). MS (+ve ion electrospray) 178 (30), (M$^+$).

f) 1-(4-Fluorophenyl)-2-trimethylsilylacetylene.

4-Fluoroiodobenzene (112 mL, 0.97 mol) and triethylamine (176 mL, 1.26 mol) are dissolved in dry tetrahydrofuran (1.2 L) and nitrogen gas was bubbled through the solution for about 20 min. Copper (I) iodide (1.08 g, 5.7 mmol) and bis(triphenyphosphine)palladium dichloride (2.15 g, 3 mmol) are added and then trimethylsilylacetylene (178 mL, 1.3 mol) was added dropwise over about 40 min with the temperature being maintained at about 23° C. A large amount of precipitate forms (presumably Et$_3$NHCl) which necessitates mechanical stirring. Following complete addition of the trimethylsilylacetylene the mixture was allowed to stir at room temperature for about 18 hours. The mixture was filtered and the solid washed with cyclohexane. The combined filtrates are concentrated under reduce pressure to give a brown oil. Application of this oil to a pad of silica gel followed by elution with cyclohexane gave a yellow solution. Removal of the solvent gave the title compound as a yellow oil; 182.8 g (95%).

EXAMPLE 27

2-(4-Fluorophenyl)-7-methyl-3-(4-pyridinyl)pyrazolo[1,5-a]pyridine

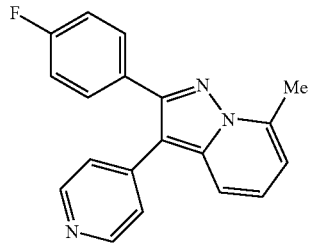

a) 2-(4-Fluorophenyl)-7-methyl-3-(4-pyridinyl)pyrazolo[1,5-a]pyridine.

In a similar manner as described in Example 26, from 2-(4-fluorophenyl)-3-bromo-7-methylpyrazolo[1,5-a]pyridine (0.1 g, 0.33 mmol) and 4-(tri-n-butyl)stannylpyridine (0.17 g, 0.46 mmol) was obtained the title compound as a white solid, 0.016 g (14%). This material was dissolved in diethyl ether and treated with HCl in diethyl ether to afford the corresponding hydrochloride salt. $^1$H NMR (DMSO-d6) δ 8.74 (d, 2H, J=6.6 Hz), 7.91 (d, 1H, J=8.9 Hz), 7.81 (d, 2H, J=6.6 Hz), 7.61 (m, 2H), 7.56 (t, 1H, J=15.9 Hz), 7.34 (t, 2H, J=17.6 Hz), 7.15 (d, 1H, J=6.9 Hz), 2.79 (s, 3H). MS (+ve electrospray) 303 (100), (M+).

b) 2-(4-Fluorophenyl)-3-bromo-7-methyl-pyrazolo[1,5-a]pyridine.

Following the procedure outlined in Example 26, from 2-(4-fluorophenyl)-7-methyl-pyrazolo[1,5-a]pyridine-3-carboxylic acid was obtained the title compound, $^1$H NMR (CDCl$_3$) δ 8.00 (m, 2H), 7.38 (d, 1H, J=8.8 Hz), 7.11 (m, 3H), 6.62 (d, 1H, J=6.9 Hz), 2.71 (s, 3H). MS (+ve electrospray) 306 (25), (MH+).

c) 2-(4-Fluorophenyl)-7-methyl-pyrazolo[1,5-a]pyridine-3-carboxylic acid.

In a similar manner as described in Example 26, from methyl 2-(4-fluorophenyl)-7-methyl-pyrazolo[1,5-a]pyridine-3-carboxylate was obtained the title compound as a white solid, $^1$H NMR (DMSO-d6) δ 8.08 (d, 1H, J=8.8 Hz), 7.84 (m, 2H), 7.76 (m, 1H), 7.53 (m, 1H), 7.30 (t, 2H, J=17.8 Hz), 7.09 (d, 1H, J=6.8 Hz), 2.75 (s, 3H). MS (+ve electrospray) 270 (100), (M+).

d) Methyl 2-(4-fluorophenyl)-7-methyl-pyrazolo[1,5-a]pyridine-3-carboxylate.

To a stirred solution of methyl 3-(4-fluorophenyl)propiolate (3.47 g, 19.5 mmol) and 1-amino-2-methylpyridinium 2,4,6-trimethylbenzenesulfonate (6.0 g, 19.5 mmol) in dry acetonitrile (75 mL) was added, dropwise over 10 min a solution of 1,8-diazabicycloundec-7-ene (5.82 mL, 39 mmol) in dry acetonitrile (25 mL). The mixture was allowed to stir at room temperature for about 18 hours. The solvent was evaporated under reduced pressure and the residue was partitioned between water (500 mL) and ethyl acetate (250 mL) and the organic phase separated. The aqueous was extracted with ethyl acetate and the combined organic extracts are dried over anhydrous magnesium sulfate, and the solvent removed under vacuum. The residue was purified by chromatography on silica gel using 10:1 hexanes:ethyl acetate as eluent to give the title compound as a white solid, 4.65 g (86%). $^1$H NMR (CDCl$_3$) δ 8.15 (d, 1H, J=8.8 Hz), 7.86 (m, 2H), 7.41 (t, 1H, J=8.9 Hz), 7.19 (t, 2H, J=17.6 Hz), 6.87 (d, 1H, J=7.0 Hz), 3.89 (s, 3H), 2.85 (s, 3H). MS (+ve ion electrospray) 285 (100), (MH+).

e) 1-Amino-2-methylpyridinium 2,4,6-trimethylbenzenesulfonate.

To cold (0° C.) trifluoroacetic acid (50 mL) was added N-tert-butoxycarbonyl-O-(mesitylsulfonyl)hydroxylamine (16.09 g, 51 mmol) in portions over about 15 minutes. The solution was then stirred for about 15 minutes at room temperature. The solution was poured into ice water (250 mL) and the resulting white precipitate was collected by filtration and air-dried for 5 minutes. The solid was dissolved in chloroform (100 mL) and this solution was dried over anhydrous magnesium sulfate. The magnesium sulfate was removed by filtration and the filtrate was added to a solution of 2-picoline (5.0 g, 54 mmol) in chloroform (5 mL). The mixture was stirred for 45 min and then filtered. To the filtrate was added diethyl ether (225 ml) and the product allowed to precipitate. The solid was collected by filtration, washed with diethyl ether (50 mL) and dried to give the title compound as a white solid, 12.9 g (82%). $^1$H NMR (CDCl$_3$) δ 9.45 (d, 1H), 8.4 (br s, 2H), 7.84 (t, 1H), 7.55 (t, 1H), 7.50 (d, 1H), 6.80 (s, 2H), 2.81 (s, 3H), 2.62 (s, 6H), 2.25 (s, 3H). MS (+ve electrospray) 109 (100), (M+).

EXAMPLE 28

2-(4-Fluorophenyl)-7-methoxy-3-(4-pyridinyl)pyrazolo[1,5-a]-pyridine

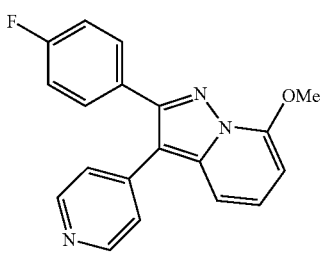

In a similar manner as described in Examples 26 and 27, from 2-methoxypyridine was obtained the title compound.

$^1$H NMR (400 MHz, DMSO-d$_6$) δ 4.12 (s, 3H), 6.52 (d, 1H, J=7.2 Hz), 7.24 (m, 4H), 7.35 (m, 2H), 7.51 (dd, 2H, J=5.6 Hz, 8.8 Hz), 8.53 (d, 2H, J=6.0 Hz). MS (ES+) m/z 320 (M++H).

Alternatively, 2-(4-fluorophenyl)-7-methoxy-3-(4pyridinyl)pyrazolo[1,5-a]-pyridine can be prepared from 7-chloro-2-(4-fluorophenyl)-3-(4-pyridinyl)pyrazolo[1,5-a]pyridine (see Example 29) by the following procedure: 7-chloro-2-(4-fluorophenyl)-3-(4-pyridinyl)pyrazolo[1,5-a]pyridine (0.05 g, 0.15 mmol) was added to a solution of sodium methoxide (0.75 mmol) in dry methanol (5 mL) and the mixture was heated at reflux for about 24 hours. Water was added and the mixture was extracted with ethyl acetate. The combined organic extracts are washed with brine and dried over anhydrous magnesium sulfate. The solution was filtered through a short pad of silica gel and the solvent was evaporated under vacuum. The residue was purified by silica gel chromatography using 1:10 MeOH:Ethyl acetate to give the title compound, 0.039 g (80%). $^1$H NMR and MS are identical to those described above.

EXAMPLE 29

7-Chloro-2-(4-fluorophenyl)-3-(4-pyridinyl)pyrazolo[1,5-a]-pyridine

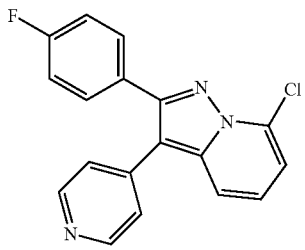

A stirred solution of 2-(4-fluorophenyl)-3-(4-pyridinyl)-pyrazolo[1,5-a]pyridine (from Example 26, 100 mg, 0.346 mmol) in dry tetrahydrofuran (4 mL) was cooled to about −78° C. under N$_2$ and n-butyllithium in hexanes (2.5 M in hexanes, 0.27 mL, 0.7 mmol) was added dropwise. The mixture was stirred at −78° C. for about 30 min and a solution of p-toluenesulfonyl chloride (0.15 g, 0.76 mmol) in dry tetrahydrofuran (1 mL) was added. The mixture was allowed to warm to room temperature over 30 min and was stirred at room temperature for 1 hour. Water was added and the mixture was poured into a separatory funnel. The organic layer was separated, and the aqueous layer was extracted with ethyl acetate. The combined organic layers were dried using anhydrous magnesium sulfate, filtered and evaporated. Purification by silica gel chromatography yielded the title compound, 0.087 g (78.6%). $^1$H NMR (CDCl$_3$): δ 8.65 (d, 2H, J=5.8 Hz), 7.55–7.69 (m, 3H), 7.30 (d, 2H, J=5.8 Hz), 7.11–7.21 (m, 1H), 7.04–7.13 (m, 3H). MS (ES+ve): 326 (25, M+3), 323 (50, M+), 290 (100).

EXAMPLE 30

2-(4-Fluorophenyl)-3-(2-fluoro-4-pyridinyl)-7-methoxypyrazolo[1,5-a]pyridine

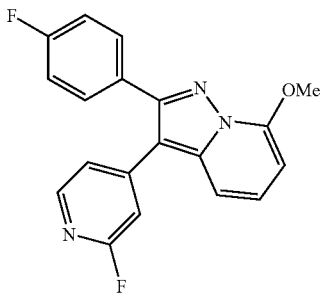

A solution of 3-bromo-2-(4-fluorophenyl)-7-methoxypyrazolo[1,5-a]pyridine (from Example 27, 180 mg, 0.560 mmol), 2-fluoropyridin-4-ylboronic acid (from Example 33, 112 mg, 0.800 mmol) and dichlorobis(triphenylphosphine) palladium (40.0 mg, 0.056 mmol) in N,N-dimethylformamide (6.00 mL) was placed in a pre-heated oil bath at 110° C. To the reaction was added, in a dropwise manner, 2M sodium carbonate (0.840 mL, 1.68 mmol). The reaction was allowed to stir for three hours before cooling to room temperature and filtering through a Celite 545 pad. The Celite filter was washed with ethyl acetate and the filtrate was concentrated to dryness at 50° C. under vacuum. The residue was dissolved in methylene chloride and dried over anhydrous magnesium sulfate. The drying agent was removed by filtration and the filtrate was concentrated and purified by silica gel chromatography to yield the title compound (110 mg, 0.326 mmol, 58%). $^1$H NMR (CDCl$_3$): δ 8.14 (d, 1H, J=5.5 Hz), 7.53(dd, 2H, J=6.0, 8.0 Hz), 7.24–7.32(m, 2H), 7.00–7.10(m, 3H), 6.89(s, 1H), 6.23(dd, 1H, J=2.0, 6.0 Hz), 4.2(s, 3H). MS (ES+ve): 338.1 (40, M$^+$), 323.1 (100).

EXAMPLE 31

N-Butyl-4-[2-(4-fluorophenyl)-7-methoxypyrazolo[1,5-a]pyridin-3-yl]-2-pyridinamine

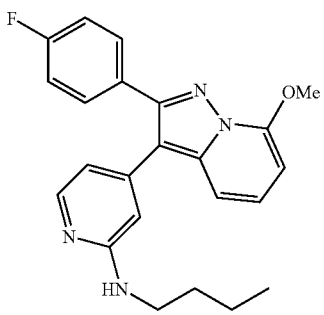

In a sealed-tube was combined 2-(4Fluorophenyl)-3-(2-fluoro-4-pyridinyl)-7-methoxypyrazolo[1,5-a]pyridine (from Example 30, 20 mg, 0.06 mmol) and n-butylamine (2.0 mL, 1.5 g, 20 mmol), and the reaction was placed in a pre-heated oil bath at 130° C. The reaction was stirred at 130° C. until consumption of starting material was indicated by TLC analysis (50% ethyl acetate in hexanes). The contents of the sealed-tube was transferred to a flask and concentrated to dryness at 50° C. under high vacuum. The residue was purified by silica gel chromatography to yield the title compound, 2.0 mg (0.005 mmol, 80%). $^1$H NMR (d$_6$-acetone): δ 8.04(d, 1H, J=5.1 Hz), 7.74(dd, 2H, J=5.7, 9.0 Hz), 7.33–7.38(m, 2H), 7.22(t, 2H, J=9.0 Hz), 6.45–6.54 (m, 3H), 4.25(s, 3H), 3.30–3.40(m, 2H), 1.60(quint, 2H, J=7.2 Hz), 1.45(sext, 2H, J=7.2 Hz), 0.9(t, 3H, J=7.2 Hz). MS (ES+ve): 391.1 (100, M$^+$), 376.3 (100).

EXAMPLE 32

N-{4-[5-Chloro-7-(ethylsulfanyl)-2-(4-fluorophenyl)pyrazolo[1,5-a]pyridin-3-yl]-2-pyrimidinyl}-N-cyclopentylamine

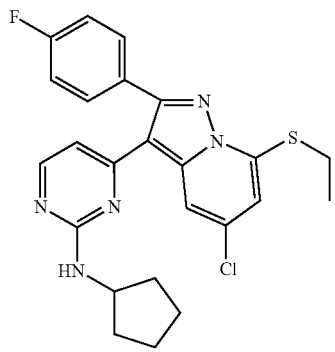

a) 2-(4-Chloro-2-pyridinyl)-1-(4-fluorophenyl)ethanone.

To a cold (0° C.) solution of 4-chloro-2-picoline (5.0 g, 39 mmol) and ethyl 4-fluorobenzoate (6.6 g, 39 mmol) in tetrahydrofuran (100 mL) was added lithium bis(trimethylsilyl)amide (80 mL, 1.0 M in tetrahydrofuran, 80 mmol) dropwise via a pressure equalizing funnel over 30 minutes. Upon complete addition, the cold bath was removed and the resulting solution was stirred at room temperature for 15 hours. The reaction mixture was concentrated under reduced pressure and methanol was added to the reaction, resulting in the formation of a white precipitate. The precipitate was collected by filtration and dried to give 2-(4-chloro-2-pyridinyl)-1-(4-fluorophenyl)ethanone (9.6 g, 99%) as a white solid. $^1$H-NMR (DMSO-d$_6$): δ 7.90 (m, 3H), 7.11 (t, 2H), 6.56 (s, 1H), 5.67 (s, 1H), 4.14 (m, 2H); $^{19}$F-NMR (DMSO-d$_6$): δ 115.67; MS m/z 250 (M+1).

b) 2-(4-Chloro-2-pyridinyl)-1-(4-fluorophenyl)ethanone oxime.

To a solution of 2-(4-chloro-2-pyridinyl)-1-(4-fluorophenyl)ethanone (9.6 g, 38 mmol) in methanol (200 mL) was added hydroxylamine hydrochloride (13.5 g, 190 mmol) followed by the addition of a sodium hydroxide solution (7.8 g, 190 mmol in 50 mL of water). The resulting suspension was heated at reflux for 2 hours and then allowed to cool to room temperature. The mixture was concentrated and water was added to the resulting slurry. A white precipitate formed, which was collected by filtration, washed with water and dried (magnesium sulfate) to give 2-(4-chloro-2-pyridinyl)-1-(4-fluorophenyl)ethanone oxime (8.45 g, 84%) as a white solid. $^1$H-NMR (DMSO-d$_6$): δ 11.56 (s, $_1$H), 8.44 (d, $_1$H), 7.80 (m, 2H), 7.40 (m, 2H), 7.22 (m, 2H), 4.29 (s, 2H); $^{19}$F-NMR (DMSO-d$_6$): δ 113.44; MS m/z 265 (M+1).

c) 5-Chloro-2-(4-fluorophenyl)pyrazolo[1,5-a]pyridine.

To a solution of 2-(4-chloro-2-pyridinyl)-1-(4-fluorophenyl)ethanone oxime (8.0 g, 30 mmol) in 1,2-dimethoxyethane (50 mL) at 0° C. was added trifluoroaceticanhydride (6.3 g, 30 mmol), keeping the temperature below 10° C. during the addition. After the addition was complete, the reaction was warmed to room temperature. The solution was then cooled to 4° C. and a solution of triethylamine (8.4 mL, 60 mmol) in 1,2-dimethoxyethane (20 mL) was added over a period of 0.5 hours. The mixture was allowed to warm to room temperature and was stirred for 1.5 hours. To this mixture was added iron(II) chloride (40 mg) and the reaction was heated at 75° C. for 15 hours. The reaction mixture was poured into water (300 mL). The resulting suspension was extracted with ethyl acetate. The combined organics were dried (magnesium sulfate), filtered and concentrated to a solid residue. This residue was purified by flash chromatography (1:1 ethyl acetate-hexane) to give 5-chloro-2-(4-fluorophenyl)pyrazolo[1,5-a]pyridine (4.2 g, 57%) as a white solid. $^1$H-NMR (CDCl$_3$): δ 8.36 (d, 1H), 7.93 (q, 2H), 7.49 (d, 1H), 7.15 (t, 2H), 6.70 (dd, 1H), 6.69 (s, 1H); $^{19}$F-NMR (CDCl$_3$): δ 113.30; MS m/z 247 (M+1).

d) 5-Chloro-2-(4-fluorophenyl)pyrazolo[1,5-a]pyridine-3-carbaldehyde.

Phosphorous oxychloride (0.6 mL, 6.4 mmol) was added to N,N-dimethylformamide (10 mL) and the resulting mixture stirred at room temperature for 10 minutes. 5-Chloro-2-(4-fluorophenyl)pyrazolo[1,5-a]pyridine (1.0 g, 4.1 mmol) was added and the reaction mixture was stirred at room temperature for 12 hours. The reaction mixture was poured into ice-water and neutralized to pH 7 with aquous ammonium hydroxide. The resulting slurry was extracted with dichloromethane (3×40 mL). The combined organics were washed with brine, dried (magnesium sulfate), filtered and concentrated to give, after recrystallization from acetonitrile, 5-chloro-2-(4-fluorophenyl)pyrazolo[1,5-a]pyridine-3-carbaldehyde (0.95 g, 85%) as a white solid. $^1$H-NMR (CDCl$_3$): δ10.07 (s, 1H), 8.49 (d, 1H), 8.44 (d, 1H), 7.78 (q, 2H), 7.22 (t, 2H), 7.07 (dd, 1H); MS m/z 275 (M+1).

e) 1-[5-Chloro-2-(4-fluorophenyl)pyrazolo[1,5-a]pyridin-3-yl]-2-butyn-1-one.

To a solution of 5-chloro-2-(4-fluorophenyl)pyrazolo[1,5-a]pyridine-3-carbaldehyde (0.93 g, 3.4 mmol) in tetrahydrofuran (20 mL) at −78° C. was added ethynylmagnesium bromide (16 mL, 0.5 M in tetrahydrofuran, 8.0 mmol). The mixture was allowed to warm to room temperature and stirred for 1 hour. Water was added to the reaction and the resulting mixture was extracted with ethyl acetate. The ethyl acetate phase was dried (magnesium sulfate), filtered and concentrated to a solid residue. This residue was dissolved in dichloromethane (50 mL) and manganese dioxide (5 g) was added. This slurry was stirred at room temperature for 2 hours. The manganese dioxide was removed by filtration and the filtrate was concentrated to a solid. This solid was purified by flash chromatography (dichloromethane) to give 1-[5-chloro-2-(4-fluorophenyl)pyrazolo[1,5-a]pyridin-3-yl]-2-butyn-1-one (0.63 g, 62% for two steps) as a white solid. $^1$H-NMR (CDCl$_3$): δ 8.52 (d, 1H), 8.47 (d, 1H), 7.69 (q, 2H), 7.18 (t, 2H), 7.07 (dd, 1H), 3.00 (s, 1H); $^{19}$F-NMR (CDCl$_3$): δ 111.69; MS m/z 299 (M+1).

f) 4-[5-Chloro-2-(4-fluorophenyl)pyrazolo[1,5-a]pyridin-3-yl]-N-cyclopentyl-2-pyrimidinamine.

To a solution of 1-[5-chloro-2-(4-fluorophenyl)pyrazolo[1,5-a]pyridin-3-yl]-2-butyn-1-one (0.61 g, 2.0 mmol) in N,N-dimethylformamide was added cyclopentyl guanidine hydrochloride (0.67 g, 4.1 mmol) followed by anhydrous potassium carbonate (0.57 g, 4.1 mmol). The resulting mixture was heated at 80° C. for 12 hours. Upon cooling to room temperature, water was added. The mixture was extracted with ethyl acetate. The ethyl acetate phase was washed with brine, dried (magnesium sulfate), filtered and concentrated in vacuo. The resulting residue was purified by flash chromatography (1:1 ethyl acetate-hexane) to give, after recrystallization from acetonitrile, 4-[5-chloro-2-(4-fluorophenyl)pyrazolo[1,5-a]pyridin-3-yl]-N-cyclopentyl-2-pyrimidinamine (0.6 g, 74%) as a white solid. $^1$H-NMR (CDCl$_3$): δ8.54 (broad s, 1H), 8.40 (d, 1H), 8.04 (d, 1H), 7.60 (q, 2H), 7.16 (t, 2H), 6.88 (dd, 1H), 6.28 (d, 1H), 5.22 (d, 1H), 4.40 (m, 1H), 1.4–2.2 (m, 8H); $^{19}$F-NMR (CDCl$_3$): δ 112.5; MS m/z 408 (M+1).

g) N-{4-[5-Chloro-7-(ethylsulfanyl)-2-(4-fluorophenyl)pyrazolo[1,5-a]pyridin-3-yl]-2-pyrimidinyl}-N-cyclopentylamine.

To a solution of 4-[5-chloro-2-(4-fluorophenyl)pyrazolo[1,5-a]pyridin-3-yl]-N-cyclopentyl-2-pyrimidinamine (150 mg, 0.37 mmol) in anhydrous tetrahydrofuran (5 mL) at −78° C. was added n-butyllithium (0.7 mL, 1.1 mmol of 1.6 M solution in hexane). The resulting solution was stirred for 10 minutes at −78° C., followed by addition of diethyldisulfide (0.14 mL, 1.1 mmol). The reaction was stirred at −78° C. for 20 minutes and then allowed to warm to room temperature. Water and ethyl acetate were added to the reaction mixture. The phases were separated, the aqueous phase washed with ethyl acetate and the combined organic phase dried (magnesium sulfate), filtered and concentrated in vacuo. The resulting solid was purified by flash chromatography (1:1 ethyl acetate-hexane) to give, after recrystallization from ethyl acetate N-{4-[5-chloro-7-(ethylsulfanyl)-2-(4-fluorophenyl)pyrazolo[1,5-a]pyridin-3-yl]-2-pyrimidinyl}-N-cyclopentylamine (90 mg, 52%) as a solid. $^1$H-NMR (CDCl$_3$): δ 8.42(broad s, 1H), 8.08 (d, 1H), 7.66 (q, 2H), 7.17 (t, 2H), 6.73 (d, 1H), 6.31 (d, 1H), 5.18 (d, 1H), 4.20 (m, 1H), 3.22 (q, 2H), 2.0–2.1 (m, 2H), 1.4–1.9 (m, 9H); $^{19}$F-NMR (CDCl$_3$): δ 112.8; MS m/z 468 (M+1).

EXAMPLE 33

2-Fluoropyridin-4-ylboronic acid

To a stirred solution of n-butyl lithium (3.2 mL, 2.5M, 8.0 mmol) in dry diethyl ether (20 mL) at −78° C. was added a solution of 2-fluoro-4-iodopyridine (1.5 g, 6.7 mmol) in dry ether (10 mL) and the reaction mixture was stirred at −78° C. for 10 minutes. Tributyl borate (2.4 mL, 2.01 g, 8.7 mmol) was added and the reaction mixture was allowed to stir to room temperature over 2 hours. Water (5 mL) was added followed by 2N aqueous sodium hydroxide solution (10 mL) to sissolve the solids. The organic phase was separated. The aqueous phase was acidified to pH3 using 6N HCl and the resulting white solid was collected by filtration and dried under vacuum to give the title compound, 0.74 g (78%). 1H NMR (DMSO-d6) δ 8.65 (br s, 2H), 8.21 (d, 1H, J=4.8 Hz), 7.59 (t, 1H, J=4.8 Hz), 7.37 (d, 1H, J=1.8 Hz).

EXAMPLE 34

Ethyl 3-[2-(cyclopentylamino)-4-pyrimidinyl]-2-(4-fluorophenyl)-7-methylpyrazolo[1,5-a]pyridine-6-carboxylate

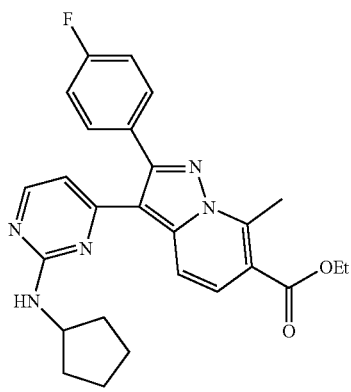

a) 1-(4-Fluorophenyl)-2-(2-(5-trifluoromethyl)pyridyl)ethanone.

To a solution of 4-fluoroacetophenone (13.8 g, 0.100 mol) and 2-chloro-5-trifluoromethylpyridine (20.0 g, 0.110 mol) in tetrahydrofuran (400 mL) was added sodium hydride (95%, 5.56 g, 0.220 mol) in several portions. The reaction was stirred at room temperature for 72 hours then carefully quenched by the addition of water (300 mL) and diethyl ether (200 mL). The organic layer was separated and extracted with 6N HCl (2×300 mL). The aqueous extracts were cooled to 0° C. and 6N NaOH was used to adjust the solution to pH12. The mixture was then extracted with diethyl ether and the combined organic extracts were dried over magnesium sulfate. The drying agent was removed by filtration and the filtrate was evaporated to dryness to afford the title compound as a tautomeric mixture, 20.9 g (73%). $^1$H NMR (CDCl$_3$): δ 8.87(s), 8.63(s), 8.14(dd, J=5.1, 8.4 Hz), 8.00–7.83(m), 7.51(d, J=8.4 Hz), 7.22–7.12(m), 6.13(s), 4.60(s). MS (ES): 284 (M+1).

b) 1-(4-Fluorophenyl)-2-(2-(5-trifluoromethyl)pyridyl)ethanone oxime.

To a solution of 1-(4-fluorophenyl)-2-(2-(5-trifluoromethyl)pyridyl)ethanone (80.0 g, 0.282 mol) in methanol (1 L) at room temperature was added 10% aqueous sodium hydroxide (436 mL, 1.09 mol). The resulting solution was stirred vigorously as solid hydroxylamine hydrochloride (98.0 g, 1.40 mol) was added. The mixture was heated to reflux for 2 hours, treated with decolorizing charcoal while hot, then filtered through Celite while hot. The filtrate was concentrated to one-half its original volume and then cooled to 0° C. with stirring for one hour. The resulting solids were collected by filtration, washed with water, and dried under vacuum at 50° C. overnight to provide the title compound as a light yellow powder, 73.9 g (88%). $^1$H NMR (DMSO-d$_6$): δ 11.60(s, 1H), 8.86(s, 1H), 8.14(dd, 1H, J=2.1, 8.1 Hz), 7.78(dd, 2H, J=5.7, 9.0 Hz), 7.53(d, 1H, J=8.4 Hz), 7.23(t, 2H, J=9.0 Hz), 4.40(s, 2H). MS (ES): 299 (M+1).

c) 3-(4-Fluorophenyl)-2-(2-(5-trifluoromethyl)pyridyl)-2H-azirine.

To a solution of 1-(4-fluorophenyl)-2-(2-(5-trifluoromethyl)pyridyl)ethanone oxime (25.0 g, 0.084 mol) in methylene chloride (400 mL) was added triethylamine (46.7 mL, 0.335 mol). The solution was cooled to 0° C. under a nitrogen atmosphere, and trifluoroacetic anhydride (14.1 mL, 0.100 mol) was added dropwise. The reaction was stirred for 0.5 hours then quenched with water. The organic layer was separated and dried over anhydrous magnesium sulfate. The drying agent was removed by filtration and the solvent was evaporated from the filtrate to leave an oil. The residue was loaded onto a silica gel column and eluted with 15% ethyl acetate in hexanes to give the title compound as an oil which solidified on standing, 19.4 g (82%). $^1$H NMR (CDCl$_3$): δ 8.76(s, 1H), 7.93(dd, 2H, J=5.4, 8.7 Hz), 7.83 (dd, 1H, J=2.1, 8.4 Hz), 7.27(t, 2H, J=8.7 Hz), 7.21(d, 1H, J=8.1 Hz), 3.54 (s, 1H). MS (ES): 281 (M+1).

d) 2-(4-Fluorophenyl)-6-(trifluoromethyl)pyrazolo[1,5-a]pyridine.

3-(4-Fluorophenyl)-2-(2-(5-trifluoromethyl)pyridyl)-2H-azirine (40.0 g, 0.143 mol) was dissolved in 1,2,4-trichlorobenzene (400 mL) and the mixture was heated to 200° C. for 10 hours. The reaction mixture was then cooled to room temperature and poured onto a silica gel column. The column was eluted with hexanes to remove the 1,2,4-trichlorobenzene; and then with 20% diethyl ether in hexanes to elute the product. The desired fractions were combined and the solvent was evaporated under reduced pressure to leave the title compound, 28.7 g (71%). $^1$H NMR (CDCl$_3$): δ 8.84(s, 1H), 7.98(dd, 2H, J=5.4, 8.7 Hz), 7.65(d, 1H, J=9.3 Hz), 7.28(d, 1H, J=9.3 Hz), 7.20(t, 2H, J=8.7 Hz), 6.88(s, 1H). MS (ES): 281 (M+1).

e) 2-(4-Fluorophenyl)-6-(trifluoromethyl)pyrazolo[1,5-a]pyridine-3-carbaldehyde.

To a cold (0° C.) solution of phosphorus oxychloride (8.0 mL, 86 mmol) in N,N-dimethylformamide (160 mL) was added 2-(4-fluorophenyl)-6-(trifluoromethyl)pyrazolo-[1,5-a]pyridine (11.0 g, 39.3 mmol). The reaction mixture was stirred at room temperature for 72 hours, then quenched with ice water. The solid precipitate was collected on a filter to provide 2-(4-fluorophenyl)-6-(trifluoromethyl)pyrazolo[1,5-a]pyridine-3-carbaldehyde (11.4 g, 94%) as a white solid. R$_f$ 0.45 (4:1 hexanes:ethyl acetate); $^1$H NMR (400 MHz, CDCl$_3$) δ 10.15 (s, 1H), 8.92 (s, 1H), 8.53 (d, 1H), 7.80 (m, 2H), 7.70 (d, 1H), 7.27 (t, 2H); $^{19}$F NMR (CDCl$_3$) δ −62.62, −110.62; MS m/z 307 (M−1).

f) 1-[2-(4-Fluorophenyl)-6-(trifluoromethyl)pyrazolo[1,5-a]pyridin-3-yl]-2-propyn-1-ol.

To a cold (−78° C.) suspension of 2-(4-fluorophenyl)-6-(trifluoromethyl)pyrazolo[1,5-a]pyridine-3-carbaldehyde (11.4 g, 37.0 mmol) in tetrahydrofuran (100 mL) was added ethynylmagnesium bromide (111 mL, 0.5 M in tetrahydrofuran, 56 mmol). The reaction mixture was warmed to room temperature and stirred for 14 hours. The reaction mixture was poured into water and adjusted to neutral pH with 1N aqueous hydrochloric acid. The aqueous mixture was extracted with ethyl acetate. The combined extracts were washed with water and brine. The organic layer was dried over magnesium sulfate. Filtration and concentration provided 1-[2-(4-fluorophenyl)-6-(trifluoromethyl)pyrazolo[1,5-a]pyridin-3-yl]-2-propyn-1-ol (11.9 g, 96%) as a tan solid. R$_f$ 0.18 (4:1 hexanes:ethyl acetate); $^1$H NMR (300 MHz, CDCl$_3$) δ 8.81 (s, 1H), 8.15 (d, 1H), 7.75 (m, 2H), 7.35 (d, 1H), 7.19 (t, 2H), 5.76 (s, 1H), 2.71 (d, 1H), 2.60 (d, 1H); MS m/z 335 (M+1).

g) 1-[2-(4-Fluorophenyl)-6-(trifluoromethyl)pyrazolo[1,5-a]pyridin-3-yl]-2-propyn-1-one.

To a cold (0° C.) solution of 1-[2-(4-fluorophenyl)-6-(trifluoromethyl)pyrazolo[1,5-a]pyridin-3-yl]-2-propyn-1-ol (5.00 g, 15.0 mmol) in chloroform (400 mL) was added manganese dioxide (130 g, 1.50 mol). The reaction mixture was stirred at 0° C. for 1.5 hours. The reaction mixture was filtered through a pad of Celite. The filtrate was concentrated in vacuo to provide 1-[2-(4-fluorophenyl)-6-(trifluoromethyl)pyrazolo-[1,5-a]pyridin-3-yl]-2-propyn-1-one (3.44 g, 69%) as a clear oil. $R_f$ 0.39 (4:1 hexanes:ethyl acetate); $^1$H NMR (400 MHz, CDCl$_3$) δ 8.90 (s, 1H), 8.61 (d, 1H), 7.72–7.69 (m, 3H), 7.17 (m, 2H), 3.06 (s, 1H); MS m/z 333 (M+1).

h) N-Cyclopentyl-4-[2-(4-fluorophenyl)-6-(trifluoromethyl)pyrazolo[1,5-a]pyridin-3-yl]-2-pyrimidinamine.

To a suspension of N-cyclopentylguanidine hydrochloride (2.20 g, 13.5 mmol) in ethanol (70 mL) was added sodium ethoxide (4.5 mL, 3 M in ethanol, 14 mmol). The mixture was stirred at room temperature for 30 minutes, then cooled to 0° C. To this mixture was added 1-[2-(4-fluorophenyl)-6-(trifluoromethyl)pyrazolo[1,5-a]pyridin-3-yl]-2-propyn-1-one (3.44 g, 10.4 mmol) portionwise. The reaction mixture was stirred at 0° C. for 30 minutes, followed by room temperature for 15 hours. The reaction mixture was diluted with water (400 mL). The solid precipitate was collected on a filter to provide N-cyclopentyl-4-[2-(4-fluorophenyl)-6-(trifluoromethyl)-pyrazolo[1,5-a]pyridin-3-yl]-2-pyrimidinamine (4.48 g 98%) as an orange solid. $^1$H NMR (400 MHz, CDCl$_3$) δ 8.84 (s, 1H), 8.51 (d, 1H), 8.11 (d, 1H), 7.64 (dd, 2H), 7.44 (dd, 1H), 7.17 (t, 2H), 6.33 (d, 1H), 5.17 (d, 1H), 4.34 (m, 1H), 2.15–2.06 (m, 2H), 1.84–1.52 (m, 6H); $^{19}$F NMR (CDCl$_3$): δ −62.70, −112.25 MS m/z 442 (M+1); mp 155–156° C.

Alternatively, N-cyclopentyl-4-[2-(4-fluorophenyl)-6-(trifluoromethyl)pyrazolo[1,5-a]pyridin-3-yl]-2-pyrimidinamine from 2-(4-Fluorophenyl)-6-(trifluoromethyl)pyrazolo[1,5-a]pyridine may be synthisized through the following steps.

aa) 1-[2-(4-Fluorophenyl)-6-(trifluoromethyl)pyrazolo[1,5-a]pyridin-3-yl]ethanone.

To a mixture of 2-(4-fluorophenyl)-6-(trifluoromethyl)pyrazolo[1,5-a]pyridine (10.30 g, 36.76 mmol) and acetic anhydride (100 mL) was added conc. sulfuric acid (10 drops) and the mixture was stirred and heated at reflux for 1 hour. The reaction mixture was cooled to room temperature and poured into ice water (300 mL). 2N Aqueous sodium hydroxide solution was added to raise the pH of the solution to about 10 and the resulting orange precipitate was collected by filtration. The solid was washed with water, air-dried, and then dried under vacuum to afford the title compound as an orange solid, 11.87 g (quant.). $^1$H NMR (DMSO-d$_6$): δ 9.58 (s, 1H), 8.41 (d, 1H, J=9.3 Hz), 7.89 (d, 1H, J=9.5 Hz), 7.74 (m, 2H), 7.39 (m, 2H), 2.22 (s, 3H). MS (ES) 323 (M+1).

bb) (2E)-3-(Dimethylamino)-1-[2-(4-fluorophenyl)-6-(trifluoromethyl)pyrazolo-[1,5-a]pyridin-3-yl]-2-propen-1-one.

A mixture of 1-[2-(4-Fluorophenyl)-6-(trifluoromethyl)pyrazolo[1,5-a]pyridin-3-yl]ethanone (11.85 g), 36.77 mmol) and N,N-dimethylformamide dimethyl acetal (100 mL) was stirred at reflux for 17 hours. The mixture was cooled to room temperature and then to 0° C. The resulting orange precipitate was collected by filtration, washed with cold hexanes, and dried under vacuum to afford the title compound as an orange solid, 10.17 g (73%). $^1$H NMR (DMSO-d$_6$): δ 9.44 (s, 1H), 8.22 (d, 1H, J=9.4 Hz), 7.75 (m, 2H), 7.65 (d, 1H, J=9.5 Hz), 7.56 (d, 1H, J=12.4 Hz), 7.35 (m, 2H), 5.05 (d, 1H, J=12.3 Hz), 3.04 (s, 3H), 2.56 (s, 3H). MS (+ve ion electrospray) 377 (80), (M+).

cc) N-Cyclopentyl-4-[2-(4-fluorophenyl)-6-(trifluoromethyl)pyrazolo[1,5-a]pyridin-3-yl]-2-pyrimidinamine.

To a solution of (2E)-3-(dimethylamino)-1-[2-(4-fluorophenyl)-6-(trifluoromethyl)-pyrazolo[1,5-a]pyridin-3-yl]-2-propen-1-one (314 mg, 0.83 mmol)) in 1-methyl-2-pyrrolidinone (3 mL) was added N-cyclopentylguanidine hydrochloride (271 mg, 1.66 mmol) and potassium carbonate (229 mg, 1.66 mmol). The mixture was heated at 140° C. for 8 hours. Upon cooling to room temperature, ether was added followed by water. The organics were washed with brine, and the aqueous layer was extracted with ether. The combined organics were dried over magnesium sulfate, filtered and concentrated in vacuo. The residue was purified by flash chromatography on silica (4:1 hexanes-ethyl acetate) to give N-cyclopentyl-4-[2-(4-fluorophenyl)-6-(trifluoromethyl)pyrazolo[1,5-a]pyridin-3-yl]-2-pyrimidinamine (204 mg, 56%) as a white solid. $^1$H NMR (CDCl$_3$): δ 8.84 (s, 1H), 8.51 (d, 1H), 8.11 (d, 1H), 7.64 (dd, 2H), 7.44 (dd, 1H), 7.17 (t, 2H), 6.33 (d, 1H), 5.17 (d, 1H), 4.34 (m, 1H), 2.15–2.06 (m, 2H), 1.84–1.52 (m, 6H); $^{19}$F NMR (CDCl$_3$): δ −62.70, −112.25; MS m/z 442 (M+1); mp 155–156° C.

i) N-Cyclopentyl-4-[2-(4-fluorophenyl)-6-(triethoxymethyl)pyrazolo[1,5-a]pyridin-3-yl]-2-pyrimidinamine.

To a dry round bottom flask was added sodium metal (1.9 g, 83 mmol). Ethanol (110 mL) was added and allowed to react with sodium at room temperature until completely dissolved. N-Cyclopentyl-4-[2-(4-fluorophenyl)-6-(trifluoromethyl)-pyrazolo[1,5-a]pyridin-3-yl]-2-pyrimidinamine (4.48 g, 10.1 mmol) was added and the reaction mixture was stirred at 60° C. for 18 hours. The reaction mixture was cooled and concentrated in vacuo to approximately one-fourth of the original volume. The resulting mixture was diluted with water and extracted with ethyl acetate. The organic layer was washed with water and brine, then dried over magnesium sulfate. Filtration and concentration provided N-cyclopentyl-4-[2-(4-fluorophenyl)-6-(triethoxymethyl)-pyrazolo[1,5-a]pyridin-3-yl]-2-pyrimidinamine (4.86 g, 92%) as an off-white solid. $R_f$ 0.15 (4:1 hexanes:ethyl acetate); $^1$H NMR (300 MHz, CDCl$_3$) δ 8.81 (s, $_1$H), 8.39 (d, $_1$H), 8.06 (d, 1H), 7.62 (m, 2H), 7.47 (d, $_1$H), 7.14 (t, 2H), 6.32 (d, 1H), 5.12 (d, 1H), 4.35 (m, 1H), 3.43 (q, 6H), 2.08 (m, 2H), 1.80–1.51 (m, 6H), 1.21 (t, 9H); MS m/z 520 (M+1).

j) 4-[7-Chloro-2-(4-fluorophenyl)-6-(triethoxymethyl)pyrazolo[1,5-a]pyridin-3-yl]-N-cyclopentyl-2-pyrimidinamine.

To a cold (0° C.) solution of diisopropylamine (4.1 mL, 29 mmol) in tetrahydrofuran (25 mL) was added butyllithium (17 mL, 1.6 M in hexanes, 28 mmol) dropwise. The resultant solution was stirred at 0° C. for 10 minutes then cooled to −78° C. The reaction mixture was transferred via syringe to a cold (−78° C.) solution of N-cyclopentyl-4-[2-(4-fluorophenyl)-6-(triethoxymethyl)pyrazolo[1,5-a]pyridin-3-yl]-

2-pyrimidinamine (4.86 g, 9.35 mmol) in tetrahydrofuran (25 mL). The reaction mixture was stirred at −78° C. for 30 minutes. Carbon tetrachloride (3.6 mL, 37 mmol) was added and the resulting mixture was warmed to room temperature and stirred for 2 hours. The reaction mixture was poured onto ice. After the ice had melted, the aqueous mixture was extracted with ethyl acetate. The organic layer was washed with water and brine, then dried over sodium sulfate. Filtration and concentration followed by flash chromatography (4:1 hexanes:ethyl acetate) provided 4-[7-chloro-2-(4-fluorophenyl)-6-(triethoxymethyl)pyrazolo[1,5-a]pyridin-3-yl]-N-cyclopentyl-2-pyrimidinamine (2.37 g, 46%) as a yellow solid. $R_f$ 0.36 (4:1 hexanes:ethyl acetate); $^1$H NMR (400 MHz, CDCl$_3$) δ 8.36 (d, 1H), 8.08 (d, 1H), 7.85 (d, 1H), 7.67 (m, 2H), 7.15 (t, 2H), 6.33 (d, 1H), 5.15 (d, 1H), 4.36 (m, 1H), 3.46 (q, 6H), 2.10 (m, 2H), 1.81–1.53 (m, 6H), 1.26 (t, 9H); MS m/z 554 (M+1).

k) Ethyl 7-chloro-3-[2-(cyclopentylamino)-4-pyrimidinyl]-2-(4-fluorophenyl)-pyrazolo[1,5-a]pyridine-6-carboxylate.

To a solution of 4-[7-chloro-2-(4-fluorophenyl)-6-(triethoxymethyl)pyrazolo[1,5-a]pyridin-3-yl]-N-cyclopentyl-2-pyrimidinamine (375 mg, 0.677 mmol) in acetone (8 mL) and water (2 mL) was added p-toluenesulfonic acid monohydrate (321 mg, 1.69 mmol). The reaction mixture was stirred at room temperature for 2 hours, then quenched with ice water. The reaction mixture was neutralized with saturated aqueous sodium bicarbonate solution, then concentrated in vacuo to remove the majority of the acetone. The resultant mixture was extracted with ethyl acetate. The organic layer was washed with water and brine, then dried over magnesium sulfate. Filtration and concentration, followed by flash chromatography (29:1 dichloromethane:methanol) provided ethyl 7-chloro-3-[2-(cyclopentylamino)-4-pyrimidinyl]-2-(4-fluorophenyl)pyrazolo[1,5-a]pyridine-6-carboxylate (175 mg, 54%) as a brown solid. $R_f$ 0.08 (29:1 dichloromethane:methanol); $^1$H NMR (400 MHz, CDCl$_3$) δ 8.36 (d, 1H), 8.09 (d, 1H), 7.82 (d, 1H), 7.65 (m, 2H), 7.14 (t, 2H), 6.30 (d, 1H), 5.19 (d, 1H), 4.46 (q, 2H), 4.32 (m, 1H), 2.06 (m, 2H), 1.77–1.21 (m, 9H); MS m/z 480 (M+1).

l) Ethyl 3-[2-(cyclopentylamino)-4-pyrimidinyl]-2-(4-fluorophenyl)-7-methylpyrazolo[1,5-a]pyridine-6-carboxylate.

To a solution of ethyl 7-chloro-3-[2-(cyclopentylamino)-4-pyrimidinyl]-2-(4-fluorophenyl)pyrazolo[1,5-a]pyridine-6-carboxylate (90 mg, 0.19 mmol) in tetrahydrofuran (1 mL) was added dimethylzinc (281 μL, 2.0 M in toluene, 0.56 mmol) and tetrakis(triphenylphosphine)palladium (21 mg, 0.018 mmol). The reaction mixture was stirred at 60° C. for 16 hours. The reaction mixture was quenched with ice water then extracted with ethyl acetate. The organic layer was washed with water and brine, then dried over magnesium sulfate. Filtration and concentration, followed by flash chromatography (49:1 dichloromethane:methanol) provided ethyl 3-[2-(cyclopentylamino)-4-pyrimidinyl]-2-(4-fluorophenyl)-7-methylpyrazolo[1,5-a]pyridine-6-carboxylate (40 mg, 45%). $^1$H NMR (300 MHz, CDCl$_3$) δ 8.34 (d, 1H), 8.11 (d, 1H), 7.91 (d, 1H), 7.70 (m, 2H), 7.19 (t, 2H), 6.36 (d, 1H), 5.33 (br, 1H), 4.47 (q, 2H), 4.38 (m, 1H), 3.26 (s, 3H), 2.12 (m, 2H), 1.83–1.43 (m, 9H); MS m/z 460 (M+1).

EXAMPLE 35

3-[2-(Cyclopentylamino)-4-pyrimidinyl]-2-(4-fluorophenyl)-7-methylpyrazolo[1,5-a]pyridine-6-carboxylic Acid

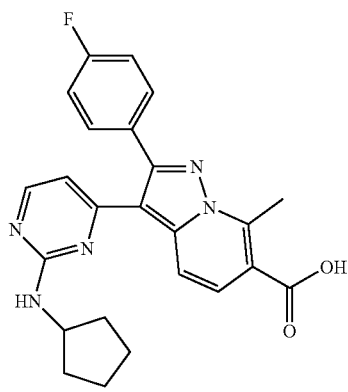

To a solution of ethyl 3-[2-(cyclopentylamino)-4-pyrimidinyl]-2-(4-fluorophenyl)-7-methylpyrazolo[1,5-a]pyridine-6-carboxylate (40 mg, 0.087 mmol) in dioxane (600 μL) was added lithium hydroxide (300 μL, 1M aqueous, 0.30 mmol). The reaction mixture was stirred at room temperature 16 hours. The reaction mixture was concentrated in vacuo to remove dioxane, then diluted with water. The aqueous mixture was acidified with 1 N aqueous hydrochloric acid. Upon standing for 72 hours, a solid precipitate had formed which was collected by filtration to provide 3-[2-(cyclopentylamino)-4-pyrimidinyl]-2-(4-fluorophenyl)-7-methylpyrazolo[1,5-a]pyridine-6-carboxylic acid (31 mg, 82%). $R_f$ 0.10 (19:1 dichloromethane:methanol); MS m/z 432 (M+1).

EXAMPLE 36

3-[2-(Cyclopentylamino)-4-pyrimidinyl]-N-cyclopropyl-2-(4-fluorophenyl)-7-methylpyrazolo[1,5-a]pyridine-6-carboxamide

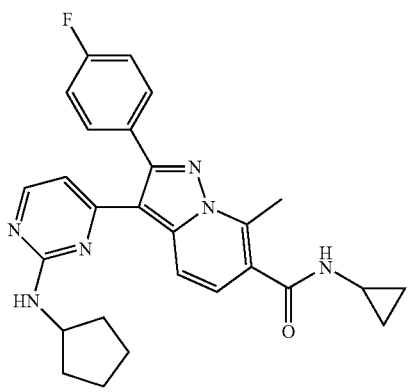

Thionyl chloride (200 μL, 2.7 mmol) was added to 3-[2-(cyclopentylamino)-4-pyrimidinyl]-2-(4-fluorophenyl)-7-methylpyrazolo[1,5-a]pyridine-6-carboxylic acid (31 mg, 0.072 mmol) which had been pre-cooled to 0° C. The reaction mixture was stirred at room temperature for 1 hour. The excess thionyl chloride was removed in vacuo. To a solution of the residue in dichloromethane (300 μL) was added cyclopropylamine (50 uL, 0.72 mmol). The reaction mixture was stirred at room temperature for 30 minutes. The resultant mixture was quenched with water and diluted with ethyl acetate. Saturated aqueous sodium bicarbonate solution was added to the biphasic mixture. The organic layer was washed with water and brine, then dried over magnesium sulfate. Filtration and concentration, followed by flash chromatography (3:2 hexanes:ethyl acetate to 2:3 hexanes:ethyl acetate) provided 3-[2-(cyclopentylamino)-4-pyrimidinyl]-N-cyclopropyl-2-(4-fluorophenyl)-7-methylpyrazolo[1,5-a]pyridine-6-carboxamide (15 mg, 44%) as a pale yellow solid. $^1$H NMR (400 MHz, CDCl$_3$) δ 8.28 (d, 1H), 8.05 (d, 1H), 7.62 (m, 2H), 7.30 (d, 1H), 7.13 (t, 2H), 6.29 (d, 1H), 5.10 (d, 1H), 4.30 (m, 1H), 2.96 (s, 3H), 2.94 (m, 1H), 2.05 (m, 2H), 1.76–1.50 (m, 6H), 0.92 (m, 2H), 0.66 (m, 2H); MS m/z 471 (M+1).

EXAMPLE 37

N-Butyl-4-[7-butyl-2-(4-fluorophenyl)pyrazolo[1,5-a]pyridin-3-yl]-2-pyrimidinamine

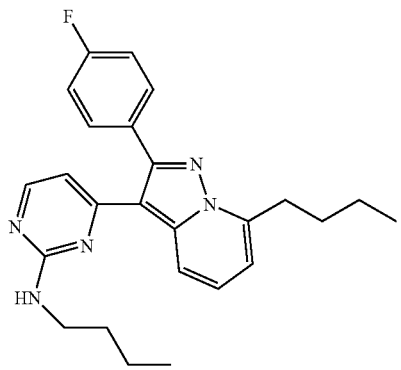

a) 2-(6-Chloro-2-pyridinyl)-1-(4-fluorophenyl)ethanone.

To a cold (0° C.) solution of 6-chloro-2-picoline (21.4 mL, 196.0 mmol) and ethyl 4-fluorobenzoate (57.5 mL 391.2 mmol) in tetrahydrofuran (311 mL) was added lithium bis(trimethylsilyl)amide (391 mL, 1.0 M in tetrahydrofuran, 391.0 mmol) dropwise via a pressure equalizing funnel over 1 hour. Upon complete addition, the cold bath was removed and the resultant solution was heated to 45° C. for 15 hours. The mixture was cooled to room temperature and quenched by the addition of water. Ether was added and the organic layer was washed with brine. The aqueous layer was extracted with ether and the combined organics were dried over magnesium sulfate. Filtration and concentration gave a solid residue which was purified by recrystallization from ethyl acetate-hexanes to provide 2-(6-chloro-2-pyridinyl)-1-(4-fluorophenyl)ethanone (32.2 g, 66%) as a tinted off-white solid existing as a keto-enol tautomeric mixture. $^1$H NMR (CDCl$_3$): for the keto tautomer δ 8.11 (m, 2 H), 7.66 (t, 1 H), 7.30–7.25 (m 2 H), 7.17 (t, 2 H), 4.48 (s 2 H), $^{19}$F NMR (CDCl$_3$) δ –104.72 (keto), –111.64 (enol); MS m/z 250 (M+1).

b) 2-(6-Chloro-2-pyridinyl)-1-(4-fluorophenyl)ethanone oxime.

To a solution of 2-(6-chloro-2-pyridinyl)-1-(4-fluorophenyl)ethanone (74.9 g, 299.8 mmol) in methanol (900 mL) was added hydroxylamine hydrochloride (104 g, 1.49 mol) followed by sodium hydroxide (600 mL, 10% aqueous, 1.5 mol). The resultant suspension was heated to reflux for 2 hours and then cooled to room temperature. The mixture was concentrated in vacuo and the residue taken up in ether and water. The organic layer was washed with brine. The aqueous layer was extracted with ether and the combined organics were dried over magnesium sulfate. Filtration and concentration gave a solid residue which was purified by recrystallization from ethyl acetate-hexanes to provide 2-(6-chloro-2-pyridinyl)-1-(4-fluorophenyl)ethanone oxime (67.9 g, 86%) as a white solid. $^1$H NMR (CDCl$_3$): δ 8.69 (s, 1 H), 7.71 (dd, 2 H), 7.53 (t, 1 H), 7.18–7.16 (m, 2 H), 7.03 (t, 2 H), 4.37 (s, 2 H); $^{19}$F NMR (CDCl$_3$) δ –111.77; MS m/z 265 (M+1).

c) 7-Chloro-2-(4-fluorophenyl)pyrazolo[1,5-a]pyridine.

To a solution of 2-(6-chloro-2-pyridinyl)-1-(4-fluorophenyl)ethanone oxime (109.2 g, 414 mmol) in 1,2-dimethoxyethane (500 mL) at 0° C. was added trifluoroacetic anhydride (59 mL, 414 mmol), keeping the temperature below 10° C. After the addition was complete, the reaction was warmed to 15° C. The solution was then cooled to 4° C. and a solution of triethylamine (116 mL, 828 mmol) in 1,2-dimethoxyethane (60 mL) was added over 0.5 hours. After warming to room temperature, the mixture was stirred for 1.5 hours. To this was added iron(II) chloride (0.52 g, 4.1 mmol) and the reaction was heated to reflux for 3 hours. The reaction was concentrated and the resulting solid was recrystallized from ethyl acetate-hexanes to give 7-chloro-2-(4-fluorophenyl)pyrazolo[1,5-a]pyridine (69.7 g, 68%) as off-white needles. $^1$H NMR (CDCl$_3$): δ 8.03 (m, 2 H), 7.54 (d, 1 H), 7.16 (m, 3 H), 6.93 (d, 1 H), 6.91 (s, 1 H); MS m/z 247 (M+1); mp 156–157° C.

d) 7-Chloro-2-(4-fluorophenyl)pyrazolo[1,5-a]pyridine-3-carbaldehyde.

N,N-Dimethylformamide (100 mL) was cooled to 0° C. and treated with phosphorous oxychloride (5.7 mL, 60.8 mmol). After the addition was complete, the mixture was warmed to room temperature and stirred for 1 hour. To this was added 7-chloro-2-(4-fluorophenyl)pyrazolo[1,5-a]pyridine (10.0 g, 40.5 mmol) and the resultant solution was stirred overnight. Water was added, followed by dichloromethane. The aqueous layer was extracted with dichloromethane. The combined organics were washed with brine, dried over magnesium sulfate, filtered and concentrated. The residue was recrystallized from diethyl ether and hexanes to give 7-chloro-2-(4-fluorophenyl)pyrazolo[1,5-a]pyridine-3-carbaldehyde (10.6 g, 95%) as a fluffy white solid. $^1$H NMR (CDCl$_3$): δ 10.07 (s, 1 H), 8.37 (d, 1 H), 7.78 (m, 2 H), 7.48 (t, 1 H), 7.20 (m, 3 H); $^{19}$F NMR (CDCl$_3$) δ –111.25; MS m/z 275 (M+1); Anal. Calcd for C$_{14}$H$_8$ClFN$_2$O: C, 61.22; H, 2.94; N, 10.20. Found: C, 61.34; H, 2.90; N, 10.15; mp 212–213° C. (decomp.).

e) 1-[7-Chloro-2-(4-fluorophenyl)pyrazolo[1,5-a]pyridin-3-yl]-2-propyn-1-ol.

In a similar manner as described in Example 34 from 7-chloro-2-(4-fluorophenyl)pyrazolo[1,5-a]pyridine-3-carbaldehyde (5.49 g, 20.0 mmol) and ethynylmagnesium bromide (100 mL, 0.5 M in tetrahydrofuran, 50.0 mmol) at 0° C., recrystallized from dichloromethane, was obtained 1-[7-chloro-2-(4-fluorophenyl)pyrazolo[1,5-a]pyridin-3-yl]-2-propyn-1-ol (5.3 g, 88%) as a pale yellow crystalline solid. $^1$H NMR (CDCl$_3$): δ 8.04 (d, 1H), 7.79 (m, 2H), 7.20 (m, 3H), 7.01 (d, 1H), 5.77 (m, 1H), 2.69 (d, 1H), 2.32 (d, 1H); MS m/z 301 (M+1).

f) 1-[7-Chloro-2-(4-fluorophenyl)pyrazolo[1,5-a]pyridin-3-yl]-2-propyn-1-one.

In a similar manner as described in Example 34, from 1-[7-chloro-2-(4-fluorophenyl)pyrazolo[1,5-a]pyridin-3-yl]-2-propyn-1-ol (5.30 g, 17.6 mmol) was obtained 1-[7-chloro-2-(4-fluorophenyl)pyrazolo[1,5-a]pyridin-3-yl]-2-propyn-1-one (4.04 g, 77%) as a yellow solid. $^1$H NMR (CDCl$_3$): δ 8.45 (d, 1H), 7.67 (m, 2H), 7.50 (t, 1H), 7.19 (d, 1H), 7.12 (t, 2H), 2.93 (s, 1H); MS m/z 299 (M+1).

g) N-Butyl-4-[7-chloro-2-(4-fluorophenyl)pyrazolo[1,5-a]pyridin-3-yl]-2-pyrimidinamine.

In a similar manner as described in Example 34 from 1-[7-chloro-2-(4-fluorophenyl)pyrazolo[1,5-a]pyridin-3-yl]-2-propyn-1-one (0.50 g, 1.7 mmol), N-butylguanidine sulfate and sodium ethoxide (0.81 mL, 21 wt % in ethanol, 2.2 mmol) at room temperature was obtained N-butyl-4-[7-chloro-2-(4-fluorophenyl)-pyrazolo[1,5-a]pyridin-3-yl]-2-pyrimidinamine (0.39 g, 59%) as a fluffy pale yellow solid. $^1$H NMR (CDCl$_3$): δ 8.40 (d, 1 H), 8.07 (d, 1 H), 7.65 (m, 2 H), 7.29 (m, 1 H), 7.15 (t, 2 H), 7.06 (d, 1 H), 6.32 (d, 1 H), 5.16 (bs, 1H), 3.49 (q, 2 H), 1.71–1.41 (m, 4 H), 0.99 (t, 3 H); $^{19}$F NMR (CDCl$_3$) δ –112.77; MS m/z 396 (M+1).

h) N-Butyl-4-[7-butyl-2-(4-fluorophenyl)pyrazolo[1,5-a]pyridin-3-yl]-2-pyrimidinamine.

To a cold (–78° C.) solution of 9-methoxy-9-borabicyclo[3.3.1]nonane (1.1 mL, 1.0 M in hexane, 1.1 mmol) in tetrahydrofuran was added n-butyllithium (696 μL, 1.6 M in hexane, 1.1 mmol) dropwise. The resultant mixture was warmed to room temperature, then potassium phosphate (371 μL, 3.0 M aqueous, 1.1 mmol) was added. A solution of N-butyl-4-[7-chloro-2-(4-fluorophenyl)pyrazolo[1,5-a]pyridin-3-yl]-2-pyrimidinamine (44 mg, 0.11 mmol) and [1,1'-bis(diphenylphosphino)-ferrocene]dichloropalladium (II) (9 mg, complex with dichloromethane, 0.011 mmol) in N,N-dimethylformamide (1.5 mL) was added to the stirring borane solution. The reaction mixture was stirred 16 hours at room temperature. The resultant mixture was diluted with ethyl acetate, washed with water and brine, then dried over magnesium sulfate. Filtration and concentration, followed by flash chromatography (4:1 hexanes:ethylacetate) provided a crude residue. To a solution of the crude residue in dioxane (10 mL) was added saturated aqueous sodium acetate solution (1 mL) and 30% aqueous hygrogen peroxide (1 mL). After stirring at room temperature for 2 hours, the mixture was diluted with ethyl acetate, washed with water and brine, then dried over magnesium sulfate. Filtration and concentration, followed by flash chromatography (59:1 dichloromethane:methanol) provided N-butyl-4-[7-butyl-2-(4-fluorophenyl)pyrazolo[1,5-a]pyridin-3-yl]-2-pyrimidinamine (7 mg, 16%). $^1$H NMR (400 MHz, CDCl$_3$) δ 8.29 (d, 1H), 8.05 (d, 1H), 7.66 (m, 2H), 7.29 (m, 1H), 7.14 (t, 2H), 6.77 (d, 1H), 6.33 (d, 1H), 5.17 (br, 1H), 3.49 (m, 2H), 3.22 (t, 2H), 1.87 (m, 2H), 1.69–1.42 (m, 6H), 1.02–0.97 (m, 6H); MS m/z 418 (M+1). To a solution of the product in ether was added 1 M HCl in ether. The precipitated solid was isolated to give the corresponding hydrochloride salt as a pale yellow solid.

EXAMPLE 38

N-Butyl-4-[2-(4fluorophenyl)-7-methylpyrazolo[1,5-a]pyridin-3-yl]-2-pyrimidinamine

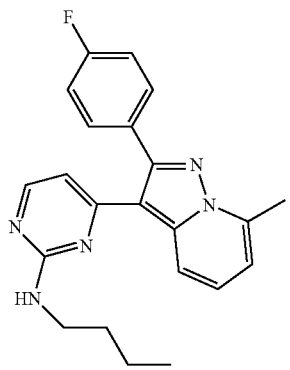

To a solution of N-butyl-4-[7-chloro-2-(4-fluorophenyl) pyrazolo[1,5-a]pyridin-3-yl]-2-pyrimidinamine (80 mg, 0.20 mmol) in tetrahydrofuran (1 mL) was added dimethylzinc (304 μL, 2.0 M in toluene, 0.60 mmol) and tetrakis(triphenyl-phosphine)palladium(0) (23 mg, 0.02 mmol). The reaction mixture was heated at 60° C. for 16 hours. The reaction mixture was cooled, then quenched with ice water. The resultant mixture was extracted with ethyl acetate. The organic layer was washed with water and brine, then dried over magnesium sulfate. Filtration and concentration, followed by flash chromatography (3:1 hexanes:ethyl acetate) provided N-butyl-4-[2-(4-fluorophenyl)-7-methylpyrazolo[1,5-a]pyridin-3-yl]-2-pyrimidinamine (24 mg, 32%) as a yellow solid. R$_f$ 0.33 (2:1 hexanes:ethyl acetate); $^1$H NMR (400 MHz, CDCl$_3$) δ 8.32 (d, 1H), 8.04 (d, 1H), 7.64 (m, 2H), 7.27 (m, 1H), 7.13 (t, 2H), 6.77 (d, 1H), 6.31 (d, 1H), 5.17 (br, 1H), 3.48 (m, 2H), 2.80 (s, 3H), 1.65 (m, 2H), 1.45 (m, 2H), 0.97 (t, 3H); MS m/z 376 (M+1).

EXAMPLE 39

N-Butyl-4-[2-(4-fluorophenyl)-7-octylpyrazolo[1,5-a]pyridin-3-yl]-2-pyrimidinamine

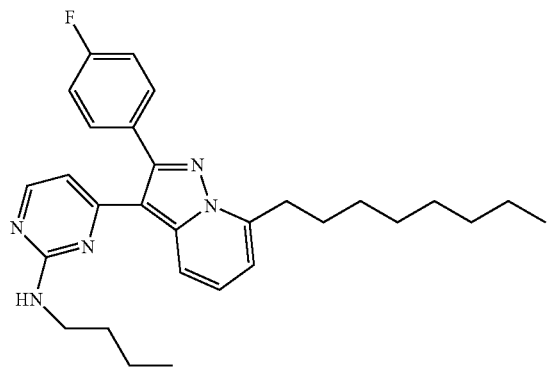

A mixture of 9-borabicyclo[3.3.1]nonane dimer (32 mg, 0.13 mmol) and tetrahydrofuran was stirred at room temperature for 2 hours. To the resultant solution was added 1-octene (38 μL, 0.24 mmol) and the reaction mixture was stirred 4 hours at room temperature. Potassium phosphate (169 μL, 3 M aqueous, 0.507 mmol) was added and the reaction was stirred for 15 minutes. A solution of N-butyl-4-[7-chloro-2-(4-fluorophenyl)pyrazolo[1,5-a]pyridin-3-yl]-2-pyrimidinamine (80 mg, 0.20 mmol) and [1,1'-bis(diphenylphosphino)-ferrocene]dichloropalladium(II) (8 mg, 0.01 mmol) in N,N-dimethylformamide was added to the borane solution and stirred 18 hours. In a separate flask, 9-borabicyclo[3.3.1]nonane dimer (32 mg, 0.13 mmol) was stirred with tetrahydrofuran for 2 hours, to which 1-octene (38 μL, 0.24 mmol) was added and stirred 4 hours. Potassium phosphate (169 μL, 3 M aqueous, 0.507 mmol) was added and the solution was stirred for 15 minutes. This fresh borane solution was added to the original reaction mixture. Additional [1,1'-bis(diphenylphosphino)-ferrocene]dichloropalladium(II) (8 mg, 0.01 mmol) was added and the reaction mixture was stirred 24 hours at room temperature. The reaction mixture was diluted with ethyl acetate. The organic layer was washed with water and brine, then dried over magnesium sulfate. Filtration and concentration, followed by flash chromatography (39:1 dichloromethane: methanol) provided N-butyl-4-[2-(4-fluorophenyl)-7-octylpyrazolo[1,5-a]pyridin-3-yl]-2-pyrimidinamine (8 mg, 8%). $^1$H NMR (300 MHz, CD$_3$OD) δ 8.80–8.55 (br, 1H), 7.84 (br, 1H), 7.71–7.65 (m, 3H), 7.35 (t, 2H), 7.17 (d, 1H), 6.55 (br, 1H), 3.32 (m, 2H), 3.26 (t, 2H), 1.90 (m, 2H), 1.75 (m, 2H), 1.54–1.25 (m, 12H), 1.03 (t, 3H), 0.89 (t, 3H); MS m/z 474 (M+1).

EXAMPLE 40

N-Cyclopropyl-4-[7-ethyl-2-(4-fluorophenyl)pyrazolo[1,5-a]pyridin-3-yl]-2-pyrimidinamine

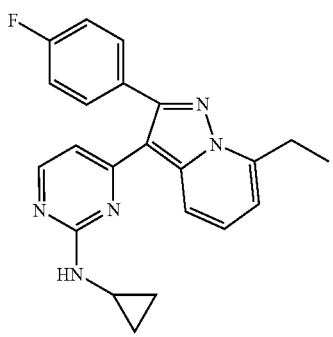

a) 4-[7-Chloro-2-(4-fluorophenyl)pyrazolo[1,5-a]pyridin-3-yl]-N-cyclopropyl-2-pyrimidinamine.

In a similar manner as described in Example 37, from 1-[7-chloro-2-(4-fluorophenyl)pyrazolo[1,5-a]pyridin-3-yl]-2-propyn-1-one (2.65 g, 8.9 mmol) and N-cyclopropylguanidine sulfate (2.27 g, 11.5 mmol) was prepared 4-[7-chloro-2-(4-fluorophenyl)pyrazolo[1,5-a]pyridin-3-yl]-N-cyclopropyl-2-pyrimidinamine (1.59 g, 47%) as a yellow solid. $^1$H NMR (CDCl$_3$): δ 8.66 (m, 1 H), 8.03 (m, 1 H), 7.66 (m, 2 H), 7.35 (t, 1 H), 7.18 (m, 3 H), 6.40 (d, 1 H), 6.06 (broad, 1 H), 2.90 (m, 1 H), 0.91 (m, 2 H), 0.70 (m, 2 H); $^{19}$F NMR (CDCl$_3$) δ −112.22; MS m/z 380 (M+1).

b) N-Cyclopropyl-4-[7-ethyl-2-(4-fluorophenyl)pyrazolo[1,5-a]pyridin-3-yl]-2-pyrimidinamine.

In a similar manner as described in Example 38, from 4-[7-chloro-2-(4-fluorophenyl)pyrazolo[1,5-a]pyridin-3-yl]-N-cyclopropyl-2-pyrimidinamine (100 mg, 0.26 mmol) and diethylzinc was prepared N-cyclopropyl-4-[7-ethyl-2-(4-fluorophenyl)pyrazolo[1,5-a]pyridin-3-yl]-2-pyrimidinamine (51.6 mg, 52%) as an off-white solid. $^1$H NMR (CDCl$_3$): δ 8.51 (m, 1 H), 7.99 (m, 1 H), 7.63 (m, 2 H), 7.35 (m, 1 H), 7.16 (t, 2 H), 6.82 (d, 1 H), 6.37 (d, 1 H), 3.25 (q, 2 H), 2.87 (m, 1 H), 1.45 (t, 3 H), 0.88 (m, 2 H), 0.67 (m, 2 H); $^{19}$F NMR (CDCl$_3$) δ −113.32; MS m/z 374 (M+1).

EXAMPLE 41

4-[7-Butoxy-2-(4-methoxyphenyl)pyrazolo[1,5-a]pyridin-3-yl]-N-cyclopentyl-2-pyrimidinamine

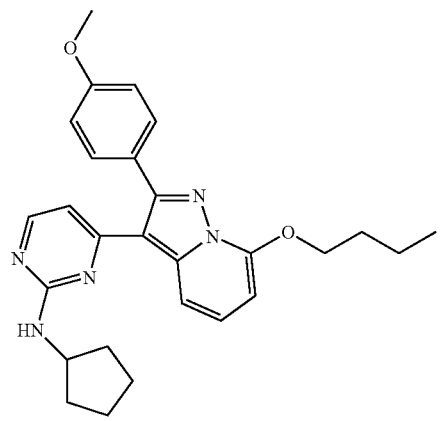

The title compound was prepared in a similar manner as described in above examples to give a yellow solid. $^1$H NMR (CDCl$_3$): δ 8.08 (d, 1H), 8.02 (d, 1H), 7.59 (d, 2H), 7.30 (m, 1H), 6.97 (d, 2H), 6.34 (d, 1H), 6.23 (d, 1H), 5.13 (d, 1H), 4.41–4.34 (m, 3H), 3.87 (s, 3H), 2.10 (m, 2H), 1.99 (m, 2H), 1.80–1.54 (m, 8H), 1.02 (t, 3H); MS m/z 458 (M+1).

EXAMPLE 42

4-[5-Chloro-2-(3-chlorophenyl)-7-(methylsulfanyl)pyrazolo[1,5-a]pyridin-3-yl]-N-cyclopentyl-2-pyrimidinamine

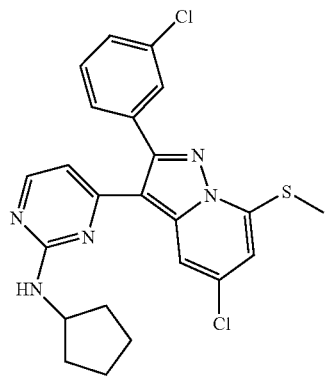

The title compound was prepared in a similar manner as described in above examples to give a yellow solid. R$_f$ 0.23 (4:1 hexanes:ethyl acetate); $^1$H NMR (CDCl$_3$) δ 8.37 (s, 1H), 8.02 (d, 1H), 7.70 (s, 1H), 7.50 (d, 1H), 7.45–7.33 (m, 2H), 6.61 (s, 1H), 6.29 (d, 1H), 5.20 (d, 1H), 4.36 (m, 1H), 2.65 (s, 3H), 2.15 (m, 2H), 1.84–1.52 (m, 6H); MS m/z 470 (M+1).

EXAMPLE 43

N-cyclopentyl-6-[2-(4-fluorophenyl)-7-(methylthio)pyrazolo[1,5-a]pyridin-3-yl]pyrimidin-4-amine

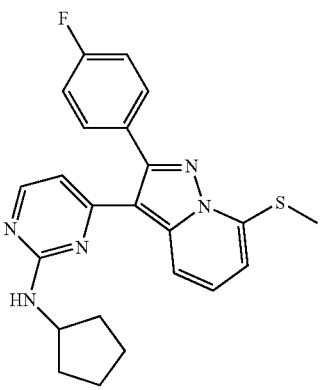

The title compound was prepared in a similar manner as described in above examples to give a peach colored solid. $^1$H NMR (CDCl$_3$) δ 8.60 (s, 1H), 8.26 (d, 1H), 7.86 (m, 2H), 7.32 (t, 1H), 7.15 (t, 2H), 6.70 (d, 1H), 6.08 (s, 1H), 4.95 (br, 1H), 3.58 (br, 1H), 2.65 (s, 3H), 1.85–1.50 (m, 6H), 1.38–1.22 (m, 2H); MS m/z 420 (M+1).

EXAMPLE 44

N-Cyclopentyl-4-[2-(4-fluorophenyl)-7-(methylthio)-5-morpholin-4-ylpyrazolo[1,5-a]pyridin-3-yl]pyrimidin-2-amine

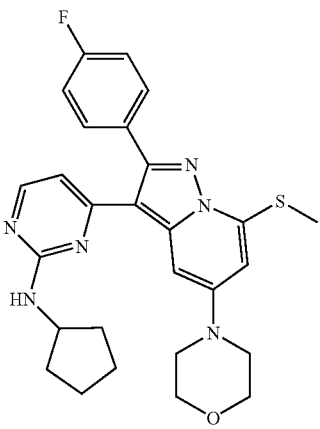

In a similar manner as described for above examples the title compound was prepared as a solid. $^1$H NMR (CDCl$_3$): δ 8.01 (d, 1H), 7.64 (m, 3H), 7.15 (t, 2H), 6.45 (d, 1H), 6.26 (d, 1H), 5.17 (d, 1H), 4.46 (m, 1H), 3.93 (m, 4H), 3.33 (m, 4H), 2.66 (s, 3H), 2.1–1.5 (m, 8H); $^{19}$F NMR (CDCl$_3$): δ −113.5; MS m/z 505 (M+1).

EXAMPLE 45

N-Cyclopentyl-4-[2-(4-fluorophenyl)-7-(isopropylthio)-5-morpholin-4-ylpyrazolo[1,5-a]pyridin-3-yl]pyrimidin-2-amine

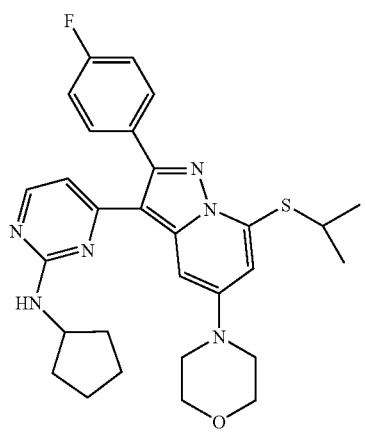

In a similar manner as described for above examples the title compound was prepared as a solid. $^1$H NMR (CDCl$_3$): δ 8.01 (d, 1H), 7.66 (m, 3H), 7.15 (t, 2H), 6.71 (d, 1H), 6.27 (d, 1H), 5.21 (d, 1H), 4.44 (m, 1H), 3.93 (m, 4H), 3.31 (m, 4H), 2.1–1.5 (m, 9H), 1.44 (d, 6H); $^{19}$F NMR (CDCl$_3$): δ −113.6; MS m/z 534 (M+1).

EXAMPLES 46–179

Using the techniques described above for Examples 1–45, the following additional compounds are prepared.

| Example No. | Structure |
| --- | --- |
| 46 | (structure shown) |

-continued
| Example No. | Structure |
|---|---|
| 47 | 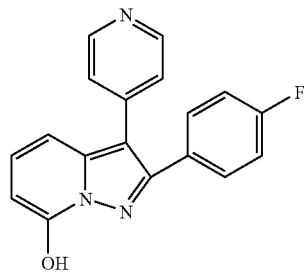 |
| 48 | 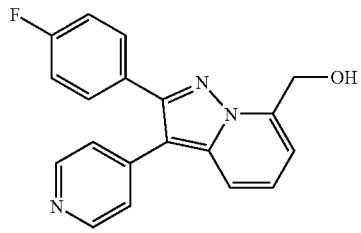 |
| 49 | 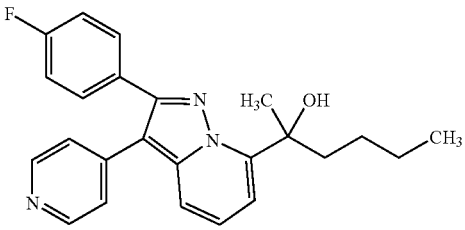 |
| 50 | 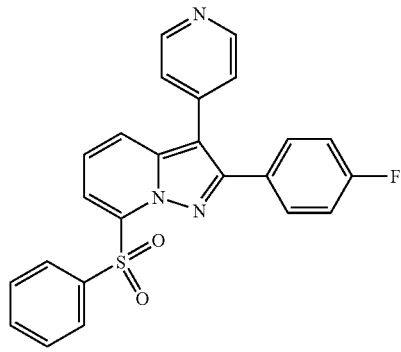 |
| 51 | 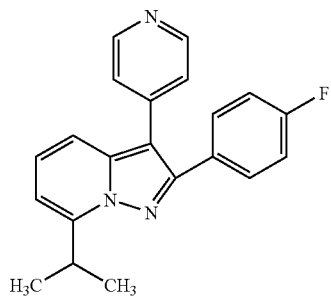 |

-continued
| Example No. | Structure |
|---|---|
| 52 | 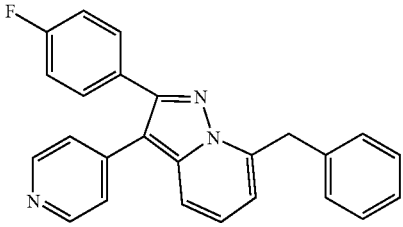 |
| 53 | 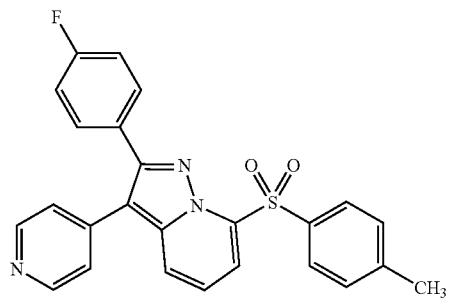 |
| 54 | 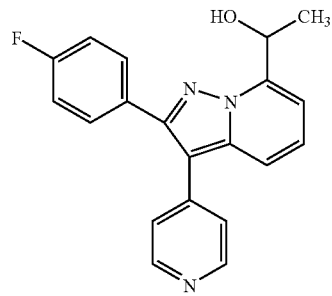 |
| 55 | 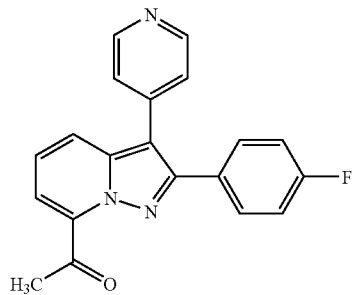 |
| 56 | 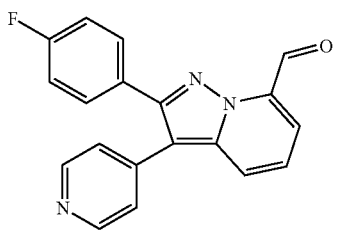 |

-continued
| Example No. | Structure |
|---|---|
| 57 | 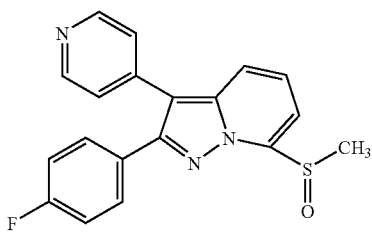 |
| 58 | 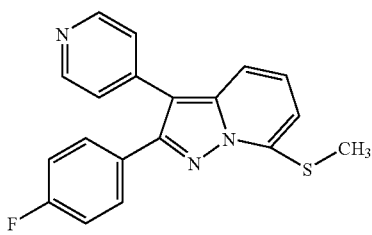 |
| 59 | 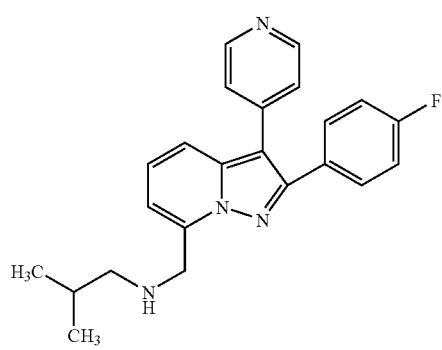 |
| 60 | 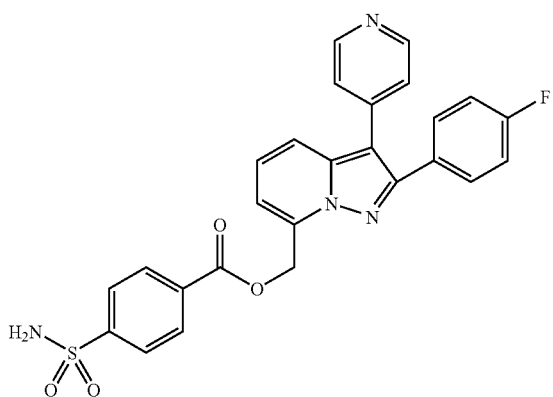 |
| 61 | 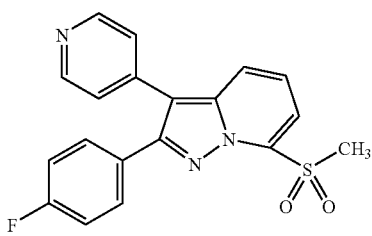 |

-continued
| Example No. | Structure |
|---|---|
| 62 | 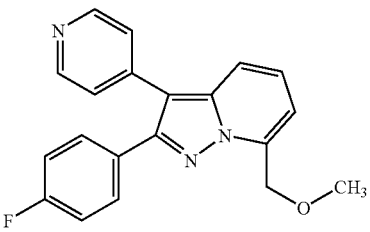 |
| 63 | 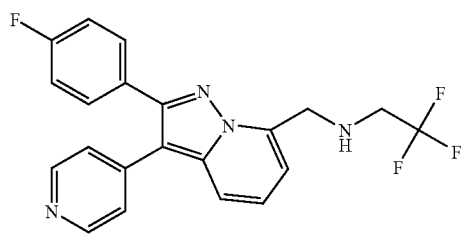 |
| 64 | 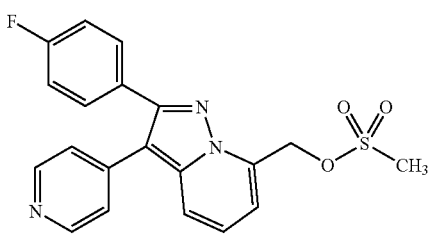 |
| 65 | 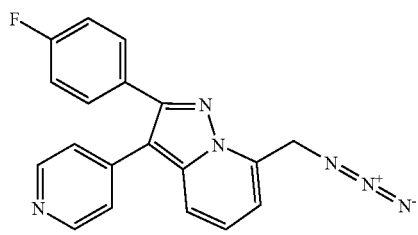 |
| 66 | 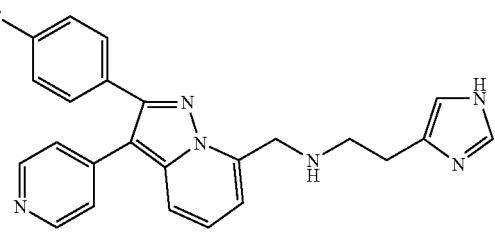 |
| 67 | 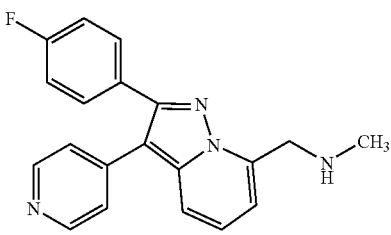 |

-continued
| Example No. | Structure |
|---|---|
| 68 | 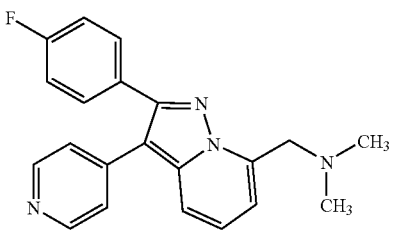 |
| 69 | 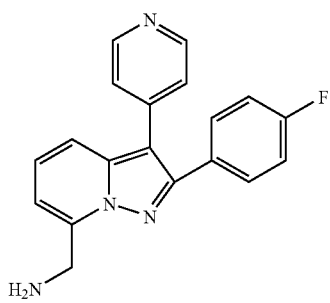 |
| 70 | 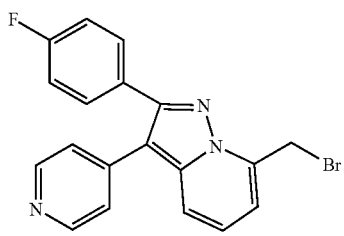 |
| 71 | 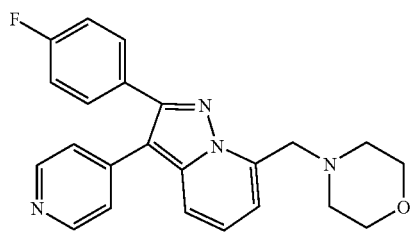 |
| 72 | 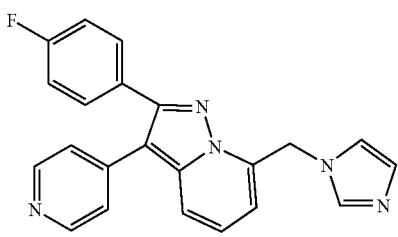 |
| 73 | 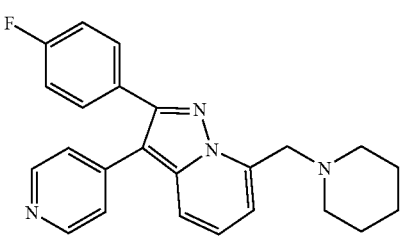 |

-continued
| Example No. | Structure |
|---|---|
| 74 | 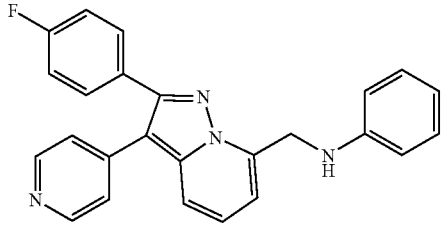 |
| 75 | 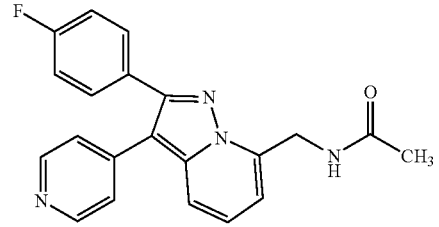 |
| 76 | 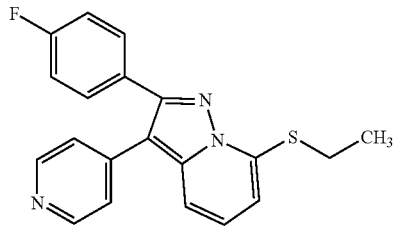 |
| 77 | 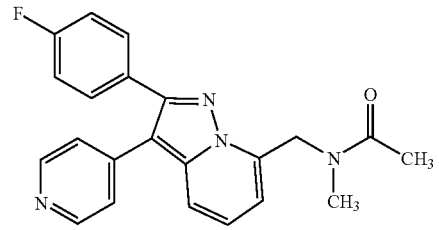 |
| 78 | 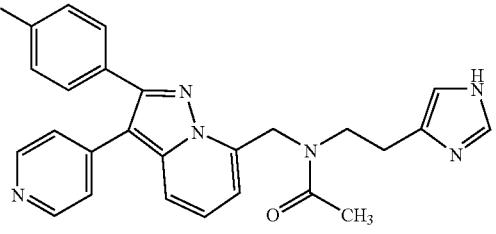 |
| 79 | 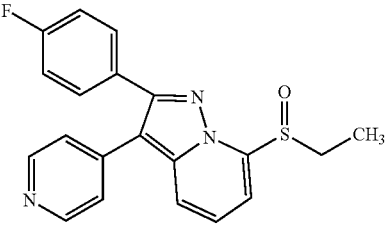 |

-continued

| Example No. | Structure |
|---|---|
| 80 | 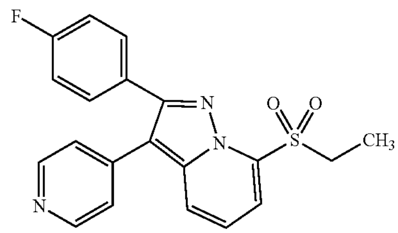 |
| 81 | 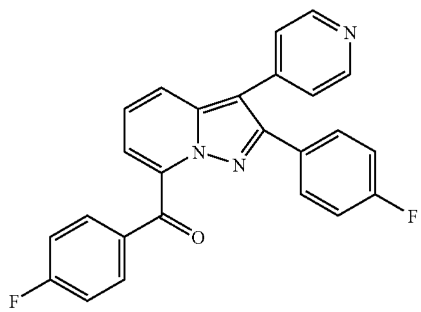 |
| 82 | 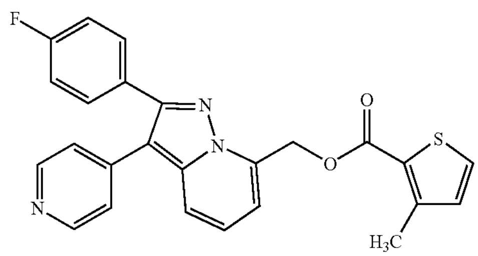 |
| 83 | 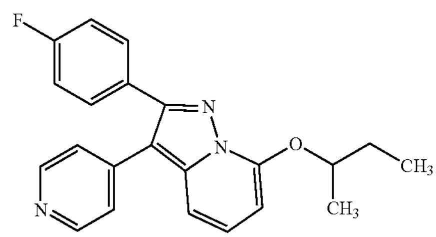 |
| 84 | 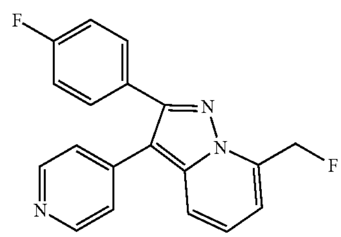 |
| 85 | 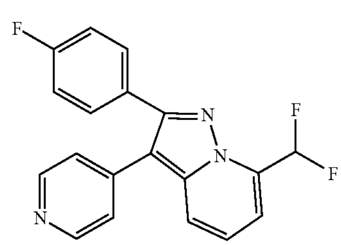 |

-continued
| Example No. | Structure |
|---|---|
| 86 | 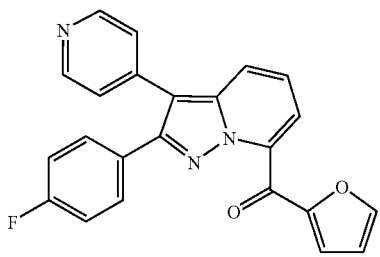 |
| 87 | 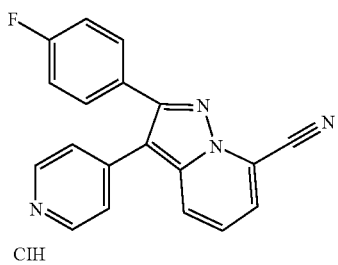
ClH |
| 88 | 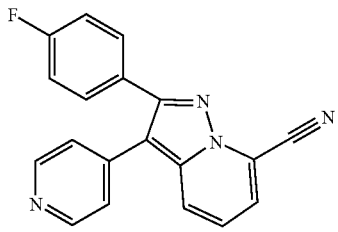 |
| 89 | 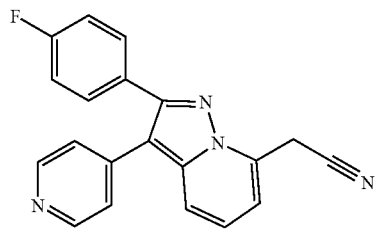 |
| 90 | 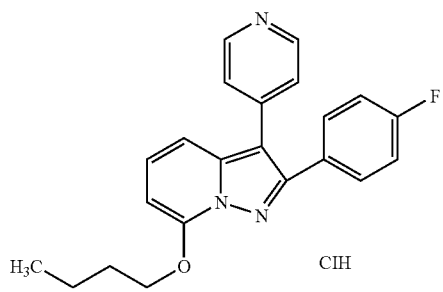
ClH |
| 91 | 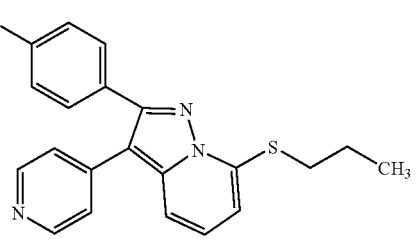 |

-continued
| Example No. | Structure |
|---|---|
| 92 | 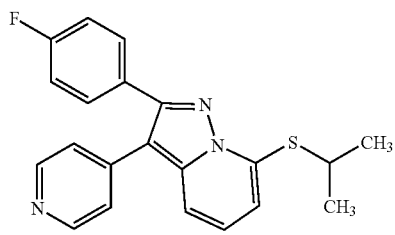 |
| 93 | 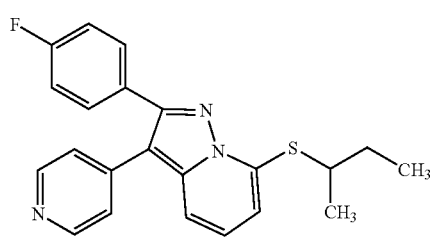 |
| 94 | 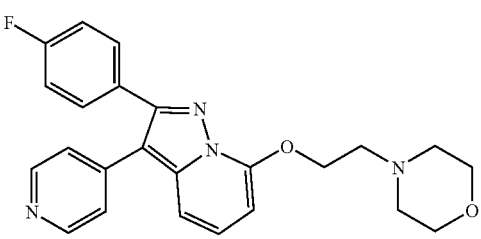 |
| 95 | 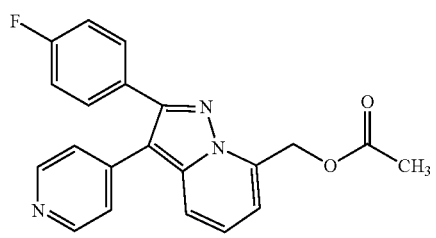 |
| 96 | 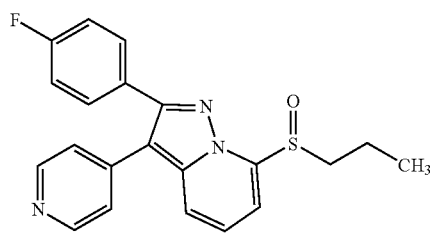 |
| 97 | 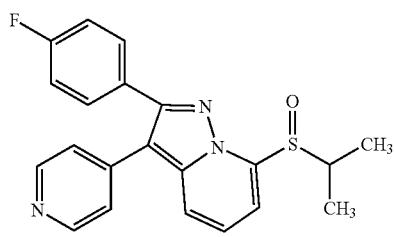 |

-continued
| Example No. | Structure |
|---|---|
| 98 | 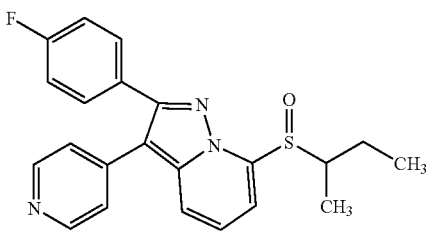 |
| 99 | 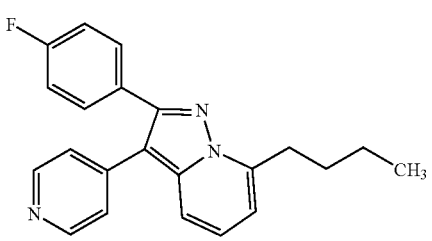 |
| 100 | 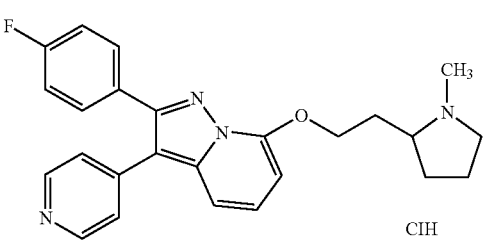 |
| 101 | 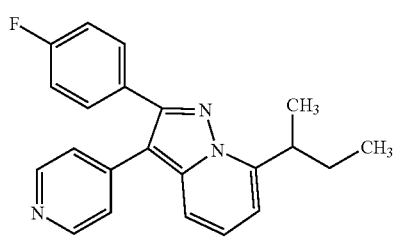 |
| 102 | 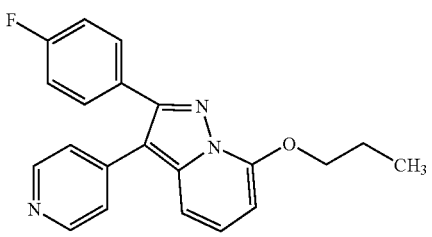 |
| 103 | 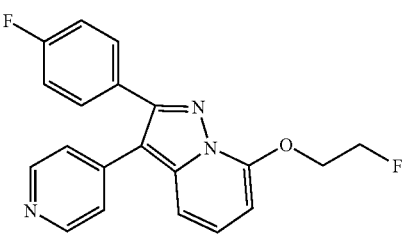 |

| Example No. | Structure |
|---|---|
| 104 | 2-(4-fluorophenyl)-3-(6-butylpyrimidin-4-yl)-7-(methylthio)pyrazolo[1,5-a]pyridine |
| 105 | 7-ethoxy-2-(4-fluorophenyl)-3-(pyridin-4-yl)pyrazolo[1,5-a]pyridine |
| 106 | 7-ethyl-2-(4-fluorophenyl)-3-(pyridin-4-yl)pyrazolo[1,5-a]pyridine |
| 107 | 2-(4-fluorophenyl)-7-(2,2,3,3,3-pentafluoropropoxy)-3-(pyridin-4-yl)pyrazolo[1,5-a]pyridine |
| 108 | 2-(4-fluorophenyl)-3-(pyrimidin-4-yl)-7-(2,2,2-trifluoroethoxy)pyrazolo[1,5-a]pyridine |
| 109 | 2-(4-fluorophenyl)-7-propyl-3-(pyridin-4-yl)pyrazolo[1,5-a]pyridine |

-continued
| Example No. | Structure |
|---|---|
| 110 | 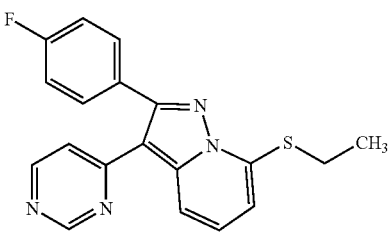 |
| 111 | 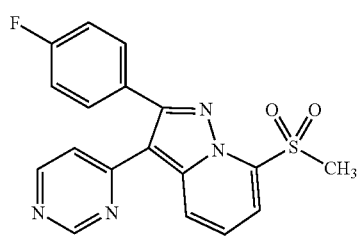 |
| 112 | 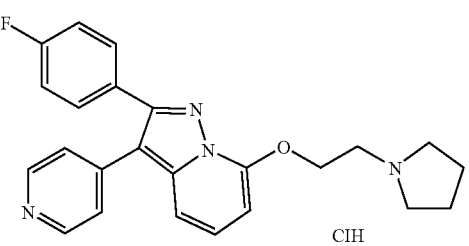 |
| 113 | 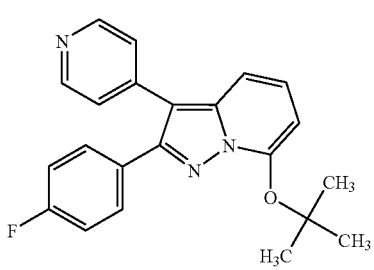 |
| 114 | 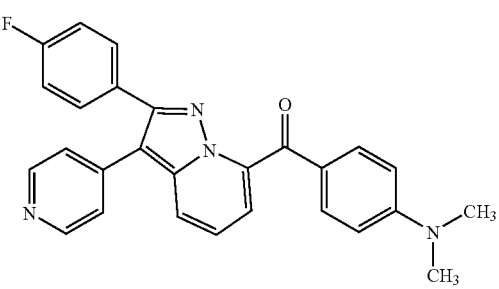 |
| 115 | 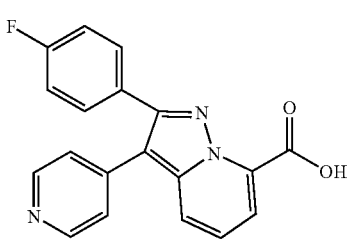 |

-continued
| Example No. | Structure |
|---|---|
| 116 | 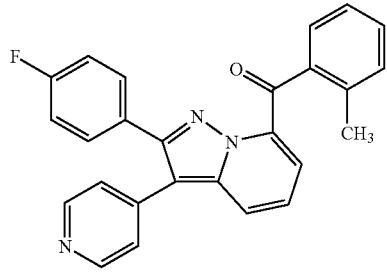 |
| 117 | 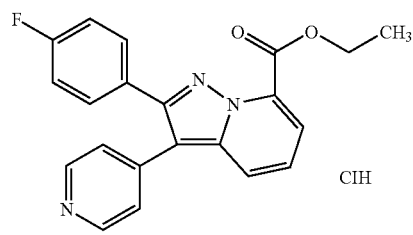 ClH |
| 118 | 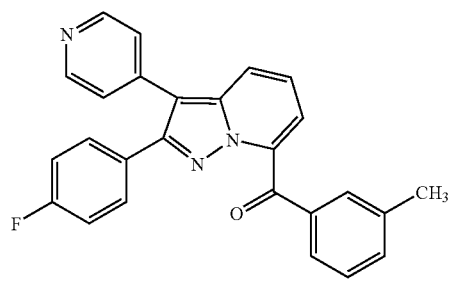 |
| 119 | 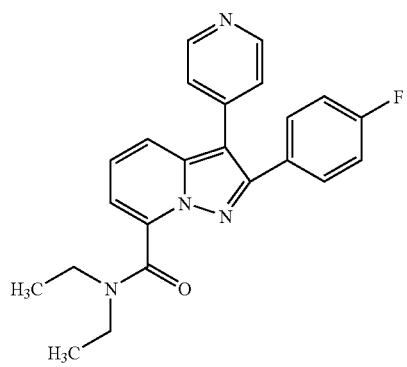 |
| 120 | 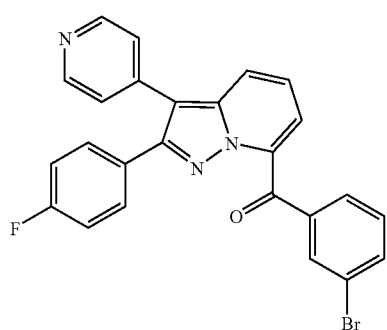 |

-continued

| Example No. | Structure |
|---|---|
| 121 | 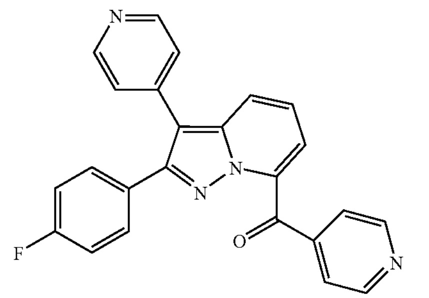 |
| 122 | 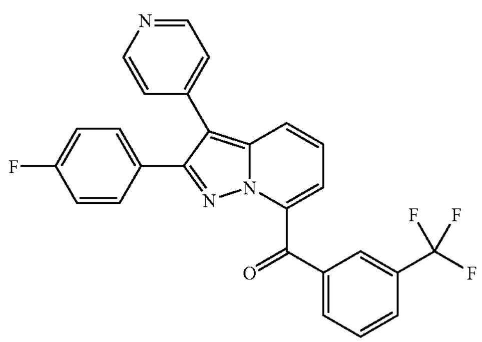 |
| 123 | 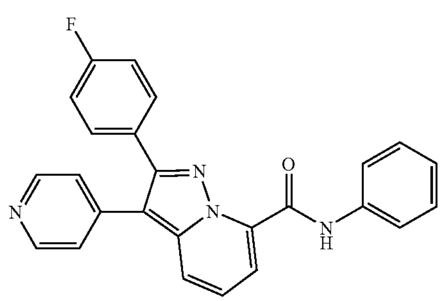 |
| 124 | 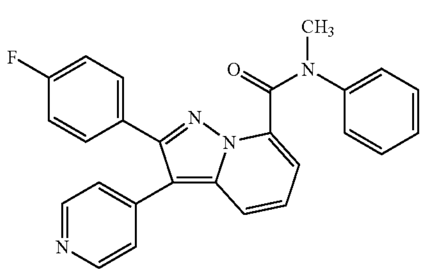 |
| 125 | 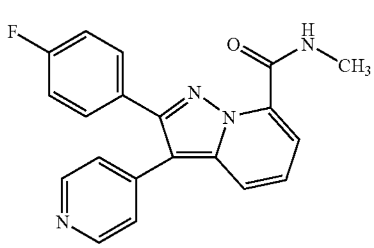 |

-continued
| Example No. | Structure |
|---|---|
| 126 | 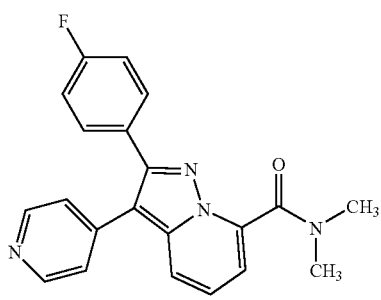 |
| 127 | 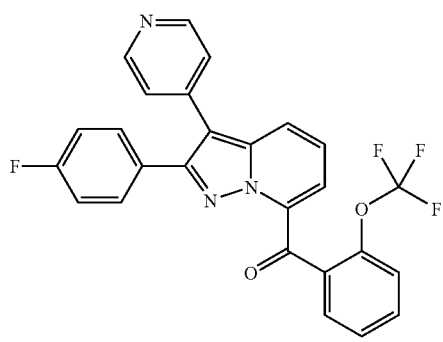 |
| 128 | 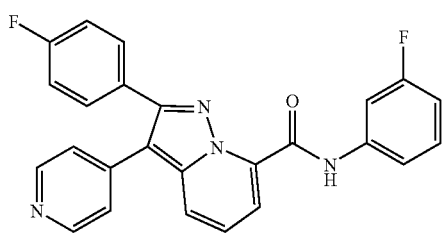 |
| 129 | 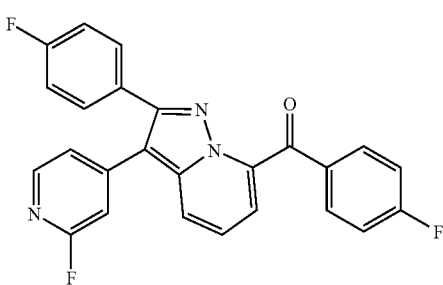 |
| 130 | 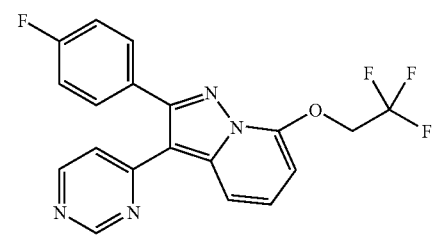 |

-continued

| Example No. | Structure |
|---|---|
| 131 | (structure) |
| 132 | (structure) |
| 133 | (structure) |
| 134 | (structure) |
| 135 | (structure) |
| 136 | (structure) |

-continued
| Example No. | Structure |
|---|---|
| 137 | 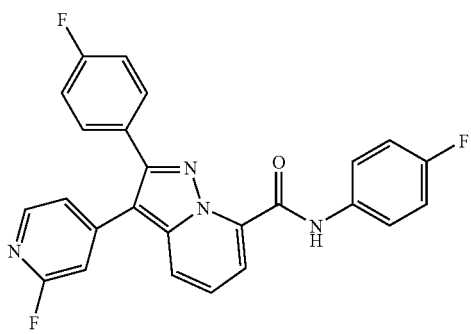 |
| 138 | 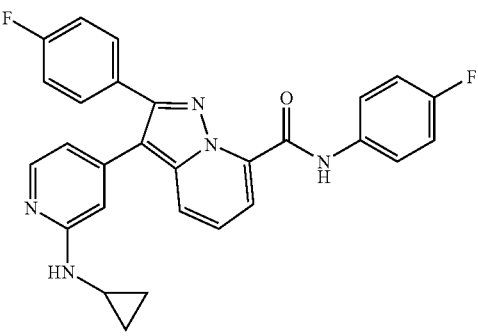 |
| 139 | 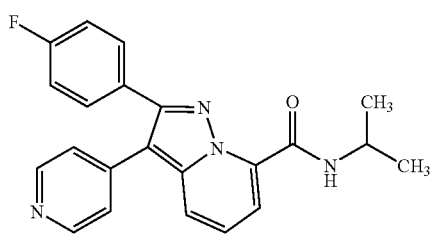 |
| 140 | 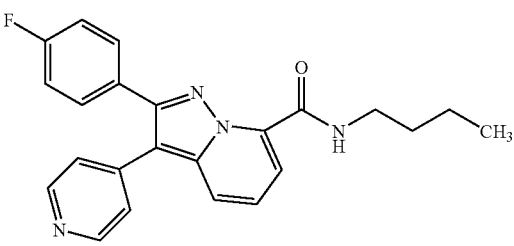 |
| 141 | 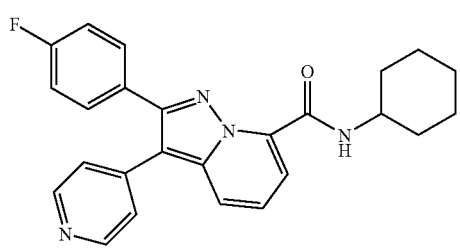 |

-continued
| Example No. | Structure |
|---|---|
| 142 | 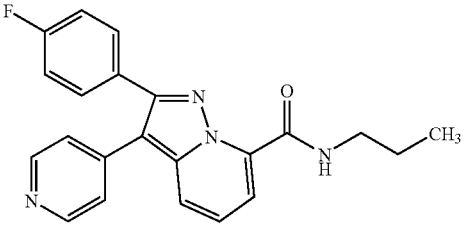 |
| 143 | 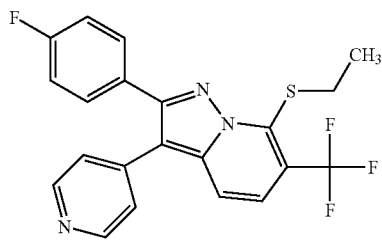 |
| 144 | 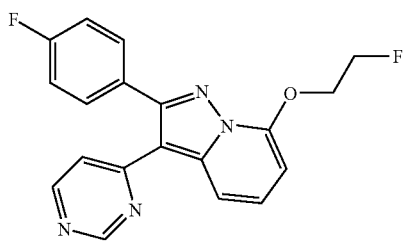 |
| 145 | 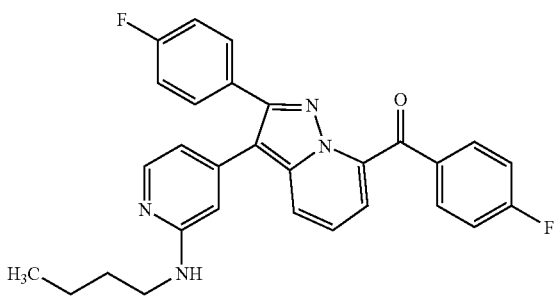 |
| 146 | 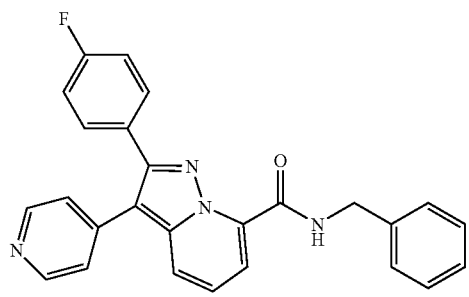 |

-continued
| Example No. | Structure |
|---|---|
| 147 | 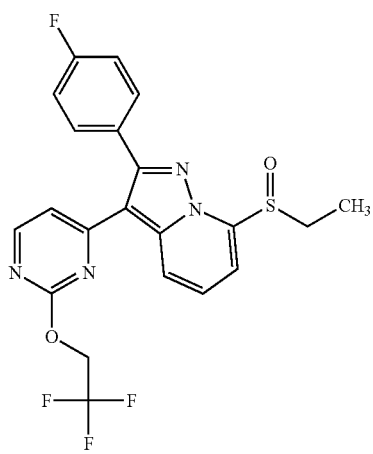 |
| 148 | 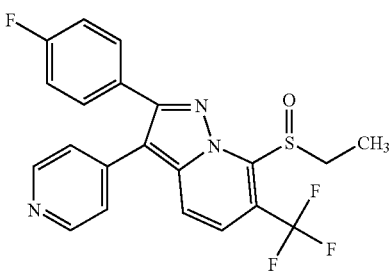 |
| 149 | 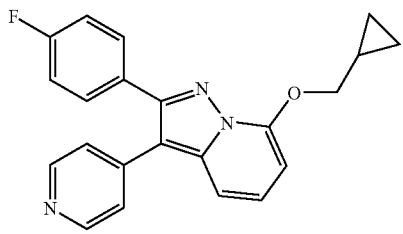 |
| 150 | 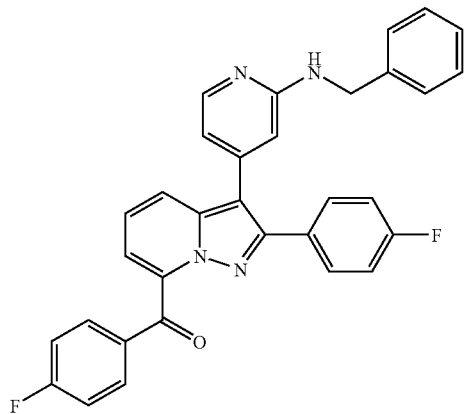 |

-continued

| Example No. | Structure |
|---|---|
| 151 | 2-(4-fluorophenyl)-3-(pyridin-4-yl)-7-(trifluoroacetyl)pyrazolo[1,5-a]pyridine |
| 152 | 2-(4-fluorophenyl)-7-(4-nitrobenzoyl)-3-(pyridin-4-yl)pyrazolo[1,5-a]pyridine |
| 153 | 2-(4-fluorophenyl)-7-isopropoxy-3-(pyridin-4-yl)pyrazolo[1,5-a]pyridine |
| 154 | 2-(4-fluorophenyl)-7-(2-fluoroethoxy)-3-(pyridin-4-yl)-6-(trifluoromethyl)pyrazolo[1,5-a]pyridine |
| 155 | 7-(ethylthio)-2-(4-fluorophenyl)-3-(2-(ethylthio)pyridin-4-yl)pyrazolo[1,5-a]pyridine |

-continued
| Example No. | Structure |
|---|---|
| 156 | 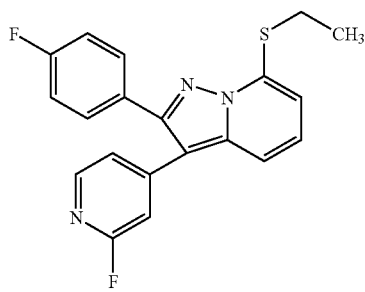 |
| 157 | 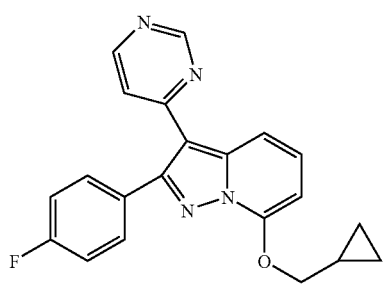 |
| 158 | 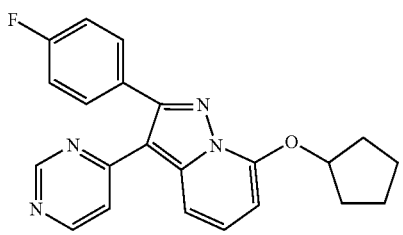 |
| 159 | 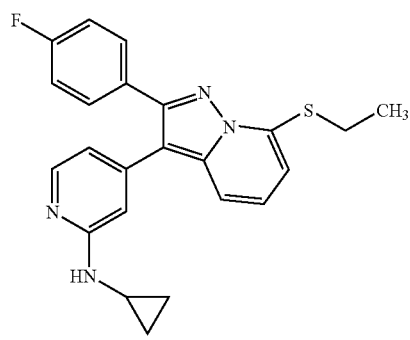 |
| 160 | 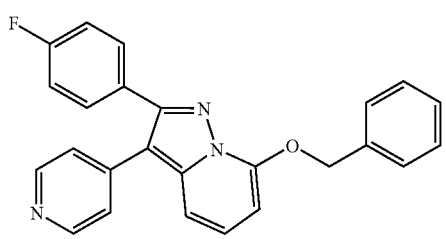 |

-continued
| Example No. | Structure |
|---|---|
| 161 | 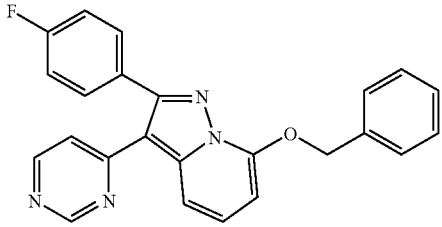 |
| 162 | 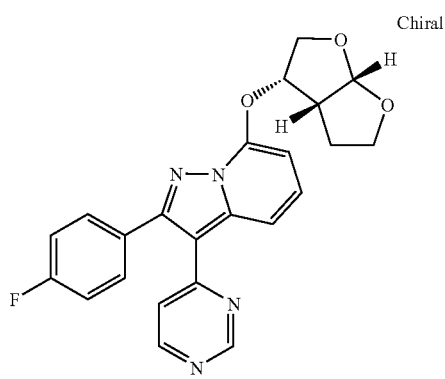 Chiral |
| 163 | 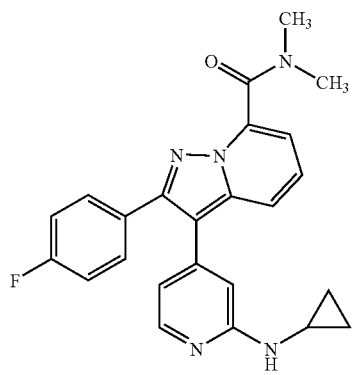 |
| 164 | 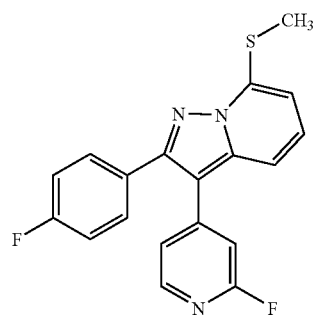 |

-continued
| Example No. | Structure |
|---|---|
| 165 | 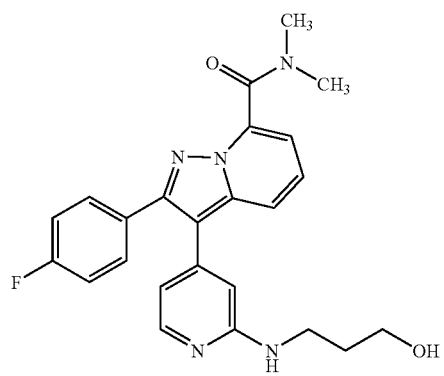 |
| 166 | 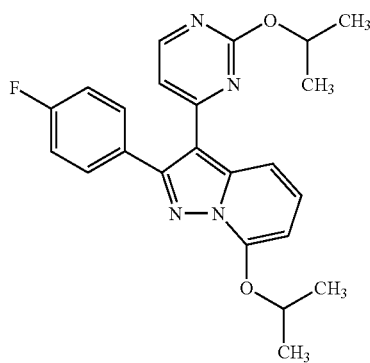 |
| 167 | 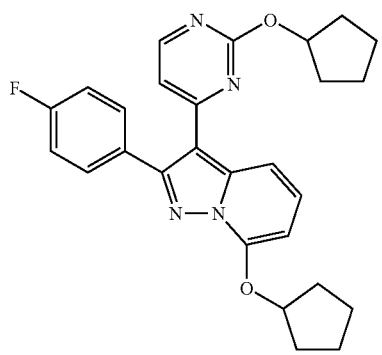 |
| 168 | 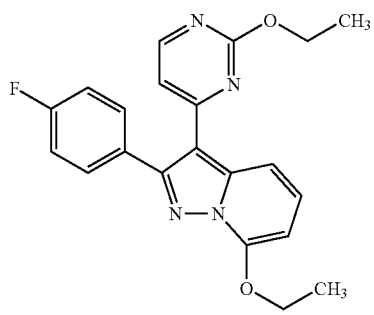 |

| Example No. | Structure |
|---|---|
| 169 | 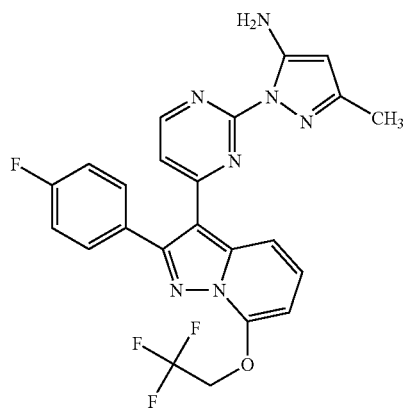 |
| 170 | 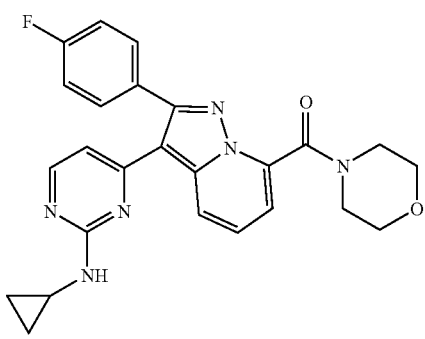 |
| 171 | 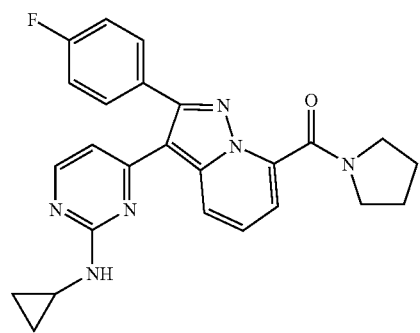 |
| 172 | 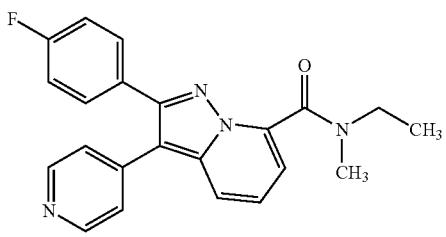 |

-continued
| Example No. | Structure |
|---|---|
| 173 | 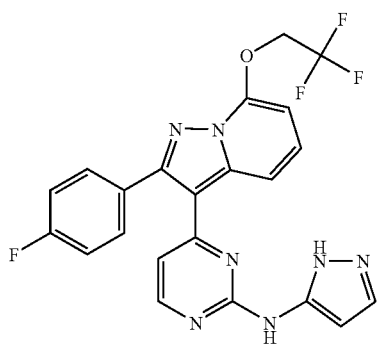 |
| 174 | 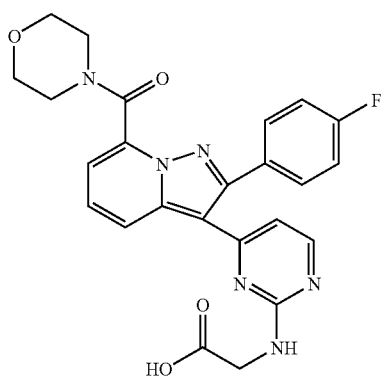 |
| 175 | 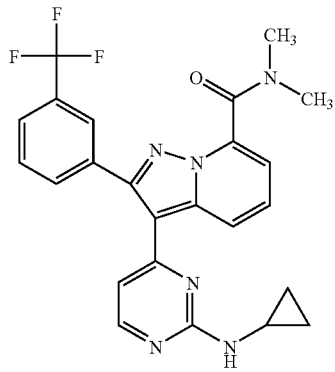 |
| 176 | 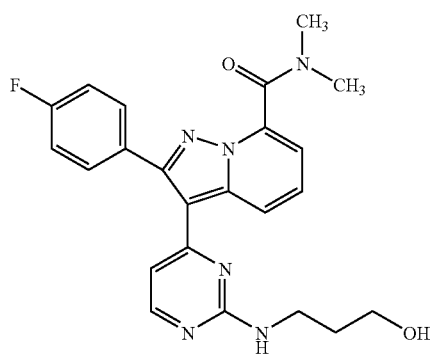 |

| Example No. | Structure |
|---|---|
| 177 | 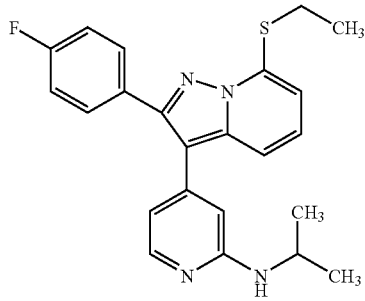 |
| 178 | 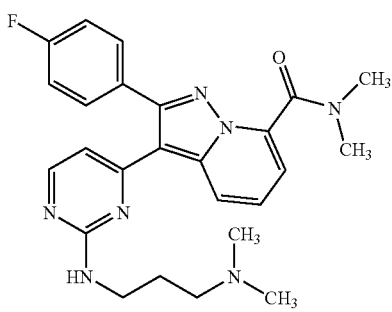 |
| 179 | 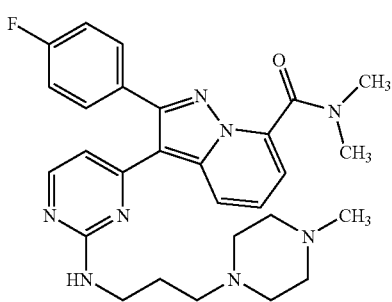 |

EXAMPLE 180

Biological Activity

In the following example, "MEM" means Minimal Essential Media; "FBS" means Fetal Bovine Serum; "NP40" and "Igepal" are detergents; "MOI" means Multiplicity of Infection; "NaOH" means sodium hydroxide; "MgCl$_2$" means magnesium chloride; "dATP" means deoxyadenosine 5' triphosphate; "dUTP" means deoxyuridine 5' triphosphate; "dCTP" means dexoxycytidine 5' triphosphate; "dGTP" means deoxyguanosine 5' triphosphate; "GuSCN" means Guanidinium thiocyanate; "EDTA" means ethylenediamine tetraacetic acid; "TE" means Tris-EDTA; "SCC" means sodium chloride/sodium citrate; "APE" means a solution of ammonia acetate, ammonia phosphate, EDTA; "PBS" means phosphate buffered saline; and "HRP" means horseradish peroxidase.

a) Tissue Culture and HSV Infection.

Vero 76 cells were maintained in MEM with Earle's salts, L-glutamine, 8% FBS (Hyclone, A-1111-L) and 100 units/mL Penicillin-100 µg/mL Streptomycin. For assay conditions, FBS was reduced to 2%. Cells are seeded into 96-well tissue culture plates at a density of $5 \times 10^4$ cells/well after being incubated for 45 min at 37° C. in the presence of HSV-1 or HSV-2 (MOI=0.001). Test compounds are added to the wells and the plates are incubated at 37° C. for 40–48 hours. Cell lysates are prepared as follows: media was removed and replaced with 150 µL/well 0.2 N NaOH with 1% Igepal CA 630 or NP-40. Plates were incubated up to 14 days at room temperature in a humidified chamber to prevent evaporation.

(b) Preparation of Detection DNA.

For the detection probe, a gel-purified, digoxigenin-labeled, 710-bp PCR fragment of the HSV UL-15 sequence was utilized. PCR conditions included 0.5 µM primers, 180 µM dTTP, 20 µM dUTP-digoxigenin (Boehringer Mannheim 1558706), 200 µM each of dATP, dCTP, and dGTP, 1×PCR Buffer II (Perkin Elmer), 2.5 mM MgCl$_2$, 0.025 units/µL of AmpliTaq Gold polymerase (Perkin Elmer), and 5 ng of gel-purified HSV DNA per 100 µL. Extension conditions were 10 min at 95° C., followed by 30 cycles of 95° C. for 1 min, 55° C. for 30 sec. and 72° C. for 2 min. The amplification was completed with a 10-min incubation at 72° C. Primers were selected to amplify a 278 bp prove spanning a section of the HSV1 UL15 open reading frame (nucleotides 249–977). Single-stranded transcripts were purified with Promega M13 Wizard kits. The final product was mixed 1:1 with a mixture of 6 M GuSCN, 100 mM EDTA and 200 μg/mL herring sperm DNA and stored at 4° C.

(c) Preparation of Capture Plates.

The capture DNA plasmid (HSV UL13 region in pUC) was linearized by cutting with Xba I, denatured for 15 min at 95° C. and diluted immediately into Reacti-Bind DNA Coating Solution (Pierce, 17250, diluted 1:1 with TE buffer, pH 8) at 1 ng/μL 75 μL/well were added to Corning (#3922 or 9690) white 96-well plates and incubated at room temperature for at least 4 hrs before washing twice with 300 μL/well 0.2× SSC/0.05% Tween-20 (SSC/T buffer). The plates were then incubated overnight at room temperature with 150 μL/well 0.2 N NaOH, 1% IGEPAL and 10 μg/mL herring sperm DNA.

(d) Hybridization.

Twenty-seven (27) μL of cell lysate was combined with 45 μL of hybridization solution (final concentration: 3M GuSCN, 50 mM EDTA, 100 μg/ml salmon sperm DNA, 5× Denhardt's solution, 0.25×APE, and 5 ng of the digoxigenin-labeled detection probe). APE is 1.5 M $NH_4$-acetate, 0.15 M ammonium phosphate monobasic, and 5 mM EDTA adjusted to pH 6.0. Mineral oil (50 μL) was added to prevent evaporation. The hybridization plates were incubated at 95° C. for 10 minutes to denature the DNA, then incubated at 42° C. overnight. The wells were washed 6× with 300 μL/well SSC/T buffer then incubated with 75 μL/well anti-digoxigenin-HRP-conjugated antibody (Boehringer Mannheim 1207733, 1:5000 in TE) for 30 min at room temperature. The wells were washed 6× with 300 μL/well with PBS/0.05% Tween-20 before 75 μL/well SuperSignal LBA substrate (Pierce) was added. The plates were incubated at room temperature for 30 minutes and chemiluminescence was measured in a Wallac Victor reader.

e) Results.

The following results were obtained for HSV-1.

| Example No. | $IC_{50}$ (μM) |
|---|---|
| 9 | 2.5 |
| 11 | 10 |
| 12 | 5 |
| 14 | 2 |
| 16 | 0.9 |
| 18 | 25 |
| 19 | 15 |
| 20 | 15 |
| 23 | 15 |
| 32 | 2 |
| 36 | 1 |
| 37 | 0.6 |
| 38 | 1 |
| 39 | 6 |
| 40 | 3 |
| 41 | 0.28 |
| 42 | 1.0 |
| 43 | 1.3 |
| 44 | 0.5 |
| 45 | 0.9 |

The results demonstrated that the compounds of the present invention are useful for The treatment and prophylaxis of herpes viral infections.

The invention claimed is:
1. A compound of formula (I):

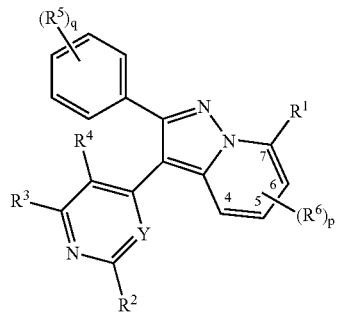

wherein:
$R^1$ is selected from the group consisting of alkyl, alkenyl, alkynyl, cycloalkyl, cycloalkenyl, —$R^{10}$cycloalkyl, —$R^{10}$Ay, —$R^{10}$Het, —$OR^7$, —OAy, —OHet, —$OR^{10}$Ay, —$OR^{10}$Het, —$R^{10}OR^9$, —$R^{10}NR^7R^8$, —$R^{10}NR^7$Ay, —$R^{10}C(O)R^9$, —$C(O)R^9$, —C(O)Ay, —C(O)Het, —$R^{10}OC(O)R^9$, —$R^{10}OC(O)$Ay, —$R^{10}OC(O)$Het, —$CO_2R^9$, —$R^{10}CO_2R^9$, —C(O)$NR^7R^8$, —C(O)$NR^7$Ay, —C(O)NH$R^{10}$Ay, —$R^{10}C(O)NR^9R^{11}$, —C(S)$NR^9R^{11}$, —$R^{10}C(S)NR^9R^{11}$, —$R^{10}$NHC(NH)$NR^9R^{11}$, —C(NH)$NR^7R^8$, —C(NH)$NR^7$Ay, —$R^{10}C(NH)NR^9R^{11}$, —$S(O)_2NR^7R^8$, —$S(O)_2NR^7$Ay, —$R^{10}SO_2NHCOR^9$, —$R^{10}SO_2NR^9R^{11}$, —$R^{10}SO_2R^9$, —$R^{10}OS(O)_nR^9$, —$R^{10}NHSO_2R^9$, —$R^{10}NHCOR^9$, —$S(O)_nR^9$, —$S(O)_n$Ay, —$S(O)_n$Het, cyano, azido and nitro;
each $R^7$ and $R^8$ are the same or different and are independently selected from the group consisting of H, alkyl, cycloalkyl, alkenyl, cycloalkenyl, —$R^{10}$cycloalkyl, —$OR^9$, —$R^{10}OR^9$, —$R^{10}NR^9R^{11}$, —$R^{10}C(O)R^9$, —$C(O)R^9$, —$CO_2R^9$, —$R^{10}CO_2R^9$, —C(O)$NR^9R^{11}$, —$R^{10}C(O)NR^9R^{11}$, —C(S)$NR^9R^{11}$, —$R^{10}C(S)NR^9R^{11}$, —$R^{10}$NHC(NH)$NR^9R^{11}$, —$R^{10}C(NH)NR^9R^{11}$, —C(NH)$NR^9R^{11}$, —$SO_2NR^9R^{11}$, —$R^{10}SO_2NR^9R^{11}$, —$R^{10}NHSO_2R^9$, —$SO_2R^{10}$, —$R^{10}SO_2R^{10}$, —$R^{10}NHCOR^9$ and —$R^{10}SO_2NHCOR^9$;
each $R^9$ and $R^{11}$ are the same or different and are independently selected from the group consisting of H, alkyl, cycloalkyl, —$R^{10}$cycloalkyl, —$R^{10}OH$, —$R^{10}(OR^{10})$w where w is 1–10, and —$R^{10}NR^{10}R^{10}$;
each $R^{10}$ is the same or different and is independently selected from the group consisting of alkyl, cycloalkyl, alkenyl, cycloalkenyl and alkynyl;
Ay is an aryl;
Het is a 5- or 6-membered heterocyclic or heteroaryl group;
n is 0, 1 or 2;
$R^2$ is selected from the group consisting of H, halo, alkyl, cycloalkyl, alkenyl, cycloalkenyl, —$NR^7R^8$, Ay, —NHR$^{10}$Ay, —$OR^7$, —OAy, —$S(O)_nR^9$, —$S(O)_n$Ay, —$R^{10}NR^7R^8$, —$R^{10}NR^7$Ay, Het, —NHHet, —NHR$^{10}$Het, —OHet and —OR$^{10}$Het;
Y is N;
$R^3$ and $R^4$ are the same or different and are each independently selected from the group consisting of H, halo, alkyl, cycloalkyl, alkenyl, Ay, —$OR^7$, —OAy, —$R^{10}OR^7$, —$R^{10}$OAy, —$NR^7R^8$, —$NR^7$Ay, —R$^{10}$NR$^7$R$^8$, —R$^{10}$NR$^7$Ay, —C(O)R$^7$, C(O)Ay, —CO$_2$R$^7$, —CO$_2$Ay, —SO$_2$NHR$^9$, Het, —NHHet and —NHR$^{10}$Het;

q is 0, 1, 2, 3, 4 or 5;

each R$^5$ is the same or different and is independently selected from the group consisting of halo, alkyl, alkenyl, alkynyl, cycloalkyl, cycloalkenyl, —R$^{10}$cycloalkyl, Ay, —NHR$^{10}$Ay, —NR$^7$Ay, Het, —NHHet, —NHR$^{10}$Het, —OR$^7$, —OAy, —OHet, —R$^{10}$OR$^9$, —NR$^7$R$^8$, —R$^{10}$NR$^7$R$^8$, —R$^{10}$NR$^7$Ay, —R$^{10}$C(O)R$^9$, —C(O)R$^9$, —C(O)Ay, —C(O)Het, —CO$_2$R$^9$, —R$^{10}$CO$_2$R$^9$, —C(O)NR$^7$R$^8$, —C(O)NR$^7$Ay, —C(O)NHR$^{10}$Het, —R$^{10}$C(O)NR$^9$R$^{11}$, —C(S)NR$^9$R$^{11}$, —R$^{10}$C(S)NR$^9$R$^{11}$, —R$^{10}$NHC(NH)NR$^9$R$^{11}$, —C(NH)NR$^7$R$^8$, —C(NH)NR$^7$Ay, —R$^{10}$C(NH)NR$^9$R$^{11}$, —S(O)$_2$NR$^7$R$^8$, —S(O)$_2$NR$^7$Ay, —R$^{10}$SO$_2$NHCOR$^9$, —R$^{10}$SO$_2$NR$^9$R$^{11}$, —R$^{10}$SO$_2$R$^9$, —S(O)$_n$R$^9$, cyano, azido and nitro; or two adjacent R$^5$ groups together with the atoms to which they are bonded form a C$_{5-6}$ cycloalkyl or aryl;

p is 0, 1, 2 or 3; and each R$^6$ is the same or different and is independently selected from the group consisting of halo, alkyl, alkenyl, alkynyl, cycloalkyl, cycloalkenyl, —R$^{10}$cycloalkyl, Ay, Het, —R$^{10}$Ay, —R$^{10}$Het, —OR$^7$, —OAy, —OHet, —R$^{10}$OR$^9$, —OR$^{10}$Ay, —OR$^{10}$Het, —R$^{10}$NR$^7$R$^8$, —R$^{10}$NR$^7$Ay, —R$^{10}$C(O)R$^9$, —C(O)R$^9$, —C(O)Ay, —C(O)Het, —CO$_2$R$^9$, —R$^{10}$CO$_2$R$^9$, —C(O)NR$^7$R$^8$, —C(O)NR$^7$Ay, —C(O)NHR$^{10}$Het, —R$^{10}$C(O)NR$^9$R$^{11}$, —C(S)NR$^9$R$^{11}$, —R$^{10}$C(S)NR$^9$R$^{11}$, —R$^{10}$NHC(NH)NR$^9$R$^{11}$, —C(NH)NR$^7$R$^8$, —C(NH)NR$^7$Ay, —R$^{10}$C(NH)NR$^9$R$^{11}$, —S(O)$_2$NR$^7$R$^8$, —S(O)$_2$NR$^7$Ay, —R$^{10}$SO$_2$NHCOR$^9$, —R$^{10}$SO$_2$NR$^9$R$^{11}$, —R$^{10}$SO$_2$R$^9$, —S(O)$_n$R$^9$, cyano, azido and nitro; or two adjacent R$^6$ groups together with the atoms to which they are bonded form a C$_{5-6}$ cycloalkyl or a 5- or 6-membered heterocyclic group containing 1 or 2 heteroatoms;

wherein when Y is CH, R$^3$ is not —NR$^7$Ay;

or a pharmaceutically acceptable salt or solvate thereof.

2. The compound according to claim 1 wherein R$^1$ is selected from the group consisting of alkyl, cycloalkyl, —R$^{10}$cycloalkyl, —OR$^7$, —OAy, —R$^{10}$OR$^9$, —R$^{10}$NR$^7$R$^8$, —C(O)R$^9$, —CO$_2$R$^9$, —C(O)NR$^7$R$^8$, —S(O)$_2$NR$^7$R$^8$, —S(O)$_n$R$^9$, cyano, nitro and azido.

3. The compound according to claim 1 wherein R$^1$ is selected from the group consisting of alkyl, —OR$^7$, —C(O)NR$^7$R$^8$ and —S(O)$_n$R$^9$.

4. The compound according to claim 1 wherein R$^2$ is selected from the group consisting of —NR$^7$R$^8$, —OR$^7$, —S(O)$_n$R$^9$, Het, —NHHet and —NHR$^{10}$Het.

5. The compound according to claim 1 wherein R$^2$ is —NR$^7$R$^8$ or Het.

6. The compound according to claim 1 wherein R$^3$ and R$^4$ are the same or different and are each independently selected from the group of H, halo, alkyl, Ay, —OR$^7$, —R$^{10}$OR$^7$, —NR$^7$R$^8$, —R$^{10}$NR$^7$R$^8$ and —CO$_2$R$^7$.

7. The compound according to claim 1 wherein R$^3$ and R$^4$ are both H.

8. The compound according to claim 1 wherein q is 0, 1 or 2.

9. The compound according to claim 1 wherein each R$^5$ is the same or different and is independently selected from the group consisting of halo, alkyl, alkenyl, Ay, —OR$^7$, —OAy, —NR$^7$R$^8$, —NR$^7$Ay, —NHR$^{10}$Ay, Het, —CO$_2$R$^9$, —C(O)NR$^7$R$^8$, —C(O)NR$^7$Ay, —S(O)$_2$NR$^7$R$^8$, cyano, nitro and azido.

10. The compound according to claim 1, wherein each R$^5$ is the same or different and is independently selected from the group consisting of halo, alkyl, —OR$^7$, —NR$^7$R$^8$ and cyano.

11. The compound according to claim 1, wherein p is 0 or 1.

12. The compound according to claim 1 wherein each R$^6$ is the same or different and is independently selected from the group consisting of halo, alkyl, Ay, Het, —OR$^7$, —OAy, —OHet, —R$^{10}$OR$^9$, —R$^{10}$NR$^7$R$^8$, —C(O)R$^9$, —CO$_2$R$^9$, —C(O)NR$^7$R$^8$, —C(O)NR$^7$Ay, —C(O)NHR$^{10}$Het, —R$^{10}$C(O)NR$^9$R$^{11}$, —S(O)$_2$NR$^7$R$^8$, —R$^{10}$SO$_2$NHCOR$^9$, —S(O)$_n$R$^9$, cyano, azido and nitro.

13. The compound according to claim 1, wherein each R$^6$ is the same or different and is independently selected from the group consisting of halo, alkyl, Het, —OR$^7$, —C(O)NR$^7$R$^8$, —S(O)$_2$NR$^7$R$^8$, —S(O)$_n$R$^9$ and cyano.

14. A compound selected from the group consisting of:
2-(4-Fluorophenyl)-7-methyl-3-(4-pyrimidinyl)pyrazolo [1,5-a]pyridine;
2-(4-Fluorophenyl)-7-methylthio-3-(4-pyrimidinyl)pyrazolo[1,5-a]pyridine;
2-(4-Fluorophenyl)-7-methylsulfinyl-3-(4-pyrimidinyl) pyrazolo[1,5-a]-pyridine;
7-(2-Fluoroethoxy)-2-(4-fluorophenyl)-3-(4-(2-methylthio)pyrimidinyl)-pyrazolo[1,5-a]pyridine;
N-Butyl-4-[7-(2-fluoroethoxy)-2-(4-fluorophenyl)pyrazolo[1,5-a]pyridin-3-yl]-2-pyrimidinamine;
N-Benzyl-4-[7-(2-fluoroethoxy)-2-(4-fluorophenyl)pyrazolo[1,5-a]pyridin-3-yl]-2-pyrimidinamine;
2-(4-Fluorophenyl)-3-(4-(2-methylthio)pyrimidinyl)-7-(2,2,2-trifluoroethoxy)pyrazolo[1,5-a]pyridine;
N-Butyl-4-[2-(4-fluorophenyl)-7-(2,2,2-trifluoroethoxy) pyrazolo[1,5-a]pyridin-3-yl]-2-pyrimidinamine;
N-Benzyl-4-[2-(4-fluorophenyl)-7-(2,2,2-trifluoroethoxy)pyrazolo[1,5-a]-pyridin-3-yl]-2-pyrimidinamine;
N-Cyclopropyl-4-[2-(4-fluorophenyl)-7-(2,2,2-trifluoroethoxy)pyrazolo [1,5-a]pyridin-3-yl]-2-pyrimidinamine;
N-Cyclopentyl-4-[2-(4-fluorophenyl)-7-(2,2,2-trifluoroethoxy)pyrazolo [1,5-a]pyridin-3-yl]-2-pyrimidinamine;
N-Cyclohexyl-4-[2-(4-fluorophenyl)-7-(2,2,2-trifluoroethoxy)pyrazolo [1,5-a]pyridin-3-yl]-2-pyrimidinamine;
3-(4-[2-(4-Fluorophenyl)-7-(2,2,2-trifluoroethoxy)pyrazolo[1,5-a]pyridin-3-yl]-2-pyrimidinylamino)-1-propanol;
2-(4-Fluorophenyl)-3-(4-(2-methyloxy)pyrimidinyl)-7-(2,2,2-trifluoroethoxy)pyrazolo[1,5-a]pyridine;
2-(4-Fluorophenyl)-3-(4-(2-phenyloxy)pyrimidinyl)-7-(2,2,2-trifluoroethoxy)pyrazolo[1,5-a]pyridine;
2-(4-Fluorophenyl)-3-(4-(2-(2,2,2-trifluoroethoxy))pyrimidinyl)-7-(2,2,2-trifluoroethoxy)pyrazolo[1,5-a]pyridine;
2-(4-Fluorophenyl)-3-(4-(2-methylsulfinyl)pyrimidinyl)-7-(ethylsulfinyl)pyrazolo[1,5-a]pyridine;
2-(4-Fluorophenyl)-3-(4-(2-methylthio)pyrimidinyl)-7-(ethylthio)pyrazolo[1,5-a]pyridine;
Dimethyl 2-(4-fluorophenyl)-3-(4-(2-cyclopropylamino) pyrimidinyl)-7-pyrazolo[1,5-a]pyridinylcarboxamide;
7-(2-Fluoroethoxy)-2-(4-fluorophenyl)-3-(4-(2-methylsulfinyl)pyrimidinyl)-pyrazolo[1,5-a]pyridine;
2-(4-Fluorophenyl)-3-(4-(2-methylsulfinyl)pyrimidinyl)-7-(2,2,2-trifluoroethoxy)-pyrazolo[1,5-a]pyridine;
N-{4-[5-Chloro-7-(ethylsulfanyl)-2-(4-fluorophenyl) pyrazolo[1,5-a]pyridin-3-yl]-2-pyrimidinyl}-N-cyclopentylamine Ethyl 3-[2-(cyclopentylamino)-4-pyrimidinyl]-2-(4-fluorophenyl)-7-methylpyrazolo[1,5-a]pyridine-6-carboxylate;

3-[2-(Cyclopentylamino)-4-pyrimidinyl]-2-(4-fluorophenyl)-7-methylpyrazolo[1,5-a]pyridine-6-carboxylic acid;

3-[2-(Cyclopentylamino)-4-pyrimidinyl]-N-cyclopropyl-2-(4-fluorophenyl)-7-methylpyrazolo[1,5-a]pyridine-6-carboxamide;

N-Butyl-4-[7-butyl-2-(4-fluorophenyl)pyrazolo[1,5-a]pyridin-3-yl]-2-pyrimidinamine;

N-Butyl-4-[2-(4-fluorophenyl)-7-methylpyrazolo[1,5-a]pyridin-3-yl]-2-pyrimidinamine;

N-Butyl-4-[2-(4-fluorophenyl)-7-octylpyrazolo[1,5-a]pyridin-3-yl]-2-pyrimidinamine;

N-Cyclopropyl-4-[7-ethyl-2-(4-fluorophenyl)pyrazolo[1,5-a]pyridin-3-yl]-2-pyrimidinamine;

4-[7-Butoxy-2-(4-methoxyphenyl)pyrazolo[1,5-a]pyridin-3-yl]-N-cyclopentyl-2-pyrimidinamine;

4-[5-Chloro-2-(3-chlorophenyl)-7-(methylsulfanyl)pyrazolo[1,5-a]pyridin-3-yl]-N-cyclopentyl-2-pyrimidinamine;

N-cyclopentyl-6-[2-(4-fluorophenyl)-7-(methylthio)pyrazolo[1,5-a]pyridin-3-yl]pyrimidin-4-amine;

N-Cyclopentyl-4-[2-(4-fluorophenyl)-7-(methylthio)-5-morpholin-4-ylpyrazolo[1,5-a]pyridin-3-yl]pyrimidin-2-amine; and N-Cyclopentyl-4-[2-(4-fluorophenyl)-7-(isopropylthio)-5-morpholin-4-ylpyrazolo[1,5-a]pyridin-3-yl]pyrimidin-2-amine;

and pharmaceutically acceptable salts and solvates thereof.

15. A pharmaceutical composition comprising a compound according to claim 1.

16. The pharmaceutical composition according to claim 15, further comprising a pharmaceutically acceptable carrier or diluent.

17. The pharmaceutical composition according to claim 15 further comprising an antiviral agent selected from the group consisting of aciclovir and valaciclovir.

18. A process for preparing a compound according to claim 1, wherein Y is N; $R^2$ is selected from the group consisting of H, alkyl, cycloalkyl, alkenyl, cycloalkenyl, —$NR^7R^8$, Ay, —$NHR^{10}Ay$, —$OR^7$, —OAy, —$S(O)_nR^9$, —$S(O)_nAy$, —$R^{10}NR^7R^8$, —$R^{10}NR^7Ay$, Het, —NHHet, —$NHR^{10}Het$, —OHet, and —$OR^{10}Het$; $R^3$ is H and $R^4$ is H, said process comprising the steps of:

a) reacting a compound of formula (IX):

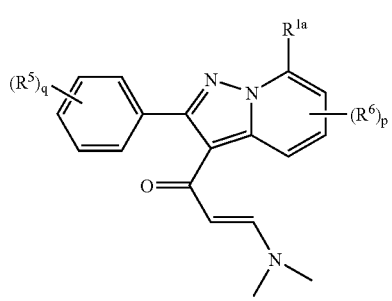

wherein $R^{1a}$ is selected from the group consisting of H, halo, alkyl, alkenyl, alkynyl, cycloalkyl, cycloalkenyl, —$R^{10}$cycloalkyl, —$R^{10}Ay$, —$R^{10}Het$, —$OR^7$, —OAy, —OHet, —$OR^{10}Ay$, —$OR^{10}Het$, —$R^{10}OR^9$, —$R^{10}NR^7R^8$, —$R^{10}NR^7Ay$, —$R^{10}C(O)R^9$, —$C(O)R^9$, —C(O)Ay, —C(O)Het, —$R^{10}OC(O)R^9$, —$R^{10}OC(O)Ay$, —$R^{10}OC(O)Het$, —$CO_2R^9$, —$R^{10}CO_2R^9$, —$C(O)NR^7R^8$, —$C(O)NR^7Ay$, —$C(O)NHR^{10}Ay$, —$R^{10}C(O)NR^9R^{11}$, —$C(S)NR^9R^{11}$, —$R^{10}C(S)NR^9R^{11}$, —$R^{10}NHC(NH)NR^9R^{11}$, —$C(NH)NR^7R^8$, —$C(NH)NR^7Ay$, —$R^{10}C(NH)NR^9R^{11}$, —$S(O)_2NR^7R^8$, —$S(O)_2NR^7Ay$, —$R^{10}SO_2NHCOR^9$, —$R^{10}SO_2NR^9R^{10}$, —$R^{11}SO_2R^9$, —$R^{10}OS(O)_nR^9$, —$R^{10}NHSO_2R^9$, —$R^{10}NHCOR^9$, —$S(O)_nR^9$, —$S(O)_nAy$, —$S(O)_n$Het, cyano, azido and nitro;

with a compound of formula (X):

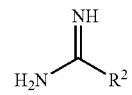

to prepare a compound of formula (XI):

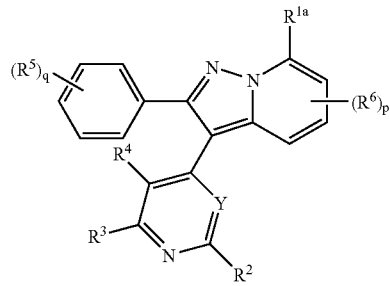

and b) when $R^{1a}$ is H or halo, converting the compound of formula (XI), to a compound of formula (I).

19. A process for preparing a compound according to claim 1 wherein Y is N; $R^2$ is selected from the group consisting of H, alkyl, cycloalkyl, alkenyl, cycloalkenyl, —$NR^7R^8$, Ay, —$NHR^{10}Ay$, —$OR^7$, —OAy, —$S(O)_nR^9$, —$S(O)_nAy$, —$R^{10}NR^7R^8$, —$R^{10}NR^7Ay$, Het, —NHHet, —$NHR^{10}Het$, —OHet, and —$OR^{10}Het$; $R^3$ is selected from the group consisting of H, alkyl, cycloalkyl, alkenyl, Ay, —$R^{10}OR^7$, —$R^{10}OAy$, —$NR^7R^8$ where $R^7$ and $R^8$ are not H, —$NR^7Ay$ where $R^7$ is not H, —$R^{10}NR^7R^8$, —$R^{10}NR^7Ay$, —$C(O)R^7$, —C(O)Ay, —$CO_2R^7$, —$CO_2Ay$, —$SO_2NHR^9$ and Het; and $R^4$ is H; said process comprising the steps of:

a) reacting a compound of formula (XV):

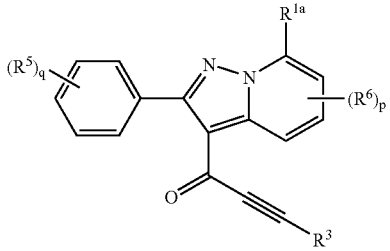

wherein $R^{1a}$ is selected from the group consisting of H, halo, alkyl, alkenyl, alkynyl, cycloalkyl, cycloalkenyl, —R$^{10}$cycloalkyl, —R$^{10}$Ay, —R$^{10}$Het, —OR$^7$, —OAy, —OHet, —OR$^{10}$Ay, —OR$^{10}$Het, —R$^{10}$OR$^9$, —R$^{10}$NR$^7$R$^8$, —R$^{10}$NR$^7$Ay, —R$^{10}$C(O)R$^9$, —C(O)R$^9$, —C(O)Ay, —C(O)Het, —R$^{10}$OC(O)R$^9$, —R$^{10}$OC(O)Ay, —R$^{10}$OC(O)Het, —CO$_2$R$^9$, —R$^{10}$CO$_2$R$^9$, —C(O)NR$^7$R$^8$, —C(O)NR$^7$Ay, —C(O)NHR$^{10}$Ay, —R$^{10}$C(O)NR$^9$R$^{11}$, —C(S)NR$^9$R$^{11}$, —R$^{10}$C(S)NR$^9$R$^{11}$, —R$^{10}$NHC(NH)NR$^9$R$^{11}$, —C(NH)NR$^7$R$^8$, —C(NH)NR$^7$Ay, —R$^{10}$C(NH)NR$^9$R$^{11}$, —S(O)$_2$NR$^7$R$^8$, —S(O)$_2$NR$^7$Ay, —R$^{10}$SO$_2$NHCOR$^9$, —R$^{10}$SO$_2$NR$^9$R$^{11}$, —R$^{10}$SO$_2$R$^9$, —R$^{10}$OS(O)$_n$R$^9$, —R$^{10}$NHSO$_2$R$^9$, —R$^{10}$NHCOR$^9$, —S(O)$_n$R$^9$, —S(O)$_n$Ay, —S(O)$_n$Het, cyano, azido and nitro;

with a compound of formula (X):

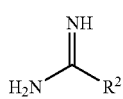

X to prepare a compound of formula (XI):

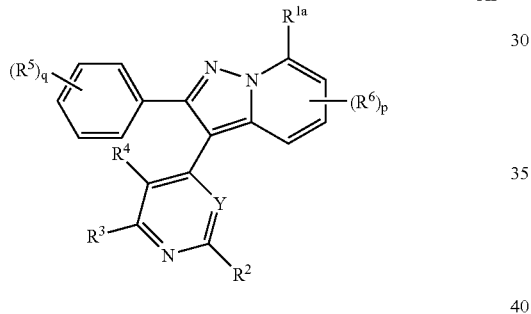

XI and b) when R$^{1a}$ is H or halo, converting the compound of formula (XI) to a compound of formula (I).

20. A process for preparing a compound according to claim 1, wherein Y is N and R$^2$ is selected from the group consisting of H, alkyl, cycloalkyl, alkenyl, cycloalkenyl, —NR$^7$R$^8$, Ay, —NHR$^{10}$Ay, —OR$^7$, —OAy, —S(O)$_n$R$^9$, —S(O)$_n$Ay, —R$^{10}$NR$^7$R$^8$, —R$^{10}$NR$^7$Ay, Het, —NHHet, —NHR$^{10}$Het, —OHet, and —OR$^{10}$Het, said process comprising the steps of:

a) reacting a compound of formula (XVIII):

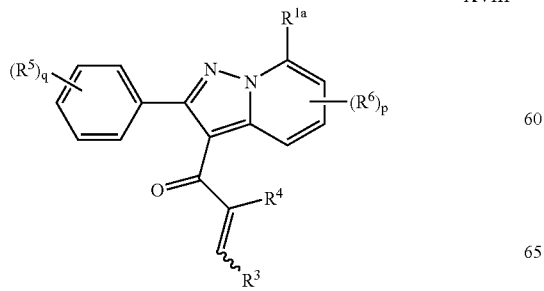

XVIII wherein R$^{1a}$ is selected from the group consisting of H, halo, alkyl, alkenyl, alkynyl, cycloalkyl, cycloalkenyl, —R$^{10}$cycloalkyl, —R$^{10}$Ay, —R$^{10}$Het, —OR$^7$, —OAy, —OHet, —OR$^{10}$Ay, —OR$^{10}$Het, —R$^{10}$OR$^9$, —R$^{10}$NR$^7$R$^8$, —R$^{10}$NR$^7$Ay, —R$^{10}$C(O)R$^9$, —C(O)R$^9$, —C(O)Ay, —C(O)Het, —R$^{10}$OC(O)R$^9$, —R$^{10}$OC(O)Ay, —R$^{10}$OC(O)Het, —CO$_2$R$^9$, —R$^{10}$CO$_2$R$^9$, —C(O)NR$^7$R$^8$, —C(O)NR$^7$Ay, —C(O)NHR$^{10}$Ay, —R$^{10}$C(O)NR$^9$R$^{11}$, —C(S)NR$^9$R$^{11}$, —R$^{10}$C(S)NR$^9$R$^{11}$, —R$^{10}$NHC(NH)NR$^9$R$^{11}$, —C(NH)NR$^7$R$^8$, —C(NH)NR$^7$Ay, —R$^{10}$C(NH)NR$^9$R$^{11}$, —S(O)$_2$NR$^7$R$^8$, —S(O)$_2$NR$^7$Ay, —R$^{10}$SO$_2$NHCOR$^9$, —R$^{10}$SO$_2$NR$^9$R$^{11}$, —R$^{10}$SO$_2$R$^9$, —R$^{10}$OS(O)$_n$R$^9$, —R$^{10}$NHSO$_2$R$^9$, —R$^{10}$NHCOR$^9$, —S(O)$_n$R$^9$, —S(O)$_n$Ay, —S(O)$_n$Het, cyano, azido and nitro;

with a compound of formula (X):

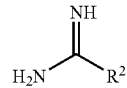

X followed by oxidative aromatization, to prepare a compound of formula (XI):

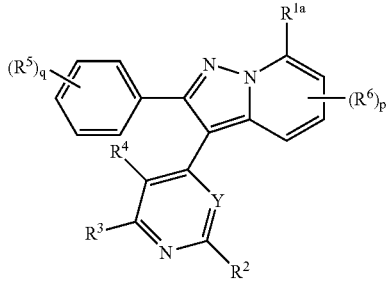

XI and b) when R$^{1a}$ is H or halo, converting the compound of formula (XI) to a compound of formula (I).

21. A process for preparing a compound according to claim 1, said process comprising the steps of:

a) reacting a compound of formula (XIX):

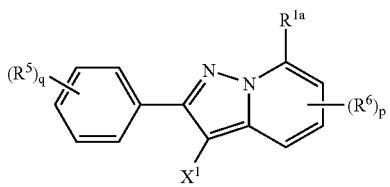

XIX wherein X¹ is halo; and wherein R¹ᵃ is selected from the group consisting of H, halo, alkyl, alkenyl, alkynyl, cycloalkyl, cycloalkenyl, —R¹⁰cycloalkyl, —R¹⁰Ay, —R¹⁰Het, —OR⁷, —OAy, —OHet, —OR¹⁰Ay, —OR¹⁰Het, —R¹⁰OR⁹, —R¹⁰NR⁷R⁸, —R¹⁰NR⁷Ay, —R¹⁰C(O)R⁹, —C(O)R⁹, —C(O)Ay, —C(O)Het, —R¹⁰OC(O)R⁹, —R¹⁰OC(O)Ay, —R¹⁰OC(O)Het, —CO₂R⁹, —R¹⁰CO₂R⁹, —C(O)NR⁷R⁸, —C(O)NR⁷Ay, —C(O)NHR¹⁰Ay, —R¹⁰C(O)NR⁹R¹¹, —C(S)NR⁹R¹¹, —R¹⁰C(S)NR⁹R¹¹, —R¹⁰NHC(NH)NR⁹R¹¹, —C(NH)NR⁷R⁸, —C(NH)NR⁷Ay, —R¹⁰C(NH)NR⁹R¹¹, —S(O)₂NR⁷R⁸, —S(O)₂NR⁷Ay, —R¹⁰SO₂NHCOR⁹, —R¹⁰SO₂NR⁹R¹¹, —R¹⁰SO₂R⁹, —R¹⁰OS(O)ₙR⁹, —R¹⁰NHSO₂R⁹, —R¹⁰NHCOR⁹, —S(O)ₙR⁹, —S(O)ₙAy, —S(O)ₙHet, cyano, azido and nitro;

with a compound of formula (XX)

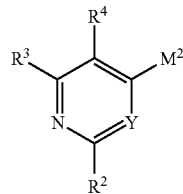

XX wherein M² is selected from the group consisting of —B(OH)₂, —B(ORa)₂, —B(Ra)₂, —Sn(Ra)₃, Zn-halide, ZnRa, Mg-halide where Ra is alkyl or cycloalkyl and halide is halo;

to prepare a compound of formula (XI):

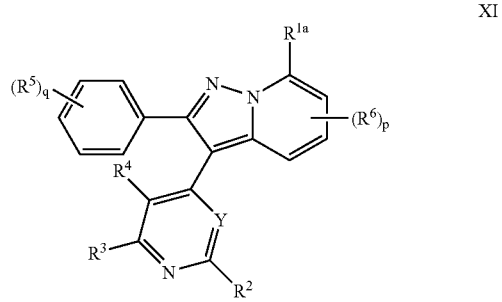

XI and b) when R¹ᵃ is H or halo, converting the compound of formula (XI), to a compound of formula (I).

22. The process according to claim 18 further comprising the step of converting a compound of formula (XI) to a pharmaceutically acceptable salt or solvate thereof.

23. The process according to claim 22 further comprising the step of converting a compound of formula (XI) or a pharmaceutically acceptable salt or solvate thereof to another compound of formula (XI) or a pharmaceutically acceptable salt or solvate thereof.

24. The process according to claim 18 further comprising the step of converting a compound of formula (I) to a pharmaceutically acceptable salt or solvate thereof.

25. The process according to claim 18 further comprising the step of converting a compound of formula (I) or a pharmaceutically acceptable salt or solvate thereof to another compound of formula (I) or a pharmaceutically acceptable salt or solvate thereof.

* * * * *

UNITED STATES PATENT AND TRADEMARK OFFICE
CERTIFICATE OF CORRECTION

PATENT NO. : 7,034,030 B2  
APPLICATION NO. : 10/473196  
DATED : April 25, 2006  
INVENTOR(S) : Alberti et al.

Page 1 of 1

It is certified that error appears in the above-identified patent and that said Letters Patent is hereby corrected as shown below:

Title Page
Item (56) References Cited
Please add: -- FR2757059 6/1998 --

Column 154, Line 9
Should read:
-- -$R^{10}SO_2NHCOR^9$, -$R^{10}SO_2NR^9R^{11}$ --

Column 154, Line 10
Should read:
-- -$R^{10}SO_2R^9$, -$R^{10}OS(O)_nR^9$, - $R^{10}NHSO_2R^9$ --

Signed and Sealed this

Tenth Day of April, 2007

JON W. DUDAS  
*Director of the United States Patent and Trademark Office*